United States Patent
Skerra et al.

(10) Patent No.: US 10,081,657 B2
(45) Date of Patent: *Sep. 25, 2018

(54) BIOSYNTHETIC PROLINE/ALANINE RANDOM COIL POLYPEPTIDES AND THEIR USES

(71) Applicants: TECHNISCHE UNIVERSITÄT MÜNCHEN, München (DE); XL-PROTEIN GMBH, Freising (DE)

(72) Inventors: Arne Skerra, Freising (DE); Uli Binder, Freising (DE); Martin Schlapschy, Freising (DE)

(73) Assignees: TECHNISCHE UNIVERSITAT MUNCHEN, Munich (DE); XL-PROTEIN GMBH, Freising (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/939,626

(22) Filed: Nov. 12, 2015

(65) Prior Publication Data
US 2016/0137698 A1 May 19, 2016

Related U.S. Application Data

(62) Division of application No. 13/697,569, filed as application No. PCT/EP2011/058307 on May 20, 2011, now Pat. No. 9,221,882.

(60) Provisional application No. 61/428,016, filed on Dec. 29, 2010.

(30) Foreign Application Priority Data

May 21, 2010 (EP) .................................. 10163564

(51) Int. Cl.
| | | |
|---|---|---|
| C07K 14/00 | (2006.01) | |
| C07K 16/00 | (2006.01) | |
| C07K 14/56 | (2006.01) | |
| C07K 14/615 | (2006.01) | |
| C07K 7/08 | (2006.01) | |
| A61K 47/64 | (2017.01) | |
| A61K 38/00 | (2006.01) | |
| A61K 39/00 | (2006.01) | |

(52) U.S. Cl.
CPC ............ *C07K 14/00* (2013.01); *A61K 47/645* (2017.08); *C07K 7/08* (2013.01); *C07K 14/001* (2013.01); *C07K 14/56* (2013.01); *C07K 14/615* (2013.01); *C07K 16/00* (2013.01); A61K 38/00 (2013.01); A61K 2039/505 (2013.01); C07K 2317/55 (2013.01); C07K 2319/31 (2013.01)

(58) Field of Classification Search
CPC .............. A61K 2039/505; A61K 38/00; A61K 47/48315; C07K 14/00; C07K 14/001; C07K 14/56; C07K 14/615; C07K 16/00; C07K 2317/55; C07K 2319/31; C07K 7/08

See application file for complete search history.

(56) References Cited

U.S. PATENT DOCUMENTS

| | | |
|---|---|---|
| 5,677,172 A | 10/1997 | Makarow |
| 9,221,882 B2 | 12/2015 | Skerra et al. |
| 2003/0190740 A1 | 10/2003 | Altman |
| 2006/0252120 A1 | 11/2006 | Kieliszewski |
| 2009/0192087 A1 | 7/2009 | Glass et al. |
| 2010/0292130 A1 | 11/2010 | Skerra et al. |

FOREIGN PATENT DOCUMENTS

| | | | |
|---|---|---|---|
| EP | 1 739 167 A1 | 1/2007 | |
| EP | 2 173 890 B1 | 3/2011 | |
| JP | 2007-529522 | 10/2007 | |
| WO | WO-01/78503 A2 | 10/2001 | |
| WO | WO-02/02597 A2 | 1/2002 | |
| WO | WO-2005/089796 A1 | 9/2005 | |
| WO | WO-2007/103515 A2 | 9/2007 | |
| WO | WO-2008/145400 A2 | 12/2008 | |
| WO | WO 2008155134 A1 * | 12/2008 | ............. C07K 14/47 |
| WO | WO-2010/091122 A1 | 8/2010 | |
| WO | WO 2011/144756 A1 | 11/2011 | |

OTHER PUBLICATIONS

"Cell Therapeutics Inc.'s Polyglutamate (PG) Technology Highlighted at International Polymer Therapeutics Meeting; Novel Recombinant Technology Extends PG Platform to G-CSF," PR Newswire, 2002, pp. 1-2, http://www.cticseattle.com/.

Affranchino, J.L., et al., "Indentification of a Trypanosoma cruzi antigen that is shed during the acute phase of Chagas' disease," Molecular and Biochemical Parasitology, 1989, pp. 221-228, vol. 34.

Alvarez, et. al., Improving protein pharmacokinetics by genetic fusion to simple amino acid sequences. J Biol Chem, 2004, 279, 3375-81.

Axelsson, et al., Studies of the release and turnover of a human neutrophil lipocalin. Scand J Clin Lab Invest, 1995, 55,577-88.

(Continued)

*Primary Examiner* — Hasan Syed Ahmed
*Assistant Examiner* — Erinne R Dabkowski
(74) *Attorney, Agent, or Firm* — Foley & Lardner LLP

(57) ABSTRACT

The present invention relates to a biosynthetic random coil polypeptide or a biosynthetic random coil polypeptide segment or biosynthetic conjugate, in which the biosynthetic random coil polypeptide, the biosynthetic random coil polypeptide segment, or the biosynthetic conjugate comprises an amino acid sequence consisting solely of proline and alanine amino acid residues, wherein the amino acid sequence consists of at least about 50 proline (Pro) and alanine (Ala) amino acid residues. The at least about 50 proline (Pro) and alanine (Ala) amino acid residues may be (a) constituent(s) of a heterologous polypeptide or an heterologous polypeptide construct. Also uses and methods of use of these biosynthetic random coil polypeptides or polypeptide segments or conjugates are described.

14 Claims, 23 Drawing Sheets

Figure 2:
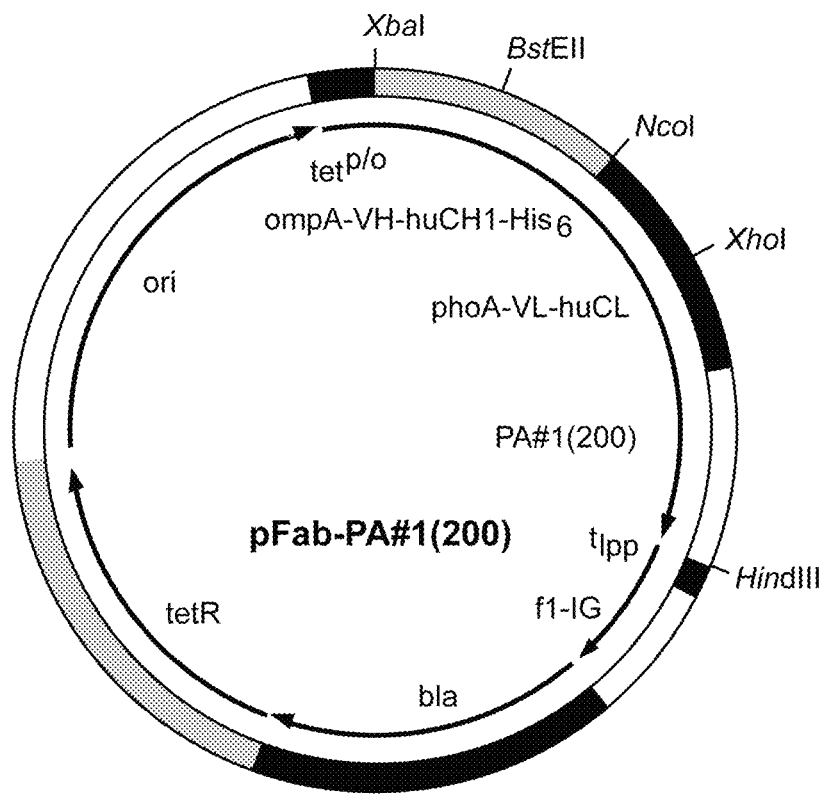
Figure 2:
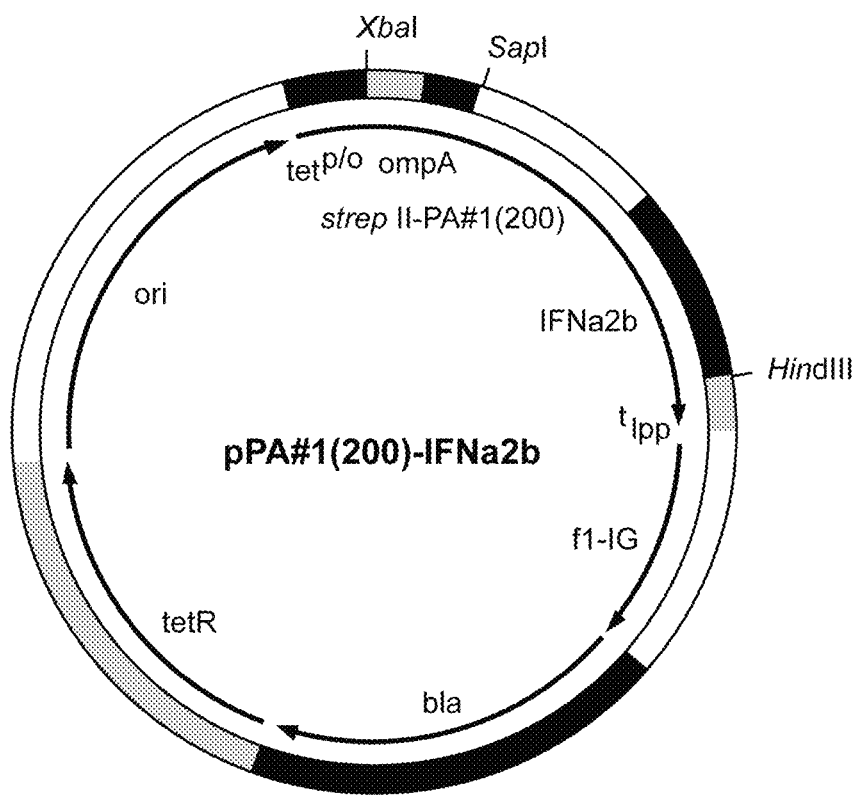

Specification includes a Sequence Listing.

(56) References Cited

OTHER PUBLICATIONS

Bamford, et. al., Synthetic polypeptides, preparation, structure, and properties, Academic Press Inc., 1956.
Benito et al., "A Polymorphic tandem repeat potentially useful for typing in the chromosome of Yersinia enterocolitica", Microbiology, 2004, vol. 150, pp. 199-204.
Berendsen, A Glimpae of the Holy Grail?, Science, 1998, 282, pp. 642-643.
Besheer et al, "Enzymatically Catalyzed HES Conjugation Using Microbial Transglutaminase: Proof of Feasibility," Journal of Pharmaceutical Sciences, vol. 98, No. 11, Nov. 2009, pp. 4420-4428.
Bhandari, D. et al., "H-NMR study of mobility and conformational constraints within the proline-rich N-terminal of the LC1 alkali light chain of skeletal myosin," Eur. J. Biochem, vol. 160, 1986, pp. 349-356.
Binz, et al., Engineering novel binding proteins from nonimmunoglobulin domains. Nat Biotechnol, 2005, 23, 1257-68.
Bohm, et al., "Quantitative analysis of protein far UV circular dichroism spectra by neural networks", Protein Engineering, vol. 5, No. 3, 1992, pp. 191-195.
Bradley et al., Limits of Cooperativity in a Structurally Modular Protein: Response of the Notch Ankyrin Domain to Analogous Alanine Substitutions in Each Repeat, J. Mol. Biol. (2002) 324, 373-386.
Brant, et al., Conformational energy estimates for statistically coiling polypeptide chains. J. Mol. Biol., 1967, 23,47-65.
Breustedt, et al., The 1.8-A crystal structure of human tear lipocalin reveals an extended branched cavity with capacity for multiple ligands. J Biol Chem, 2005, 280,484-93.
Breustedt, et al.,) Comparative ligand-binding analysis of ten human lipocalins. Biochim Biophys Acta, 2006, 1764, 161-73.
Bullock, et al., XLI-Blue: A High Efficiency Plasmid Transforming recA *Escherichia coli* Strain with Beta-Galactosidase Selection. BioTechniques, 1987, vol. 5, No. 4; pp. 376-378.
Buscaglia, C.A., et al., "Tandem Amino Acid Repeats From Trypanosoma cruzi Shed Antigens Increase the Half-Life of Proteins in Blood," Blood, The American Society of Hematology, 1999, pp. 2025-2032, vol. 93, No. 6.
Buscaglia, C.A., et al., "The Repetitive Domain of Trypanosoma cruzi trans-Sialidase Enhances the Immune Response against the Catalytic Domain," The Journal of Infectious Diseases, 1998, pp. 431-436, vol. 177.
Caliceti, et al.,) Pharmacokinetic and biodistribution properties of poly(ethylene glycol)-protein conjugates. Adv Drug Deliv Rev, 2003, 55, 1261-77.
Cantor, et. al., The Conformation of Biological Macromolecules, Biophysical Chemistry, 1996, Part I, pp. 425-428, Part II, pp. 1006-1010.
Carter, et al., Purification, cloning, expression and biological characterization of an interleukin-I receptor antagonist protein. Nature, 1990, 344, 633-8.
Chan et al., "Review on Medusa® : a Polymer-Based Sustained Release Technology for Protein and Peptide Drugs," Expert Opinion Drug Delivery, vol. 4, No. 4, 2007, pp. 441-451.
Chou, et al., Prediction of protein conformation. Biochemistry, 1974, 13,222-45.
Chu, et al., The hydrophobic pocket of 24p3 protein from mouse uterine luminal fluid: fatty acid and retinol binding activity and predicted structural similarity to lipocalins. J Pept Res., 1998, 52,390-7.
Clark, et al.,) Long-acting growth hormones produced by conjugation with polyethylene glycol. J Biol Chem, 1996, 271, 21969-77.
Constancis et al., "Macromolecular Colloids of Diblock Poly(amino acids) That Bind Insulin," Journal of Colloid and Interface Science, vol. 217,1999, pp. 357-368.
The Extended Search Report received in the related European Patent Application No. 10163564.7, dated Feb. 3, 2011.
The International Preliminary Report on Patentability received in the corresponding International Application No. PCT/EP2011/058307, dated Nov. 27, 2012.
The International Search Report received in the parent application PCT/EP2011/058307, dated Oct. 7, 2011.
Cowan, et al., Structure of poly-1-proline, Nature, 1955, pp. 501-503, vol. 176.
Creighton, Thomas E., "Proteins structures and molecular properties", European Molecular Biology Laboratory, Second Edition, pp. 190-191, 176-177.
de Benito, et al., "A polymorphic tandem potentially useful for typing in the chromosome of Yersinia enterocolitica", Microbiology, 2004, vol. 150, pp. 199-204.
Dennis, et al., "Albumin binding as a general strategy for improving the pharmacokinetics of proteins", J Biol Chem, 2002, 277,35035-43.
Elliott, et al., Enhancement of therapeutic protein in vivo activities through glycoengineering. Nat Biotechnol, 2003, 21, 414-21.
Estevez, et al., "Characterization of Synthetic Hydroxyproline-Rich Proteoglycans with Arabinogalactan Protein and Extensin Motifs in *Arabidopsis*[1]", Plant Physiology, 2006, 142. pp. 458-470.
Fandrich, et al., "The behaviour of polyamino acids reveals an inverse side chain effect in amyloid structure formation", Embo J., 2002, 21, 5682-90.
Fares et al., "Design of a Long-Acting Follitropin Agonist by Fusing the C-Terminal Sequence of the Chorionic Gonadotropin β Subunit to the Follitropin β Subunit," Proc. Natl. Acad. Sci. USA, vol. 89, May 1992, pp. 4304-4308.
Flo, et al., "Lipocalin 2 mediates an innate immune response to bacterial infection by sequestrating iron", Nature, 2004, 432, 917-21.
Ghetie, et al., Transcytosis and catabolism of antibody. Immunol Res, 2002, 25, 97-133.
Gill, et al., Calculation of protein extinction coefficients from amino acid sequence data. Anal Biochem, 1989, 182, 319-26.
Goetz, et al.,) The neutrophil lipocalin NGAL is a bacteriostatic agent that interferes with siderophore-mediated iron acquisition. Mol Cell, 2002, 10, 1033-43.
Goldenberg, M. M., Etanercept, a novel drug for the treatment of patients with severe, active rheumatoid arthritis. Clin Ther, 1999, 21, 75-87; discussion 1-2.
Greenfield, et. al., Computed circular dichroism spectra for the evaluation of protein conformation, Biochemistry, 1969, pp. 4108-4116, vol. 8, No. 10.
Gregoriadis et al., "Polysialic Acids: Potential in Improving Stability and Pharmacokinetics of Proteins and Other Therapeutics," Cell. Mol. Life Sci., vol. 57, 2000, pp. 1964-1969.
Harris, et al., Effect of pegylation on pharmaceuticals. Nat Rev Drug Discov., 2003, 2, 214-21.
Holmes, et al., Siderocalin (Lcn 2) also binds carboxymycobactins, potentially defending against mycobacterial infections through iron sequestration. Structure, 2005, 13, 29-41.
Homsi et al., "Phase I Trial of Poly-L-Glutamate Camptothecin (CT-2106) Administered Weekly in Patients with Advanced Solid Malignancies," Clinical Cancer Research, vol. 13., No. 19, Oct. 2007, pp. 5855-5861.
Huang et al., "Engineering a Pharmacologically Superior Form of Granulocyte-Colony-Stimulating Factor by Fusion with Gelatin-Like-Protein Polymer," European Journal of Pharmaceutics and Biopharmaceutics, vol. 74, 2010, pp. 435-441.
Hvidberg, et al., "The endocytic receptor megalin binds the iron transporting neutrophil-gelatinase-associated lipocalin with high affinity and mediates its cellular uptake". FEBS Lett, 2005, 579, 773-7.
Iizuka, et al., "Synthesis and Properties of High Molecular Weight Polypeptides Containing Proline", Bull. Chem. Soc. of Japan, 1998, col. 66, pp. 1269-1272.
Ivens, et al. "The Genome of the Kinetoplastid Parasite, Leishmania major", Science, 2005, 309(5733), pp. 436-442.
Johnson, et al., "SPAK, a STE20/SPS1-related kinase that activates the p38 pathway", Oncogene, 2000, vol. 19, pp. 4290-4297.
Klein et al., "Development and Characterization of a Long-Acting Recombinant hFSH Agonist," Human Reproduction, vol. 18, No. 1, 2003, pp. 50-56.
Klinke, et al., Physiologie, 5th Ed., Georg Thieme Verlag, Stuttgart. pp. 872-876.

(56) References Cited

OTHER PUBLICATIONS

Kojima, Y., et al., "Conjugation Cu,Zn-Superoxide Dismutase with Succinylated Gelatin: Pharmacological Activity and Cell-Lubricating Function," BloconJugate Chem., American Chemical Society, 1993, pp. 490-498, vol. 4.
Macewan S.R., et al., Invited Review Elastin-Like Polypeptides: Biomedical Applications of Tunable Biopolymers, PeptideScience, 2010, pp. 60-77, vol. 94, No. 1.
Makrides, et al., Extended in vivo half-life of human soluble complement receptor type I fused to a serum albumin-binding receptor. J Pharmacol Exp Ther, 1996, 277, 534-42.
Miller, et al., Dimensions of protein random coils. Biochemistry, 1968, 7, 3925-35.
Mori, et al., Endocytic delivery of lipocalin-siderophore-iron complex rescues the kidney from ischemia-reperfusion injury. J Clin Invest, 2005, 115, 610-21.
Na et al., "Effect of Molecular Size of PEGylated Recombinant Human Epidermal Growth Factor on the Biological Activity and Stability in Rat Wound Tissue," Pharmaceutical Development and Technology, vol. 11, 2006, pp. 513-519.
Ngo et al, Computational Complexity, Protein Structure Protection, and the Levinthal Paradox, 1994, pp. 491-494.
Nguyen, et al., The pharmacokinetics of an albumin-binding Fab (AB.Fab) can be modulated as a function of affinity for albumin. Protein Eng Des Sel, 2006, 19, 291-7.
Osborn, et al., Pharmacokinetic and pharmacodynamic studies of a human serum albumin-interferon-alpha fusion protein in cynomolgus monkeys. J Pharmacol Exp Ther, 2002, 303, 540-8.
Perelygina Ludmila, et al., "Complete sequence and comparative analysis of the genome of herpes B virus (Cercopithecine herpesvirus 1) from a rhesus monkey", Journal of Virology, vol. 77, No. 11, 2003, pp. 6167-6177. (XP002598446).
Perlman, et al., Glycosylation of an N-terminal extension prolongs the half-life and increases the in vivo activity of follicle stimulating hormone. J Clin Endocrinol Metab, 2003, 88, 3227-35.
Plückthun, A., IBC Conference on "Antibodies and Beyond Antibodies", Loews Coronado Bay Resort, Coronado, CA, Jun. 1-2, 2006. www.IBCLifeSciences.com/3198, pp. 1-6.
Qu et al., "Development of Compstatin Derivative-Albumin Binding Peptide Chimeras for Prolonged Plasma Half-Life," in Lebl (ed) Breaking Away: Proceedings of the 21st American Peptide Symposium, pp. 219-220, American Peptide Society, 2009.
Quadrifoglio, et al., Ultraviolet rotatory properties of polypeptides in solution. II. Poly-L-serine. J Am Chem Soc, 1968, 90, 2760-5.
Radhakrishnan et al., Zinc mediated dimer of human interferon-alpha 2b revealed by X-ray crystallography. Structure, 1996, 4, 1453-63.
Ray, et al., A simple procedure for removing contaminating aldehydes and peroxides from aqueous solutions of polyethylene glycols and of nonionic detergents that are based on the polyoxyethylene linkage. Anal Biochem, 1985, 146, 307-12.
Rosendahl, et al., Site-Specific Protein PEGylation. BioProcess International, 2005, 3, 52-61.
Rudinger, Peptide Hormones, JA Parsons, Ed., 1976, pp. 1-7.
Schellenberger, V, "AMUNIX—Engineering of Microproteins for Pharmaceutical Applications," Powerpoint presentation, pp. 1-35, Menlo Park, CA.
Schellenberger, V., et al., "A recombinant polypeptide extends the in vivo half-life of peptides and proteins in a tunable manner," Nature Biotechnology, 2009, pp. 1186-1190, vol. 27, No. 12.
Schimmel, et al., Conformational energy and configurational statistics of poly-L-proline. Proc Natl Acad Sci USA, 1967, 58, 52-9.
Schiweck, et al., Fermenter production of an artificial fab fragment, rationally designed for the antigen cystatin, and its optimized crystallization through constant domain shuffling. Proteins, 1995, 23, 561-5.

Schlapschy, et al., A system for concomitant overexpression of four periplasmic folding catalysts to improve secretory protein prodcution in *Escherichia coli*. Protein Engineering, Design & Selection, 2006, vol. 19, No. 8, pp. 385-390.
Schlapschy, et. al., Fusion of a recombinant antibody fragment with a homo-amino-acid polymer: effects on biophysical properties and prolonged plasma half-life, Protein Engineering, Design & Selection: PEDS, 2007, pp. 273-284, vol. 20, No. 6.
Schreuder, et al., A new cytokine-receptor binding mode revealed by the crystal structure of the IL-I receptor with an antagonist. Nature, 1997, 386, 194-200.
Shamji M.F., et al., "Development and Characterization of a Fusion Protein Between Thermally Responsive Elastin-like Polypeptide and Interleukin-1 Receptor Antagonist," Arthritis & Rheumatism, 2007, pp. 3650-3661, vol. 56, No. 11.
Shental-Bechor, et al., Monte Carlo studies of folding, dynamics, and stability in alpha-helices. Biophys J, 2005, 88, 2391-402.
Sigma, 2004, pp. 1-2.
Singer, J.W., "Paclitaxel poliglumex (XYOTAX™, CT-2103): A macromolecular taxane," Journal of Controlled Release, 2005, pp. 120-126, vol. 109.
Skerra, A, Use of the tetracycline promoter for the tightly regulated production of a murine antibody fragment in *Escherichia coli*. Gene, 1994, 151, 131-5.
Skerra, A., Engineered protein scaffolds for molecular recognition. J Mol Recognit, 2000, 13, 167-87.
Skerra, et al., Use of the Strep-Tag and streptavidin for detection and purification of recombinant proteins. Methods Enzymol, 2000, vol. 326, pp. 271-304.
Smith, et al., The concept of a random coil. Residual structure in peptides and denatured proteins. Fold Des, 1996, 1, R95-106.
Squire, P. G., Calculation of hydrodynamic parameters of random coil polymers from size exclusion chromotography and comparison with parameters by conventional methods. Journal of Chromatography, 1981, 5,433-442.
Sung et al., "An IFN-β-Albumin Fusion Protein That Displays Improved Pharmacokinetic and Pharmacodynamic Properties in Nonhuman Primates," Journal of Interferon & Cytokine Research, vol. 23, 2003, pp. 25-36.
Tan et al., "Glycosylation Motifs That Direct Arabinogalactan Addition to Arabinogalactan-Proteins," Plant Physiology, vol. 132, 2003, pp. 1362-1369.
UniProt Protein Database, Very large tegument protein, UL36, protein accession Q7T5D9, accessed on Nov. 25, 2014.
U.S. Office Action dated Jun. 28, 2013.
Voet et al, Biochemistry, John Wiley & Sons Inc., 1995, pp. 235-241.
Walker, et. al., Using protein-based motifs to stabilize peptides, Journal of Peptide Research, 2003, pp. 214-226, vol. 62, No. 5.
Walsh, G., Biopharmaceutical benchmarks—2003. Nat Biotechnol, 2003, 21, 865-70.
Walsh, G., Second-generation biopharmaceuticals. Eur. J Pharm Biopharm, 2004, 58, 185-96.
Wood, W. B., Host specificity of DNA produced by *Escherichia coli*: bacterial mutations affecting the restriction and modification of DNA. J Mol Biol, 1966, 16, 118-33.
Xu et al., "Human Growth Hormone Expressed in Tobacco Cells as an Arabinogalactan-Protein Fusion Glycoprotein has a Prolonged Serum Life," Transgenic Res, vol. 19, 2010, pp. 849-867.
Yang, et al., An iron delivery pathway mediated by a lipocalin. Mol Cell, 2002, 10, 1045-56.
Yanisch-Perron, et al., Improved M13 phage cloning vectors and host strains: nucleotide sequences of the M13mp18 and pUC19 vectors. Gene, 1985, 33, 103-19.
Canadian Office Action with Examination Search Report issued in Application No. 2,794,614 dated Feb. 10, 2017.

\* cited by examiner

Figure 1

```
gccGCTCCAGCTGCACCTGCTCTCCAGCAGCACCTGCTGCACCAGCTCCGGCTGCTCCTGCT
   |||||||||||||||||||||||||||||||||||||||||||||||||||||||||
   CGAGGTCGACGTGGACGAGGTCGTCGTGGACGACGTGGTCGAGGCCGACGAGGACGAcgg
 AlaAlaProAlaAlaProAlaAlaProAlaAlaProAlaAlaProAlaAlaProAlaAlaProAla
```

Figure 2

A

```
          SapI    SapI
AAGAGCTTCAACCGCGGAGAGTGCTCTTCTGCCCTGAAGAGCTTAAGCTT
+-|-----------------------------|-----------------+
TTCTCGAAGTTGGCGCCCTCTCACGAGAAGACGGACTTCTCGAATTCGAA
 LysSerPheAsnArgGlyGlyGluCysSerSerAlaEnd
```

B

```
                                                                                          SapI
GAGTGCTCTTCTGCCGCTCCAGCTGCACCTGCTCCAGCAGCACCTGCTCTGCACCAGCTCCGGCTGCTCCTGCTCCTGAAGAGCTT
+-|-------|-------------------------------------------------------------|-------------+
CTCACGAGAAGACGGCGAGGTCGACGTGGACGAGGTCGTCGTGGACGACGTGGTCGAGGCCGACGAGGACACTTCTCGAA
 GluCysSerSerAlaAlaProAlaAlaProAlaAlaProAlaAlaProAlaAlaProAlaAlaProAlaAla
 SapI
```

C

Figure 2 cont.

D

```
                   SapI
                   |     |
GAAAAAGGCGGCCAGCTCTTCTGCCCTGTGATCTGCCTCAAACCCACAGCCTGGGTAGC...
--------+---------+---------+---------+---------+---------+---
CTTTTTCCGCGGTCGAGAAGACGGGACACTAGACGGAGTTTGGGTGTCGGACCCATCG...
GluLysGlyAlaSerSerSerAlaCysAlaLeuProGlnThrHisSerLeuGlySer...
                               +1
```

E

```
                   SapI
                   |     |
GAAAAAGGCGGCCAGCTCTTCTGCGCTCCAGCTGCACCTGCTGCACCAGCTCCGGCTCCGCTCCTGCTGCCTGTGAT...
--------+---------+---------+---------+---------+---------+---------+---------+---------+---
CTTTTTCCGCGGTCGAGAAGACGCGAGGTCGACGTGGACGACGTGGTCGAGGCCGAGGCGAGGACGACGGACACTA...
GluLysGlyAlaSerSerSerAlaAlaProAlaAlaProAlaAlaProAlaAlaProAlaAlaProAlaAlaCysAsp...
                                                                            (1)
```

F

Figure 3
A
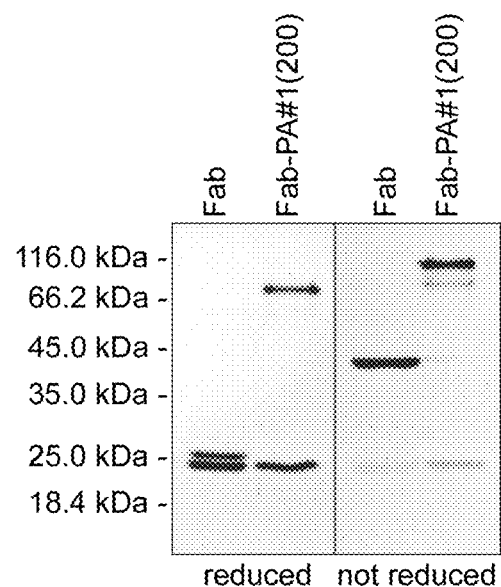
B
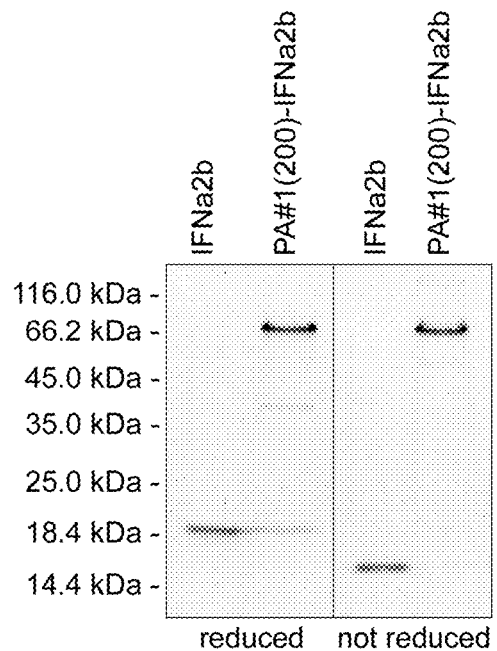

Figure 4
A
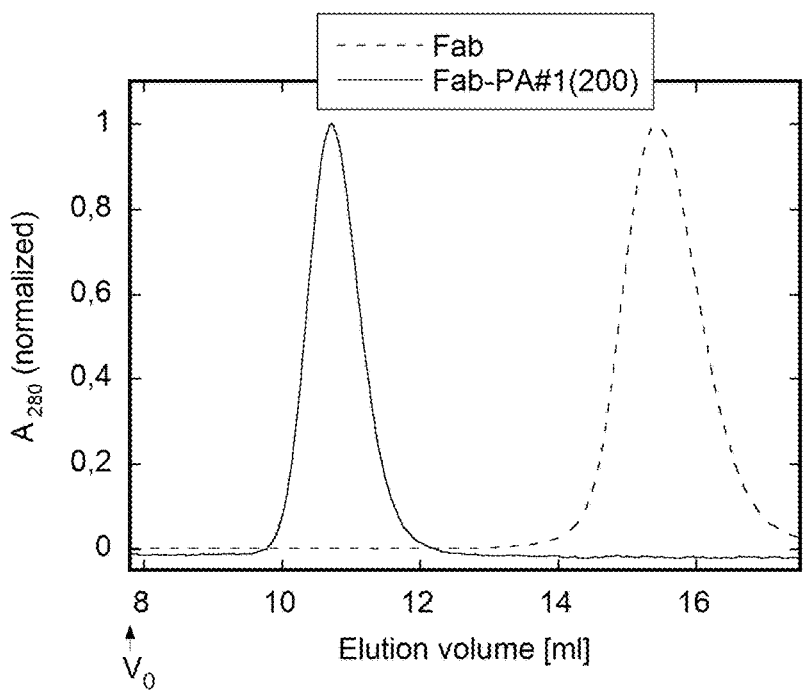
B
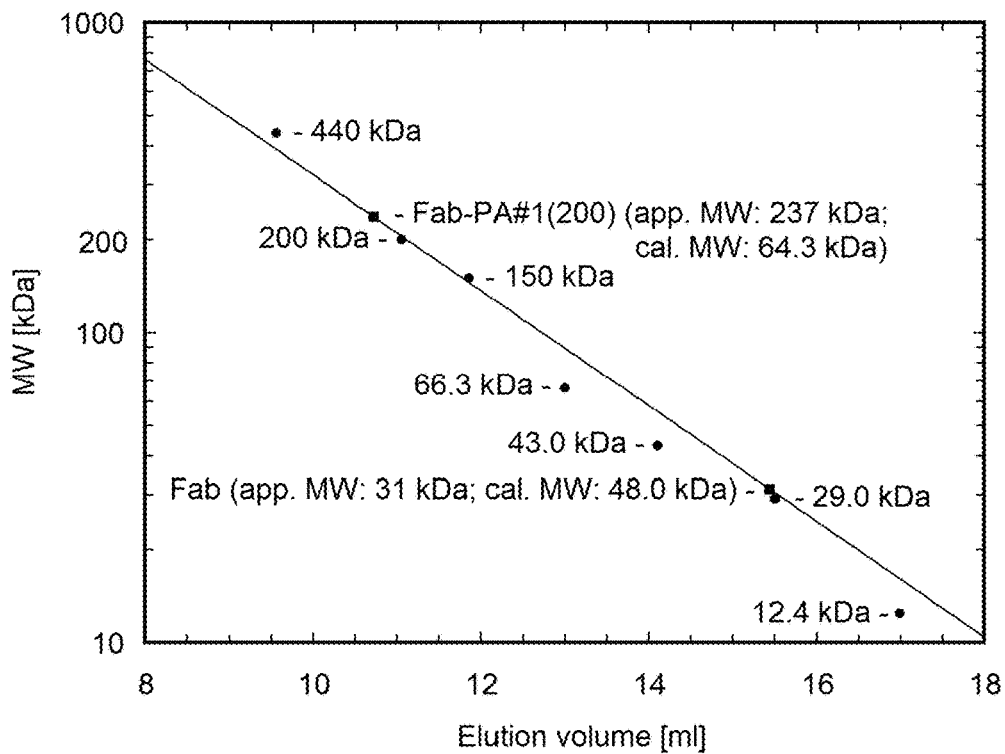

Figure 4 cont.
C
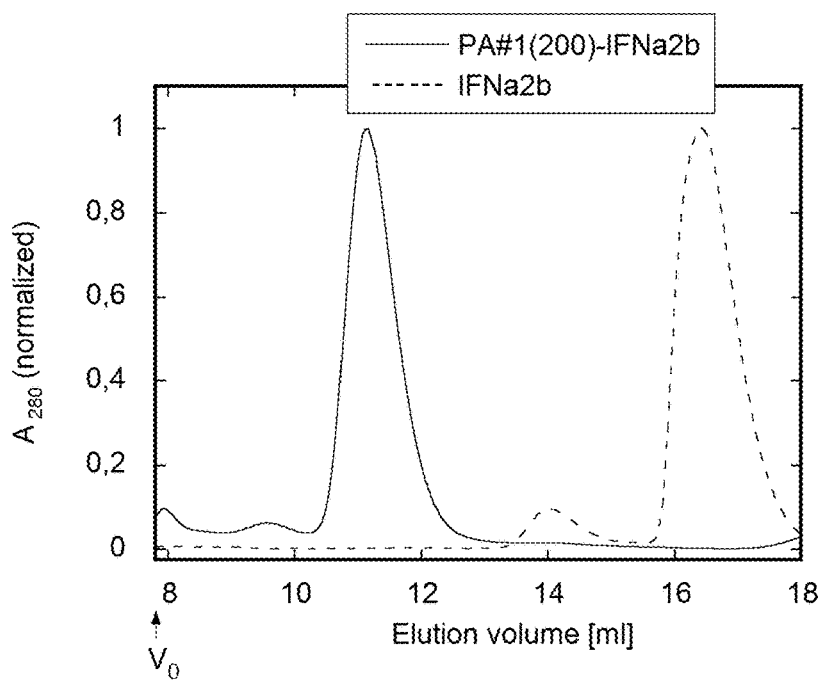
D
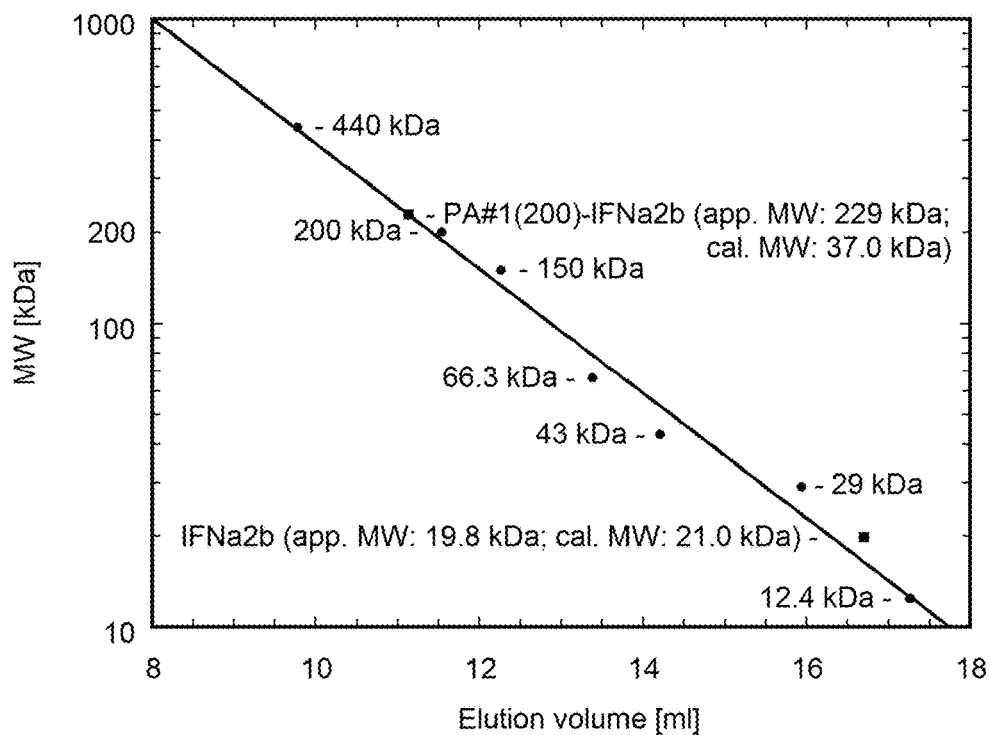

Figure 5
A
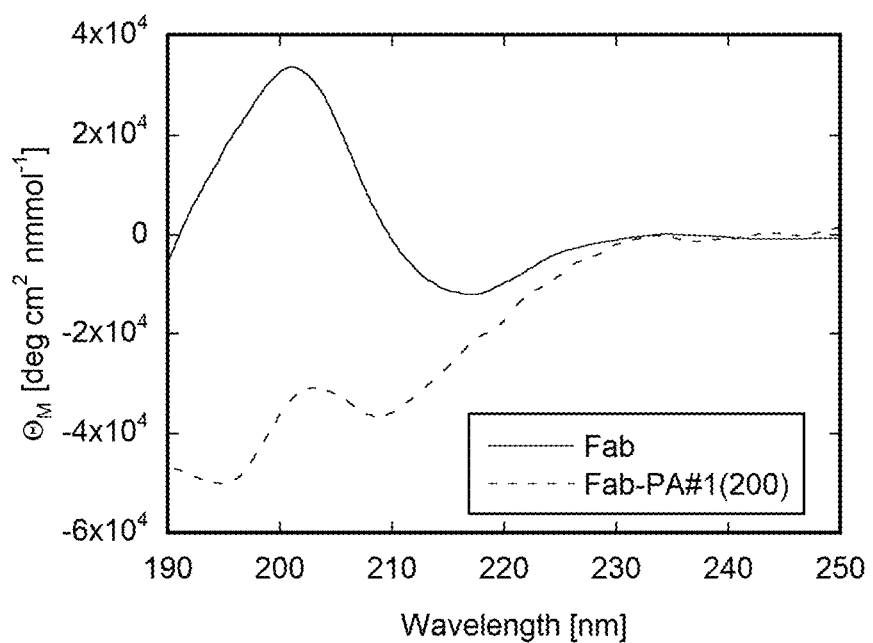
B
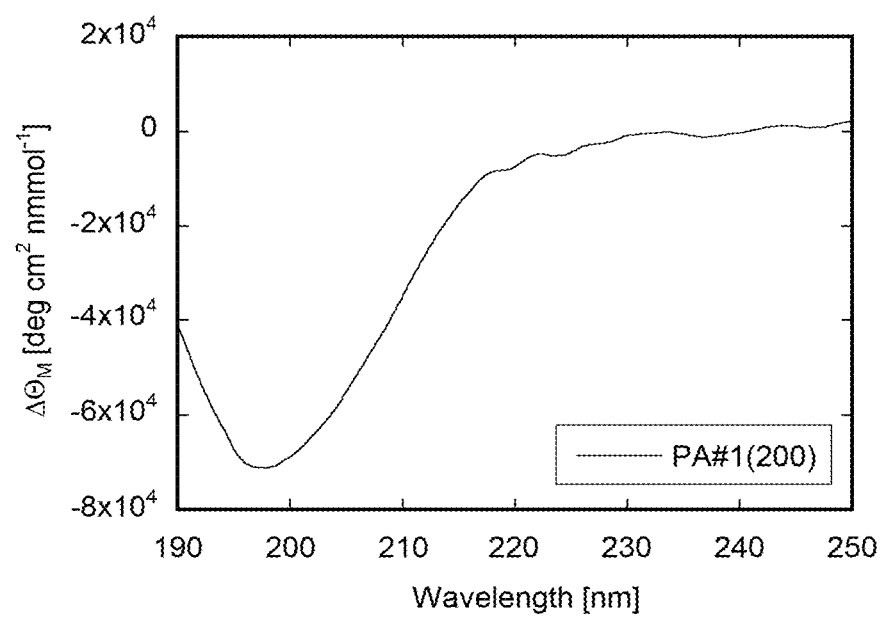

Figure 5 cont.
C
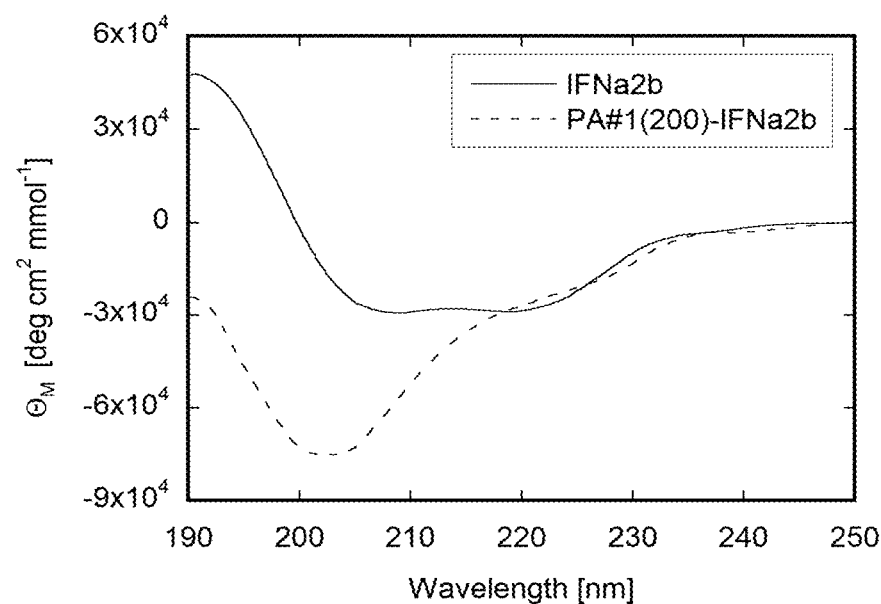
D
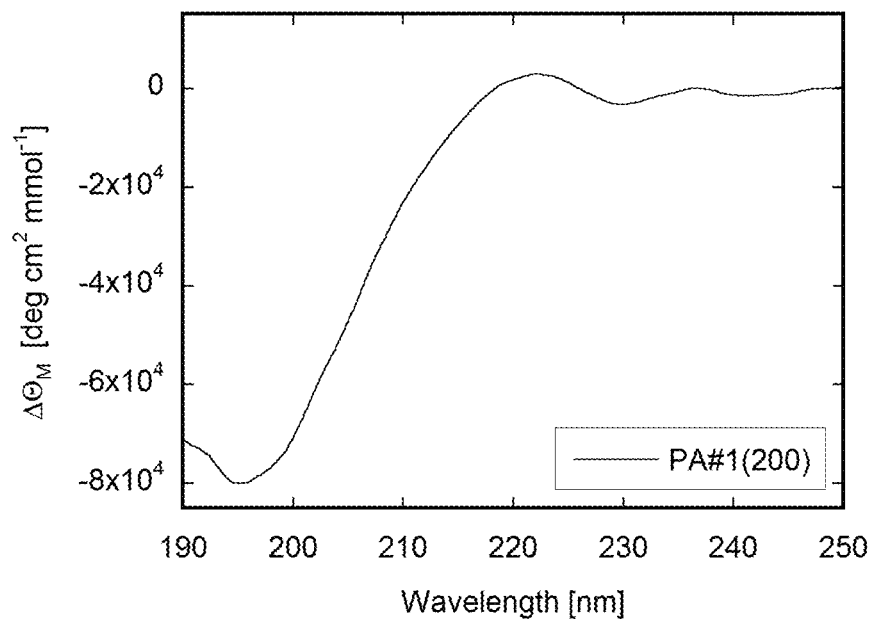

Figure 6

A

```
NheI                                          SapI
 |                                             |
GCCGCTAGCCATCACCACCATCACCATGGCGCCAGCTCTTCTGCCTTCCCAACC...
---------+---------+---------+---------+-----+----+----...
CGGCGATCGGTAGTGGTGGTAGTGGTACCGCGGTCGAGAAGACGGAAGGGTTGG...
AlaAlaSerHisHisHisHisHisHisGlyAlaSerSerSerAlaPheProThr... -
                                              +1
```

Figure 6 cont.

B

```
        NheI                                                                SapI
        |                                                                   |
GCCGCTAGCCATCACCACCATCACCATGGCGGCCGCCAGCTCTTCTGCGCCTCCAGCTGCCACCTGCTCTGCCACCAGCTCCG
--------+---------+---------+---------+---------+---------+---------+---------+
CGGCGATCGGTAGTGGTGGTAGTGGTACCGCGGTCGAGAAGACGCGGAGGTCGACGGTGGACGAGGTCGACGTGGTCGAGGC
 AlaAlaSerHisHisHisHisHisHisGlyAlaAlaSerSerSerAlaProAlaAlaProAlaAlaProAlaAlaProAlaPro

GCTGCTCCTGCTGCCTTCCCAACC...
--------+---------+------
CGACGAGGACGACGGAAGGGTTGG...
 AlaAlaProAlaAlaPheProThr...
             (1)
```

C

Figure 6:
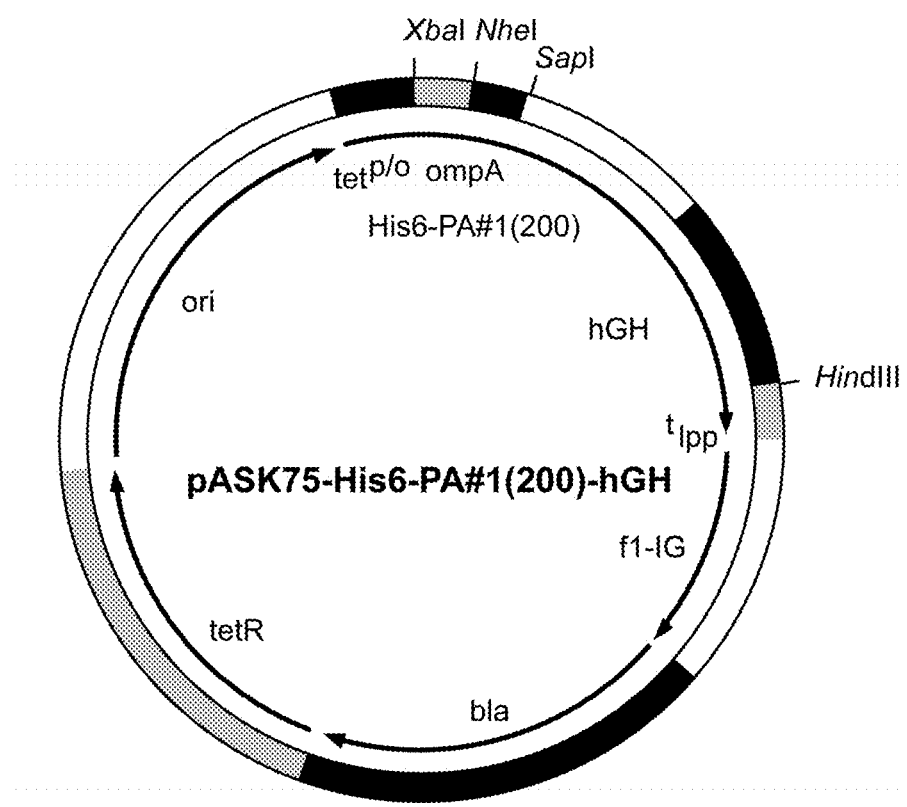

Figure 6 cont.
D
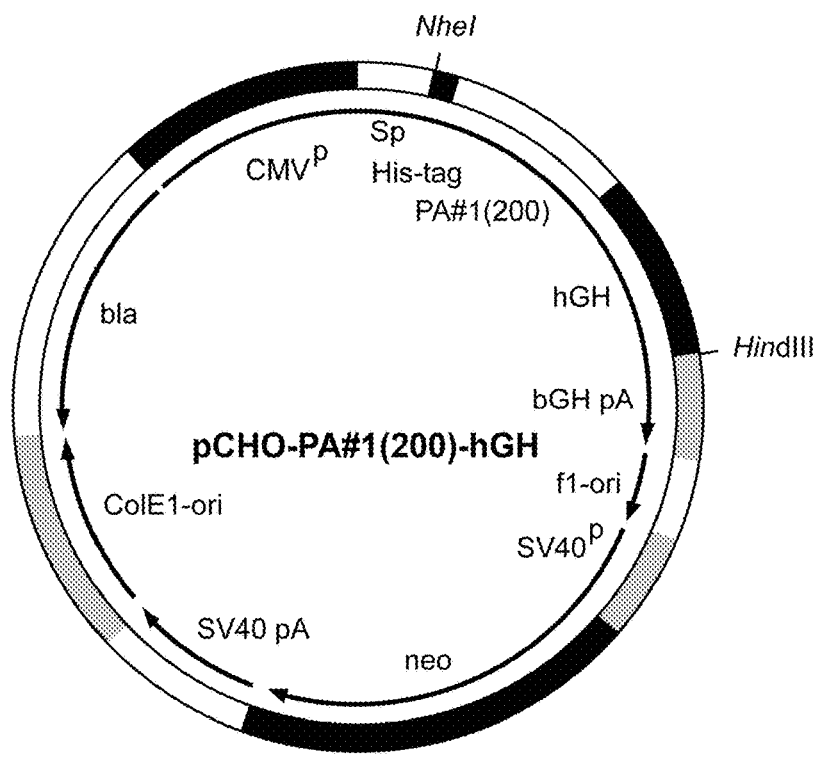
E
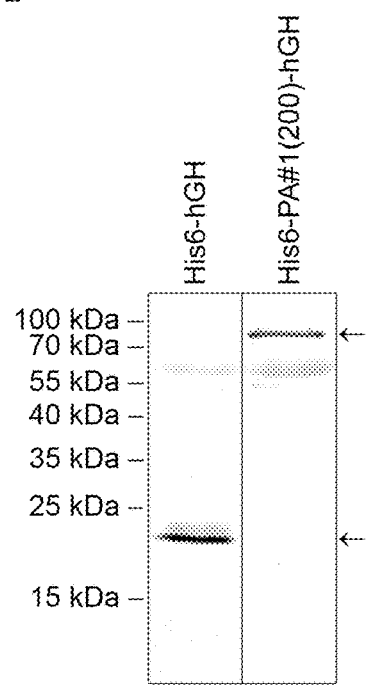

Figure 7

Chou-Fasman plot, 60 aa:

```
         AAPAAPAPAAPAAPAPAAPAAPAPAAPAAPAPAAPAAPAPAAPAAPAPAAPAAPAPAAPA
helix <------------------------------------------------------------>
sheet
turns Residue totals:  H: 59    E: 0    T: 0
       percent:  H: 98.3  E: 0.0  T: 0.0
```

Fig. 11
A
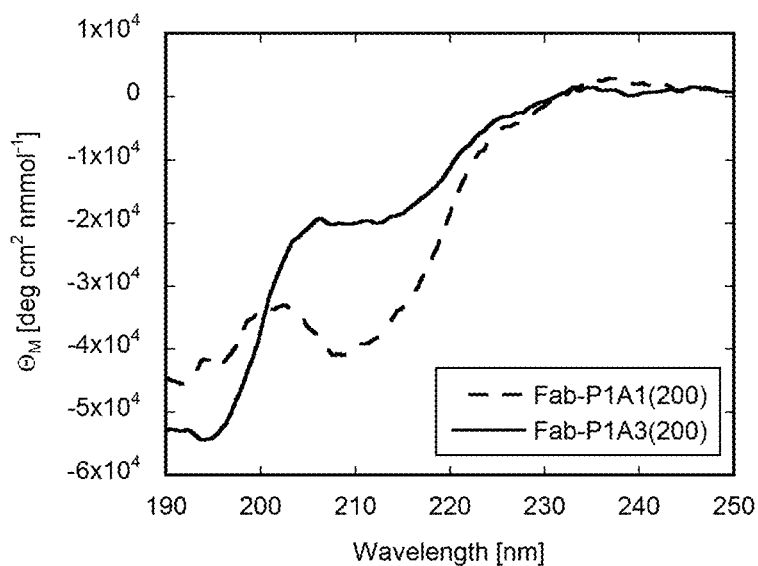
B
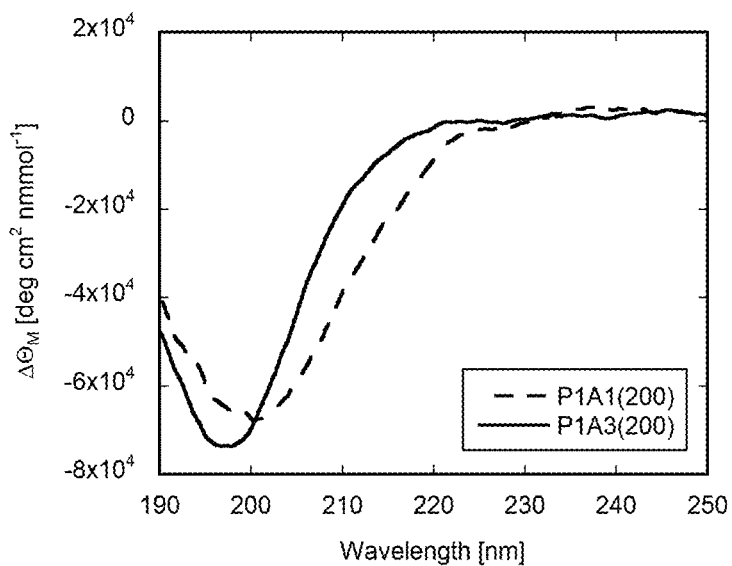

Fig. 12
A
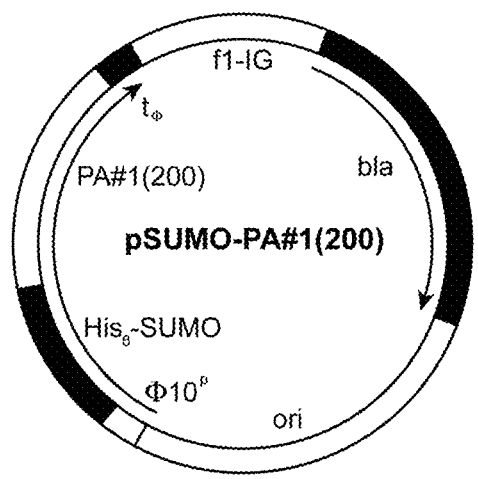
B
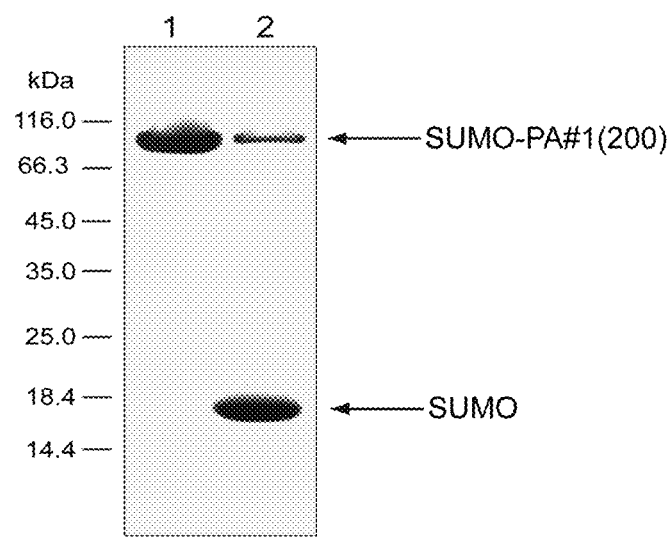
1: SUMO-PA#1(200) prior to cleavage
2: SUMO-PA#1(200) cleaved with SUMO protease Fig. 13 cont.
L
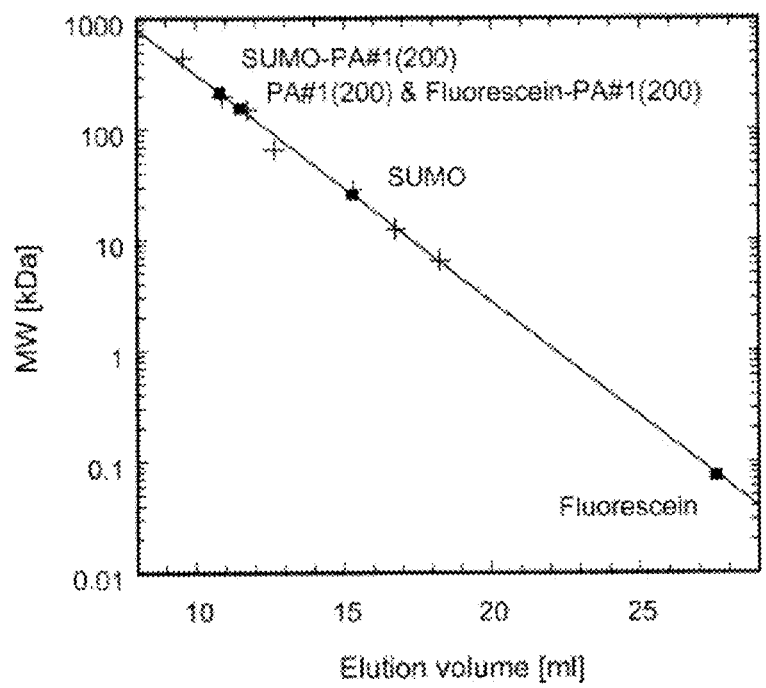
M
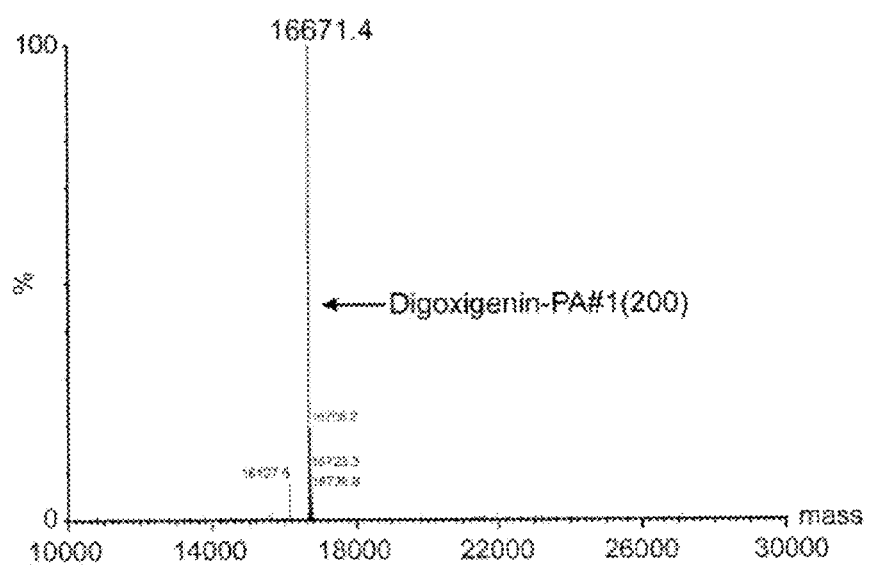

Fig. 14
A
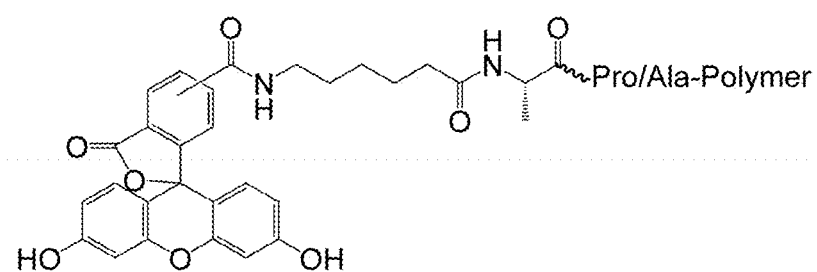
B
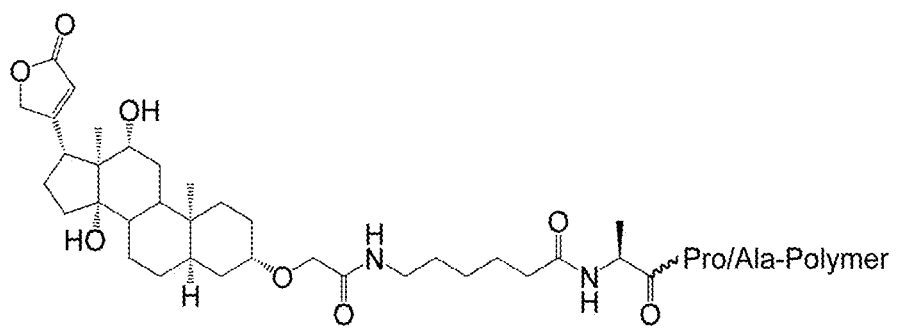

BIOSYNTHETIC PROLINE/ALANINE RANDOM COIL POLYPEPTIDES AND THEIR USES

CROSS-REFERENCE TO RELATED PATENT APPLICATIONS

This application is a Divisional of U.S. application Ser. No. 13/697,569, which entered U.S. National Phase on Nov. 13, 2012 from International Application No. PCT/EP2011/058307, filed May 20, 2011; which claims priority to Provisional U.S. Application 61/428,016, filed Dec. 29, 2010; and European Patent Office Priority Application 10163564.7, filed May 21, 2010. The foregoing applications are incorporated herein by reference in their entirety.

This application contains a Sequence Listing which has been submitted in ASCII format via EFS-Web and is hereby incorporated by reference in its entirety.

The present invention relates to a biosynthetic random coil polypeptide or a biosynthetic random coil polypeptide segment or a conjugate, said biosynthetic random coil polypeptide or a biosynthetic random coil polypeptide segment or a conjugate comprising an amino acid sequence consisting solely of proline and alanine amino acid residues, wherein said amino acid sequence consists of at least about 50 proline (Pro) and alanine (Ala) amino acid residues. Said at least about 50 proline (Pro) and alanine (Ala) amino acid residues may be (a) constituent(s) of a heterologous polypeptide or an heterologous polypeptide construct. Also uses and methods of use of these biosynthetic random coil polypeptides, said polypeptide segments or said conjugates are described. The uses may, inter alia, comprise medical uses, diagnostic uses or uses in the food industry as well as other industrial applications, like in the paper industry, in oil recovery and the like. The present invention relates, also, to (a) specific use(s) of the herein provided biosynthetic random coil polypeptide or biosynthetic random coil polypeptide segment or conjugates, said biosynthetic random coil polypeptide or biosynthetic random coil polypeptide segment or conjugates comprising an amino acid sequence consisting solely of proline and alanine amino acid residues. The amino acid sequence of the herein provided biosynthetic random coil polypeptide or biosynthetic random coil polypeptide segment consists of at least about 50, of at least about 100, of at least about 150, of at least about 200, of at least about 250, of at least about 300, of at least about 350 or of at least about 400 proline (Pro) and alanine (Ala) amino acid residues. Said at least about 50, at least about 100, at least about 150, at least about 200, at least about 250, at least about 300, at least about 350 or at least about 400 proline (Pro) and alanine (Ala) amino acid residues are preferably (a) a constituent of a heterologous polypeptide or a heterologous polypeptide construct or are preferably (b) a constituent of a conjugate, like a drug conjugate, like a conjugate with a food or cosmetic ingredient or additive, like a conjugate with a biologically active compound or like a conjugate with a spectroscopically active compound. In particular, heterologous proteins are provided herein whereby these proteins comprise at least two domains, wherein a first domain of said at least two domains comprises an amino acid sequence having and/or mediating an activity, like a biological activity, and a second domain of said at least two domains comprising the biosynthetic random coil proline/alanine polypeptide or proline/alanine polypeptide segment of the present invention. The present invention relates in particular to a drug conjugate comprising (i) a biosynthetic random coil polypeptide or polypeptide segment comprising an amino acid sequence consisting solely of proline and alanine amino acid residues, wherein said amino acid sequence consists of at least 50 proline (Pro) and alanine (Ala) amino acid residues, and (ii) a drug selected from the group consisting of (a) a biologically active protein or a polypeptide that comprises or that is an amino acid sequence that has or mediates a biological activity and (b) a small molecule drug. A further subject of the present invention is a drug conjugate comprising the biosynthetic random coil proline/alanine polypeptide or proline/alanine polypeptide segment as provided herein and, additionally, (a) pharmaceutically or medically useful molecule(s), like small molecules, peptides or biomacromolecules (such as proteins, nucleic acids, carbohydrates, lipid vesicles) and the like, linked and/or coupled to said biosynthetic random coil proline/alanine polypeptide or proline/alanine polypeptide segment. Furthermore, nucleic acid molecules encoding the biosynthetic random coil polypeptide or polypeptide segment and/or the biologically active, heterologous proteins as well as vectors and cells comprising said nucleic acid molecules are disclosed. Furthermore, methods for the production of the herein described inventive biosynthetic random coil polypeptides or polypeptide segments and corresponding drug or food conjugates, i.e.conjugates comprising the herein defined biosynthetic random coil polypeptides or polypeptide segments and a food ingredient or a food additive, are disclosed. Also disclosed are corresponding conjugates (comprising as one constituent the herein disclosed biosynthetic random coil polypeptide or polypeptide segment) which comprise, inter alia, a cosmetic ingredient or additive or a biologically or spectroscopically active compound. In addition, the present invention provides compositions comprising the compounds of the invention (i.e. the herein disclosed the random coil polypeptides or random coil polypeptide segments comprising an amino acid sequence consisting solely of proline and alanine amino acid residues and nucleic acid molecules encoding the same) as well as specific uses of said random coil polypeptide or polypeptide segment, of the biologically active proteins comprising said random coil polype random coil polypeptides or random coil polypeptide segments ptides or random coil polypeptide segments, the drug conjugates, the food conjugates or the nucleic acid molecules, vectors and cells of the invention. Also methods of producing and/or obtaining the inventive biosynthetic random coil polypeptides or polypeptide segments as well as of producing and/or obtaining the inventive biologically active, heterologous proteins, and/or polypeptide constructs or drug conjugates are provided. In addition, medical, pharmaceutical as well as diagnostic uses are provided herein for the biosynthetic random coil polypeptide or polypeptide segment comprising an amino acid sequence consisting solely of proline and alanine amino acid residues (or for molecules and conjugates comprising the same) as defined herein. Such a medical or pharmaceutical use can comprise the use of said biosynthetic random coil polypeptide or polypeptide segment as plasma expander and the like. However, the means and methods provided herein are not limited to pharmaceutical, medical and biological uses but can also be employed in other industrial areas, like in the paper industry, in oil recovery, etc.

Rapid clearance from blood circulation by renal filtration is a typical property of small molecules (including small proteins and peptides). However, by expanding the apparent molecular dimensions beyond the pore size of the kidney glomeruli plasma half-life of therapeutic proteins can be extended to a medically useful range of several days. One strategy to achieve such an effect is chemical conjugation of the biologic with the synthetic polymer poly-ethylene glycol (PEG). This has led to several approved drugs, for example PEG-interferon alpha2a (Pegasys®), PEG-G-CSF (Neulasta®) and, recently, a PEGylated alphaTNF-Fab fragment (Cimzia®). Nevertheless, the "PEGylation" technology has several drawbacks: clinical grade PEG derivatives are expensive and their covalent coupling to a recombinant protein requires additional downstream processing and purification steps, thus lowering yield and raising the costs. Furthermore, PEG is not biodegradable, which can cause side effects such as vacuolation of kidney epithelium upon continuous treatment; see, e.g., Gaberc-Porekar (2008) Curr Opin Drug Discov Devel 11:242-50; Knop (2010) Angew Chem Int Ed Engl 49:6288-308 or Armstrong in: Veronese (Ed.), "PEGylated Protein Drugs: Basic Science and Clinical Applications"; Birkhäuser Verlag, Basel 2009.

In order to overcome some of the drawbacks of PEG technology, certain recombinant polypeptide mimetics have been provided in the art, some of which are based on naturally occurring amino acid sequences or synthetic amino acid stretches.

Most natural amino acid sequences do not behave like an ideal random chain in physiological solution because they either tend to adopt a folded conformation (secondary structure) or, if unfolded, they usually are insoluble and form aggregates. In fact, most of the classical experiments to investigate the random chain behaviour of polypeptides were conducted under denaturing conditions, i.e. in the presence of chemical denaturants like urea or guanidinium chloride (see, e.g., Cantor (1980) Biophysical Chemistry. W.H. Freeman and Company, New York). Hence, such technologies generally rest upon peculiar amino acid sequences that resist folding, aggregation as well as unspecific adsorption and, thus, provide stable random chains under physiological buffer conditions and temperature even if genetically fused to a folded therapeutic protein domain. Under these circumstances, such recombinant PEG mimetics can confer a size increase much larger than one would normally expect on the basis of their molecular mass alone, eventually retarding kidney filtration and effectively extending plasma half-life of the attached biologic by considerable factors.

A lot of these technologies have, however, further caveats and disadvantages.

For example, naturally occurring repetitive amino acid sequences have been tested for their usefulness in medical sciences and in pharmaceutical approaches. One of these approaches relates to the trans-sialidase of *Trypanosoma cruzi*. It contains a 680 amino acid residue catalytic domain followed by a C-terminal repetitive domain, dubbed "shed acute phase antigen" (SAPA), which comprises a variable number of 12 mer amino acid repeats. Pharmacokinetic (PK) studies in mice of the trans-sialidase containing 13 hydrophilic and (at physiological pH) negatively charged corresponding amino acid repeats having the natural sequence DSSAHSTPSTPA revealed a five-fold longer plasma half-life compared to the recombinant enzyme from which the C-terminal repetitive sequence had been deleted (Buscaglia (1999) Blood 93:2025-32). A similar half-life extending effect was observed after fusion of the same trans-sialidase, i.e. its 76 kDa catalytic domain, with 13 charged amino acid repeats of the sequence EPKSA that were found in the *Trypanosoma cruzi* protein antigen 13. Both the repeats from SAPA and from the antigen 13 were able to prolong the plasma half-life of the heterologous protein gluthatione S-transferase (GST) from *Schistosoma japonicum* by a factor 7-8 after genetic fusion to both C-termini of this homodimeric enzyme (see Buscaglia, loc. cit.). Yet, while these naturally occurring repetitive amino acid sequences from human pathogens in principle may appear attractive to optimize the pharmacokinetics of therapeutic proteins they were found to be highly immunogenic (see Affranchino (1989), Mol Biochem Parasitol 34:221-8 or Buscaglia (1998), J Infect Dis 1998; 177:431-6).

Another approach relates to the use of gelatin. Gelatin, hydrolyzed and denatured animal collagen, contains long stretches of Gly-Xaa-Yaa repeats, wherein Xaa and Yaa mostly constitute proline and 4-hydroxyproline, respectively. Succinylation of gelatin, primarily via the ε-amino groups of naturally interspersed lysine side chains, increases the hydrophilicity of this biopolymer and lowers its isoelectric point (pI). The intramolecular electrostatic repulsion between the negatively charged carboxylate groups of the modified side chains supposedly spreads out the molecule into a more or less extended conformation. The resulting expanded volume makes succinylated gelatin a macromolecule for use as plasma expander in humans and is, inter alia, marketed as Volplex® (Beacon Pharmaceuticals Ltd) or Gelofusine® (B. Braun Melsungen AG). Furthermore, a half-life extending effect was achieved by genetic fusion of granulocyte-colony-stimulating factor (G-CSF) to an artificial gelatin-like polypeptide (Huang (2010) Eur J Pharm Biopharm 74:435-41). To this end, all hydrophobic side chains in a natural gelatin were exchanged by hydrophilic residues, resulting in a 116 amino acid gelatin-like protein (GLK) comprising the amino acids G, P, E, Q, N, S, and K in varying order. G-CSF was fused at its N-terminus with 4 copies of this GLK sequence and secreted in *Pichia pastoris*. *Pichia pastoris* appeared as a favourable production organism for GLK fusion proteins; yet, if GLKs can also be produced in other organisms remains to be determined as it is known that recombinant gelatin fragments can be expressed with only low yield in *E. coli*, for example, as illustrated in Olsen (2003), Adv Drug Deliv Rev 55:1547-67.

Elastin is a component of the extracellular matrix in many tissues. It is formed from the soluble precursor tropoelastin, which consists of a hydrophilic Lys/Ala-rich domain and a hydrophobic, elastomeric domain with repetitive sequence. Enzymatic crosslinking of lysine side chains within the hydrophilic domain leads to insoluble elastin formation. Elastin-like polypeptides (ELPs) are artifically designed, repetitive amino acid sequences derived from the hydrophobic domain of tropoelastin. The most common repeat sequence motif of ELPs is V-P-G-X-G, wherein "X" can be any amino acid except Pro (MacEwan (2010) Biopolymers 94:60-77; Kim (2010) Adv Drug Deliv Rev 62:1468-78). Suitable ELPs can be fused with therapeutic proteins and produced in *E. coli*. Consequently, the ability of ELPs to form gel-like depots after injection can significantly prolong the in vivo half-life of an attached biologic, albeit by a mechanism different from the other unstructured polypeptides. Yet, ELP attachment can hamper the bioactivity of the fusion partner as demonstrated for the interleukin-1 receptor antagonist in an IL-1-induced lymphocyte proliferation bioassay (Shamji (2007) Arthritis Rheum. 11:3650-3661). In addition, ELPs are subject to degradation by endogenous proteases such as collagenase. Also, aggregated proteins are generally more susceptible to immunogenicity.

Further approaches relate to the use of polyanionic polymers. For example, polyglutamate (PG) has been chemically coupled to poorly soluble cytotoxic small molecule drugs for cancer treatment. A corresponding product would be Opaxio™, a paclitaxel drug conjugate currently in clinical phase III studies. Half-life of a paclitaxel PG conjugate was prolonged by a factor 3 to 14 in comparison with the unmodified compound (Singer (2005) J Control Release 109:120-6). Further fusion proteins, for example G-CSF fused at its N-terminus with a stretch of 175 consecutive Glu residues or IFN-alpha2 carrying at its C-terminus a PG tail of 84 residues, were produced in a soluble state in the cytoplasm of E. coli (see WO2002/077036). For efficient translation, the N-terminal fusion required a leader peptide, which was later removed by Tobacco Etch Virus (TEV) protease cleavage. Polyglutamate fusions of G-CSF and INFα2 showed bioactivity in cell culture assays. However, to date no pharmacokinetic data of these PG fusions have been reported. Also, the highly negative charge of PG fusions is a general disadvantage with respect to biomolecular interactions (e.g. binding of the target receptor or soluble factor) due to artificial electrostatic attraction or repulsion effects.

WO 2006/081249 describes a polypeptide sequence with about 2 to 500 repeat units of 3 to 6 amino acids, wherein G, N or Q represent the major constituents while minor constituents can be A, S, T, D or E. This amino acid composition allows integration of the glycosylation sequon Asn-Xaa-Ser/Thr (where Xaa is any amino acid except Pro) for N-linked glycosylation of the Asn side chain in eukaryotic expression systems. The increased macromolecular size of a resulting fusion protein, including posttranslational modification with bulky solvated carbohydrate structures, can extend the pharmacokinetics of the genetically conjugated protein. Such oligosaccharide attachments ("glycoengineering") in general can both reduce susceptibility to proteolysis and increase the hydrodynamic volume (Sinclair (2005) J Pharm Sci 94:1626-35). A disadvantage is the intrinsic molecular heterogeneity of the glycosylated biomacromolecule, which causes additional effort during biotechnological production and quality control.

WO 2010/091122 (and WO 2007/103515) and Schellenberger (2009) Nat Biotechnol 27:1186-90 disclose unstructured non-repetitive amino acid polymers encompassing and comprising the residues P, E, S, T, A and G. This set of amino acids, which shows a composition not unlike the PSTAD repeat described further above, was systematically screened for sequences to yield a solvated polypeptide with large molecular size, suitable for biopharmaceutical development, by avoiding hydrophobic side chains—in particular F, I, L, M, V and W—that can give rise to aggregation and may cause an HLA/MHC-II mediated immune response. Also, potentially crosslinking Cys residues, the cationic amino acids K, R and H, which could interact with negatively charged cell membranes, and the amide side chains of N and Q, which are potentially prone to hydrolysis, were excluded (see Schellenberger (2009) loc. cit.). Synthetic gene libraries encoding non-repetitive sequences comprising the PESTAG set of residues, which were fused to the green fluorescent protein (GFP), were screened with respect to soluble expression levels in E. coli, and a resulting subset was further investigated for genetic stability, protein solubility, thermostability, aggregation tendency, and contaminant profile. Eventually, an 864 amino acid sequence containing 216 Ser residues (25.0 mole %), 72 Ala residues (8.3 mole %) and 144 amino acids (16.7 mole %) of each Pro, Thr, Glu, and Gly was further tested for fusion to the GLP-1 receptor agonist Exendin-4 (E-XTEN) and a few other biologics. The fusion proteins—typically carrying a cellulose binding domain, which was later cleaved off—were produced in a soluble state in the cytoplasm of E. coli and isolated. Investigation of of E-XTEN by circular dichroism (CD) spectroscopy revealed lack of secondary structure while during size exclusion chromatography (SEC) the fusion protein showed substantially less retention than expected for a 84 kDa protein, thus demonstrating an increased hydrodynamic volume (Schellenberg (2009) loc. cit.). The disordered structure of the PESTAG polypeptide and the associated increase in hydrodynamic radius may be favoured by the electrostatic repulsion between amino acids that carry a high net negative charge which are distributed across the XTEN sequence (see WO 2010/091122). However, a further study Geething (2010) PLoS One 2010; 5:e10175 demonstrated that XTEN decreases potency of its therapeutic fusion partner. In a cell culture assay, a glucagon XTEN fusion showed merely 15% bioactivity of the non-modified peptide. An even stronger loss in receptor affinity (17-fold increased $EC_{50}$) was described for an XTEN fusion of human growth hormone (hGH); see WO 2010/144502.

Also glycine, as the smallest and structurally simplest amino acid, has been considered as the conformationally most flexible amino acid based on theoretical grounds; see, e.g. Schulz G E, Schirmer R H. Principles of Protein Structure. Springer, N.Y. 1979. Furthermore, computer simulations have indicated that Gly polymers lack secondary structure and are likely to form a random coil in solution; see Shental-Bechor (2005) Biophys J 88:2391-402. From a chemical perspective, polyglycine is a linear unbranched polyamide that shows certain resemblance to the polyether PEG in so far as both are essentially one-dimensional macromolecules with many rotational degrees of freedom along the chain, which are made of repeated short hydrocarbon units that are regularly interrupted by hydrogen-bonding and highly solvated polar groups. Consequently, polyglycine should constitute the simplest genetically encodable PEG mimetic with prospects for extending the plasma half-life of therapeutic proteins. This concept was employed in form of "homo-amino-acid polymer (HAP)" or as glycine rich sequence (GRS), respectively; see, Schlapschy (2007) Protein Eng Des Sel 20:273-84; WO 2007/103515. However, it has long been known that chemically synthesized pure polymers of Gly show poor solubility in water; see, inter alia, in Bamford C H et al. Synthetic Polypeptides—Preparation, Structure, and Properties. Academic Press, New York 1956. Hence, different attempts were made to increase hydrophilicity, either by introducing hydrogen-bonding serine alcohol side chains (WO 2007/103515 as well as Schlapschy (2007) loc. cit.) or, in addition, negatively charged glutamate residues (WO 2007/103515). It is of note that peptide spacers with the composition $(Gly_4Ser)_n$ have already been described in the art in order to link domains in fusion proteins in a flexible manner. A significantly increased hydrodynamic volume was detected for these fusion proteins in analytical SEC. In the case of the 200 residue HAP version the apparent size increase was 120% compared with the unfused Fab fragment, while the true mass was only bigger by 29%, hence revealing the effect of an enhanced hydrodynamic volume due to the solvated random coil structure of the polyglycine tag. Furthermore, CD difference spectra were characteristic for disordered secondary structure for the HAP moiety. Finally, terminal plasma half-life of the Fab fragment carrying the 200 residue HAP in mice was prolonged by approximately a factor 3. Though moderate, this effect could be appropriate for certain (specialized) diagnostic applications, such as in vivo imaging; see Schlapschy (2007); loc. cit. Unfortunately, the production of fusion proteins with longer $(Gly_4Ser)_n$ repeat sequences appeared less feasible due to an increasing tendency to form aggregates, thus posing a natural limitation to the use of—more or less pure—glycine polymers as PEG mimetics.

WO 2008/155134 discloses that sequences with an appropriate mixture of Pro, Ala, and Ser (i.e. PAS) residues lead to mutual cancellation of their distinct secondary structure preferences and, thus, result in a stably disordered polypeptide. However, WO 2008/155134 also documents that fusion proteins with a domain composed only of serine and alanine (SA) residues, i.e. a domain comprising only two types of amino acids, do not form a random coil, but a β-sheet structure instead.

The chemical synthesis of polypeptides is well known and has been described in the art. Izuka discloses the chemical synthesis of polypeptides containing proline (see Izuka (1993), Bull. Chem. Soc. Jpn 66, 1269-1272). These copolypeptides contain random sequences of proline and either glycine, L-alanine, L-α-aminobutyric acid (Abu), L-norvaline (Nva) or L-leucine, respectively, and are synthesized by chemical copolymerization. Izuka discloses that such copolypeptides mostly have a defined collagen-like conformation. Further, it is described in this publication that copolypeptides of proline and alanine (or proline and L-α-aminobutyric acid) are partially soluble in water, while other copolypeptides were completely insoluble. It is speculated in Izuka that proline/alanine copolypeptides may have a partial disordered conformation. Izuka emphasizes that chemically synthesized polypeptides with a random proline/alanine sequence occur predominantly in a collagen-like conformation, i.e. in a structured conformation.

Thus, the technical problem underlying the present invention is the provision of large polypeptides with true random coil conformation. The technical problem is solved by provision of the embodiments characterized in the claims and as provided herein.

Accordingly, the invention relates to the provision and use of a biosynthetic random coil polypeptide or polypeptide segment comprising an amino acid sequence consisting of at least about 50, in particular of at least about 100, in particular of at least about 150, in particular of at least about 200, in particular of at least about 250, in particular of at least about 300, in particular of at least about 350, in particular of at least about 400 proline and alanine amino acid residues. The invention therefore relates to the provision of biosynthetic random coil polypeptides or polypeptide segments comprising an amino acid sequence of at least 50 amino acid residues, said amino acid sequence consisting solely of proline and alanine amino acid residues and comprising at least one proline and at least one alanine. The invention also provides for a drug conjugate comprising (i) a biosynthetic random coil polypeptide or polypeptide segment comprising an amino acid sequence consisting solely of proline and alanine amino acid residues, wherein said amino acid sequence consists of at least 50 proline (Pro) and alanine (Ala) amino acid residues, and (ii) a drug selected from the group consisting of (a) a biologically active protein or a polypeptide that comprises or that is an amino acid sequence that has or mediates a biological activity and (b) a small molecule drug. The polypeptides with true random coil conformation and polypeptide segments with true random coil conformation as provided herein are also useful in the context of cosmetic uses as well as uses in food industry and the production of beverages. The large polypeptides provided herein which show true random coil confirmation consist soley and merely of proline (P, Pro) and alanine (A, Ala) residues and comprise more than at least 50 amino acids, in particular of at least about 100, in particular of at least about 150, in particular of at least about 200, in particular of at least about 250, in particular of at least about 300, in particular of at least about 350, in particular of at least about 400 proline and alanine amino acid residues. Both amino acids, P and A, need to be present in the herein provided large polypeptides with true random coil conformation and polypeptide segments with true random coil conformation. Also provided herein are nucleic acid molecules that encode for the herein disclosed biosynthetic random coil polypeptides or polypeptide segments as well as for drug or food conjugates that comprise said biosynthetic random coil polypeptides or polypeptide segments and a (covalently linked) protein of interest, like a biologically active protein.

The biosynthetic random coil polypeptide or biosynthetic random coil polypeptide segment as described herein and to be used in drug or food conjugates as provided herein and comprising an amino acid sequence consisting of at least about 50, of at least about 100, of at least about 150, of at least about 200, of at least about 250, of at least about 300, of at least about 350, of at least about 400 proline (P) and alanine (A) amino acid residues is, inter alia, to be used in a heterologous context, i.e. in a biologically active heterologous protein, protein construct and/or in a drug conjugate comprising said biosynthetic random coil polypeptide or polypeptide segment and pharmaceutically or medically useful molecules, like small molecules, peptides or biomacromolecules such as proteins, nucleic acids, carbohydrates, lipid vesicles and the like. As illustrated in the appended examples, the inventors could successfully provide for drug conjugates which consist of the true random coil polypeptides as defined herein and biologically active proteins or protein stretches as well as drug conjugates that consist of small molecules or small molecule drugs that comprise and/or are linked to the herein described random coil polypeptides, consisting solely of proline and alanine amino acid residues (i.e. of both amino acids P and A).

Accordingly, the present invention provides, inter alia, for a biologically active, heterologous protein comprising at least two domains wherein (a) a first domain of said at least two domains comprises an amino acid sequence having and/or mediating said biological activity; and (b) a second domain of said at least two domains comprises the biosynthetic random coil polypeptide or polypeptide segment consisting of an amino acid sequence consisting of at least about 50, of at least about 100, of at least about 150, of at least about 200, of at least about 250, of at least about 300, of at least about 350, of at least about 400 proline and alanine amino acid residues. In accordance with this invention, said "first domain" and said "second domain" are not comprised in either a natural (i.e. occurring in nature) protein or a hypothetical protein as deduced from naturally occurring coding nucleic acid sequences, like open reading frames etc.

Furthermore, this invention provides for a drug conjugate consisting of the biosynthetic random coil polypeptide or polypeptide segment comprising an amino acid sequence consisting of at least about 50, of at least about 100, of at least 150, of at least about 200, of at least about 250, of at least about 300, of at least about 350, of at least about 400 proline and alanine amino acid residues and (a) pharmaceutically, therapeutically and/or medically useful molecule(s), like (a) small molecule(s), (a) peptide(s) or (a) biomacromolecule(s) such as protein(s), a nucleic acid(s), (a) carbohydrate(s), (a) lipid vesicle(s) and the like, that is/are conjugated to said biosynthetic random coil polypeptide or polypeptide segment. Again, it is of note that the term "biologically active" in context of herein disclosed conjugates is not limited to pure biological molecules but also comprise medically active, therapeutically active, pharmacuticlly active molecules and the like. It is evident for the skilled artisan that the means and methods provided herein are not limited to pharmaceutical and medical uses, but can be employed in a wide variety of technologies, including, but not limited to cosmetic, food, beverage and nutrition technologies, oil industry, paper industry and the like.

In contrast to chemically synthesized copolypeptides (like in Izuka, loc. cit.), the random coil polypeptides provided herein are biosynthetically produced. The term "biosynthetic" as used herein refers to the synthesis by means of biotechnological methods (in contrast to chemical synthesis). Such biotechnological methods are well known in the art and also described herein further below. The biosynthesis of the random coil polypeptides of the present invention allows the production of polypeptides with a defined sequence of proline and alanine residues, a defined length and/or a defined ratio of proline and alanine residues. Further, the polypeptides provided in accordance with the present invention are substantially pure, i.e. the produced polypeptides are essentially uniform and share the above characteristics (i.e. defined sequence, defined length and/or defined amino acid ratio). The random coil polypeptides consisting of at least about 50, in particular of at least about 100, in particular of at least about 150, in particular of at least about 200, in particular of at least about 250, in particular of at least about 300, in particular of at least about 350, in particular of at least about 400 proline and alanine amino acid residues are, in accordance with this invention for example comprised in biologically active, heterologous polypeptides/polypeptide constructs and/or in drug or food conjugates as well as in other conjugates useful in further industrial areas, like, but not limited to paper industry, oil industry and the like.

Overall, the above features of the polypeptides of the present invention permit the formation of a stable random coil of the polypeptides and these random coil polypeptides have surprising and advantageous properties. For example, the polypeptides of the present invention are completely soluble in aqueous solution and have an increased hydrodynamic volume. Unexpectedly, the random coil polypeptides as defined herein are also capable of conferring an increased in vivo/in vitro stability. This is particularly important for medical applications, for example, for biologically active proteins or drug conjugates comprising the random coil polypeptide of this invention. However, the numerous advantageous properties of the random coil polypeptides of the present invention not only permit their use in the medical field but also in other fields, like in cosmetics/cosmetic treatments or in the fields of nutrition and food technology, like in the dairy industry or in meat processing. Examples of conjugates useful in food industry and the like are conjugates that comprise the herein disclosed random coil polypeptide or polypeptide segment comprising an amino acid sequence consisting solely of proline and alanine amino acid residues and compounds that are useful in these technologies, like, e.g. polyoxypropylene or polyoxyethylene polymers, which are non-ionic surfactants used as emulsifiers. Also envisaged herein is the use of the biosynthetic random coil polypeptide as defined herein in biochemical methods and in technical processes, such as paper production, oil recovery and the like. The surprising and advantageous characteristics of the biosynthetic random coil polypeptides consisting merely of proline and alanine residues as provided herein (and as also of the herein disclosed conjugates and constructs, like drug or food conjugates/constructs, comprising said biosynthetic, true random coil polypeptides) are described below in greater detail. Furthermore, illustrative uses and means and methods employing these inventive biosynthetic random coil polypeptides are provided below. Also means and methods for the production of such biosynthetic random coil polypeptides as well as biologically active, heterologous polypeptides or polypeptide constructs and of the herein dislosed conjugates and constructs, like drug constructs, comprising said random coil polypeptides are provided herein.

In context of this invention, it has been surprisingly found that proline-alanine polymers/polypeptides with a uniform composition form stable random coil conformation. This is also demonstrated in the appended examples, where random coil structure of biosynthetic proline/alanine (co)-polymers/polypeptides is confirmed by circular dichroism (CD) spectroscopy. Obtaining and employing such biosynthetic, truly random coil polypeptides/polymers was surprising since the established Chou-Fasman method (Chou and Fasman (1974), Biochemistry 13, 223-245) predicts a 100% α-helical secondary structure of polymers/polypeptides (or segments thereof) composed of proline and alanine, as shown in FIG. 7. Yet, herein it has been surprisingly found and experimentally shown that proline-alanine polymers/polypeptides with a uniform composition form a stable random coil conformation. This is also demonstrated in the appended examples, where random coil structure of proline/alanine (co)-polymers/polypeptides is confirmed by experimental techniques like circular dichroism (CD) spectroscopy and size exclusion chromatography (SEC).

In contrast to the polypeptides/polymers of the present invention, the chemically synthesized polypeptides described, for example, in Izuka (1993), loc. cit. have an arbitrary/undefined and stochastic sequence and a diverse length. Thus, the chemically synthesized polypeptides comprise a mixture of completely different peptides with various proline/alanine ratios, lengths, and so on. As mentioned in Izuka, the chemically synthesized polypeptides of such a mixture do not (or only partially) form a random coil and, accordingly, do not have any of the advantageous properties of the biosynthetic polypeptides provided and described herein below. Accordingly, the present invention comprises and relates to compositions comprising the inventive biosynthetic random coil polypeptides/polymers as disclosed herein, whereby said biosynthetic random coil polypeptides/polymers are defined, inter alia, by their sequence comprising solely proline and alanine residues. In one particular embodiment, the present invention relates to conjugates, like drug or food conjugates comprising, as one constituent, these random coil polypeptides/polymers disclosed herein. These inventive biosynthetic random coil polypeptides/polymers comprised in said compositions are, in one embodiment, of uniform length.

As mentioned above, the biosynthetic random coil polypeptides (or random coil polypeptide segments) of this invention consisting solely of proline and alanine residues unexpectedly form a stable random coil conformation. The term "random coil" as used herein relates generally to any conformation of a polymeric molecule, including amino acid polymers/amino acid sequences/polypeptides, in which the individual monomeric elements that form said polymeric structure are essentially randomly oriented towards the adjacent monomeric elements while still being chemically bound to said adjacent monomeric elements. In particular, a polypeptide, amino acid sequence or amino acid polymer adopting/having/forming "random coil conformation" substantially lacks a defined secondary and tertiary structure. In context of the polypeptides of the present invention, the monomeric elements forming the polymeric structure (i.e. the polypeptide/amino acid sequence) are either single amino acids such as proline and alanine per se or peptide stretches such as the "amino acid repeats"/"amino acid cassettes"/"cassette repeats"/"building blocks"/"modules" (or fragments thereof) which are described and defined further below.

The nature of polypeptide random coils and their methods of experimental identification are known to the person skilled in the art and have been described in the scientific literature (Cantor (1980) Biophysical Chemistry, 2nd ed., W.H. Freeman and Company, New York; Creighton (1993) Proteins-Structures and Molecular Properties, 2nd ed., W.H. Freeman and Company, New York; Smith (1996) Fold Des 1:R95-R106). The term "segment" as used herein refers to a part of the herein defined biosynthetic random coil polypeptide, whereby such a part may be an internal part of the biosynthetic random coil polypeptide described herein. Such a "segment" may be, for example, a biosynthetic random coil polypeptide as defined herein where one (or more) amino acid(s) has/have been deleted, e.g. from the start and/or from the end of the polypeptide of the invention. Furthermore, such a "segment" may be used as or may form part of a larger protein or polypeptide, for example, of a fusion protein with a biologically active protein. Such a "fusion protein" would also be an example of a heterologous, biologically active polypeptide/protein/polypeptide construct of the present invention. The term "heterologous" as used herein is defined herein below.

The random coil polypeptide (or random coil segment thereof), as provided in the present invention and to be employed in context of this invention, adopts/forms random coil conformation, for example, in aqueous solution or at physiological conditions. The term "physiological conditions" is known in the art and relates to those conditions in which proteins usually adopt their native, folded conformation. More specifically, the term "physiological conditions" relates to the biophysical parameters as they are typically valid for higher forms of life and, particularly, in mammals, most preferably human beings. The term "physiological conditions" may relate to the biochemical and biophysical parameters as they are normally found in the body (in particular in body fluids) of mammals and in particular in humans. Said "physiological conditions" may relate to the corresponding parameters found in the healthy body as well as the parameters found under disease conditions or in human patients. For example, a sick mammal or human patient may have a higher, yet "physiological" temperature condition when said mammal or said human suffers from fever. With respect to "physiological conditions" at which proteins adopt their native conformation/state, the most important parameters are temperature (37° C. for the human body), pH (7.35-7.45 for human blood), osmolarity (280-300 mmol/kg $H_2O$), and, if necessary, protein content (66-85 g/l serum). Yet, the person skilled in the art is aware that at physiological conditions these parameters may vary, e.g. the temperature, pH, osmolarity, and protein content may be different in given body or tissue fluids such as blood, liquor cerebrospinalis, peritoneal fluid and lymph (Klinke (2005) Physiologie, 5th ed., Georg Thieme Verlag, Stuttgart). For example, in the liquor cerebrospinalis the osmolarity may be around 290 mmol/kg $H_2O$ and the protein concentration may be between 0.15 g/l to 0.45 g/l while in the lymph the pH may be around 7.4 and the protein content may be between 3 g/l and 5 g/l. When determining whether a polypeptide (or segment thereof)/amino acid sequence forms/adopts random coil conformation under experimental conditions using the methods as described herein below, the biophysical parameters such as temperature, pH, osmolarity and protein content may be different to the physiological conditions normally found in vivo. Temperatures between 1° C. and 42° C. or preferably 4° C. to 25° C. may be considered useful to test and/or verify the biophysical properties and biological activity of a protein under physiological conditions in vitro.

Several buffers, in particular in experimental settings (for example in the determination of protein structures, in particular in CD measurements and other methods that allow the person skilled in the art to determine the structural properties of a protein/amino acid stretch) or in buffers, solvents and/or excipients for pharmaceutical compositions, are considered to represent "physiological solutions"/"physiological conditions" in vitro. Examples of such buffers are, e.g. phosphate-buffered saline (PBS: 115 mM NaCl, 4 mM $KH_2PO_4$, 16 mM $Na_2HPO_4$ pH 7.4), Tris buffers, acetate buffers, citrate buffers or similar buffers such as those used in the appended examples. Generally, the pH of a buffer representing "physiological solution conditions" should lie in a range from 6.5 to 8.5, preferably in a range from 7.0 to 8.0, most preferably in a range from 7.2 to 7.7 and the osmolarity should lie in a range from 10 to 1000 mmol/kg $H_2O$, more preferably in a range from 50 to 500 mmol/kg $H_2O$ and most preferably in a range from 200 to 350 mmol/kg $H_2O$. Optionally, the protein content of a buffer representing physiological solution conditions may lie in a range from 0 to 100 g/l, neglecting the protein with biological activity itself, whereby typical stabilizing proteins may be used, for example human or bovine serum albumin.

It has been found herein that the polypeptides (or segments thereof) not only form random coil conformation under physiological conditions but, more generally, in aqueous solution. The term "aqueous solution" is well known in the art. An "aqueous solution" may be a solution with a water ($H_2O$) content of at least about 20%, of at least about 30%, of at least about 40%, of at least about 50%, of at least about 60%, of at least about 70%, of at least about 80% or of at least about 90% $H_2O$ (weight/weight). Accordingly, the polypeptide (or segment thereof) of the present invention may form random coil conformation in aqueous solution, possibly containing other miscible solvents, or in aqueous dispersions with a wider range of temperatures, pH values, osmolarities or protein content. This is particularly relevant for applications of the random coil polypeptide (or segment thereof) outside medical therapy or in vivo diagnostics, for example in cosmetics, nutrition or food technology.

Accordingly, it is also envisaged in the context of this invention that the random coil conformation of the proline/alanine biosynthetic polypeptide (or segment thereof) of the present invention is maintained in and/or is used in context of pharmaceutical compositions, like liquid pharmaceuticals/biologicals or lyophilized pharmaceutical compositions. This is particularly important in context of the herein provided biologically active, heterologous proteins or the drug conjugates comprising, inter alia, the inventive random coil polypeptide (or polypeptide segment). Preferably, "physiological conditions" are to be used in corresponding buffer systems, solvents and/or excipients. Yet, for example in lyophilized or dried compositions (like, e.g. pharmaceutical compositions/biologicals), it is envisaged that the random coil conformation of the herein provided random coil polypeptide (or polypeptide segment) is transiently not present and/or cannot be detected. However, said random coil polypeptide (or polypeptide segment) will adopt/form again its random coil after reconstitution in corresponding buffers/solutions/excipients/solvents or after administration to the body. Methods for determining whether a polypeptide (or segment thereof) forms/adopts random coil conformation are known in the art (Cantor (1980) loc. cit.; Creighton (1993) loc. cit.; Smith (1996) loc. cit.). Such methods include circular dichroism (CD) spectroscopy as exemplified herein below. CD spectroscopy represents a light absorption spectroscopy method in which the difference in absorbance of right- and left-circularly polarized light by a substance is measured. The secondary structure of a protein can be determined by CD spectroscopy using far-ultraviolet spectra with a wavelength between approximately 190 and 250 nm. At these wavelengths, the different secondary structures commonly found in polypeptides can be analyzed, since α-helix, parallel and anti-parallel β-sheet, and random coil conformations each give rise to a characteristic shape and magnitude of the CD spectrum. Accordingly, by using CD spectrometry the skilled artisan is readily capable of determining whether polypeptide (or segment thereof) forms/adopts random coil conformation in aqueous solution or at physiological conditions. Other established biophysical methods include nuclear magnetic resonance (NMR) spectroscopy, absorption spectrometry, infrared and Raman spectroscopy, measurement of the hydrodynamic volume via size exclusion chromatography, analytical ultracentrifugation or dynamic/static light scattering as well as measurements of the frictional coefficient or intrinsic viscosity (Cantor (1980) loc. cit.; Creighton (1993) loc. cit.; Smith (1996) loc. cit.).

In addition to the experimental methods above, theoretical methods for the prediction of secondary structures in proteins have been described. One example of such a theoretical method is the Chou-Fasman method (Chou and Fasman, loc. cit.) which is based on an analysis of the relative frequencies of each amino acid in α-helices, β-sheets, and turns based on known protein structures solved, for example, with X-ray crystallography. However, theoretical prediction of protein secondary structure is known to be unreliable. As exemplified herein below, amino acid sequences expected to adopt an α-helical secondary structure according to the Chou-Fasman method were experimentally found to form a random coil. Accordingly, theoretical methods such as the Chou-Fasman algorithm may only have limited predictive value whether a given polypeptide adopts random coil conformation, as also illustrated in the appended examples and figures. Nonetheless, the above described theoretical prediction is often the first approach in the evaluation of a putative secondary structure of a given polypeptide/amino acid sequence. A theoretical prediction of a random coil structure also often indicates that it might be worthwhile verifying by the above experimental means whether a given polypeptide/amino acid sequence has indeed a random coil conformation.

Homo-polymers of most amino acids, in particular the hydrophobic amino acids, are usually insoluble in aqueous solution (Bamford (1956) Synthetic Polypeptides—*Preparation, Structure, and Properties,* 2nd ed., Academic Press, New York). Homo-polymers of several hydrophilic amino acids are known to form secondary structures, for example α-helix in the case of Ala (Shental-Bechor (2005) Biophys J 88:2391-2402) and β-sheet in the case of Ser (Quadrifoglio (1968) J Am Chem Soc 90:2760-2765) while poly-proline, the stiffest homooligopeptide (Schimmel (1967) Proc Natl Acad Sci USA 58:52-59), forms a type II trans helix in aqueous solution (Cowan (1955) Nature 176:501-503).

Using the theoretical principles of polymer biophysics the random coil diameter of a chain of 200 amino acid residues would amount in the case of poly-glycine, for example, to ca. 75 Å—calculated as the average root mean square end-to-end distance of $\sqrt{\langle r^2 \rangle} = l \cdot \sqrt{n \cdot C_\infty}$, with n=200 rotatable bonds of length l=3.8 Å for each Cα-Cα distance and the 'characteristic ratio' $C_\infty \approx 2.0$ for poly(Gly) (Brant (1967) J Mol Biol 23:47-65; Creighton, (1993) loc. cit.). This relation shows that the person skilled in the art would expect that the hydrodynamic volume of a random chain amino acid polymer can be either extended by (a) using a longer chain length l or by (b) using amino acids that exhibit a larger characteristic ratio, $C_{28}$. $C_{28}$ is a measure for the inherent stiffness of the molecular random chain and has a general value of 9 for most amino acids (Brant (1967) loc. cit.). Only Gly, which lacks a side chain, and also the imino acid Pro exhibit significantly smaller values. Hence, Gly and Pro (under denaturing conditions) are expected to contribute to reducing the dimensions of random coil proteins (Miller (1968) Biochemistry 7:3925-3935) Amino acid sequences comprising proline residues, accordingly, are expected to have a relatively compact hydrodynamic volume. In contrast to this teaching, however, it is shown herein that the hydrodynamic volume of the amino acid polymers/polypeptides of the invention that comprise a mixture of proline and alanine residues have a dramatically increased hydrodynamic volume as determined by analytical gel permeation/size exclusion chromatography when compared to the expected hydrodynamic volume. In fact, it is surprising that polypeptides comprising mixtures of these two amino acids (proline and alanine), of which each alone tends to form a homooligopeptide with defined secondary structure, adopt random coil conformation under physiological conditions. Such inventive proline/alanine polypeptides have a larger hydrodynamic radius than homo-polymers comprising the same number of Gly residues, for example, and they confer better solubility to the biologically active proteins or constructs, i.e. biologically active heterologous proteins or drug conjugates, according to the invention.

As mentioned above, the biosynthetic random coil proline/alanine polypeptides of the present invention differ from chemically synthesized polypeptides in that they can adopt a defined, uniform length by easy means and methods. Whereas the prior art provides mixtures/compositions of polypeptides with enormous variations in terms of the length of the peptides, the present invention can provide mixtures/compositions of biosynthetic random coil polypeptides with a defined length. Preferably, essentially all polypeptides of the invention comprised in such a mixture/composition have the same defined length, and, hence, share the same biochemical characteristics. Such a uniform composition is more advantageous in the various medical, cosmetic, nutritional applications, wherein the biosynthetic random coil polypeptides can be employed. Furthermore, in particular in a medical or pharmaceutical context, the herein defined biosynthetic random coil polypeptide or polypeptide segment comprising an amino acid sequence consisting of at least about 50, in particular of at least about 100, in particular of at least about 150, in particular of at least about 200, in particular of at least about 250, in particular of at least about 300, in particular of at least about 350, in particular of at least about 400 proline and alanine amino acid residues can also be used in the prevention, amelioration and/or treatment of disorders linked and/or affiliated with an impaired blood plasma situation, for example after injuries, burns, surgery and the like. One medical use of said biosynthetic random coil polypeptides or polypeptide segments is, accordingly, the use as plasma expander. However, it is of note that in accordance with this invention also the herein described drug conjugates and heterologous polypeptides or heterologous polypeptide constructs may be employed in context of the medical or pharmaceutical intervention of a disorder related to an impaired blood plasma amount or blood plasma content or of a disorder related to an impaired blood volume.

Accordingly, the present invention relates in one embodiment to a biosynthetic random polypeptide (or segment thereof) which comprises an amino acid sequence consisting solely of at least about 50 proline and alanine amino acid residues, of at least about 100 proline and alanine amino acid residues, of at least about 150 proline and alanine amino acid residues or of at least about 200 proline and alanine residues, in particular when comprised in a heterologous protein/polypeptide/polypeptide construct or in a drug conjugate. The present invention also relates to biosynthetic random coil polypeptides which comprise an amino acid sequence consisting solely of at least about 200 proline and alanine amino acid residues, even more preferably of at least about 300 proline and alanine amino acid residues, particularly preferably of at least about 400 proline and alanine amino acid residues, more particularly preferably of at least about 500 proline and alanine amino acid residues and most preferably of at least about 600 proline and alanine amino acid residues. The amino acid sequence forming random coil conformation may consist of maximally about 3000 proline and alanine amino acid residues, of maximally about 2000 proline and alanine amino acid residues, of maximally about 1500 proline and alanine amino acid residues, of maximally about 1200 proline and alanine amino acid residues, of maximally about 800 proline and alanine amino acid residues. Accordingly, the proline/alanine amino acid sequence stretch may consist of about 50, of about 100, of about 150, of about 200, of about 250, of about 300, of about 350, of about 400, of about 500, of about 600, of about 700, of about 800, of about 900 to about 3000 proline and alanine amino acid residues. In certain embodiments, the inventive biosynthetic amino acid sequence comprises about 200 to about 3000 proline and alanine residues, about 200 to about 2500 proline and alanine residues, about 200 to about 2000 proline and alanine residues, about 200 to about 1500 proline and alanine residues, about 200 to about 1000 proline and alanine residues, about 300 to about 3000 proline and alanine residues, about 300 to about 2500 proline and alanine residues, about 300 to about 2000 proline and alanine residues, about 300 to about 1500 proline and alanine residues, about 300 to about 1000 proline and alanine residues, about 400 to about 3000 proline and alanine residues, about 400 to about 2500 proline and alanine residues, about 400 to about 2000 proline and alanine residues, about 400 to about 1500 proline and alanine residues, about 400 to about 1000 proline and alanine residues, about 500 to about 3000 proline and alanine residues, about 500 to about 2500 proline and alanine residues, about 500 to about 2000 proline and alanine residues, about 500 to about 1500 proline and alanine residues, about 500 to about 1000 proline and alanine residues, about 600 to about 3000 proline and alanine residues, about 600 to about 2500 proline and alanine residues, about 600 to about 2000 proline and alanine residues, about 600 to about 1500 proline and alanine residues, about 600 to about 1000 proline and alanine residues, about 700 to about 3000 proline and alanine residues, about 700 to about 2500 proline and alanine residues, about 700 to about 2000 proline and alanine residues, about 700 to about 1500 proline and alanine residues, about 700 to about 1000 proline and alanine residues, about 800 to about 3000 proline and alanine residues, about 800 to about 2500 proline and alanine residues, about 800 to about 2000 proline and alanine residues, about 800 to about 1500 proline and alanine residues, about 800 to about 1000 proline and alanine residues. As is evident from the content of this invention, also larger biosynthetic amino acid sequences (consisting essentially of proline and alanine) are within the scope of this invention and can readily be employed in the herein defined biologically active proteins or protein constructs which comprise as one domain of at least two domains an amino acid sequence having and/or mediating said biological activity and as another domain of at least two domains the biosynthetic random coil polypeptide or polypeptide segment consisting of at least about 50 proline and alanine amino acid residues, of at least about 100 proline and alanine amino acid residues, of at least about 150 proline and alanine amino acid residues, of at least about 200, of at least about 250, of at least about 300, of at least about 350, of at least about 400 proline and alanine amino acid residues. Such a biosynthetic random coil polypeptide or polypeptide segment corresponds to the biosynthetic random coil part of a heterologous protein/protein construct. These biosynthetic proline/alanine stretches consist of maximally about 3000 proline and alanine amino acid residues. These amino acid sequences (proline/alanine stretches) comprise proline and alanine as main or unique residues as explained further below.

It is envisaged that it is the herein defined biosynthetic amino acid sequence consisting solely of proline (P) and alanine (A) amino acid residues, which forms/adopts/has a random coil conformation. In the simplest case, the biosynthetic polypeptide or polypeptide segment consists of the amino acid sequence having a random coil conformation as defined herein. However, the biosynthetic polypeptide (or segment thereof) may, in addition to the herein described amino acid sequence forming/adopting/having a random coil conformation, comprise further amino acid sequences/amino acid residues which do not contribute to the formation of the random coil conformation or which are not capable of forming/adopting/having a random coil conformation on their own. Without deferring from the gist of the invention, also such biosynthetic polypeptides (or segments thereof) are biosynthetic "random coil" polypeptides or polypeptide segments. The further amino acid sequences/amino acid residues may, for example, be useful as linkers. Inter alia, dimers, trimers, i.e. in general multimers of the biosynthetic random coil polypeptide are also envisaged in context of the present invention and such multimers may be linked by amino acid sequences/residues which do not form random coil conformation. An example of a protein which may comprise such a random coil polypeptide is the herein provided biologically active protein, which may, in addition to the random coil polypeptide consisting of proline and alanine amino acid residues as defined herein further comprise another polypeptide having/mediating biological activity. Again, such a construct may be a heterologous, biologically active protein or polypeptide construct as described herein.

The term "at least about 50/100/150/200/300/400/500/600/700/800/etc amino acid residues" is not limited to the concise number of amino acid residues but also comprises amino acid stretches that comprise either additional about 1-20%, like 10% to 20% residues or about 1-20%, like 10% to 20% less residues. For example "at least about 100 amino acid residues" may also comprise about 80 to 100 and about 100 to 120 amino acid residues without deferring from the gist of the present invention. For example "at least about 200 amino acid residues" may also comprise about 160 to 200 and about 200 to 240 amino acid residues without deferring from the gist of this invention. The definition and explanations given herein above, apply, mutatis mutandis, also to the term "maximally about 3000/2000/1500/1200/800 amino acid residues" etc. Accordingly, the term "about" is not limited or restricted to the concise number of amino acid residues in context of longer amino acid sequences (e.g. amino acid sequences comprising or consisting of maximally 3000 amino acid residues). Therefore, the term "maximally about 3000/2000/1500/1200/800 amino acid residues" but may also comprise amino acid stretches that comprise additional 10% to 20% or 10% to 20% less residues without deferring from this invention.

Furthermore, the biosynthetic random coil polypeptides (or segments thereof) are characterised by a defined content or ratio of amino acid residues, in particular of the main constituents proline and alanine. As mentioned above, the present invention relates to a biosynthetic random coil polypeptide or polypeptide segment comprising an amino acid sequence consisting solely of proline and alanine amino acid residues, wherein said amino acid sequence consists of at least about 50, of at least about 100, of at least about 150, of at least about 200 of at least about 250, of at least about 300, of at least about 350, of at least about 400 proline (Pro) and alanine (Ala) amino acid residues in particular when comprised in a heterologous biological active protein/protein construct/polypeptide or drug conjugate. The term "solely" as used herein means that preferably at least about 90% or at least about 95% of the amino acids are proline and alanine, whereby proline and alanine constitute the majority but may not be the only amino acid residues, i.e. these inventive amino acid sequences are not necessarily 100% proline and alanine amino acid stretches. Hence, the biosynthetic polypeptides/amino acid sequences of the present invention may also comprise other amino acids than proline and alanine as minor constituents as long as the amino acid sequence forms/adopts/has random coil conformation. Such a random coil conformation can be easily determined by herein provided means and methods. Accordingly, also in context of the term "solely", a minor amount (less than about 10% or less than about 5%) of other amino acid residues may be comprised. Said "other", minor amino acid residues are defined herein below.

Accordingly, the present invention relates in one embodiment to a biosynthetic random coil polypeptide (or segment thereof) whereby the amino acid sequence consists mainly of proline and alanine, and wherein the proline residues constitute more than about 10% and less than 75% of the amino acid sequence. The alanine residues comprise the remaining at least 25% to 90% of said amino acid sequence (or the random coil polypeptide or polypeptide segment if it consists of the amino acid sequence).

Preferably, the amino acid sequence comprises more than about 10%, preferably more than about 12%, even more preferably more than about 14%, particularly preferably more than about 18%, more particularly preferably more than about 20%, even more particularly preferably more than about 22%, 23% or 24% and most preferably more than about 25% proline residues. The amino acid sequence preferably comprises less than about 75%, more preferably less than 70%, 65%, 60%, 55% or 50% proline residues, wherein the lower values are preferred. Even more preferably, the amino acid sequence comprises less than about 48%, 46%, 44%, 42% proline residues. Particular preferred are amino acid sequences comprising less than about 41%, 40%, 39% 38%, 37% or 36% proline residues, whereby lower values are preferred. Most preferably, the amino acid sequence comprise less than about 35% proline residues; see also the herein below provided PA constructs.

Vice versa, the amino acid sequence preferably comprises less than about 90%, more preferably less than 88%, 86%, 84%, 82% or 80% alanine residues, wherein the lower values are preferred. Even more preferably, the amino acid sequence comprises less than about 79%, 78%, 77%, 76% alanine residues, whereby lower values are preferred. Most preferably, the amino acid sequence comprises less than about 75% alanine residues.

Also preferred herein is an amino acid sequence comprising more than about 25%, preferably more than about 30%, even more preferably more than about 35%, particularly preferably more than about 40%, more particularly preferably more than about 45% or 50%, even more particularly preferably more than about 52%, 54%, 56%, 58% or 59% alanine residues, wherein the higher values are preferred. Even more preferably, the amino acid sequence comprises more than about 60%, 61%, 62%, 63% or 64% alanine residues and most preferably more than about 65% alanine residues.

Accordingly, the random coil polypeptide (or segment thereof) may comprise an amino acid sequence consisting of about 25% proline residues, and about 75% alanine residues. Alternatively, the random coil polypeptide (or segment thereof) may comprise an amino acid sequence consisting of about 35% proline residues and about 65% alanine residues. The term "about X %" as used herein above is not limited to the concise number of the percentage, but also comprises values of additional 10% to 20% or 10% to 20% less residues. For example the term 10% may also relate to 11% or 12% and to 9% and 8%, respectively.

However, as mentioned above and further detailed herein below said random coil polypeptide (or polypeptide segment), and, in particular the amino acid sequence, may also comprise additional amino acids differing from proline and alanine as minor constituents. As already discussed herein above, said minor constituent(s), i.e. (an)other amino acid(s) than proline or alanine, may comprise less than about 10%, less than about 9%, less than about 8%, less than about 7%, less than about 6%, less than about 5%, less than about 4%, less than about 4%, less than about 3% or less than about 2% of the biosynthetic random coil polypeptide/polymer of this invention.

The skilled person is aware that an amino acid sequence/polypeptide (or segment thereof) may also form random coil conformation when other residues than proline and alanine are comprised as a minor constituent in said amino acid sequence/polypeptide (polypeptide segment). The term "minor constituent" as used herein means that maximally 5% or maximally 10% amino acid residues are different from proline or alanine in the inventive biosynthetic random coil polypepitdes/polymers of this invention. This means that maximally 10 of 100 amino acids may be different from proline and alanine, preferably maximally 8%, i.e. maximally 8 of 100 amino acids may be different from proline and alanine, more preferably maximally 6%, i.e. maximally 6 of 100 amino acids may be different from proline and alanine, even more preferably maximally 5%, i.e. maximally 5 of 100 amino acids may be different from proline and alanine, particularly preferably maximally 4%, i.e. maximally 4 of 100 amino acids may be different from proline and alanine, more particularly preferably maximally 3%, i.e. maximally 3 of 100 amino acids may be different from proline and alanine, even more particularly preferably maximally 2%, i.e. maximally 2 of 100 amino acids may be different from proline and alanine and most preferably maximally 1%, i.e. maximally 1 of 100 of the amino acids that are comprised in the random coil polypeptide (or segment thereof) may be different from proline and alanine. Said amino acids different from proline and alanine, may be selected from the group consisting of Arg, Asn, Asp, Cys, Gln, Glu, Gly, His, Ile, Leu, Lys, Met, Phe, Thr, Trp, Tyr, and Val, including posttranslationally modified amino acids or non-natural amino acids (see, e.g., Budisa (2004) Angew Chem Int Ed Engl 43:6426-6463 or Young (2010) J Biol Chem 285:11039-11044). In case that the "minor constituent" (i.e. an amino acid other than proline and alanine) of the biosynthetic random coil polypeptide/construct/polymer (or a fragment thereof) comprises as "other amino acid"/"different amino acid" (a) Ser(s), said Ser amino acid/Ser amino acids constitute preferably less than 50%, more preferably less than 40%, less than 30%, less than 20% or less than 10% of these (minor) amino acid residues. In a most preferred embodiment, the biosynthetic random coil polypeptide/construct/polymer as described herein or the random coil polypeptide part of a (e.g.) fusion protein as described herein does not comprise (a) serine residue(s). It is, generally, preferred herein that these "minor" amino acids (other than proline and alanine) are not present in the herein provided biosynthetic random coil polypeptide/construct/polymer as described herein or the random coil polypeptide part of a (e.g.) fusion protein. In accordance with the invention, a biosynthetic random coil polypeptide (or segment thereof)/ the amino acid sequence may, in particular, consist exclusively of proline and alanine amino acid residues (i.e. no other amino acid residues are present in the random coil polypeptide or in the amino acid sequence).

Whereas the above relates to the overall length and proline/alanine content of the amino acid sequence comprised in the random coil polypeptide (or segment thereof), the following relates in greater detail to the specific, exemplary amino acid sequences (or fragments thereof).

In one embodiment, the amino acid sequences/polypeptides adopting random coil conformation (the random coil polypeptide or segment thereof as defined herein), for example, in aqueous solution or under physiological conditions may comprise a plurality of "amino acid repeats"/ "amino acid cassettes"/"cassette repeats", wherein said "amino acid repeats"/"amino acid cassettes"/"cassette repeats"/"building block"/"modules" (these terms are used herein interchangeably) mainly or exclusively consist of proline (Pro, P) and alanine (Ala, A) amino acid residues (depicted herein as "PA", or as "AP"), wherein no more than 6 consecutive amino acid residues are identical. An illustrative "building block" is, e.g. "AP" and this has also been provided in the appended illustrative examples as functional biosynthetic random coil domain of the present invention. This illustrative example is the sequence "P1A1" as also provided in form of APAPAPAPAPAPAPAPAPAP (SEQ ID NO: 51). i.e. a "poly PA" "amino acid repeat"/"amino acid cassette"/"cassette repeat". In a preferred embodiment, the amino acid sequence/polypeptide comprising the above defined "amino acid repeats"/"amino acid cassettes"/"cassette repeats" and the like comprises no more than 5 identical consecutive amino acid residues. Other alternative embodiments are provided herein below in context of exemplified, individual building blocks.

Within a random coil polypeptide (or segment thereof) according to this invention the amino acid repeats may be identical or non-identical. Non-limiting examples of "amino acid repeats", "building blocks", "modules", "repeats", "amino acid cassettes" etc. consisting of proline and alanine residues are provided herein below; see, e.g. SEQ ID NO: 1, SEQ ID NO: 2, SEQ ID NO: 3, SEQ ID NO: 4, SEQ ID NO: 5, SEQ ID NO: 6 and SEQ ID NO. 51 (The enclosed sequence listing also comprises illustrative nucleic acid sequences which encode such "repeats"/"modules", etc. The appended sequences in said sequence listing as filed herewith constitute part of this specification and description). Also the use of (identical and/or non-identical) fragments of these sequences is envisasged herein, whereby a "fragment" comprises at least 2 amino acids and comprises at least one proline and/or alanine, preferably at least one proline and one alanine. "Fragments" of these sequences to be employed in accordance with this invention for the generation of the random coil polypeptide (or segment thereof) may consist of at least 3, preferably of at least 4, more preferably of at least 5, even more preferably of at least 6, still more preferably of at least 8, particularly preferably of at least 10, more particularly preferably of at least 12, even more particularly preferably of at least 14, still more particularly preferably of at least 16, and most preferably of at least 18 consecutive amino acids of the amino acid sequence selected from the group consisting of said SEQ ID NOs: 1, 2, 3, 4, 5, 6 and 51 (here it is of note that SEQ ID No. 51 consists of an illustrative "AP" or "PA" repeat).

Based on the teaching given herein, the person skilled in the art is readily in a position to generate further amino acid sequences/polypeptides that form random coil conformation for example under aqueous or under physiological conditions and are constituted of mainly proline and alanine as defined herein. Further examples of random coil conformation forming amino acid sequences/polypeptides to be used as building blocks or modules of the herein defined random coil polypeptide (or segment thereof) may, inter alia, comprise combinations and/or fragments or circularly permuted versions of the specific "building blocks", "polymer cassettes", or "polymer repeats" shown above. Accordingly, the exemplified modules/sequence units/polymer repeats/polymer cassettes of the random coil polypeptide/amino acid sequence may also provide for individual fragments which may be newly combined to form further modules/sequence units/polymer repeats/polymer cassettes in accordance with this invention.

The terms "module(s)", "sequence unit(s)", "polymer repeat(s)", "polymer cassette(s)" and "building block(s)" are used as synonyms herein and relate to individual amino acid stretches which may be used to form the herein defined random coil polypeptide (or segment thereof)/amino acid sequence.

An amino acid repeat (used as "building block" etc. of a biosynthetic random coil polypeptide of the present invention) may consist of at least 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid residues, wherein each repeat comprises (an) proline and alanine residue(s). However, as illustrated in appended SEQ ID No. 51, said "building block" can also merely consist of the 2 herein provided amino acid residues P and A, namely in form of "PA" or "AP". In one embodiment, the amino acid repeat according to the present invention does not comprise more than 50 amino acid residues. However, it is evident for the skilled artisan that such a "repeat" may comprise even more than 50 amino acid residues, for example in cases wherein said inventive biosynthetic random coil polypeptide/polymer comprises more than about, e.g., 100 amino acids, more than about 150 amino acids, more than about 200 amino acids, etc. Accordingly, the maximal amount of amino acid residues comprised in such a "repeat" is conditioned by the over-all length of the biosynthetic polypeptide (or segment thereof)/polymer as provided herein.

Yet, it is of note that the biosynthetic random coil polypeptides/amino acid sequences comprising the above repeats etc. should preferably have the overall length and/or proline/alanine content as defined and explained herein above, i.e. consist of about 50, of about 100, of about 150, of about 200, of about 250, of about 300, of about 350, of about 400 to about 3000 amino acids and/or comprise more than about 10% and less than about 75% proline residues. All the definitions given herein above in this context also apply here, mutatis mutandis.

As discussed in detail herein and as provided herein above, the present invention provides for (a) biologically active, heterologous protein(s) or (a) protein construct(s) that is/are particularly useful in a pharmaceutical, medical and/or medicinal setting. These biologically active, heterologous proteins/protein constructs comprise as at least one domain of said at least two domains the random coil polypeptide or polypeptide segment comprising an amino acid sequence consisting solely of proline and alanine residues, wherein said amino acid sequence consist of about 50, of about 100, of about 150, of about 200, of about 250, of about 300, of about 350, of about 400 to about 3000 proline (Pro) and alanine (Ala) residues.

In context of the biologically active, heterologous proteins, polypeptides or protein constructs as disclosed herein, the term "heterologous" relates to at least two domains within said proteins, polypeptides or protein constructs wherein a first of said at least two domains confers, has and/or mediates a defined biological activity and wherein a second of said at least two domains comprises the biosynthetic random coil polypeptide consisting solely of proline and alanine amino acid residues and whereby said at least two domains are not found operationally linked to each other in nature or are not encoded by a single coding nucleic acid sequence (like an open reading frame) existing in nature. The biosynthetic random coil polypeptide/polypeptide segment consisting solely of proline and alanine amino acid residues as provided herein and as employed in the biologically active, heterologous proteins/protein constructs of this invention are preferably not further (chemically) modified, for example they are preferably neither glycosylated nor hydroxylated.

It is of note that certain naturally occurring proteins or hypothetical proteins as deduced from sequenced nucleic acid stretches found in nature are described as comprising a relatively high (i.e. above average) content of proline and alanine. For example, a homologous hypothetical protein has been described for Leishmania major strain Friedlin (Ivens (2005) Science 309, 436-442.). The disclosed reading frame comprising 1514 codon triplets includes a stretch of 412 triplets composed of 240 Ala, 132 Pro, 34 Lys and 4 Val codons. The Lys residues, which are positively charged under physiological buffer conditions, are almost evenly distributed among this sequence, suggesting a solubilizing effect. However, as is evident from the disclosure herein, such a homologous hypothetical protein as deduced from a naturally occurring nucleic acid molecule or open reading frame, comprising a high proline and alanine content above average is not part of this invention. The invention is based on the fact that a rather large random coil polypeptide or polypeptide segment that does not occur in nature in an isolated manner and that comprises an amino acid sequence consisting solely of proline and alanine residues, wherein said amino acid sequence consist of about 50, of about 100, of about 150, of about 200, of about 250, of about 300, of about 350, of about 400 to about 3000 proline (Pro) and alanine (Ala) residues is provided that is particularly useful in medical/pharmaceutical context. The herein described isolated biosynthetic random coil polypeptides or polypeptide segments that do not occur in nature in an isolated manner are also comprised in the herein disclosed (a) biologically active, heterologous protein(s) or (a) protein construct(s) that is/are particularly useful in a pharmaceutical, medical and/or medicinal setting. These biologically active, heterologous proteins/protein constructs comprise as at least one domain of said at least two domains the random coil polypeptide or polypeptide segment comprising an amino acid sequence consisting solely of proline and alanine residues, wherein said amino acid sequence consists of about 50, of about 100, of about 150, of about 200, of about 250, of about 300, of about 350, of about 400 to about 3000 proline (Pro) and alanine (Ala) residues.

Also, arabinogalactan proteins (AGPs), Pro-rich proteins, and extensins belong to a large group of glycoproteins, known as hydroxyproline (Hyp)-rich glycoproteins (HRGPs), which are expressed throughout the plant kingdom. One such AGP motif comprising an Ala-Pro repeat (AP)51 was expressed as a synthetic glycomodule peptide with N-terminal signal sequence and C-terminal green fluorescent protein in transgenic *Arabidopsis thaliana* and investigated as a substrate for prolyl hydroxylases and subsequent O-glycosylation of the hydroxyproline residues (Estevez (2006) Plant Physiol. 142, 458-470). Again, the disclosed hydroxylated and/or glycosylated Pro side chains, which can form hydrogen bonds to water molecules, appear to have a solubilizing effect.

It is of note that the herein described "biologically active proteins or protein constructs comprising as (at least) one domain a biosynthetic random coil polypeptide or peptide segment comprising an amino acid sequence consisting solely of proline and alanine residues" relate to proteins or protein constructs that do not normally occur in nature and, thus, are "heterologous". Furthermore, and in contrast to proline-rich sequences described in the plant kingdom, the biosynthetic random coil polypeptides/polypeptide segments described herein are preferably not chemically modified, i.e. they are preferably not glycosylated or hydroxylated.

A particular advantage of the biosynthetic random coil polypeptides or polypeptide segments of this invention is their intrinsically hydrophilic but uncharged character. Accordingly, as "minor" amino acids (other than proline and alanine) in the herein described biosynthetic random coil polypeptide or polypeptide stretch such amino acids are preferred that do not have hydrophobic side chains, like Val, Ile, Leu, Met, Phe, Tyr or Trp, and/or that do not have charged side chains, like Lys, Arg, Asp or Glu. In accordance with this invention, it is envisaged that (in cases where such individual amino acids are nevertheless comprised in the inventive biosynthetic random coil polypeptide/polypeptide segment) the overall content of each individual amino acid having a hydrophobic side chain, like Val, Ile, Leu, Met, Phe, Tyr or Trp, and/or having a charged side chain, like Lys, Arg, Asp, or Glu, within the herein defined biosynthetic random coil polypeptide (or segment thereof) does not exceed 8%, 7%, 6%, 5%, 4%, 3%, 2% or 1%.

The biosynthetic random coil polypeptide/amino acid sequences of the present invention may comprise concatamers of individual blocks comprising combined proline/alanine stretches of the sequence $(Pro)_x$-$(Ala)_y$, whereby x can have an integer value from 1 to preferably 15, more preferably 1 to 10, even more preferably 1 to 5, and y can have an integer value from 1 to preferably 15, more preferably 1 to 10, even more preferably 1 to 5, and x and y can vary between subsequent blocks. Said x and y can also be an integer of 1, 2, 3, 4, 5, 6, 7, 8, 9, 10, 11, 12, 13, 14 or 15.

The amino acid sequences/polypeptides forming random coil conformation in aqueous solution or under physiological conditions may have the formula (I):

$$[Pro_xAla_y]_n$$

wherein x is independently selected from integer 1 to 5. Furthermore, for each n, y is independently selected from integer 1 to 5. n, finally, is any integer provided that random coil polypeptide (or segment thereof)/amino acid sequence consists preferably of at least about 50, of at least about 100, of at least about 150, of at least about 200, of at least about 250, of at least about 300, of at least about 350, of at least about 400 amino acid residues and up to about 3000 amino acid residues. Also in this context it is of note that the polypeptides/amino acid sequences comprising the above concatemers or having the above formula (I) should preferably have the overall length and/or proline/alanine content as defined and explained herein above, i.e. consist of about 50, of about 100, of about 150, of about 200, of about 250, of about 300, of about 350, of about 400 to about 3000 amino acids and/or comprise more than about 10% and less than about 75% proline residues. Again, all the definitions given herein above in this context also apply here, mutatis mutandis.

The present invention also relates to random coil polypeptides ((a)polypeptide segment(s))/amino acid sequences comprising an amino acid stretch selected from the group consisting of AAPAAPAAPAAPAAPAPAAPA (SEQ ID NO: 1); AAPAAAPAPAAPAAPAPAAP (SEQ ID NO: 2); AAAPAAAPAAAAPAAAPAAAP (SEQ ID NO: 3 being an example for [Pro$_1$Ala$_3$]$_5$); AAPAAPAAPAAPAAPAAPAAP (SEQ ID NO: 4); APAAAPAPAAAPAPAAAPAAAP (SEQ ID NO: 5); AAAPAAPAAPPAAAAPAAPAAPPA (SEQ ID NO: 6) and APAPAPAPAPAPAPAPAP (SEQ ID NO: 51 being an example for [Pro$_1$Ala$_1$]$_{10}$) or circular permuted versions or (a) multimers(s) of these sequences as a whole or parts of these sequences. Accordingly, the random coil polypeptide ((a) polypeptide segment(s) thereof)/amino acid sequence may comprise the amino acid stretch AAPAAPAPAAPAA-PAPAAPA (SEQ ID NO: 1), AAPAAPAPAAPAAPAPAAPA (SEQ ID NO: 1); AAPAAAPAPAAPAAPAPAAP (SEQ ID NO: 2); AAAPAAAPAAAAPAAAPAAAP (SEQ ID NO: 3); AAPAAPAAPAAPAAPAAPAAP (SEQ ID NO: 4); APAAAPAPAAAPAPAAAPAAAP (SEQ ID NO: 5); AAAPAAPAAPPAAAAPAAPAAPPA (SEQ ID NO: 6) and APAPAPAPAPAPAPAPAP (SEQ ID NO: 51), as well as combinations of these motifs or combinations of fragments and parts of this motifs as long as the resulting biosynthetic random coil polypeptide consists solely of proline and alanine amino acid residues, wherein said amino acid sequence consists of at least 50 proline (Pro) and alanine (Ala) amino acid residues.

Also circular permuted versions of the above amino acid sequences may be used in accordance with the present invention. Exemplary circular permuted versions of e.g. AAPAAPAPAAPAAPAPAAPA (SEQ ID NO: 1) can be easily generated, for example by removing the first alanine and adding another alanine at the end of the above sequence. Such a cicular permuted version of SEQ ID NO: 1 would then be APAAPAPAAPAAPAPAAPAA (SEQ ID NO: 7). Further, non-limiting examples of cicular permuted versions of SEQ ID NO: 1 are:

```
                               (SEQ ID NO: 8)
PAAPAPAAPAAPAPAAPAAA, (SEQ ID NO: 9)
AAPAPAAPAAPAPAAPAAAP, (SEQ ID NO: 10)
APAPAAPAAPAPAAPAAAPA, (SEQ ID NO: 11)
PAPAAPAAPAPAAPAAAPAA, (SEQ ID NO: 12)
APAAPAAPAPAAPAAAPAAP, (SEQ ID NO: 13)
PAAPAAPAPAAPAAAPAAPA, (SEQ ID NO: 14)
AAPAAPAPAAPAAAPAAPAP, (SEQ ID NO: 15)
APAAPAPAAPAAAPAAPAPA, (SEQ ID NO: 16)
PAAPAPAAPAAAPAAPAPAA,
``` and the like. Based on the teaching of the present invention, a skilled person is easily in the position to generate corresponding circular permuted versions of the amino acid stretches as shown in SEQ ID NO: 2, SEQ ID NO: 3, SEQ ID NO: 4, SEQ ID NO: 5, SEQ ID NO: 6 and SEQ ID NO. 51 (said SEQ ID No. 51 being entirely based on "AP" repeats and a circular permutated version could be based entirely on "PA" or "AP" repeats/building blocks).

Such circular permuted versions may also be considered as examples of a further "module"/"building block" etc. of the herein provided polypeptides/amino acid sequences which can be used accordingly herein.

It is evident for the person skilled in the art that also "modules" and (shorter) fragments or circularly permuted versions of the herein provided amino acid stretches may be used as "modules", "repeats" and/or building blocks for the herein defined random coil polypeptide (or segment thereof)/amino acid sequence.

In accordance with the above, the random coil polypeptide/amino acid sequence forming random coil conformation may comprise a multimer of any of the above amino acid stretches (or circular permuted versions or fragments thereof), preferably those shown in SEQ ID NO: 1, SEQ ID NO: 2, SEQ ID NO: 3, SEQ ID NO: 4, SEQ ID NO: 5, SEQ ID NO: 6 and SEQ ID NO. 51. It is to note that these sequences are by no means limiting in context of this invention.

Again, the polypeptides/amino acid sequences comprising the above amino acid stretches (or fragments thereof), circular mutated versions (or fragments thereof) should preferably have the overall length and/or proline/alanine content as defined and explained herein above, i.e. consist of about 50, of about 100, of about 150, of about 200, of about 250, of about 300, of about 350, of about 400 to about 3000 amino acids and/or comprise more than about 10% and less than about 75% proline residues. All the definitions given herein above in this context also apply here, mutatis mutandis. Also the term "fragment" has been defined above.

As mentioned above, in context of this invention it was surprisingly found that the biosynthetic random coil polypeptides (or polypeptide segment)/polymers as provided herein are characterized by a relatively large hydrodynamic volume. This hydrodynamic volume, also called apparent size, can easily be determined by analytical gel filtration (also known as size exclusion chromatography, SEC). Preferably, the random coil polypeptide (or segment thereof) has an apparent size of at least 10 kDa, preferably of at least 25 kDa, more preferably of at least 50 kDa, even more preferably of at least 100 kDa, particularly preferably of at least 200 kDa and most preferably of at least 400 kDa. The person skilled in the art is readily capable of determining the hydrodynamic volume of specific proteins. Such methods may include dynamic/static light scattering, analytical ultracentrifugation or analytical gel filtration as exemplified herein below. Analytical gel filtration represents a known method in the art for measuring the hydrodynamic volume of macromolecules. Alternatively, the hydrodynamic volume of a globular polypeptide can be estimated by its molecular weight (Creighton (1993) loc. cit.). As described herein the hydrodynamic volume of the polypeptides of the invention consisting preferably of at least about 50, of at least about 100, of at least about 150, of at least about 200, of at least about 250, of at least about 300, of at least about 350, of at least about 400 to about 3000 proline and alanine amino acid residues and having random coil conformation show unexpectedly high values in relation to the hydrodynamic volume that would be estimated for a corresponding folded, globular protein based on the molecular weight. The following relates to biologically active, heterologous proteins or protein constructs comprising, inter alia, the biosynthetic random coil polypeptide (or segment thereof) as described and defined herein above which represent a preferred embodiment of the present invention. Without being bound by theory, it was surprisingly found in context of the present invention that the biosynthetic random coil polypeptide stretches as provided herein and consisting solely of proline and alanine can, even provide for a higher hydrodynamic volume than a corresponding biosynthetic random coil stretch having the same total number of amino acid residues but consisting solely of proline, alanine and serine (as provided in WO 2008/155134).

Common human plasma proteins such as serum albumin (HSA) and immunoglobulins (Igs), including humanized antibodies, show long half-lifes, typically of 2 to 3 weeks, which is attributable to their specific interaction with the neonatal Fc receptor (FcRn), leading to endosomal recycling (Ghetie (2002) Immunol Res, 25:97-113). In contrast, most other proteins of pharmaceutical interest, in particular recombinant antibody fragments, hormones, interferons, etc. suffer from rapid (blood) clearance. This is particularly true for proteins whose size is below the threshold value for kidney filtration of about 70 kDa (Caliceti (2003) Adv Drug Deliv Rev 55:1261-1277). In these cases the plasma half-life of an unmodified pharmaceutical protein may be considerably less than one hour, thus rendering it essentially useless for most therapeutic applications. In order to achieve sustained pharmacological action and also improved patient compliance—with required dosing intervals extending to days or even weeks—several strategies were previously established for purposes of biopharmaceutical drug development.

First, the recycling mechanism of natural plasma proteins has been employed by producing fusion proteins with the Fc portion of Igs, for example Enbrel®, a hybrid between the extracellular domain of TNFα receptor and human IgG1 (Goldenberg (1999) Clin Ther 21:75-87) or with serum albumin, for example Albuferon® (albinterferon alfa-2b, ZALBIN™, JOULFERON®), a corresponding fusion of IFNalpha with HSA (Osborn (2002) J Pharmacol Exp Ther 303:540-548). Albumin with its high plasma concentration of 600 μM has also been utilized in an indirect manner, serving as carrier vehicle for biopharmaceuticals that are equipped with an albumin-binding function, for example via fusion with a bacterial albumin-binding domain (ABD) from *Streptococcal* protein G (Makrides (1996) J Pharmacol Exp Ther 277:534-542) or with a peptide selected against HSA from a phage display library (Dennis (2002) J Biol Chem, 277:35035-35043; Nguyen (2006) Protein Eng Des Sel 19:291-297).

Second, a fundamentally different methodology for prolonging the plasma half-life of biopharmaceuticals is the conjugation with highly solvated and physiologically inert chemical polymers, thus effectively enlarging the hydrodynamic radius of the therapeutic protein beyond the glomerular pore size of approximately 3-5 nm (Caliceti (2003) loc. cit.). Covalent coupling under biochemically mild conditions with activated derivatives of polyethylene glycol (PEG), either randomly via Lys side chains (Clark (1996) J Biol Chem 271:21969-21977) or by means of specifically introduced Cys residues (Rosendahl (2005) BioProcess International: 52-60) has been moderately successful and is currently being applied in several approved drugs. Corresponding advantages have been achieved especially in conjunction with small proteins possessing specific pharmacological activity, for example Pegasys®, a chemically PEGylated recombinant IFNa-2a (Harris (2003) Nat Rev Drug Discov, 2:214-221; Walsh (2003) Nat Biotechnol 21:865-870).

However, the chemical coupling of a biologically active protein with synthetic polymers has disadvantages with respect to biopharmaceutical development and production. Suitable PEG derivatives are expensive, especially as high purity is needed, and their conjugation with a recombinant protein requires additional in vitro processing and purification steps, which lower the yield and raise the manufacturing costs. In fact, PEG is often contaminated with aldehydes and peroxides (Ray (1985) Anal Biochem 146:307-312) and it is intrinsically prone to chemical degradation upon storage in the presence of oxygen. Also, the pharmaceutical function of a therapeutic protein may be hampered if amino acid side chains in the vicinity of its biochemical active site become modified by the PEGylation process. Furthermore, chemical coupling with synthetic polymers usually results in a heterogeneous mixture of molecules which may show a substantial variance of in vivo activity.

Third, the use of glycosylation analogs of biologically active proteins in which new N-linked glycosylation consensus sequences are introduced has been proposed to prolong plasma half-life; see WO 02/02597; Perlman (2003) J Clin Endocrinol Metab 88:2327-2335; or Elliott (2003) Nat Biotechnol 21:414-420). The described glycoengineered proteins, however, displayed an altered in vivo activity, which indicates that the new carbohydrate side chains influence the biological activity of the engineered protein. Moreover, the additional carbohydrate side chains are likely to increase the antigenicity of the resulting biological active molecules, which raises substantial safety concerns. Furthermore, fusion proteins comprising the *Trypanosoma cruzi* derived artificial repetitive sequence PSTAD have been reported to induce a prolonged plasma half-life of trans-sialidase (Alvarez (2004) JBC 279:3375-3381). Yet, such *Trypanosoma cruzi* derived repeats have been reported to induce a humoral immune response (Alvarez (2004) loc.

cit.). Accordingly, alternative strategies to prolong the action of biologically active proteins are desired.

The biosynthetic amino acid sequences/polypeptides as disclosed herein and consisting solely of proline and alanine according to the invention were surprisingly found to adopt random coil conformation in particular under physiological conditions. Therefore, they are advantageous molecules to provide for the herein below defined "second domain" of the biologically active protein(s)/polypeptide(s), i.e. comprising a polypeptide stretch that forms under physiological conditions a random coil conformation and thereby mediates an increased in vivo and/or in vitro stability to biologically active ("functional") protein(s) or polypeptide(s), in particular, an increased plasma half-life. The hydrodynamic volume of a functional protein that is fused to said random coil domain is dramatically increased as can be estimated by using standard methods mentioned herein. Since the random coil domain is thought not to interfere with the biological activity of the first domain of the biologically active protein, the biological activity mediated by the functional protein of interest to which it is fused is essentially preserved. Moreover, the amino acid polymers/polypeptides that form random coil domain as disclosed herein are thought to be biologically largely inert, especially with respect to proteolysis in blood plasma, immunogenicity, isoelectric point/electrostatic behaviour, binding to cell surface receptors as well as internalisation, but still biodegradable, which provides clear advantages over synthetic polymers such as PEG.

In accordance with the above, the present invention relates to a biologically active protein comprising the herein described biosynthetic random coil polypeptide. Such a biologically active protein/protein construct comprising the biosynthetic random coil polypeptide decribed herein is a heterologous biological active protein/protein construct. In particular, herein disclosed is/are also (a) biologically active, heterologous protein(s) comprising or consisting of at least two domains wherein (a) a first domain of said at least two domains comprises or consists of an amino acid sequence having and/or mediating said biological activity; and (b) a second domain of said at least two domains comprises or consists of the herein described and defined random coil polypeptide or polypeptide segment.

It is of note that in accordance with the present invention that "first domain" and said "second domain" relate to protein stretches that are not naturally occurring within the same protein or that are not expected to be part of the same hypothetical protein as encoded by a coding nucleic acid sequence (like an open reading frame) as found in nature.

The definitions and explanations given herein above in context of the random coil polypeptide or polypeptide segment thereof apply, mutatis mutandis, in the context of biologically active proteins comprising said random coil polypeptide (or (a) polypeptide segment(s) thereof).

Preferably, said random coil conformation mediates an increased in vivo and/or in vitro stability of said biologically active protein, like the in vivo and/or in vitro stability in biological samples or in physiological environments.

For example, it is envisaged herein that proteins comprising a herein defined, additional "second domain" adopting a random coil conformation in aqueous solution or under physiological conditions (for example polymers consisting of about 200 or about 400 or about 600 amino acid residues and comprising PA#1/SEQ ID NO. 1, PA#2/SEQ ID NO. 2, PA#3/SEQ ID NO. 3, PA#4/SEQ ID NO. 4, PA#5/SEQ ID NO. 5, PA#6/SEQ ID NO. 6 and/or P1A1/SEQ ID NO. 51 as "building blocks") have an advantageous serum stability or plasma half-life, even in vivo, (in particular if intravenously administered) as compared to a control lacking said random coil conformation.

In WO 2008/155134 (as discussed herein above) it has been shown that biologically active proteins which comprise a domain with an amino acid sequence adopting a random coil conformation have an increased in vivo and/or in vitro stability. The random coil domains disclosed in WO 2008/155134 consist, in particular, of proline, alanine, and serine (PAS) residues. The presence of these three residues is described in this prior art document as an essential requirement for the formation of a stable and soluble random coil in aqueous solution.

As discussed in the introduction herein above, WO 2007/103515 describes unstructured recombinant polymers which comprise as main constituents a large variety of amino acids, inter alia, glycine, aspartate, alanine, serine, threonine, glutamate and proline. However, the term "unstructured recombinant polymer" has, in contrast to the terms "biosynthetic" and "random coil", no recognized, clear meaning.

Also mentioned herein above was WO 2006/081249. This document describes protein conjugates comprising a biologically active protein coupled to a polypeptide comprising 2 to 500 units of an amino acid repeat having Gly, Asn, and Gln as a major constituent and Ser, Thr, Asp, Gln, Glu, His, and Asn as a minor constituent. Said protein conjugates are described to have either an increased or a decreased plasma half-life when compared to the unconjugated biologically active protein. WO 2006/081249, however, does not provide any teaching to predict whether a specific amino acid repeat reduces or augments the plasma half-life of the conjugate. Moreover, WO 2006/081249 does not teach or suggest that the plasma half-life of proteins can be increased when the conjugated protein comprises an amino acid repeat that forms random coil conformation as shown in the present invention. Furthermore, the amino acid repeats disclosed in WO 2006/081249 comprise at least two residues selected from Gly, Asn, and Gln, which is in clear contrast with the biosynthetic random coil polypeptides of the present invention which comprise an amino acid sequence that solely consists of proline and alanine amino acid residues.

Surprisingly, it has been found herein that biosynthetic random coil amino acid sequences as provided herein which, in contrast to the prior art, solely comprise proline and alanine residues (i.e. which preferably do not comprise a substantial amount of any other amino acid, also not a substantial amount of serine or no serine at all) do also form a useful random coil structure. This is particularly unexpected given the disclosure in WO 2008/155134 of fusion proteins with a domain composed only of serine and alanine (SA) residues, i.e. where proline residues were omitted, demonstrating that such a domain comprising only two types of amino acids did not form a random coil, but a β-sheet structure. These serine-alanine domains did also not show such an increased hydrodynamic volume as observed with "PAS" or, in particular, with the "P/A" sequences as provided herein.

As used herein, the term "biological activity" describes the biological effect of a substance on living matter. Accordingly, the terms "biologically active protein" as used herein relate to proteins that are capable of inducing a biological effect in living cells/organisms that are exposed to said protein or polypeptide. Yet, it is of note that in the context of the present invention, the term "biologically active protein" relates to the whole protein of the invention which both comprises an amino acid sequence having and/or mediating said biological activity (said first domain) and the inventive amino acid sequence adopting/forming random coil conformation and consisting solely of proline and alanine (said second domain).

Accordingly, the terms "amino acid sequence having and/or mediating biological activity" or "amino acid sequence with biological activity" as used herein to the above-defined "first domain" of the biologically active protein of the invention, which mediates or has or is capable of mediating or having the above defined "biological activity". Also comprised in the terms "amino acid sequence having and/or mediating biological activity" or "amino acid sequence with biological activity" are any proteins of interest (and functional fragments thereof, such as antibody fragments, fragments comprising extracellular or intracellular domain(s) of a membrane receptor, truncated forms of a growth factor or cytokine and the like), the half-life of which, either in vivo or in vitro, needs to be prolonged. In one embodiment of this invention, the amino acid sequence having and/or mediating biological activity in accordance with the present invention may be deduced from any "protein of interest", i.e. any protein of pharmaceutical or biological interest or any protein that is useful as a therapeutic/diagnostic agent.

Accordingly, the biologically active proteins may comprise a first domain comprising a biologically active amino acid sequence which is derived from naturally produced polypeptides or polypeptides produced by recombinant DNA technology. In a preferred embodiment, the protein of interest may be selected from the group consisting of binding proteins/binding molecules, immunoglobulins, antibody fragments, transport proteins, membrane receptors, signaling proteins/peptides such as cytokines, growth factors, hormones or enzymes and the like.

As explained herein above, the random coil polypeptide (or polypeptide segment) comprised in the second domain of the biologically active protein forms the random coil conformation in particular under physiological conditions. This is particularly relevant in context of biologically active proteins which may form part of a pharmaceutical composition that is to be administered to a subject or patient.

It is of note that the inventive biosynthetic random coil domain (said "second domain") of the biologically active protein natively (ie. under physiologic conditions) adopts/forms/has random coil conformation, in particular in vivo and when administered to mammals or human patients in need of medical intervention. In contrast, it is known in the art that proteins having a non-random secondary and/or tertiary structure as native conformation tend to adopt a random coil conformation under non-physiological conditions (i.e. under denaturing conditions). However, such denatured proteins have completely different characteristics compared to the biologically active protein comprising the random coil polypeptide of the present invention. Hence, it is the gist of this invention that the "biologically active protein" and the biologically active part of the fusion proteins/fusion constructs as provided herein maintain their biological function also when combined and/or linked with the biosynthetic random coil polypeptide (or polypeptide segment) of this invention.

Furthermore, the random coil polypeptide (or polypeptide segment) retains solubility under physiological conditions. Accordingly, it is also envisaged that the protein construct of the present invention (comprising the above defined "first" and "second domain") may comprise the "second", random coil forming/adopting domain transiently or temporarily not in random coil conformation, for example, when in form of a specific composition, like a lyophylisate or dried composition. Yet, it is important that such a "second domain" of the inventive protein construct again adopts after, e.g., reconstitution in corresponding buffers (preferably "physiological" buffers/excipients and/or solvents), the herein defined random coil conformation. Said "second domain" is (if necessary, after corresponding reconstitution) capable of mediating an increased in vivo and/or in vitro stability of the inventive biologically active protein. It is preferred herein that the "second domain" as defined herein consists of the random coil polypeptide (or polypeptide segment) of the present invention.

As used herein, the term "domain" relates to any region/part of an amino acid sequence that is capable of autonomously adopting a specific structure and/or function. In the context of the present invention, accordingly, a "domain" may represent a functional domain or a structural domain. As described herein, the proteins of the present invention comprise at least one domain/part having and/or mediating biological activity and at least one domain/part forming random coil conformation. Yet, the proteins of the invention also may consist of more than two domains and may comprise e.g. an additional linker or spacer structure between the herein defined two domains/parts or another domain/part like, e.g. a protease sensitive cleavage site, an affinity tag such as the $His_6$-tag or the Strep-tag, a signal peptide, retention peptide, a targeting peptide like a membrane translocation peptide or additional effector domains like antibody fragments for tumour targeting associated with an anti-tumour toxin or an enzyme for prodrug-activation etc.

In another embodiment, the biologically active protein of the invention has a hydrodynamic volume as determined by analytical gel filtration (also known as size exclusion chromatography, SEC) of at least 50 kDa, preferably of at least 70 kDa, more preferably of at least 80 kDa, even more preferably of at least 100 kDa, particularly preferably of at least 125 kDa and most preferably of at least 150 kDa. The person skilled in the art is readily capable of determining the hydrodynamic volume of specific proteins. Exemplary methods have been described herein above in context of the random coil polypeptide. A skilled person is easily in the position to adapt such methods also in context of the biologically active protein of the present invention. As described herein below, the hydrodynamic volume of the biologically active proteins of the invention that comprise the above defined second domain, i.e. the domain comprising or consisting of the herein provided random coil polypeptide (or segment thereof) are shown to have an unexpectedly large hydrodynamic volume in relation to the estimated hydrodynamic volume for a corresponding folded, globular protein based on their molecular weight or number/composition of amino acid residues.

It should be noted that the first domain comprising an "amino acid sequence having and/or mediating biological activity" may also adopt its biological activity in the context of or after association with another polypeptide or amino acid sequence. For example, the Fab fragment of an antibody such as the one of the anti-tumour antibody Herceptin (Eigenbrot (1993) J. Mol. Biol. 229:969-995) consists of two different polypeptide chain, the immunoglobulin light chain and a fragment of the immunoglobulin heavy chain, which may furthermore be linked via (an) interchain disulfide bond(s). According to the present invention, it may be sufficient to link one of those chains (e.g. via gene fusion) to the random coil polypeptide (or polypeptide segment) while the full biologically active protein is reconstituted by means of association with the other chain. Such reconstitution may be achieved, for example, by co-expression of the different polypeptides (on the one hand a fusion protein of one chain and the random coil polypeptide, on the other hand the other chain) in the same host cell, as described in the appended examples, or by reconstitution in vitro, for example, as part of a refolding protocol.

Accordingly, also such proteins (comprising tow separate polypeptide chains) are considered as biologically active proteins in accordance with the present invention. In such a case, the first domain as defined herein may comprise two separate polypeptide chains which are linked only non-covalently. Furthermore, the independent chains of the biologically active protein/domain may each be linked to the random coil polypeptide (or polypeptide segment). Beside antibody fragments there are many other homo- or hetero-oligomeric proteins of interest (for example, insulin, hemoglobin and the like) that are composed of several associated polypeptide chains and which are subject to this invention.

As used herein, the term "binding protein" relates to a molecule that is able to specifically interact with (a) potential binding partner(s) so that it is able to discriminate between said potential binding partner(s) and a plurality of different molecules as said potential binding partner(s) to such an extent that, from a pool of said plurality of different molecules as potential binding partner(s), only said potential binding partner(s) is/are bound, or is/are significantly bound. Methods for the measurement of binding between a binding protein and a potential binding partner are known in the art and can be routinely performed, e.g., by using ELISA, isothermal titration calorimetry, equilibrium dialysis, pull down assays, surface plasmon resonance or a Biacore apparatus. Exemplary binding proteins/binding molecules which are useful in the context of the present invention include, but are not limited to antibodies, antibody fragments such as Fab fragments, F(ab')$_2$ fragments, single chain variable fragments (scFv), isolated variable regions of antibodies (VL and/or VH regions), CDRs, single domain antibodies/immunoglobulins, CDR-derived peptidomimetics, lectins, immunoglobulin domains, fibronectin domains, protein A domains, SH3 domains, ankyrin repeat domains, lipocalins or various types of scaffold-derived binding proteins as described, for example, in Skerra (2000) J Mol Recognit 13:167-187, Gebauer (2009) Curr Opin Chem Biol 13:245-255, Binz (2005) Nat Biotechnol 23:1257-1268 or Nelson (2009) Nat Biotechnol 27:331-337.

Other exemplary biologically active proteins of interest (in particular proteins comprised in the first domain or constituting/being the first domain of the biologically active protein) which are useful in the context of the present invention include, but are not limited to, granulocyte colony stimulating factor, human growth hormone, alpha-interferon, beta-interferon, gamma-interferon, lambda-interferone, tumor necrosis factor, erythropoietin, coagulation factors such as coagulation factor VIII, coagulation factor VIIa, coagulation factor IX, gp120/gp160, soluble tumor necrosis factor I and II receptor, thrombolytics such as reteplase, peptides with metabolic effects such as GLP-1 or exendin-4, immunosuppressive/immunoregulatory proteins like interleukin-1 receptor antagonists or anakinra, interleukin-2 and neutrophil gelatinase-associated lipocalin or other natural or engineered lipocalins or those proteins or compounds listed, for example, in Walsh (2003) Nat Biotechnol 21:865-870 or Walsh (2004) Eur J Pharm Biopharm 58:185-196 or listed in online databases such as biopharma.com/approvals.html or drugbank.ca. Further biologically active proteins (in particular proteins comprised in the first domain or constituting/being the first domain of the biologically active protein) which may be employed in context of the present invention are, inter alia, follicle-stimulating hormone, glucocerebrosidase, thymosin alpha 1, glucagon, somatostatin, adenosine deaminase, interleukin 11, hematide, leptin, interleukin-20, interleukin-22 receptor subunit alpha (IL-22ra), interleukin-22, hyaluronidase, fibroblast growth factor 18, fibroblast growth factor 21, glucagon-like peptide 1, osteoprotegerin, IL-18 binding protein, growth hormone releasing factor, soluble TACI receptor, thrombospondin-1, soluble VEGF receptor Flt-1, α-galactosidase A, myostatin antagonist, gastric inhibitory polypeptide, alpha-1 antitrypsin, IL-4 mutein, and the like. As will be evident from the disclosure herein, the present invention also relates to comprising the biosynthetic random coil proline/alanine polypeptide or proline/alanine polypeptide segment and pharmaceutically or medically useful molecules, like small molecules, peptides or biomacromolecules such as proteins, nucleic acids, carbohydrates, lipid vesicles and the like, in particular pharmaceutically or medically useful proteins, like (but not limited to) binding proteins/binding molecules, immunoglobulins, antibody fragments, transport proteins, membrane receptors, signaling proteins/peptides, cytokines, growth factors, hormones or enzymes and the like may be comprised in the herein defined drug constructs btu they may also be part of the herein defined biologically active, heterologous protein comprising or consisting of said defined at least two domains. In such a case, said particular pharmaceutically or medically useful proteins (or functional fragments thereof) may be the "first domain" of said at least two domains comprising or consisting of an amino acid sequence having and/or mediating said biological activity Functional fragments, in this context, are fragments of said pharmaceutically or medically useful proteins that are still capable to elucidate the desired biological or pharmaceutical response in vivo and/or in vitro and/or still have or mediate the desired biological activity.

The above-mentioned polypeptide linker/spacer, inserted between said first and said second domains, preferably comprises plural hydrophilic, peptide-bonded amino acids that are covalently linked to both domains. In yet another embodiment said polypeptide linker/spacer comprises a plasma protease cleavage site which allows the controlled release of said first domain comprising a polypeptide having and/or mediating a biological activity. Linkers of different types or lengths may be identified without undue burden to obtain optimal biological activity of specific proteins.

In a preferred embodiment, the biologically active proteins of the present invention are fusion proteins. A fusion protein as described herein may comprise at least one domain which can mediate a biological activity and at least one other domain which comprises the biosynthetic random coil polypeptide (or polypeptide segment) as described herein in a single multi-domain polypeptide. Again, it is of note that the present invention is not limited to fusion proteins wherein one domain mediates a biological activity. Also other "fusion proteins"/"fusion constructs" are provided herein wherein one part/domain is or comprises the inventive random coil polypeptide/polymer of proline/alanine and the other part/domain comprises another protein stretch/structure.

In particular, in the case of fusion proteins the random coil polypeptide (or polypeptide segment) according to this invention does not necessarily carry Pro or Ala residues at its amino or carboxyl terminus. In an alternative embodiment, the biologically active protein in accordance with the present invention may represent a protein conjugate wherein a protein of interest or a polypeptide/polypeptide stretch/peptide/amino acid sequence having and/or mediating biological activity is conjugated via a non-peptide bond to an amino acid sequence which forms/adopts random coil conformation, in particular, the random coil polypeptide (or polypeptide segment) as provided herein and consisting solely of proline and alanine residues. Non-peptide bonds that are useful for cross-linking proteins are known in the art with the biosynthetic random coil polypeptide or polypeptide segment comprising an amino acid sequence consisting solely of proline and alanine amino acid residues, wherein said amino acid sequence consists of at least 50 proline (Pro) and alanine (Ala) amino acid residues as provided herein. Such Non-peptide bonds may include disulfide bonds, e.g. between Cys side chains, thioether bonds or non-peptide covalent bonds induced by chemical cross-linkers, such as disuccinimidyl suberate (DSS) or sulfosuccinimidyl 4-[p-maleimidophenyl] butyrate (Sulfo-SMPB), metal-chelating/complexing groups, as well as non-covalent protein-protein interactions.

It is of note that the "biologically active protein" of the present invention may also comprise more than one "amino acid sequence having and/or mediating a biological activity". Furthermore, the biologically active protein may also comprise more than biosynthetic random coil polypeptide (or segment thereof). In the simplest case, the biologically active protein consists of two domains, i.e. a first domain comprising an amino acid sequence having and/or mediating a biological activity and a second domain comprising the biosynthetic polypeptide (or segment thereof). It is of note that the present invention is not limited to "biologically or therapeutically active proteins" linked to the herein disclosed biosynthetic random coil polypeptide or polypeptide segment comprising an amino acid sequence consisting solely of proline and alanine amino acid residues, wherein said amino acid sequence consists of at least 50 proline (Pro) and alanine (Ala) amino acid residues. Also other proteins or molecules of interest, as relevant for other industries, like food or beverage industry, cosmetic industry and the like, may be manufactured by the means and methods provided herein.

The person skilled in the art is aware that the "domain comprising an amino acid sequence having and/or mediating a biological activity" and the "second domain comprising the random coil polypeptide (or segment thereof) as comprised in the biologically active proteins of the invention may be organized in a specific order.

Accordingly, and in the context of the invention, the order of the herein defined "first" and "second" domain of the inventive biologically active polypeptide may be arranged in an order, whereby said "first domain" (i.e. protein of interest; "amino acid sequence having and/or mediating said biological activity") is located at the amino (N—) terminus and said "second domain" (i.e. the domain that comprises the herein provided random coil polypeptide (or segment thereof)) is located at the carboxy (C—) terminus of the biologically active protein. However, this order may also be reversed, e.g. said "first domain" (i.e. protein of interest; "amino acid sequence having and/or mediating said biological activity") is located at the carboxy (C—) terminus and said "second domain" (i.e. the domain that comprises the herein provided random coil polypeptide (or segment thereof)) is located at the amino (N—) terminus of the biologically active protein. If the biologically active protein consists only of one first domain and one second domain, the domain order may, accordingly, be (from N-terminus to C-terminus): first domain (amino acid sequence having and/or mediating a biological activity)—second domain (random coil polypeptide (or segment thereof)). Vice versa, the domain order may be (from N-terminus to C-terminus): second domain (random coil polypeptide (or segment thereof))—first domain (amino acid sequence having and/or mediating a biological activity).

It is also envisaged that more than one domain comprising or consisting of an amino acid sequence having and/or mediating said biological activity are to be used in context of the inventive protein construct. For example, the biologically active protein may comprise two "first domain", i.e. two specific amino acid sequences having and/or mediating a biological activity, whereby this biological activity may be the same or a different activity. If the biologically active protein consists of two such "first domains", i.e two specific amino acid sequences having and/or mediating a biological activity, and one "second domain" (comprising the biosynthetic random coil polypeptide (or segment thereof), the domain order may be (from N-terminus to C-terminus): first domain (amino acid sequence having and/or mediating a specific biological activity)—second domain (random coil polypeptide (or segment thereof))—first domain (amino acid sequence having and/or mediating a specific (optionally different) biological activity).

The same explanations apply in cases where the biologically active protein comprises more than one "second domain" (i.e. the biologically active protein comprises more than one random coil polypeptide (or segment thereof). If the biologically active protein consists of two such "second domains", i.e two domains comprising the biosynthetic random coil polypeptide (or segment thereof), and one "first domain" (comprising an amino acid sequence having and/or mediating a biological activity), the domain order may be (from N-terminus to C-terminus): second domain (random coil polypeptide (or segment thereof))—first domain (amino acid sequence having and/or mediating a specific biological activity)—second domain (random coil polypeptide (or segment thereof)). If the biologically active protein comprises more than one "second domain" it is envisaged herein that these "second domains" may be identical or may be different.

As mentioned above, the biologically active protein may comprise more than one "first domain", i.e. more than one specific amino acid sequences having and/or mediating a biological activity and more than one "second domain" (biosynthetic random coil polypeptide (or segment thereof)) whereby these "first domains" may be identical or different and/or whereby said "second domains" may be identical or different. In such cases the following, exemplary domain orders are conceivable (from N-terminus to C-terminus):

first domain (amino acid sequence having and/or mediating a specific biological activity)—second domain (random coil polypeptide (or segment thereof))—first domain (amino acid sequence having and/or mediating a specific biological activity)—second domain (random coil polypeptide (or segment thereof));

second domain (random coil polypeptide (or segment thereof))—first domain (amino acid sequence having and/or mediating a specific biological activity)—first domain (amino acid sequence having and/or mediating a specific biological activity)—second domain (random coil polypeptide (or segment thereof));

first domain (amino acid sequence having and/or mediating a specific biological activity)—second domain (random coil polypeptide (or segment thereof))—second domain (random coil polypeptide (or segment thereof))—first domain (amino acid sequence having and/or mediating a specific biological activity);

second domain (random coil polypeptide (or segment thereof))—first domain (amino acid sequence having and/or mediating a specific biological activity)—second domain (random coil polypeptide (or segment thereof))—first domain (amino acid sequence having and/or mediating a specific biological activity);

second domain (random coil polypeptide (or segment thereof))—second domain (random coil polypeptide (or segment thereof))—first domain (amino acid sequence having and/or mediating a specific biological activity)—first domain (amino acid sequence having and/or mediating a specific biological activity); or first domain (amino acid sequence having and/or mediating a specific biological activity)—first domain (amino acid sequence having and/or mediating a specific biological activity)—second domain (random coil polypeptide (or segment thereof))—second domain (random coil polypeptide (or segment thereof)).

For a person skilled in the art further corresponding domain orders (in particular in cases where more than two "first domains" or more than two "second domains" are comprised in the biologically active protein) are easily conceivable.

As with all embodiments of the present inventive polypeptide/biologically active protein, said domain(s) comprising an amino acid sequence having and/or mediating the said biological activity may also be a biologically active fragment of a given protein with a desired biological function. Therefore, the herein defined "second domain" (preferably comprising the herein provided random coil polypeptide (or segment thereof)) may also be located between two biologically active fragments of a protein of interest or between biologically active fragments of two proteins of interest. All the explanations and definitions given herein above in context of "full length" proteins/polypeptides of interest (i.e. when the amino acid sequences has/mediates a certain biological activity on its own) apply, mutatis mutandis, in context of such fragments.

Again the above invention is not limited to the constructs that comprise a "domain" with a "biological active function". The constructs of the present invention may also comprise domains with other functions and are not limited to biological activities. These are merely embodiments of the present invention and it is evident for the skilled artisan that other constructs can easily be made and used without deferring from the gist of the present invention. Accordingyl, the herein said in context of "amino acid sequence having and/or mediating a specific biological activity" applies, mutatis mutnatis, for other constructs, for example constructs to be used in other technical fields, like in cosmetics, food processing, dairy products, paper production, etc. As mentioned herein above, the biosynthetic polypeptides/polymers of the rpesent invention can also be used to be linked with e.g. small molecules and the like.

Again, it has to be pointed out that the term "amino acid sequence having and/or mediating first biological activity" is not limited to full-length polypeptides that have and/or mediate said biological activity or function, but also to biologically and/or pharmacologically active fragments thereof. Especially, but not only, in a context wherein two or more "first domains" as defined herein are comprised in the inventive "biologically active protein" it is also envisaged that these "first domains" are or represent different parts of a protein complex or fragments of such parts of protein complex.

As exemplified herein below, the biologically active proteins of the invention which are modified to comprise a random coil polypeptide surprisingly exhibit an increased in vivo and/or in vitro stability when compared to unmodified biologically active proteins that lack said random coil domain. As used herein, the term "in vivo stability" relates to the capacity of a specific substance that is administered to the living body to remain biologically available and biologically active. In vivo, a substance may be removed and/or inactivated due to excretion, kidney filtration, liver uptake, aggregation, degradation and/or other metabolic processes. Accordingly, in the context of the present invention biologically active proteins that have an increased in vivo stability may be less rapidly excreted through the kidneys (urine) or via the feces and/or may be more stable against proteolysis, in particular against in vivo proteolysis in biological fluids, like blood, liquor cerebrospinalis, peritoneal fluid, and lymph. In one embodiment, the increased in vivo stability of a biologically active protein manifests in a prolonged plasma half-life of said biologically active protein. In particular, the increased in vivo stability of the biologically active protein is a prolonged plasma half-life of said biologically active protein comprising said second domain when compared to the biologically active protein lacking the second domain.

Methods for measuring the in vivo stability of biologically active proteins are known in the art. As exemplified herein below, biologically active proteins may be specifically detected in the blood plasma using Western blotting techniques or enzyme linked immunosorbent assay (ELISA). Yet, the person skilled in the art is aware that other methods may be employed to specifically measure the plasma half-life of a protein of interest. Such methods include, but are not limited to the physical detection of a radioactively labelled protein of interest. Methods for radioactive labelling of proteins e.g. by radioiodination are known in the art.

The term "increased in vitro stability" as used herein relates to the capacity of a biologically active protein to resist degradation and/or aggregation and to maintain its original biological activity in an in vitro environment. Methods for measuring the biological activity of biologically active proteins are well known in the art.

Furthermore, a drug conjugate is provided which comprises the herein described and defined random coil polypeptide or polypeptide segment and a small molecule drug that is conjugated to said random coil polypeptide or polypeptide segment. Non-limiting examples of the small molecules are digoxigenin, fluorescein doxorubicin, calicheamicin, camptothecin, fumagillin, dexamethasone, geldanamycin, paclitaxel, docetaxel, irinotecan, cyclosporine, buprenorphine, naltrexone, naloxone, vindesine, vancomycin, risperidone, aripiprazole, palonosetron, granisetron, cytarabine, NX1838, leuprolide, goserelin, buserelin, octreotide, teduglutide, cilengitide, abarelix, enfuvirtide, ghrelin and derivatives, tubulysins, platin derivatives, alpha 4 integrin inhibitors, antisense nucleic acids, small interference RNAs, micro RNAs, steroids, DNA or RNA aptamers, peptides, peptidomimetics. In general, the present invention also relates to drug constructs comprising the herein defined random coil polypeptide or polypeptide segment and in particular pharmaceutically or medically useful molecules, like small molecules, peptides or biomacromolecules such as proteins, nucleic acids, carbohydrates, lipid vesicles and the like. In the appended illustrative experimental part (see, e.g. Example 22) the successful generation of constructs/conjugates of the present invention are provided, also constructs wherein "small chemical molecules" have been conjugated to the herein disclosed random coil polypeptide. Therefore, the present Figures and experimental information in the corresponding figure legends provide for illustrative examples, wherein the herein disclosed drug conjugates comprise (i) a biosynthetic random coil polypeptide or polypeptide segment comprising an amino acid sequence consisting solely of proline and alanine amino acid residues, wherein said amino acid sequence consists of at least 50 proline (Pro) and alanine (Ala) amino acid residues, and (ii) a small molecule, which is, as illustration, selected from digoxigenin and fluorescein. It is of note that these are not only academic examples. Fluorescein or fluorescein derivates are are commonly used as diagnostics, and medical fluorescein solutions are sold under the trade names Fluoescite®, AK-FLUOR® or Fluress®. Such compounds can certainly profit from the means and methods provided herein. Digoxigenin forms the steroid part of digoxin, a well known secondary plant metabolite with cardioactive function which furthermore contains three digitoxose sugars. Digoxin, and to a lesser extent the closely related compound digitoxin, are widely used for the treatment of ventricular tachyarrhythmias and congestive heart failure (Hauptman (1999) Circulation 99: 1265-1270). All cardioactive steroids are potent and highly specific inhibitors of the $Na^+/K^+$-ATPase located in the cellular plasma membrane, thereby exerting sympatholytic or positive inotropic effects.

The definitions and explanations given herein above in context of the random coil polypeptide or polypeptide segment thereof apply, mutatis mutandis, in context of drug conjugate comprising the random coil polypeptide (or polypeptide segment thereof) and a drug selected from the group consisting of (a) a biologically active protein or a polypeptide that comprises or that is an amino acid sequence that has or mediates a biological activity and (b) a small molecule drug.

The amino acid polymer forming random coil conformation/the random coil polypeptide (or segment thereof) as defined and provided herein can be conjugated to a small molecule/small molecule drug. By this means, plasma half-life and/or solubility of the small molecule/small molecule drug may be increased, unspecific toxicity may be decreased, and the prolonged exposure of active drug to target cells or structures in the body may result in enhanced pharmacodynamics.

A site-specific conjugation of the N-terminus of the random coil polypeptide with an activated drug derivative, e.g. as N-hydroxysuccinimide (NHS) ester derivative (Hermanson (1996) Bioconjugate Techniques, Academic Press, San Diego, Calif.), is possible. Generally, the N-terminal amino group can be chemically coupled with a wide variety of functional groups such as aldehydes and ketones (to form Schiff bases, which may be reduced to amines using sodium borohydride or sodium cyanoborohydride, for example) or to activated carbonic acid derivatives (anhydrides, chlorides, esters and the like, to form amides) or to other reactive chemicals such as isocyanates, isothiocyanates, sulfonly chlorides etc. Also, the N-terminus of the amino acid polymer/polypeptide can first be modified with a suitable protective group, for example an acetyl group, a BOC group or an FMOC group (Jakubke (1996) Peptide. Spektrum Akdemischer Verlag, Heidelberg, Germany) Furthermore, the amino terminus may be protected by a pyroglutamyl group, which can form from an encoded Gln amino acid residue preceding the Pro/Ala polypeptide or polypeptide segment. After activation of the C-terminal carboxylate group, e.g. using the common reagents EDC (N-(3-dimethylaminopropyl)-N'-ethylcarbodiimide) and NHS, site-specific coupling to the C-terminus of the protected random coil polypeptide can be achieved if the drug carries a free amino group, for example.

Alternatively, the N-terminus or the C-terminus of the amino acid polymer forming random coil conformation/the random coil polypeptide can be modified with a commercially available linker reagent providing a maleimide group, thus allowing chemical coupling to a thiol group as part of the drug molecule. In this manner uniform drug conjugates can be easily obtained. Similar techniques, which are well known in the art (Hermanson (1996) loc. cit.), can be used to couple the random coil polypeptide to a peptide or even to a protein drug. Such peptides or proteins can easily be prepared carrying a Lys or Cys side chain, which allows their in vitro coupling to the amino acid polymer forming random coil conformation via NHS ester or maleimide active groups. Generally, similar drug conjugates can be prepared with fusion proteins comprising the random coil polypeptide (or segment thereof). Yet, and as illustrated in the appended Examples and Figures the present invention also provides for the preparation of a random coil polypeptides or a random coil polypeptide segments as comprised in the innovative conjugates of the present invention.

As an alternative to a single site-specific conjugation the random coil polypeptide may be equipped with additional side chains, at the N- or C-terminus or internally, suitable for chemical modification such as lysine residues with their ε-amino groups, cysteine residues with their thiol groups, or even non-natural amino acids, allowing the conjugation of multiple small molecules using, for example, NHS ester or maleimide active groups.

Apart from stable conjugation, a prodrug may be linked transiently to the random coil polypeptide. The linkage can be designed to be cleaved in vivo, in a predictable fashion, either via an enzymatic mechanism or by slow hydrolysis initiated at physiological pH similarly as, for example, the poorly soluble antitumor agent camptothecin was conjugated to a PEG polymer, thus achieving increased biodistribution, decreased toxicity, enhanced efficacy and tumor accumulation (Conover (1998) Cancer Chemother Pharmacol, 42:407-414). Examples for further prodrugs are chemotherapeutic agents like docetaxel (Liu (2008) J Pharm Sci. 97:3274-3290), doxorubicin (Veronese (2005) Bioconjugate Chem. 16: 775-784) or paclitaxel (Greenwald (2001) J Control Release 74:159-171).

Furthermore, the small molecule may be coupled to a fusion protein comprising the amino acid polymer/polypeptide genetically fused to a targeting domain, e.g. an antibody fragment, thus resulting in a specific delivery of the small molecule drug. In the latter case immunotoxins can be easily generated by conjugation with a cytotoxic small molecule if the targeting domain is directed against a cell-surface receptor which undergoes internalization, for example.

In accordance with the above, the present invention also relates, therefore, to the provision of the herein disclosed biosynthetic random coil polypeptide or polypeptide segment comprising an amino acid sequence consisting solely of proline and alanine amino acid residues for further and additional coupling with other compounds of choice. Said further and/or additional coupling may be and/or may comprise the first coupling of said biosynthetic random coil polypeptide or biosynthetic random coil polypeptide segment with or to another compound.

In another embodiment, the present invention relates to nucleic acid molecules encoding the random coil polypeptides (or segments thereof) or biologically active proteins as described herein. Accordingly, said nucleic acid molecule may comprise a nucleic acid sequence encoding a polypeptide having biological activity and a nucleic acid sequence encoding the random coil polypeptide (or segment thereof) . . . . The term "nucleic acid molecule", as used herein, is intended to include nucleic acid molecules such as DNA molecules and RNA molecules. Said nucleic acid molecule may be single-stranded or double-stranded, but preferably is double-stranded DNA. Preferably, said nucleic acid molecule may be comprised in a vector.

Accordingly, the present invention also relates to a nucleic acid molecule encoding the random coil polypeptide or polypeptide segment as comprised in the conjugates provided herein, like a drug conjugate as defined herein, or a nucleic acid molecule encoding a protein conjugate that comprises a biologically active protein as defined above and that comprises, additionally, a biosynthetic random coil polypeptide or polypeptide segment comprising an amino acid sequence consisting solely of proline and alanine amino acid residues, wherein said amino acid sequence consists of at least 50 proline (Pro) and alanine (Ala) amino acid residues.

In one embodiment a nucleic acid molecule is provided that encodes a conjugate, like a drug conjugate or food conjugate as defined above, said nucleic acid molecule comprising
  (i) a nucleic acid sequence encoding a translated amino acid and/or a leader sequence;
  (ii) a nucleic acid sequence encoding a biosynthetic random coil polypeptide or polypeptide segment comprising an amino acid sequence consisting solely of proline and alanine amino acid residues, wherein said amino acid sequence consists of at least 50 proline (Pro) and alanine (Ala) amino acid residues;
  (iii) a nucleic acid sequence encoding biologically active protein or said a polypeptide that comprises or that is an amino acid sequence that has or that mediates a biological activity or a protein of interest, like a protein to be employed in other industrial areas like the food industry; and
  (iv) a nucleic acid sequence that represents or is a translational stop codon.

The above mentioned "translated amino acid and/or a leader sequence" under (i) may for example be the starting "M", i.e. a methionine derived from a corresponding starting codon, it may also comprise non-translated sequences of an mRNA like the 5' sequence up to a start codon which comprises for example a ribosome binding site. Such a sequence may however also comprise classical leader and/or signal sequences for example for secretion of an expressed protein into the periplasm or in a culture medium. Prokaryotic signal peptides are for example OmpA, MalE, PhoA, DsbA, pelB, Afa, npr, STII. Eukaryotic signal peptides are for example Honeybee melittin signal sequence, acidic glycoprotein gp67 signal sequence, mouse IgM signal sequence, hGH signal sequence.

Biologically active proteins or polypeptides that comprises or that is an amino acid sequence that has or that mediates a biological activity as well as other proteins of interest, like a protein to be employed in other industrial areas, have been provided herein above. Said embodiments apply, mutatis mutandis, for the nucleic acid molece (part/segments (iii)) as illustrated herein above.

Translational stop codons to be employed in the nucleic acid molecule provided herein are well known in the art and are, e.g. codons UAA, UAG or UGA.

In one embodiment of the nucleic acid molecule as provided herein above said nucleic acid molecule parts/segments (ii) and (iii) are interchanged in their position on said nucleic acid molecule encoding for a conjugate, like a drug conjugate or a food conjugate. Such a nucleic acid molecule would comprise the following order of parts/segments:
  (i) a nucleic acid sequence encoding a translated amino acid and/or a leader sequence;
  (ii) a nucleic acid sequence encoding biologically active protein or said a polypeptide that comprises or that is an amino acid sequence that has or that mediates a biological activity or a protein of interest, like a protein to be employed in other industrial areas, like the food industry;
  (iii) a nucleic acid sequence encoding a biosynthetic random coil polypeptide or polypeptide segment comprising an amino acid sequence consisting solely of proline and alanine amino acid residues, wherein said amino acid sequence consists of at least 50 proline (Pro) and alanine (Ala) amino acid residues; and
  (iv) a nucleic acid sequence that represents or is a translational stop codon.

The nucleic acid molecules as provided herein above may also, optionally, comprise, between parts/segments (i) and (ii) and/or between parts/segments (ii) and (iii), a protease and/or a chemical cleavage site and/or a recognition site. Such chemical cleavage sites are well known in the art, and comprise for example specific, individual amino acid sequences (see, e.g. Lottspeich and Engels (Hrsg.) (2006) Bioanalytik. 2. Auflage. Spektrum Akademischer Verlag, Elsevier, Munchen, Germany). For example, cyanogen bromide or cyanogen chloride cleaves the peptide bond following a Met residue; hydroxylamine cleaves the asparaginyl-glycyl bond; formic acid cleaves Asp-Pro; 2-(2'-nitrophenylsulfenyl)-3-methyl-3-bromoinolenine, 2-iodosobenzoic acid or N-chlorosuccinimide after Trp; 2-nitro-5-thiocyanatobenzoic acid after Cys. It is also envisaged and possible that the residue preceding the Pro/Ala polypeptide or polypeptide segment may be substituted to Met via site-directed mutagenesis and the resulting fusion protein can then be cleaved by BrCN. Similarly, other amino acid sequences comprising cleavage site can be introduced into the recombinant fusion protein or its encoding nucleic acid by way of site-directed mutagenesis.

Also useful protease recognition/cleavage sites are known in the art. These comprise, but are not limited to: trypsin, chymotrypsin, enterokinase, Tobacco Etch Virus (TEV) protease, PreScission protease, HRV 3C Protease, SUMO Protease, Sortase A, granzyme B, furin, thrombin, factor Xa or self cleavable inteins. Factor Xa hydrolyses the peptide bond at the C-terminal end of the amino acid sequence IleGluGlyArg, which may be inserted between the N-terminal fusion partner and the Pro/Ala polypeptide or polypeptide segment. A particularly simple method to achieve proteolytic cleavage would be by insertion or substitution of a Lys or Arg side chain at the N-terminal end of the Pro/Ala polypeptide or polypeptide segment followed by digest with trypsin, which does not cleave within the Pro/Ala polypeptide or polypeptide segment as long as internal Lys or Arg side chains are avoided. Illustrative recognition sites are, without being limited, D-D-D-D-K (enterokinase), ENLYFQ(G/S) (TEV protease), I-(E/D)-G-R (Factor Xa), L-E-V-L-F-Q-G-P (HRV 3C), R-X-(K/R)-R (Fuxin), LPXTG (Sortase A), L-V-P-R-G (Thrombin) or I-E-X-D-X-G (Granzyme B).

As is evident form the disclosure herein above, the present invention provides for recombinantly produced biosynthetic random coil polypeptides and polypeptide segments that can be conjugated with molecules of choice, like useful proteins, pharmaceutically active polypeptides or small molecules, diagnostically useful polypeptides or small molecules or, inter alia, other useful proteins or small molecules of other industrial areas, like food or paper industry or in oil recovery. Therefore, the present invention also provide for a nucleic acid encoding for a biosynthetic random coil polypeptide or polypeptide segment comprising an amino acid sequence consisting solely of proline and alanine amino acid residues wherein said amino acid sequence consists of at least 50 proline (Pro) and alanine (Ala) amino acid residues, said nucleic acid molecule comprising (i) a nucleic acid sequence encoding for a translated amino acid and/or leader sequence;
(ii) a nucleic acid sequence encoding for said a biosynthetic random coil polypeptide or polypeptide segment comprising an amino acid sequence consisting solely of proline and alanine amino acid residues; and
(iii) a nucleic acid sequence that represents or is a translational stop codon.

Such a nucleic acid molecule may, optionally, comprise, between (i) and (ii) a protease and/or a chemical cleavage site and/or a recognition site).

Also for this nucleic acid molecule, the embodiments provided herein above in context of the first two described nucleic acid molecules (i.e. a protease and/or a chemical cleavage site and/or a recognition), apply here mutatis mutantis.

Useful and illustrative signal sequences to be employed in context of this invention comprise, but are not limited, prokaryotic sequences like: OmpA, MalE, PhoA, DsbA, pelB, Afa, npr, STII or eukaryotic sequences like: Honeybee melittin signal sequence, acidic glycoprotein gp67 signal sequence, mouse IgM signal sequence, hGH signal sequence In particular the nucleic acid molecule encoding the biosynthetic random coil polypeptide or polypeptide segment comprising an amino acid sequence consisting solely of proline and alanine amino acid residues of the present invention is useful in methods as also provided herein below and as illustrated in the appended examples and figures. Such an expressed random coil polypeptide or random coil polypeptide segment can be isolated form, e.g. host cells expressing such a random coil polypeptide or random coil polypeptide segment. Such host cells may be transfected cells, for example with an vector as provided herein.

Therefore, it is envisaged to transfect cells with the nucleic acid molecule or vectors as described herein. In a further embodiment, the present invention relates to nucleic acid molecules which upon expression encode the random coil polypeptide (or segment thereof) or biologically active proteins of the invention. Yet, in a further embodiment, the present invention relates to nucleic acid molecules which upon expression encode the herein disclosed polypeptides that, entirely or in part, form/adopt random coil conformation in aqueous solution or under physiological conditions. Said nucleic acid molecules may be fused to suitable expression control sequences known in the art to ensure proper transcription and translation of the polypeptide as well as signal sequences to ensure cellular secretion or targeting to organelles. Such vectors may comprise further genes such as marker genes which allow for the selection of said vector in a suitable host cell and under suitable conditions.

Preferably, the nucleic acid molecule of the invention is comprised in a recombinant vector in which a nucleic acid molecule encoding the herein described biologically active protein is operatively linked to expression control sequences allowing expression in prokaryotic or eukaryotic cells. Expression of said nucleic acid molecule comprises transcription of the nucleic acid molecule into a translatable mRNA. Regulatory elements permitting expression in prokaryotic host cells comprise, e.g., the lambda PL, lac, trp, tac, ara, phoA, tet or T7 promoters in E. coli. Possible regulatory elements ensuring expression in eukaryotic cells, preferably mammalian cells or yeast, are well known to those skilled in the art. They usually comprise regulatory sequences ensuring initiation of transcription and optionally poly-A signals effecting termination of transcription and stabilization of the transcript. Additional regulatory elements may include transcriptional as well as translational enhancers, and/or naturally associated or heterologous promoter regions. Examples for regulatory elements permitting expression in eukaryotic host cells are the AOX1 or GAL1 promoters in yeast or the CMV, SV40, RSV (Rous sarcoma virus) promoters, CMV enhancer, SV40 enhancer or a globin intron in mammalian and other animal cells. Apart from elements which are responsible for the initiation of transcription such regulatory elements may also comprise transcription termination signals, such as the SV40-poly-A site or the tk-poly-A site, downstream of the coding region.

Methods which are well known to those skilled in the art can be used to construct recombinant vectors (see, for example, the techniques described in Sambrook (1989), Molecular Cloning: A Laboratory Manual, Cold Spring Harbor Laboratory NY and Ausubel (1989), Current Protocols in Molecular Biology, Green Publishing Associates and Wiley Interscience, NY). In this context, suitable expression vectors are known in the art such as Okayama-Berg cDNA expression vector pcDV1 (Pharmacia), pCDM8, pRc/CMV, pcDNA1, pcDNA3, pP1CZalpha A (Invitrogen), or pSPORT1 (GIBCO BRL). Furthermore, depending on the expression system that is used, leader sequences capable of directing the polypeptide to a cellular compartment or secreting it into the culture medium may be added to the coding sequence of the nucleic acid molecule of the invention.

The present invention also relates to vectors, particularly plasmids, cosmids, viruses, and bacteriophages that are conventionally employed in genetic engineering, comprising a nucleic acid molecule encoding the the random coil polypeptide (or segment thereof) or the biologically active protein of the invention. Preferably, said vector is an expression vector and/or a gene transfer or targeting vector. Expression vectors derived from viruses such as retroviruses, vaccinia virus, adeno-associated virus, herpes viruses or bovine papilloma virus may be used for delivery of the polynucleotides or vector of the invention into targeted cell populations.

The vectors containing the nucleic acid molecules of the invention can be transfected into the host cell by well known methods, which vary depending on the type of cell. Accordingly, the invention further relates to a cell comprising said nucleic acid molecule or said vector. Such methods, for example, include the techniques described in Sambrook (1989), loc. cit. and Ausubel (1989), loc. cit. Accordingly, calcium chloride transfection or electroporation is commonly utilized for prokaryotic cells, whereas calcium phosphate treatment or electroporation may be used for other cellular hosts (Sambrook (1989), loc. cit.). As a further alternative, the nucleic acid molecules and vectors of the invention can be reconstituted into liposomes for delivery to target cells. The nucleic acid molecule or vector of the invention which is present in the host cell may either be integrated into the genome of the host cell or it may be maintained extra-chromosomally. Accordingly, the present invention also relates to a host cell comprising the nucleic acid molecule and/or the vector of this invention. Host cells for the expression of polypeptides are well known in the art and comprise prokaryotic cells as well as eukaryotic cells, e.g. *E. coli* cells, yeast cells, invertebrate cells, CHO cells, CHO-K1 cells, HEK 293 cells, Hela cells, COS-1 monkey cells, melanoma cells such as Bowes cells, mouse L-929 cells, 3T3 cell lines derived from Swiss, Balb-c or NIH mice, BHK or HaK hamster cell lines and the like.

In a further aspect, the present invention comprises methods for the preparation of the conjugates of the present invention as well as the biosynthetic random coil polypeptide (or segment thereof) or biologically active proteins provided herein and comprising culturing the (host) cell of this invention and isolating said random coil polypeptide (or segment thereof) or the conjugate or a biologically active protein from the culture as described herein. In general, the inventive random coil polypeptide (or segment thereof), the conjugate or biologically active protein comprising a random coil domain may be produced by recombinant DNA technology, e.g. by cultivating a cell comprising the described nucleic acid molecule or vectors which encode the inventive biologically active protein or random coil polypeptide (or segment thereof) and isolating said protein/polypeptide from the culture. The inventive biologically active protein or random coil polypeptide (or segment thereof) may be produced in any suitable cell culture system including prokaryotic cells, e.g. *E. coli* BL21, KS272 or JM83, or eukaryotic cells, e.g. *Pichia pastoris*, yeast strain X-33 or CHO cells. Further suitable cell lines known in the art are obtainable from cell line depositories like the American Type Culture Collection (ATCC).

The term "prokaryotic" is meant to include bacterial cells while the term "eukaryotic" is meant to include yeast, higher plant, insect and mammalian cells. The transformed hosts can be grown in fermentors and cultured according to techniques known in the art to achieve optimal cell growth. In a further embodiment, the present invention relates to a process for the preparation of a random coil polypeptide (or segment thereof) or a biologically active protein described above comprising cultivating a cell of the invention under conditions suitable for expression of the biologically active protein or random coil polypeptide (or segment thereof) and isolating said protein/polypeptide from the cell or the culture medium.

The random coil polypeptide (or segment thereof) per se of the present invention does, preferably not comprises any chemically reactive group, except for, possibly, one N-terminal primary (or, in the case of proline, secondary) amino group and one carboxylate group at the C-terminus of the polymer. However, it is evident for the skilled artisan that the biosynthetic random coil polypeptide/polymer as provided herein may comprise a chemically reactive group, for example when said random coil polypeptide/polymer is part of a "fusion protein"/"fusion construct". As also described above, the biosynthetic random coil polypeptide (or segment thereof) can be prepared by recombinant expression in a transformed cell in several ways according to methods well known to the person skilled in the art, for example: (i) direct expression in the cytoplasm with the help of an N-terminal Met residue/start codon; (ii) secretion via an N-terminal signal peptide, for example OmpA, PhoA (Monteilhet (1993) Gene. 1993 125:223-228), mellitin (Tessier (1991) Gene 98: 177-183), interleukin 2 (Zhang (2005) J Gene Med 7: 354-365), hGH (Pecceu (1991) Gene 97(2):253-258) and the like, followed by intracellular cleavage resulting in the mature N-terminus, such as Ala or Pro; (iii) expression as a fusion protein with another soluble protein, e.g., maltose-binding protein at the N-terminus and with a protease cleavage site interspersed (Kapust and Waugh (2000) Protein Expr. Purif. 19:312-318), followed by specific protease cleavage in vitro or in vivo, thus releasing the amino acid polymer/polypeptide with its mature N-terminus such, as Ala or Pro. Another suitable fusion partner is the SUMO protein, which can be cleaved by SUMO protease, as described in Examples 20 and 21. Further fusion partners include, without limitation, glutathion-S-transferase, thioredoxin, a cellulose-binding domain, an albumin-binding domain, a fluorescent protein (such as GFP), protein A, protein G, an intein and the like (Malhotra (2009) Methods Enzymol. 463:239-258).

As explained above, the random coil polypeptides (or polypeptide segments)/polymers described consist predominantly of alanine and proline residues, whereas serine, threonine or asparagine, which are required for O- or N-glycosylation, are preferably absent. Thus, the production of the polypeptide itself or of a biologically active protein comprising the random coil polypeptide (or polypeptide segment thereof) or, generally, a fusion protein comprising the random coil polypeptide (or polypeptide segment thereof) surprisingly can result in a monodisperse product preferably devoid of post-translational modifications within the Pro-Ala sequence This is an advantage for recombinant protein production in eukaryotic cells, like chinese hamster ovarian cells (CHO) or yeast, which are often chosen for the biosynthesis of complex proteins. For example, yeast has been used for the production of approved therapeutic proteins such as insulin, granulocyte-macrophage colony stimulating factor, platelet-derived growth factor or hirudin (Gerngross (2004) Nat. Biotechnol. 22:1409-1414). CHO cells have served for the production of therapeutic proteins such as coagulation factor IX, interferone β-1a, tenecteplase (Chu (2001) Curr. Opin. Biotechnol. 12:180-187) or gonadotropins, where the glycocomponent may positively influence several aspects like functional activity, folding, dimerization, secretion as well as receptor interaction, signal transduction, and metabolic clearance (Walsh (2006) Nat. Biotechnol. 24:-1241-1252). Accordingly, the preparation of the inventive constructs, random coil polypeptides and conjugates in eukaryotic expression systems is also disclosed in context of the present invention.

With the means and methods provided herein it is now possible to manufacture and provide for the herein disclosed conjugates and molecules comprising (i) a biosynthetic random coil polypeptide or polypeptide segment comprising an amino acid sequence consisting solely of proline and alanine amino acid residues and (ii) a further molecule of interest, like a useful protein, a protein segment or a small molecule. The present invention, therefore, also provides for methods for the preparation or manufacure of such conjugates as well as of biosynthetic random coil polypeptides and/or molecules or conjugates comprising the same. Accordingly, the present invention also provides for a method for the preparation and/or manufacture of a random coil polypeptide or a random coil polypeptide segment as comprised in the conjugates, like drug conjugates, food conjugates, diagnostic conjugates and the like. Also methods for the preparation and/or manufacture of the biologically active protein or conjugate comprising the random coil polypeptide or the random coil polypeptide segment are provided. Furthermore, methods for the preparation and/or manufacture and/or for the preparation and/or manufacture of a polypeptide that comprises or that is an amino acid sequence that has or that mediates a biological activity and that additionally comprises said random coil polypeptide or random coil polypeptide segment are provided. These methods, in particular comprise (as one step) the cultivation of the (host) cell as provided herein above and (as a further step) the isolation of said random coil polypeptide or biologically active protein and/or said biologically active protein and/or said polypeptide conjugate from the culture or from said cell. This isolated random coil, a biosynthetic random coil polypeptide or polypeptide segment comprising an amino acid sequence consisting solely of proline and alanine amino acid residues as well as the isolated conjugate may than be further proceesed. For example, said biosynthetic random coil polypeptide or polypeptide segment comprising an amino acid sequence consisting solely of proline and alanine amino acid residues may be chemically linked or coupled to a molecule of interest, as also shown in the appended examples. Furthermore and as an alternative, the molecule of interest may be enzymatically conjugated e.g. via transglutaminase (Besheer (2009) J Pharm Sci. 98:4420-8) or other enzymes (Subul (2009) Org. Biomol. Chem. 7:3361-3371) to the said biosynthetic random coil polypeptide or polypeptide segment comprising an amino acid sequence consisting of proline and alanine amino acid residues.

The random coil polypeptide (or segment thereof) and/or a protein conjugate comprising random coil polypeptide (or segment thereof) and a protein of interest, like a biologically or therapeutically active protein or a protein to be used in, e.g. diagnostic methods, can be isolated (inter alia) from the growth medium, cellular lysates, periplasm or cellular membrane fractions. (Again, the present invention is not limited to (protein) conjugates that are useful in a medical or pharmaceutical setting. The means and methods provided herein are also of use in other industrial areas, like, but not limited to food and beverage industry, nutrient industry, paper industry, bioreagent industry, research tool and reagent industry, industries where enzymes are to be used, cosmetic industry, oil processing and oil recovery, and the like). The isolation and purification of the expressed polypeptides of the invention may be performed by any conventional means (Scopes (1982) "Protein Purification", Springer, New York, N.Y.), including ammonium sulphate precipitation, affinity purification, column chromatography, gel electrophoresis and the like and may involve the use of monoclonal or polyclonal antibodies directed, e.g., against a tag fused with the biologically active protein of the invention. For example, the protein can be purified via the Strep-tag II using streptavidin affinity chromatography (Skerra (2000) Methods Enzymol. 326:271-304) as described in the appended examples. Substantially pure polypeptides of at least about 90 to 95% homogeneity (on the protein level) are preferred, and 98 to 99% or more homogeneity are most preferred, in particular for pharmaceutical use/applications. Depending upon the host cell/organism employed in the production procedure, the polypeptides of the present invention may be glycosylated or may be non-glycosylated.

The invention further relates to the use of the biologically active protein, the random coil polypeptide (or segment thereof) or the conjugates, like the drug conjugates of the invention, the nucleic acid molecule of the invention, the vector of the invention or the (host) cell of the invention for the preparation of a medicament, wherein said biologically active protein or drug (or any other small molecule or protein of interest) has an increased in vivo and/or in vitro stability as compared to a control molecule that does not comprise or that is not linked to a biosynthetic random coil polypeptide or polypeptide segment comprising an amino acid sequence consisting solely of proline and alanine amino acid residues, wherein said amino acid sequence consists of at least 50 proline (Pro) and alanine (Ala) amino acid residues.

In yet another embodiment, the present invention relates to a method for the treatment of diseases and/or disorders that benefit from the improved stability of said biologically active protein or drug, comprising administering the biologically active protein or drug conjugate as described herein to a mammal in need of such treatment. Depending on the biological activity of the inventive protein or drug conjugate, the skilled person is readily capable of determining which disease/disorder is to be treated with a specific biologically active protein or drug conjugate of the invention. Some non-limiting examples are listed in the following Table:

| Biologically active protein (or a biologically active component/fragment thereof) or drug | Disorder/disease to be treated |
| --- | --- |
| granulocyte colony stimulating factor | cancer and/or chemotherapy related neutropenia |
| human growth hormone | growth hormone deficiency related hypoglycaemia and/or growth failure |
| interferon α | cancer, viral infection, hepatitis C |
| interferon β | auto-immune disease, multiple sclerosis |
| interferon γ | viral infection |
| tumor necrosis factor | cancer |
| interleukin-20 | psoriasis |
| α-galactosidase A | Fabry disease |
| myostatin antagonist | sarcopenia |
| gastric inhibitory polypeptide | type 2 diabetes |
| alpha-1 antitrypsin | enzyme replacement therapy, cystic fibrosis, chronic obstructive pulmonary diseases, acute respiratory syndrome, severe asthma. |
| erythropoietin | anaemia |
| coagulation factor VIII | haemophilia |
| gp120/gp160 | HIV |
| soluble tumor necrosis factor I and II receptor | inflammatory disease |
| reteplase | thrombosis, myocardial infarction |
| exendin-4 | diabetes |

-continued

| Biologically active protein (or a biologically active component/fragment thereof) or drug | Disorder/disease to be treated |
|---|---|
| interleukin-1 receptor antagonist (IL-1ra; anakinra) | auto-immune disease, rheumatoid arthritis |
| interleukin-2 | cancer |
| insulin | diabetes |
| asparaginase | acute lymphoblastic leukemia, non-Hodgkin's lymphoma |
| onconase | malignant mesothelioma and other types of cancer |
| streptokinase | thrombotic disorders |
| neutrophil gelatinase-associated lipocalin | microbial infection, kidney reperfusion injury |
| antibodies and their fragments, including single domain antibodies, single chain and other engineered fragments including CDR mimetic peptides and CDRs | immunological, oncological, neovascular, and infectious diseases etc. |
| granulocyte-macrophage colony-stimulating factor | chemotherapy related neutropenia |
| follicle-stimulating hormone | infertility |
| glucocerebrosidase | Gaucher's disease |
| thymosin alpha 1 | chronic hepatitis B, cancer |
| glucagon | hypoglycemia |
| somatostatin | acromegaly |
| adenosine deaminase | adenosine deaminase deficiency |
| Interleukin-11 | thrombocytopenia |
| coagulation factor VIIa | haemophilia |
| coagulation factor IX | hemophilia |
| hematide | anemia |
| interferone λ | hepatitis C |
| leptin | lipodystrophy, obesity, Alzheimer's disease, type I diabetes |
| interleukin-22 receptor subunit alpha (IL-22ra) | psoriasis |
| interleukin 22 | metastatic melanoma |
| hyaluronidase | solid tumors |
| fibroblast growth factor 18 | osteoarthritis |
| fibroblast growth factor 21 | diabetes type II, obesity, dyslipidemia, metabolic disorders |
| glucagon-like peptide 1 | diabetes |
| osteoprotegerin | cancer, osteoporosis, rheumatoid arthritis |
| IL-18 binding protein | rheumatoid arthritis |
| growth hormone-releasing factor | HIV-associated lipodystrophy |
| soluble TACI receptor | systemic lupus erythematosus, multiple sclerosis, rheumatoid arthritis |
| thrombospondin-1 | cancer |
| soluble VEGF receptor Flt-1 | cancer |
| IL-4 mutein (IL-4 receptor antagonist) | asthma |
| cyclosporine | organ rejection |
| fumagillin | cancer |
| naltrexone | alcohol dependence |
| octreotide | acromegaly, carcinoid tumors |
| teduglutide | short bowel syndrome, Crohn's disease |
| goserelin | advanced prostate cancer, breast cancer |
| camptothecin | cancer |
| vancomycin | Gram-positive pneumonias |

In accordance with the above, the biologically active protein, the random coil polypeptide (or segment thereof), the drug conjugate, the nucleic acid, the vector or the cell may be used for the preparation of a medicament which preferably has or confers an increased in vivo and/or in vitro stability, in particular for the biologically active protein and/or drug component, for the treatment of hormone deficiencies or related disorders, auto-immune disease, cancer, anaemia, neovascular diseases, infectious/inflammatory diseases, thrombosis, myocardial infarction, diabetes, infertility, Gaucher's disease, hepatitis, hypoglycaemia, acromegaly, adenosine deaminase deficiency, thrombocytopenia, haemophilia, anemia, obesity, Alzheimer's disease, lipodistrophy, psoriasis, metastatic melanoma, osteoarthritis, dyslipidemia, rheumatoid arthritis, systemic lupus erythromatosis, multiple sclerosis, asthma, osteoporosis, and reperfusion injury or other kidney diseases, for example. In one embodiment, the biologically active protein, the drug conjugate the nucleic acid, the vector or the cell is for the use as a medicament which has an increased in vivo and/or in vitro stability of said biologically active protein/drug conjugate. Similarly, the biologically active protein, the random coil polypeptide (or segment thereof), the drug conjugate, the nucleic acid, the vector or the cell are for use in the treatment of for the treatment of hormone deficiencies or related disorders, auto-immune disease, proliferative disorders, like cancer, anaemia, neovascular diseases, infectious and/or inflammatory diseases, thrombosis, myocardial infarction stroke, diabetes, infertility, penile dysfunction, Gaucher's disease, Fabry disease, sarcopenia, cystic fibrosis, obstructive pulmonary diseases, acute respiratory syndrome, hepatitis, hypoglycaemia, acromegaly, adenosine deaminase deficiency, thrombocytopenia, haemophilia, anemia, obesity, Alzheimer's disease, lipodistrophy, psoriasis, metastatic melanoma, osteoarthritis, dyslipidemia, rheumatoid arthritis, systemic lupus erythromatosis, multiple sclerosis, asthma, osteoporosis, and reperfusion injury or other kidney diseases, for example.

The present invention also relates to the use of the nucleic acid molecules, vectors as well as transfected cells as provided herein and comprising the nucleic acid molecules or vectors of the present invention in medical approaches, like, e.g. cell based gene therapy approaches or nucleic acid based gene therapy approaches.

In a further embodiment, the random coil polypeptide (or polypeptide segment thereof) as provided herein, the biologically active, heterologous protein/protein construct or the drug or food conjugate or other conjugates that comprise the biosynthetic random coil polypeptide (or polypeptide segment thereof) and/or the nucleic acid molecule or the vector or the host cell of the present invention) is part of a composition. Said composition may comprise one or more of the inventive random coil polypeptides (or polypeptide segments thereof), biologically active proteins, food conjugates, conjugates of interest, drug conjugates or nucleic acid molecules, vectors and/or host cells encoding and/or expressing the same. Said composition may be a pharmaceutical composition, optionally further comprising a pharmaceutically acceptable carrier and/or diluent. In a further embodiment, the present invention relates to the use of the herein described biologically active protein, the random coil polypeptide (or segment thereof) or the drug conjugate for the preparation of a pharmaceutical composition for the prevention, treatment or amelioration of diseases which require the uptake of such a pharmaceutical composition.

As mentioned herein above, not only the herein disclosed conjugates, like drug conjugates or diagnostic conjugates, and/or biologically active, heterologous proteins/protein constructs (comprising the inventive random coil polypeptide or polypeptide segment thereof) are in particular of medical or pharmaceutical use. Also said random coil polypeptide or polypeptide segment may be per se employed in such a medical context, for example as "plasma expander" or as blood surrogate, in the amelioration, prevention and/or treatment of a disorder related to an impaired blood plasma amount or blood plasma content or in the amelioration, prevention and/or treatment of a disorder related to an impaired blood volume. Disorders that are treated with plasma expanders are, but not limited to, disorders affiliated with blood loss, like injuries, surgeries, burns, trauma, or abdominal emergencies, infections, dehydratations etc. Yet, such a medical use is not limited to the random coil polypeptide or polypeptide segment of this invention but can also be extended to certain drug conjugates as disclosed herein or even to certain biologically active, heterologous proteins/protein constructs.

In one embodiment, the composition as described herein may be a diagnostic composition, for example an imaging reagent, optionally further comprising suitable means for detection, wherein said diagnostic composition has an increased in vivo and/or in vitro stability.

The compositions of the invention may be in solid or liquid form and may be, inter alia, in a form of (a) powder(s), (a) tablet(s), (a) solution(s) or (an) aerosol(s). Furthermore, it is envisaged that the medicament of the invention might comprise further biologically active agents, depending on the intended use of the pharmaceutical composition.

Administration of the suitable (pharmaceutical) compositions may be effected by different ways, e.g., by parenteral, subcutaneous, intravenous, intraarterial, intraperitoneal, topical, intrabronchial, intrapulmonary and intranasal administration and, if desired for local treatment, intralesional administration. Parenteral administrations include intraperitoneal, intramuscular, intradermal, subcutaneous, intravenous or intraarterial administration. The compositions of the invention may also be administered directly to the target site, e.g., by biolistic delivery to an external or internal target site, like a specifically effected organ.

Examples of suitable pharmaceutical carriers, excipients and/or diluents are well known in the art and include phosphate buffered saline solutions or other buffer solutions, water, emulsions, such as oil/water emulsions, various types of wetting agents, sterile solutions etc. Compositions comprising such carriers can be formulated by well known conventional methods. Suitable carriers may comprise any material which, when combined with the biologically active protein/drug conjugate of the invention, retains its biological and/or pharmaceutical activity (see Remington's Pharmaceutical Sciences (1980) 16th edition, Osol, A. Ed, Mack Publishing Company, Easton, Pa.). Preparations for parenteral administration may include sterile aqueous or non-aqueous solutions, suspensions, and emulsions. The buffers, solvents and/or excipients as employed in context of the pharmaceutical composition are preferably "physiological" as defined herein above. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles may include sodium chloride solution, Ringer's dextrose, dextrose and sodium chloride, lactated Ringer's, or fixed oils. Intravenous vehicles may include fluid and nutrient replenishes, electrolyte replenishers (such as those based on Ringer's dextrose), and the like. Preservatives and other additives may also be present, including antimicrobials, anti-oxidants, chelating agents and/or inert gases and the like. In addition, a pharmaceutical composition of the present invention might comprise proteinaceous carriers, like, e.g., serum albumin or immunoglobulin, preferably of human origin.

These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Pharmaceutically active matter may be present in amounts between 1 μg and 20 mg/kg body weight per dose, e.g. between 0.1 mg to 10 mg/kg body weight, e.g. between 0.5 mg to 5 mg/kg body weight. If the regimen is a continuous infusion, it should also be in the range of 1 μg to 10 mg per kilogram of body weight per minute. Yet, doses below or above the indicated exemplary ranges also are envisioned, especially considering the aforementioned factors.

Furthermore, it is envisaged that the pharmaceutical composition of the invention might comprise further biologically or pharmaceutically active agents, depending on the intended use of the pharmaceutical composition. These further biologically or pharmaceutically active agents may be e.g. antibodies, antibody fragments, hormones, growth factors, enzymes, binding molecules, cytokines, chemokines, nucleic acid molecules and drugs.

It is of note that the present invention is not limited to pharmaceutical compositions. Also compositions to be used in research or as diagnostic(s) are envisaged. It is, for example, envisaged that the biologically active proteins or drug conjugates comprising a random coil domain or component as defined herein, are used in a diagnostic setting. For such a purpose, the inventive biologically active protein or drug conjugate of this invention may be labelled in order to allow detection. Such labels comprise, but are not limited to, radioactive labels (like [$^3$H]hydrogen [$^{125}$I]iodide or [$^{123}$I] iodide), fluorescent labels (including fluorescent proteins, like green fluorescent protein (GFP) or fluorophores, like fluorescein isothiocyanate (FITC)) or NMR labels (like gadolinium chelates). The here defined labels or markers are in no way limiting and merely represent illustrative examples. The diagnostic compositions of this invention are particularly useful in tracing or imaging experiments or in a diagnostic medicals setting. In the appended Examples and Figures, the preparation of a corresponding construct is provided that comprises conjugates comprising (i) a biosynthetic random coil polypeptide or polypeptide segment comprising an amino acid sequence consisting solely of proline and alanine amino acid residues, wherein said amino acid sequence consists of at least 50 proline (Pro) and alanine (Ala) amino acid residues, and (ii) fluorescein or digoxigenin; see appended FIGS. 13 and 14 and the corresponding figure legend as well as illustrative Example 22.

But not only pharmaceutical or diagnostic uses of the means and methods provided herein are within the gist of the present invention. The compounds/conjugates provided herein are also useful in certain other industrial areas, like in the food industry, the beverage industry, the cosmetic industry, the oil industry, the paper industry and the like. Therefore, the present invention also provides for uses of the biosynthetic random coil polypeptide as provided herein in such industrial areas. Also part of this invention is, accordingly, a method for the production of a cosmetic, of a compound to be used in cosmetic treatments, of a food or of a beverage, said method comprising the culture of the cell comprising a nucleic acid molecule (or a vector) encoding a random coil polypeptide as defined herein or encoding a biologically active protein and/or a biologically active protein and/or a polypeptide that comprises or that is an amino acid sequence that has or that mediates an activity. Such a method also includes the isolation of said random coil polypeptide, said biologically active protein and/or said biologically active protein or said polypeptide that comprises or that is an amino acid sequence that has or that mediates an activity, like a biological activity, and that additionally comprises said random coil polypeptide or random coil polypeptide segment from the culture or from said cell. In the same context, other conjugates of interest can be produced, for example conjugates which are useful in different areas of industry, like in the oil or paper industry. The person skilled in the art is readily in a position to adapt the herein provided means and methods for the generation of corresponding molecular/recombinant constructs as well as for the generation of conjugates that comprise a biosynthetic random coil polypeptide or polypeptide segment comprising an amino acid sequence consisting solely of proline and alanine amino acid residues, wherein said amino acid sequence consists of at least 50 proline (Pro) and alanine (Ala) amino acid residues, and a small molecule or a polypeptide of interest.

In yet another embodiment, the present invention provides for a kit comprising the random coil polypeptide (or polypeptide segment thereof), the biologically active protein, the drug conjugate, the nucleic acid molecule encoding said biologically active protein encoding said biologically active protein and/or encoding said biologically active protein and/or encoding said polypeptide that comprises or that is an amino acid sequence that has or that mediates an activity (for example a biological activity), the vector comprising said nucleic acid molecule or the cell comprising said nucleic acid or said vector as described herein. The kit of the present invention may further comprise, (a) buffer(s), storage solutions and/or additional reagents or materials required for the conduct of medical, scientific or diagnostic assays and purposes. Furthermore, parts of the kit of the invention can be packaged individually in vials or bottles or in combination in containers or multicontainer units.

The kit of the present invention may be advantageously used, inter alia, for carrying out the method of the invention and could be employed in a variety of applications referred herein, e.g., as diagnostic kits, as research tools or as medical tools. Additionally, the kit of the invention may contain means for detection suitable for scientific, medical and/or diagnostic purposes. The manufacture of the kits preferably follows standard procedures which are known to the person skilled in the art.

The invention is further illustrated by the following, non-limiting Figures and Examples.

FIG. 1. Gene design for the PA#1 Pro/Ala polymer/polypeptide sequence.

Nucleotide and encoded amino acid sequence of a building block for PA#1 (SEQ ID NO: 1) obtained by hybridization of two complementary oligodeoxynucleotides (upper/coding strand oligodeoxynucleotide SEQ ID NO: 17, lower/non-coding strand oligodeoxynucleotide SEQ ID NO: 18). The resulting nucleic acid has two sticky ends (shown in lower case letters), corresponding to an Ala codon and anti-codon, respectively, and are mutually compatible. Upon repeated ligation of such a building block, concatamers encoding Pro-Ala polypeptides of varying lengths can be obtained and subsequently cloned, for example, via (a) SapI restriction site(s).

FIG. 2. Cloning strategies for a Pro/Ala polymer/polypeptide sequence as fusion to a Fab fragment or to human IFNa2b.

(A) Nucleotide and encoded amino acid sequence stretch (upper/coding strand SEQ ID NO: 19, lower/non-coding strand SEQ ID NO: 20, encoded amino acid sequence SEQ ID NO: 21) around the C-terminus of the immunoglobulin light chain of an antibody Fab fragment as encoded on pASK88-Fab-2xSapI (SEQ ID NO: 22), a derivative of pASK75, used for subcloning of Pro/Ala polymer/polypeptide sequences and expression of corresponding biologically active proteins. The nucleotide sequence carries two SapI recognition sites in mutually reverse orientation, which leads upon digest to protruding DNA ends that are compatible with the synthetic gene cassette shown in FIG. 1. The recognition sequences and the C-terminal amino acids of the light chain are underlined.

(B) Nucleotide sequence and encoded amino acid sequence (upper/coding strand SEQ ID NO: 23, lower/non-coding strand SEQ ID NO: 24, encoded amino acid sequence SEQ ID NO: 25) of a PA#1 polymer/polypeptide with 20 residues after insertion of a single cassette as shown in FIG. 1 into the pASK88-Fab-2xSapI plasmid. Similar ligation/insertion of 10 such repeated cassettes resulted in the plasmid vector pFab-PA#1(200) (Seq ID NO: 28) coding for a polymer/polypeptide with 200 residues (SEQ ID NO:

26 and 27). The SapI restriction sites flanking the Pro/Ala polymer-encoding sequence are labelled (recognition sequences are underlined).

(C) Plasmid map of pFab-PA#1(200) (SEQ ID NO: 28). The structural genes for the heavy chain (HC) and light chain (LC) of the Fab-PA#1(200) are under transcriptional control of the tetracycline promoter/operator (tet$^{p/o}$) and the operon ends with the lipoprotein terminator ($t_{1pp}$). HC comprises the bacterial OmpA signal peptide, the variable (VH) and the first human IgG1 heavy chain constant C domain (CH) as well as the His$_6$-tag. LC comprises the bacterial PhoA signal peptide, the variable (VL) and human light chain constant (CL) domain, the PA#1 polymer/polypeptide with 200 residues. The plasmid backbone of pFab-PA#1(200) outside the expression cassette flanked by the XbaI and HindIII restriction sites is identical with that of the generic cloning and expression vector pASK75 (Skerra (1994) Gene 151:131-135). Singular restriction sites are indicated.

(D) Nucleotide and amino acid sequence stretch (upper/coding strand SEQ ID NO: 29, lower/non-coding strand SEQ ID NO: 30, encoded amino acid sequence SEQ ID NO: 31) around the N-terminus of human IFNa2b as cloned on pASK-IFNa2b (SEQ ID NO: 32). The single restriction site SapI that can be used for insertion of the Pro/Ala polymer-encoding sequence is labelled (recognition sequence is underlined). The two C-terminal amino acids of the Strep-tag II are underlined. The first amino acid of the mature IFNa2b is labelled with +1.

(E) Nucleotide and encoded amino acid sequence stretch (upper/coding strand SEQ ID NO: 33, lower/non-coding strand SEQ ID NO: 34, encoded amino acid sequence SEQ ID NO: 35) of the N-terminus of IFNa2b after insertion of one PA#1 polymer sequence cassette as shown in FIG. 1. The single restriction site SapI, that remains after insertion of the Pro/Ala polymer-encoding sequence, is labelled (recognition sequences are underlined). The first amino acid of IFNa2b as part of the fusion protein is labelled (1) and the two C-terminal amino acids of the Strep-tag II are underlined. Similar ligation/insertion of 10 repeated PA#1 polymer sequence cassettes resulted in the plasmid vector pPA#1(200)-IFNa2b coding for a polymer/polypeptide with 200 residues (SEQ ID NO: 36)

(F) Plasmid map of pPA#1(200)-IFNa2b (SEQ ID NO: 37). The structural gene for biologically active protein PA#1(200)-IFNa2b (comprising the bacterial OmpA signal peptide, the Strep-tag II, the PA#1 polymer/polypeptide segment with 200 residues, and human IFNa2b) is under transcriptional control of the tetracycline promoter/operator (tet$^{p/o}$) and ends with the lipoprotein terminator ($t_{1pp}$). The plasmid backbone outside the expression cassette flanked by the XbaI and HindIII restriction sites is identical with that of the generic cloning and expression vector pASK75 (Skerra (1994) loc. cit.). Singular restriction sites are indicated.

FIG. 3. Analysis of the purified recombinant Fab fragment and the purified recombinant IFNa2b as well as their Pro/Ala polypeptide/polymer fusions by SDS-PAGE.

The recombinant proteins were produced in E. coli KS272 (Strauch (1988) Proc. Natl. Acad. Sci. USA 85:1576-80) via periplasmic secretion and purified by means of the His$_6$-tag (Fab) or the Strep-tag II (IFNa2b) using immobilized metal or streptavidin affinity chromatography, respectively.

(A) Analysis of the purified recombinant Fab and its PA#1 fusion with 200 residues by 12% SDS-PAGE. The gel shows 2 µg protein samples each of Fab and Fab-PA#1(200). Samples on the left were reduced with 2-mercaptoethanol whereas repeated samples on the right were left unreduced. Sizes of protein markers—applied under reducing conditions—are indicated on the left margin. Upon reduction of the interchain disulfide bridge the Fab fragment and its 200 residue PA#1 fusion appear as two homogenous bands. In the case of the reduced Fab fragment, the two bands with molecular sizes of ca. 24 and 26 kDa, respectively, correspond to the separated LC and HC. In the case of the reduced Fab-PA#1(200) fusion protein the band at 24 kDa corresponds to the HC, whereas the band at ca. 90 kDa corresponds to the LC fused with the PA#1(200) polypeptide segment. Under non-reducing conditions, the Fab fragment and its PA#1(200) fusion appear as single homogeneous bands with apparent molecular sizes of ca. 45 kDa and 100 kDa, respectively. The two apparent size values for the Fab-PA#1(200) fusion protein are significantly larger than the calculated masses of 64.3 kDa for the non-reduced Fab-PA#1(200) and of 39.1 kDa for the isolated LC-PA#1(200). This effect is due to the addition of the Pro/Ala polymer/polypeptide segment because the Fab fragment itself, with a calculated mass of 48.0 kDa, or its unfused light chain exhibit essentially normal electrophoretic mobility.

(B) Analysis of the purified recombinant IFNa2b and its PA#1 fusion protein with 200 residues by 12% SDS-PAGE. The gel shows 2 µg protein samples each of IFNa2b and of PA#1(200)-IFNa2b. Samples on the left were reduced with 2-mercaptoethanol whereas corresponding samples on the right were left unreduced. Sizes of protein markers—applied under reducing conditions—are indicated on the left margin. The two proteins appear as single homogeneous bands with apparent molecular sizes of ca. 20 kDa and ca. 80 kDa in the reduced form. The latter value is significantly larger than the calculated mass of 37.0 kDa for PA#1(200)-IFNa2b. This effect is due to the addition of the Pro/Ala polymer/polypeptide segment because the IFNa2b itself, with a calculated mass of 20.9 kDa, exhibits essentially normal electrophoretic mobility. IFNa2b in the non-reduced state has a slightly higher electrophoretic mobility, indicating a more compact form as a result of its two intramolecular disulfide bridges.

FIG. 4. Quantitative analysis of the hydrodynamic volumes of the purified recombinant Fab and IFNa2b as well as their PA#1(200) fusions.

(A) Analytical size exclusion chromatography (SEC) of Fab and Fab-PA#1(200). 250 µl of the purified protein at a concentration of 0.25 mg/ml was applied to a Superdex S200 10/300 GL column equilibrated with PBS buffer. Absorption at 280 nm was monitored and the peak of each chromatography run was normalized to a value of 1. The arrow indicates the void volume of the column (7.8 ml).

(B) Calibration curve for the chromatograms from (A) using a Superdex S200 10/300 GL column. The logarithm of the molecular weight (MW) of marker proteins (cytochrome c, 12.4 kDa; carbonic anhydrase, 29.0 kDa; ovalbumin, 43.0 kDa; bovine serum albumin, 66.3 kDa; alcohol dehydrogenase, 150 kDa, β-amylase, 200 kDa, apo-ferritin, 440 kDa) was plotted vs. their elution volumes (black circles) and fitted by a straight line. From the observed elution volumes of the Fab fragment and its PA#1 fusion protein (black squares) their apparent molecular sizes were determined as follows. Fab: 31 kDa (true mass: 48.0 kDa); Fab-PA#1(200): 237 kDa (true mass: 64.3 kDa). These data show that fusion with the PA#1 polypeptide confers a much enlarged hydrodynamic volume.

(C) Analytical size exclusion chromatography of IFNa2b and PA#1(200)-IFNa2b. 250 µl of each purified protein at a concentration of 0.25 mg/ml was applied to a Superdex S200 10/300 GL column equilibrated with phosphate-buffered saline, PBS. Absorption at 280 nm was monitored and the peak of each chromatography run was normalized to a value of 1. The arrow indicates the void volume of the column (7.8 ml).

(D) Calibration curve for the chromatogram from (C) using a Superdex S200 10/300 GL column. The logarithm of the molecular weight (MW) of marker proteins (see B) was plotted vs. their elution volumes (black circles) and fitted by a straight line. From the observed elution volumes of IFNa2b and its PA#1 fusion protein (black squares) their apparent molecular sizes were determined as follows. IFNa2b: 22.5 kDa (true mass: 20.9 kDa); PA#1(200)-IFNa2b: 229.0 kDa (true mass: 37.0 kDa). These data show that fusion with the PA#1 polypeptide confers a much enlarged hydrodynamic volume.

FIG. 5. Experimental secondary structure analysis of recombinant proteins and their PA#1 polymer/polypeptide fusions by circular dichroism (CD) spectroscopy.

Spectra were recorded at room temperature in 50 mM $K_2SO_4$, 20 mM K-phosphate pH 7.5 and normalized to the molar ellipticity, $\Theta_M$, for each protein.

(A) CD spectra of the purified recombinant Fab and Fab-PA#1(200). The CD spectrum for the Fab fragment shows the typical features of a predominant β-sheet protein with a broad negative maximum around 216 nm (Sreerama in: Circular Dichroism—Principles and Applications (2000) Berova, Nakanishi and Woody (Eds.) Wiley, New York, N.Y., pp. 601-620), which indicates the correct folding of the bacterially produced Fab fragment. The spectrum of its fusion protein with the Pro/Ala polymer/polypeptide reveals a dominant negative band below 200 nm, which is indicative of random coil conformation. In addition, there is a shoulder around 220 nm, which results from the β-sheet contribution of the Fab fragment and indicates its correct folding even as part of the fusion protein.

(B) Molar difference CD spectrum for Fab-PA#1(200) obtained by subtraction of the spectrum for the Fab fragment. The difference CD spectrum represents the secondary struture of the 200 residue PA#1 polymer/polypeptide segment and reveals a strong minimum around 200 nm, which is a clear indication of random coil conformation in the buffered aqueous solution (Greenfield (1969) Biochemistry 8: 4108-4116; Sreerama (2000) loc. cit.; Fändrich (2002) EMBO J. 21:5682-5690).

(C) CD spectra of the purified recombinant IFNa2b and PA#1(200)-IFNa2b. The CD spectrum for IFNa2b shows the typical features of a predominant α-helix protein with two negative bands around 208 nm and 220 nm (Sreerama (2000) loc. cit.), which indicates the correct folding of the bacterially produced human IFNa2b. The spectrum of its fusion protein with the Pro/Ala polymerr/polypeptide reveals characteristic deviations with a dominant minimum around 200 nm, which is indicative of random coil conformation. In addition, there is a shoulder around 220 nm, which results from the α-helical contribution of IFNa2b and indicates the correct folding of the IFNa2b even as part of the fusion protein.

(D) Molar difference CD spectrum for PA#1(200)-IFNa2b obtained by subtraction of the spectrum for IFNa2b. The difference CD spectrum represents the secondary struture of the 200 residue PA#1 polymer/polypeptide segment and reveals a strong minimum around 200 nm, essentially identical to the one shown in (B). This is again a clear indication of random coil conformation in buffered aqueous solution for a biological polymer comprising Pro and Ala residues according to the invention.

FIG. 6. Secretory production of a fusion protein between human growth hormone (hGH) and the genetically encoded PA#1 polymer in CHO cells.

(A) Nucleotide and amino acid sequence stretch (upper/coding strand SEQ ID NO: 38, lower/non-coding strand SEQ ID NO: 39, encoded amino acid sequence SEQ ID NO: 40) around the N-terminus of hGH as cloned on pASK75-His6-hGH (SEQ ID NO: 41). The single restriction sites NheI, that can be used together with HindIII (not shown) for subcloning, and SapI, that can be used for insertion of the Pro/Ala polymer-encoding sequence, are labelled (recognition sequence is underlined). The six amino acids of the His6-tag are underlined. The first amino acid of the hGH is labelled with +1.

(B) Nucleotide and encoded amino acid sequence (upper/coding strand SEQ ID NO: 42, lower/non-coding strand SEQ ID NO: 43, encoded amino acid sequence SEQ ID NO: 44) of the N-terminus of hGH after insertion of one PA#1 polymer sequence cassette as shown in FIG. 1. The single restriction sites NheI, that can be used for subcloning, and SapI, that remains after insertion of the Pro/Ala polymer-encoding sequence, is labelled (recognition sequences are underlined). The first amino acid of hGH as part of the fusion protein is labelled (1) and the amino acids of the His6-tag are underlined. Similar ligation/insertion of 10 repeated PA#1 polymer sequence cassettes resulted in the plasmid vector pASK75-His6-PA#1(200)-hGH coding for the mature fusion protein SEQ ID NO: 45.)

(C) Plasmid map of pASK75-His6-PA#1(200)-hGH (SEQ ID NO: 46). The structural gene for biologically active protein His6-PA#1(200)-hGH (comprising the bacterial OmpA signal peptide, the His6-tag, the PA#1 polymer/polypeptide segment with 200 residues, and human GH) is under transcriptional control of the tetracycline promoter/operator (tet$^{p/o}$) and ends with the lipoprotein terminator ($t_{lpp}$). The plasmid backbone outside the expression cassette flanked by the XbaI and HindIII restriction sites is identical with that of the generic cloning and expression vector pASK75 (Skerra (1994) loc. cit.). Singular restriction sites are indicated.

(D) Plasmid map of pCHO-PA#1(200)-hGH, which encodes a His6-PA#1(200)-hGH fusion protein (SEQ ID NO: 47). The structural gene, comprising the human growth hormone signal peptide (Sp), the His$_6$-tag, the PA#1 polymer/polypeptide sequence with 200 residues (PA#1(200)), the human growth hormone (hGH), and containing the bovine growth hormone polyadenylation signal (bGH pA), is under transcriptional control of the cytomegalus virus promoter (CMV$^p$). The singular restriction sites NheI and HindIII are indicated. The resistance gene for neomycin-phosphotransferase (neo) is under control of the SV40 promotor (SV40$^p$) and followed by a SV40 polyadenylation signal (SV40 pA). In addition, the plasmid contains the bacterial ColE1 origin of replication (ColE1-ori), the bacteriophage fl origin of replication (fl-ori), and the β-lactamase gene (bla) to allow propagation and selection in *E. coli*.

(E) Western blot analysis of a fusion protein between hGH and the genetically encoded PA#1 polymer of 200 residues produced in CHO cells compared with recombinant hGH. CHO-K1 cells were transfected either with pCHO-PA#1(200)-hGH (SEQ ID NO: 48) or with pCHO-hGH (SEQ ID NO: 49), a similar plasmid encoding hGH without the PA#1(200) sequence (but also carrying the His6-tag). Two days after transfection, a sample of the cell culture supernatant was subjected to SDS-PAGE and Western blotting with an anti-hGH antibody conjugated with horse radish peroxidase. The two proteins appear as single bands indicated by arrows, with apparent molecular sizes of ca. 23 kDa (His6-hGH) and ca. 90 kDa (His6-PA#1-hGH). There is also a weak band around 60 kDa arising from serum proteins in the culture medium. Whereas the His6-tagged hGH appears at the calculated mass of 23.5 kDa, the apparent molecular size of His6-PA#1-hGH is significantly larger than its calculated mass of 39.5 kDa. This effect is due to the hydrophilic random coil nature of the Pro-Ala polymer.

FIG. 7. Theoretical prediction of secondary structure for the PA#1 Pro/Ala polypeptide/polymer sequence.

This illustration shows the output from the CHOFAS computer algorithm according to the Chou-Fasman method (Chou and Fasman (1974) Biochemistry 13: 222-245) as implemented on the Sequence Comparison and Secondary Structure prediction server at the University of Virginia. To avoid boundary effects at the amino and carboxy termini, the 20mer amino acid repeat according to FIG. 1 was pasted in three consecutive copies (resulting in a concatamer similar as encoded after repeated ligation/insertion of the synthetic gene cassette) and only the output for the central 20mer sequence block (boxed) was considered. In the case of the PA#1 polypeptide sequence/segment (SEQ ID NO: 1) the Chou-Fasman algorithm predicts 100% α-helical secondary structure. This is in contrast with the experimentally observed predominant random coil conformation for the PA#1 polypeptide/polypeptide segment as part of a fusion protein (see FIG. 5B/D).

Figure 8:
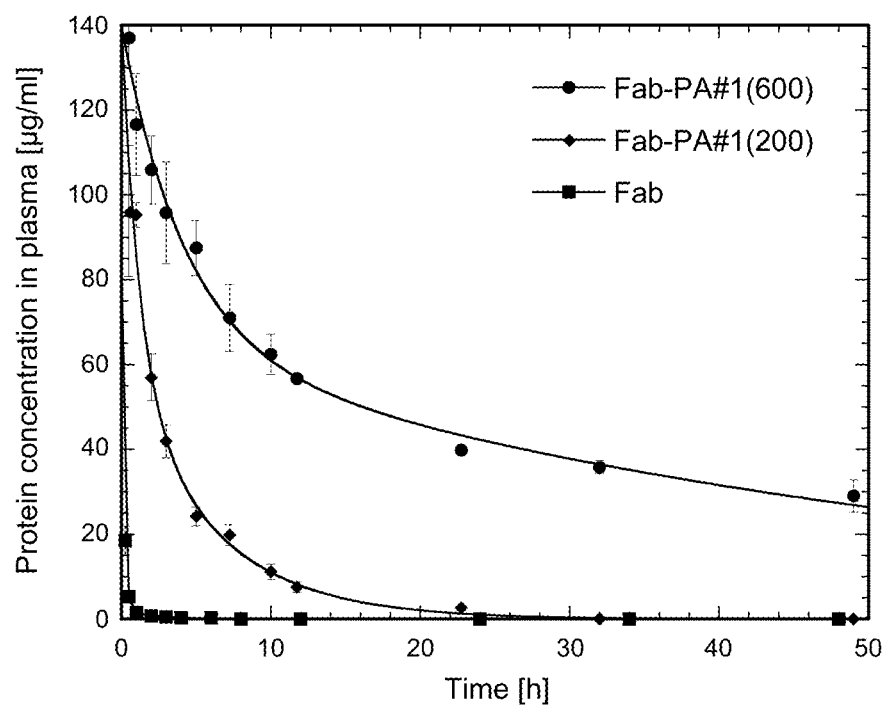

FIG. 8: Quantitative analysis of the pharmacokinetics of the purified recombinant Fab fragment and its PA#1 polymer fusions with 200 and 600 residues in BALB/c mice.

Plasma samples from Example 16 were assayed for Fab, Fab-PA#1(200), and Fab-PA#1(600) concentrations using a sandwich ELISA. To estimate the plasma half-life of Fab, Fab-PA#1(200), and Fab-PA#1(600), the measured concentration values were plotted against time post intravenous injection and numerically fitted assuming a bi-exponential decay. The unfused Fab fragment exhibited a very fast clearance with an elimination half-life of 1.3±0.1 h. In contrast, the elimination phase determined for Fab-PA#1 (200) and Fab-PA#1(600) was significantly slower, with terminal half-lives of 4.1±1.8 h and 38.8±11.2 h, respectively, thus demonstrating a ca. 3-fold and a ca. 30-fold prolonged circulation due to the Pro/Ala polymer fusion with 200 or 600 residues compared with the unfused Fab fragment.

Figure 9:
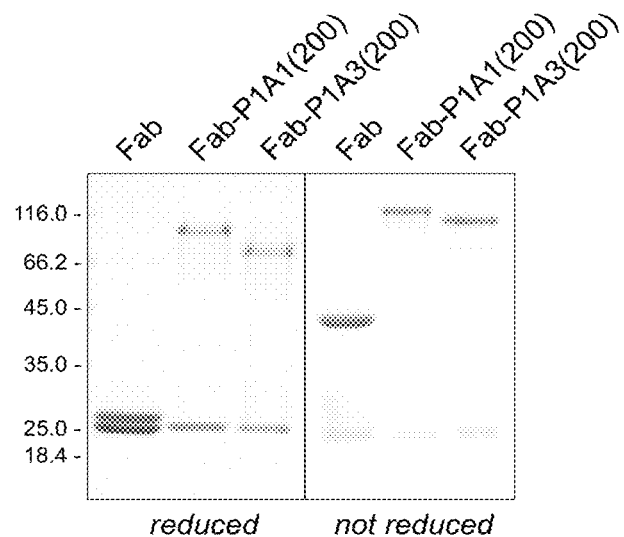

FIG. 9: Analysis of the purified recombinant Fab fragment as fusion with the P1A1 or P1A3 polymer having 200 residues.

The recombinant proteins were produced in *E. coli* KS272 via periplasmic secretion and purified by means of the His$_6$-tag using immobilized metal affinity chromatography. The purified proteins were analyzed by 12% SDS-PAGE. The gel shows 2 μg protein samples each of Fab-P1A1(200) and Fab-P1A3(200) as well as, for comparison, of the unfused Fab fragment (cf. FIG. 3A). Samples on the left were reduced with 2-mercaptoethanol whereas analogous samples on the right were left unreduced. Sizes of protein markers—applied under reducing conditions—are indicated on the left margin. After reduction of the interchain disulfide bridges the Fab fragment and its 200 residue Pro/Ala fusions appear as two homogeneous bands. In the case of the reduced Fab fragment, the two bands with molecular sizes of ca. 24 and 26 kDa, respectively, correspond to the separated light chain (LC) and heavy chain fragment (HC). In the case of the reduced Fab-P1A1(200) fusion protein the band at 24 kDa corresponds to the HC, whereas the band at ca. 90 kDa corresponds to the LC fused with the P1A1(200) polypeptide. In the case of the reduced Fab-P1A3(200) fusion protein the band at 24 kDa corresponds to the HC, whereas the band at ca. 75 kDa corresponds to the LC fused with the P1A5(200) polypeptide. Under non-reducing conditions, the Fab fragment, its P1A1(200) and its P1A3(200) fusion appear as single prominent bands with apparent molecular sizes of ca. 45 kDa, 110 kDa, and 90 kDa, respectively. The apparent sizes for the Fab-P1A1(200) and Fab-P1A3(200) fusion proteins are significantly larger than the calculated masses of 65.3 kDa for the non-reduced Fab-P1A1(200) and of 64.0 kDa for the non-reduced Fab-P1A3(200). Also, the apparent sizes for the corresponding reduced light chains are significantly larger than the calculated masses of 40.7 kDa for the P1A1(200) LC and of 39.4 kDa for the P1A3(200) LC. This effect is due to the addition of the Pro/Ala polymer/polypeptide segment because the Fab fragment itself, with a calculated mass of 48.0 kDa, or its unfused light chain, with a calculated mass of 23.4 kDa, exhibit essentially normal electrophoretic mobility.

Figure 10:
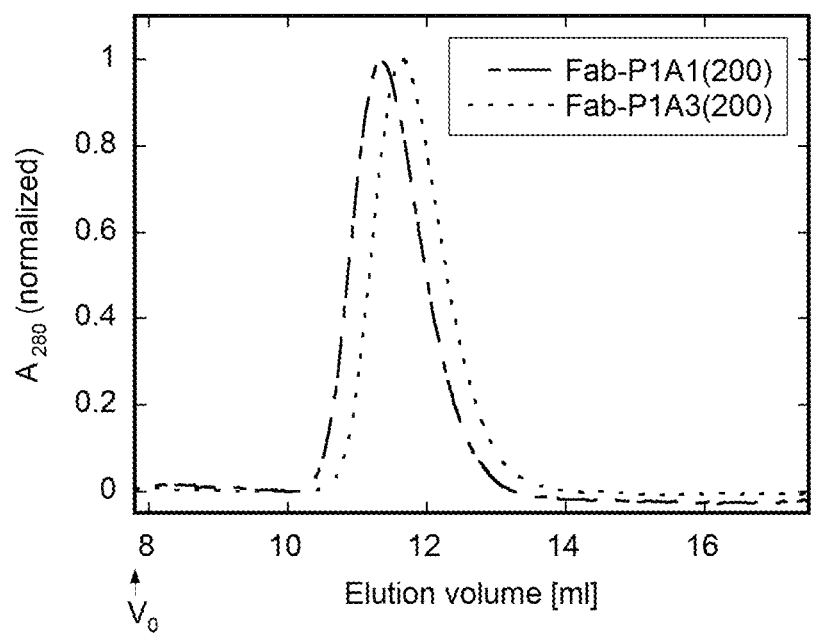

FIG. 10. Quantitative analysis of the hydrodynamic volumes of the purified recombinant Fab-P1A1(200) and Fab-P1A3(200) fusion proteins.

Analytical size exclusion chromatography (SEC) of Fab-P1A1(200) and Fab-P1A3(200). 250 μl of the purified protein at a concentration of 0.25 mg/ml was applied to a Superdex S200 10/300 GL column equilibrated with PBS. Absorption at 280 nm was monitored and the peak of each chromatography run was normalized to a value of 1. The arrow indicates the void volume of the column (7.8 ml). From the observed elution volumes of the fusion proteins their apparent molecular sizes were determined using a similar calibration curve as shown in FIG. 4B as follows. Fab-P1A1(200): 180.7 kDa (true mass: 65.3 kDa); Fab-P1A3(200): 160.2 kDa (true mass: 64.0 kDa). These data show that fusion of a protein with the P1A1 and/or P1A5 polypeptide confers a much enlarged hydrodynamic volume.

FIG. 11. Experimental secondary structure analysis of Fab-P1A1(200) and Fab-P1A3(200) fusions by circular dichroism (CD) spectroscopy.

Spectra were recorded at room temperature in 50 mM $K_2SO_4$, 20 mM K-phosphate pH 7.5 and normalized to the molar ellipticity, $\Theta_M$, for each protein.

(A) CD spectra of the purified recombinant Fab-P1A1 (200) and Fab-P1A3(200). The CD spectra of the Fab fusion proteins with both Pro/Ala polymers/polypeptides each reveal a dominant negative band below 200 nm, which is indicative of random coil conformation. In addition, there is a shoulder around 220 nm, which arises from the β-sheet contribution of the Fab fragment and indicates its correct folding even as part of the fusion protein.

(B) Molar difference CD spectra for Fab-P1A1(200) and Fab-P1A3 (200) obtained by subtraction of the spectrum for the unfused Fab fragment (see FIG. 5A). The difference CD spectra represent the secondary structures of the 200 residue P1A1 (SEQ ID NO: 51) and P1A3 (SEQ ID NO: 3) polymers/polypeptide segments, respectively, and reveal a strong minimum around 200 nm, which is a clear indication of their random coil conformation in the buffered aqueous solution (Greenfield (1969) Biochemistry 8: 4108-4116; Sreerama (2000) loc. cit.; Fändrich (2002) EMBO J. 21:5682-5690).

FIG. 12: Preparation of an isolated biosynthetic Pro/Ala polymer/polypeptide.

(A) Plasmid map of pSUMO-PA#1(200) (SEQ ID NO: 60). The structural gene for the fusion protein MK-His(6)-SUMO-PA#1(200) comprising a start methionine codon followed by a lysine codon, an N-terminal affinity tag of six consecutive His residues, the cleavable small ubiquitin-like modifier (SUMO) protein Smt3p (Panavas (2009) Methods Mol Biol. 497: 303-17), and the PA#1 polymer/polypeptide segment with 200 residues (SEQ ID NO: 60) is under transcriptional control of the gene 10 promoter of the bacteriophage T7 and ends with the tφ terminator. Additonal plasmid elements comprise the origin of replication (ori), the ampicilin resistance gene (bla), and the fl origin of replication. The plasmid backbone outside the expression cassette flanked by the NdeI and HindIII restriction sites is, except for a SapI restriction site that was eliminated by silent mutation, identical with that of the generic cloning and expression vector pRSET5a (Schoepfer (1993) 124: 83-85).

SEQ ID NO: 60 is provided in the enclosed sequence listing (which is also part of this description and specification) and is reproduced herein below.

```
gcactttcg gggaaatgtg cgcggaaccc ctatttgttt attttctaa atacattcaa    60
atatgtatcc gctcatgaga caataaccct gataaatgct tcaataatat tgaaaaagga   120
agagtatgag tattcaacat ttccgtgtcg cccttattcc ctttttcgcg gcattttgcc   180
ttcctgtttt tgctcaccca gaaacgctgg tgaaagtaaa agatgctgaa gatcagttgg   240
gtgcacgagt gggttacatc gaactggatc tcaacagcgg taagatcctt gagagtttc   300
gccccgaaga acgttttcca atgatgagca cttttaaagt tctgctatgt ggcgcggtat   360
tatcccgtat tgacgccggg caagagcaac tcggtcgccg catacactat tctcagaatg   420
acttggttga gtactcacca gtcacagaaa agcatcttac ggatggcatg acagtaagag   480
aattatgcag tgctgccata accatgagtg ataacactgc ggccaactta cttctgacaa   540
cgatcggagg accgaaggag ctaaccgctt ttttgcacaa catgggggat catgtaactc   600
gccttgatcg ttgggaaccg gagctgaatg aagccatacc aaacgacgag cgtgacacca   660
cgatgcctgt agcaatggca acaacgttgc gcaaactatt aactggcgaa ctacttactc   720
tagcttcccg gcaacaatta atagactgga tggaggcgga taaagttgca ggaccacttc   780
tgcgctcggc ccttccggct ggctggttta ttgctgataa atctggagcc ggtgagcgtg   840
ggtctcgcgg tatcattgca gcactgggc cagatggtaa gccctcccgt atcgtagtta   900
tctacacgac ggggagtcag gcaactatgg atgaacgaaa tagacagatc gctgagatag   960
gtgcctcact gattaagcat tggtaactgt cagaccaagt ttactcatat atactttaga  1020
ttgatttaaa acttcatttt taatttaaaa ggatctaggt gaagatcctt tttgataatc  1080
tcatgaccaa aatcccttaa cgtgagtttt cgttccactg agcgtcagac cccgtagaaa  1140
agatcaaagg atcttcttga gatccttttt ttctgcgcgt aatctgctgc ttgcaaacaa  1200
aaaaaccacc gctaccagcg gtggtttgtt tgccggatca agagctacca actcttttc  1260
cgaaggtaac tggcttcagc agagcgcaga taccaaatac tgtccttcta gtgtagccgt  1320
agttaggcca ccacttcaag aactctgtag caccgcctac atacctcgct ctgctaatcc  1380
tgttaccagt ggctgctgcc agtggcgata agtcgtgtct taccgggttg gactcaagac  1440
gatagttacc ggataaggcg cagcggtcgg gctgaacggg gggttcgtgc acacagccca  1500
gcttggagcg aacgacctac accgaactga gatacctaca gcgtgagcta tgagaaagcg  1560
ccacgcttcc cgaaggagaa aaggcggaca ggtatccggt aagcggcagg gtcggaacag  1620
gagagcgcac gagggagctt ccaggggaa acgcctggta tctttatagt cctgtcgggt  1680
ttcgccacct ctgacttgag cgtcgatttt tgtgatgctc gtcaggggg cggagcctat  1740
ggaaaaacgc cagcaacgcg gcctttttac ggttcctggc cttttgctgg ccttttgctc  1800
acatgttctt tcctgcgtta tcccctgatt ctgtggataa ccgtattacc gcctttgagt  1860
gagctgatac cgctcgccgc agccgaacga ccgagcgcag cgagtcagtg agcgaggaag  1920
cggagaagcg cccaatacgc aaaccgcctc tccccgcgcg ttggccgatt cattaatgca  1980
ggatctcgat cccgcgaaat taatacgact cactataggg agaccacaac ggtttccctc  2040
tagaaataat tttgtttaac tttaagaagg agatatacat atgaaacatc accaccatca  2100
```

-continued

```
ccattcggac tcagaagtca atcaagaagc taagccagag gtcaagccag aagtcaagcc    2160
tgagactcac atcaatttaa aggtgtccga tggatcttca gaaatcttct ttaagatcaa    2220
aaagaccact cctttaagaa ggctgatgga agcgttcgct aaaagacagg gtaaggaaat    2280
ggactcctta agattcttgt acgacggtat tagaattcaa gctgatcaga ccctgaaga    2340 tttggacatg gaggataacg atattattga ggctcacaga gaacagattg gtggcgccgc    2400
tccagctgca cctgctccag cagcacctgc tgcaccagct ccggctgctc ctgctgccgc    2460
tccagctgca cctgctccag cagcacctgc tgcaccagct ccggctgctc ctgctgccgc    2520
tccagctgca cctgctccag cagcacctgc tgcaccagct ccggctgctc ctgctgccgc    2580
tccagctgca cctgctccag cagcacctgc tgcaccagct ccggctgctc ctgctgccgc    2640
tccagctgca cctgctccag cagcacctgc tgcaccagct ccggctgctc ctgctgccgc    2700
tccagctgca cctgctccag cagcacctgc tgcaccagct ccggctgctc ctgctgccgc    2760
tccagctgca cctgctccag cagcacctgc tgcaccagct ccggctgctc ctgctgccgc    2820
tccagctgca cctgctccag cagcacctgc tgcaccagct ccggctgctc ctgctgccgc    2880
tccagctgca cctgctccag cagcacctgc tgcaccagct ccggctgctc ctgctgccgc    2940
tccagctgca cctgctccag cagcacctgc tgcaccagct ccggctgctc ctgctgcctg    3000
aagagcaagc ttgatccggc tgctaacaag cccgaaagga agctgagttg gctgctgcc    3060 accgctgagc aataactagc ataacccctt ggggcctcta aacgggtctt gaggggtttt    3120
ttgctgaaag gaggaactat atccggatct ggcgtaatag cgaagaggcc cgcaccgatc    3180
gcccttccca acagttgcgc agcctgaatg gcgaatggga cgcgccctgt agcggcgcat    3240
taagcgcggc gggtgtggtg gttacgcgca gcgtgaccgc tacacttgcc agcgccctag    3300 cgccgctcc tttcgctttc ttcccttcct ttctcgccac gttcgccggc tttccccgtc    3360
aagctctaaa tcggggctc cctttagggt tccgatttag tgctttacgg cacctcgacc    3420
ccaaaaaact tgattagggt gatggttcac gtagtgggcc atcgccctga tagacggttt    3480
ttcgcccttt gacgttggag tccacgttct ttaatagtgg actcttgttc caaactggaa    3540
caacactcaa ccctatctcg gtctattctt ttgatttata agggattttg ccgatttcgg    3600
cctattggtt aaaaaatgag ctgatttaac aaaaatttaa cgcgaatttt aacaaaatat    3660
taacgcttac aatttaggtg                                                 3680
```

(B) Analysis of the bacterially produced His(6)-SUMO-PA#1(200) fusion protein and its cleavage by 12% SDS-PAGE. The gel shows the SUMO-PAS#1(200) fusion protein extracted from *E. coli* and purified via immobilized metal affinity chromatography (IMAC) and size exclusion chromatography (SEC) before (lane 1) and after proteolytic cleavage with Ubl-specific protease 1 (SUMO protease) (lane 2) as described in Example 21. All samples were reduced with 2-mercaptoethanol. Sizes of protein markers (M), applied under reducing conditions, are indicated on the left margin. The His(6)-SUMO-PA#1(200) fusion protein appears as a single homogeneous band with an apparent molecular size of ca. 100 kDa. Thus, the apparent size for the His(6)-SUMO-PA#1(200) fusion protein observed in SDS-PAGE is significantly larger than the calculated mass of 28.3 kDa, which is due to the presence of the Pro/Ala polymer/polypeptide. After cleavage, the hydrophilic PA#1(200) polypeptide is not detectably stained by Coomassie blue; hence, only a small residual fraction of the fusion protein and the cleaved His(6)-SUMO protein are visible on the SDS polyacrylamide gel (lane 2). The His(6)-SUMO protein shows a homogeneous band with apparent molecular size of ca. 16 kDa (lane 2) which is well in agreement with its calculated molecular mass of 12.2 kDa.

Figure 13:
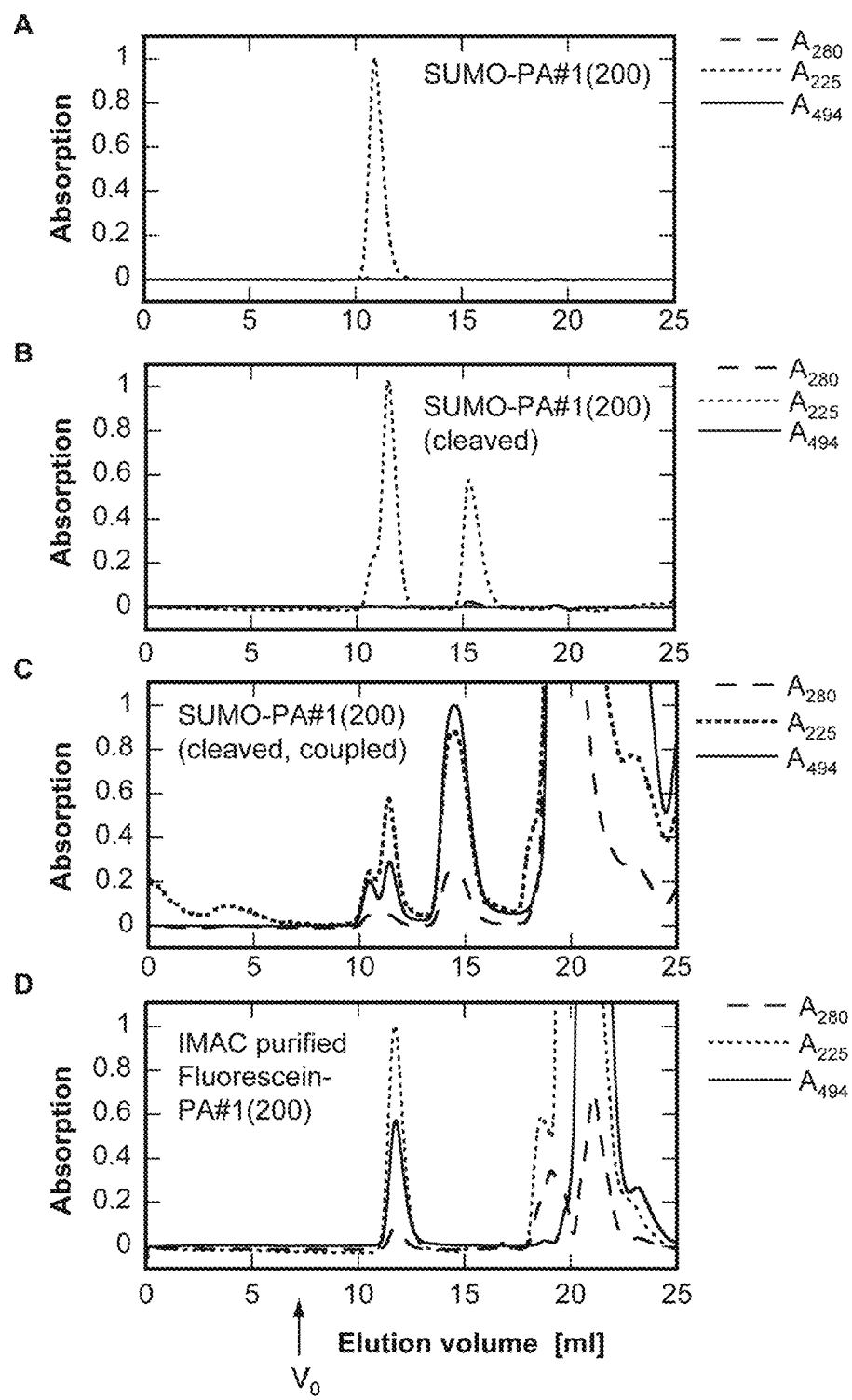
Figure 13:
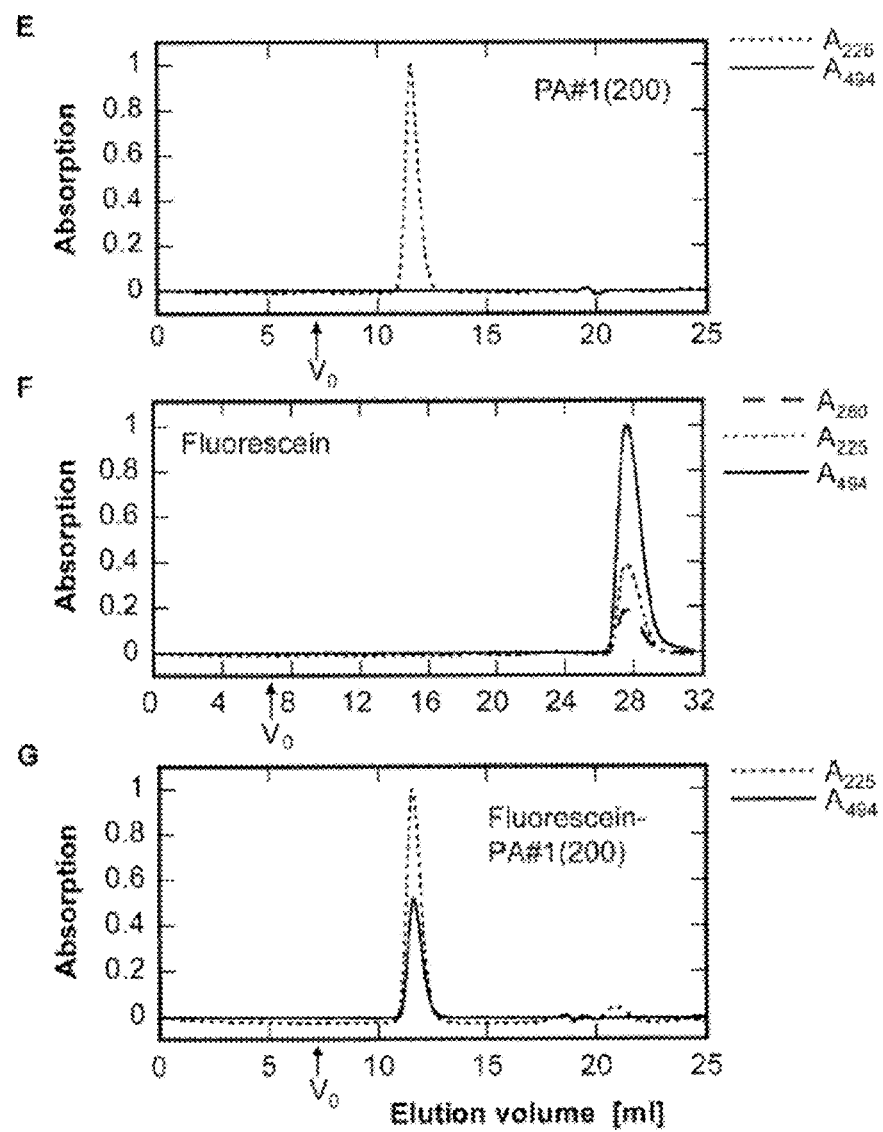
Figure 13:
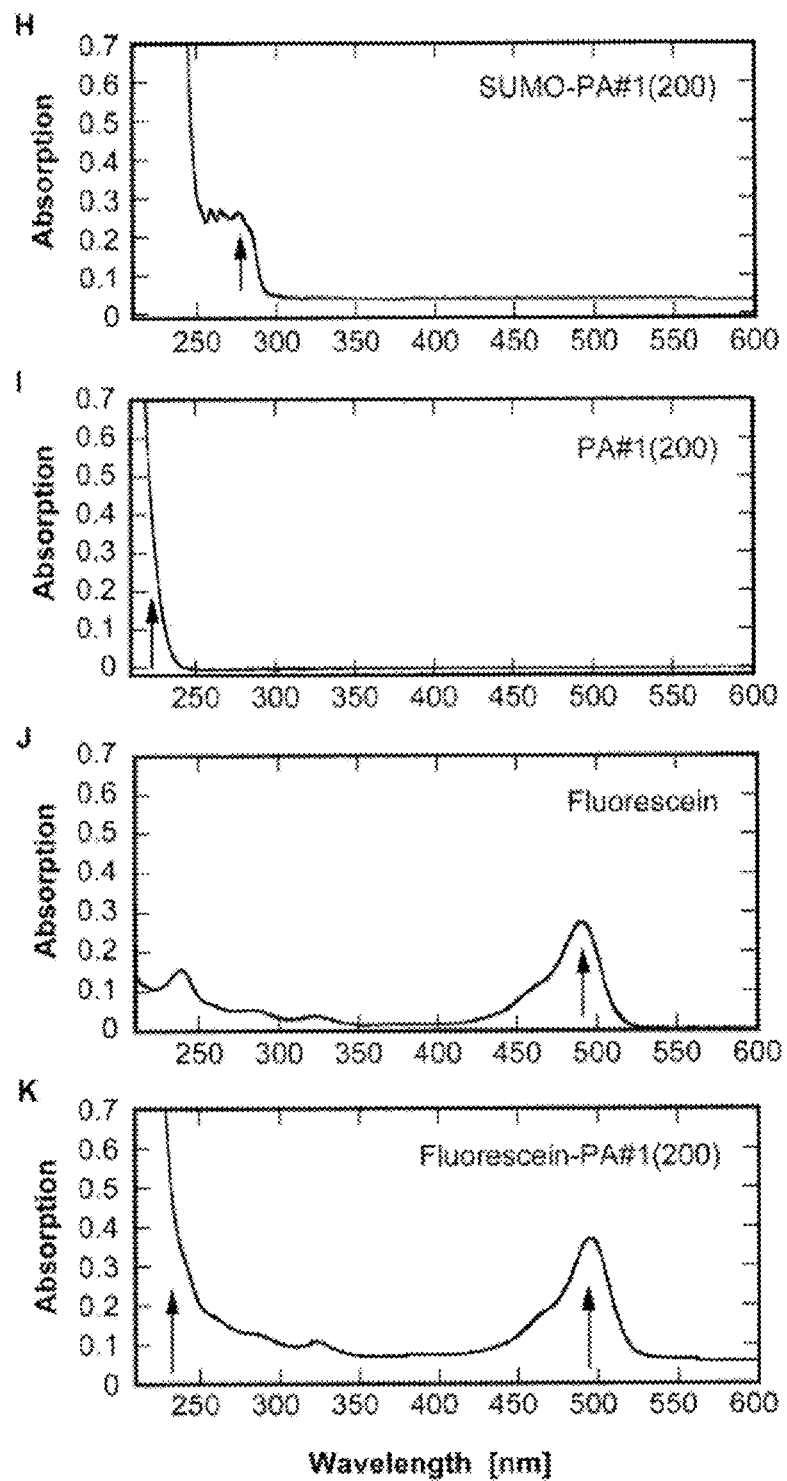

FIG. 13: Conjugation of a biosynthetic Pro/Ala polymer/polypeptide with chemical compounds and/or drugs.

(A-D) Production of a fluorescein conjugate with a biosynthetic PA#1(200) polymer/polypeptide (SEQ ID NO: 61) monitored via analytical size exclusion chromatography (SEC). The panels show (from top to bottom) SEC runs of purified His(6)-SUMO-PA#1(200) (A), His(6)-SUMO-PA#1(200) after cleavage reaction in the presence of SUMO protease (B), the cleaved His(6)-SUMO-PA#1(200) batch after chemical coupling with a fluorescein NHS ester (C), and the fluorescein-PA#1(200) conjugate after IMAC purification (D). 250 µl of protein/polypeptide at a concentration of ca. 0.5 mg/ml was applied to a Superdex S200 10/300 GL column equilibrated with PBS on an Äkta purifier system. Absorption at 225 nm, 280 nm, and 494 nm was monitored using a UV-900 UV/VIS detector (GE Healthcare) and a prominent peak of each chromatogram was normalized to a value of 1. The arrow indicates the void volume of the column (7.3 ml).

(E-K) Characterization of free fluorescein, the biosynthetic PA#1(200) polymer/polypeptide, and its fluorescein conjugate via SEC and UV/VIS spectroscopy. The three chromatograms show (from top to bottom) purified PA#1 (200) (E), the chemical compound fluorescein (F) and the purified fluorescein-PA#1(200) conjugate (G). The four UV/VIS spectra show the purified His(6)-SUMO-PA#1 (200) fusion protein (H), the purified PA#1(200) polymer/polypeptide (I), free fluorescein (J), and the purified fluorescein-PA#1(200) conjugate (K) (all in PBS). The arrows indicate characteric absorption bands/shoulders of SUMO (280 nm), PA#1(200) (225 nm), and fluorescein (494 nm).

(L) Calibration curve for the chromatograms from (A-G) using a Superdex S200 10/300 GL column. The logarithm of the molecular weight (MW) of marker proteins (aprotinin, 6.5 kDa; cytochrome C, 12.4 kDa; carbonic anhydrase, 29.0 kDa; bovine serum albumin, 66.3 kDa; alcohol dehydrogenase, 150 kDa; β-amylase, 200 kDa; apo-ferritin, 440 kDa) was plotted vs. their elution volumes (x) and fitted by a straight line. From the observed elution volumes of His(6)-SUMO-PA#1(200) (10.81 ml), PA#1(200) (11.51 ml), fluorescein-PA#1(200) (11.49 ml) and fluorescein (27.57 ml), their apparent molecular sizes were determined as follows. His(6)-SUMO-PA#1(200): 215.6 kDa, PA#1(200): 154.1 kDa (true mass: 16.1 kDa), fluorescein-PA#1(200): 155.6 kDa (true mass: 16.6 kDa); SUMO: 25.7 kDa (true mass: 12.2 kDa); fluorescein: 0.09 kDa (true mass: 0.33 kDa). These data show that fusion with the Pro/Ala polypeptide/polymer confers a much enlarged hydrodynamic volume to the conjugated drug compared with the unmodified compound.

(M) Characterization of the chemical conjugate between the biosynthetic PA#1(200) polypeptide/polymer and the steroid compound digoxigenin via Electro Spray Ionisation Mass Spectrometry (ESI-MS). A deconvoluted ESI-MS spectrum of digoxigenin-PA#1(200) reveals a mass of 16671.4 Da, which essentially coincides with the calculated mass for the digoxigenin-PA#1(200) conjugate (16670.6 Da).

FIG. 14: Illustration of chemical conjugates between the biosynthetic PA#1(200) polypeptide/polymer and small molecule drugs.

(A) Fluorescein coupled to the N-terminus of biosynthetic PA#1(200).

(B) Digoxigenin coupled to the N-terminus of biosynthetic PA#1(200).

EXAMPLES

The present invention is additionally described by way of the following illustrative non-limiting examples that provide a better understanding of the present invention and of its many advantages.

Unless otherwise indicated, established methods of recombinant gene technology were used as described, for example, in Sambrook (2001) loc. cit.

Example 1: Gene Synthesis for Pro/Ala Amino Acid Polymers/Polypeptides

As described herein above, amino acid repeats consisting of Pro and Ala residues are depicted herein as Pro/Ala or "PA". Gene fragments encoding a repetitive polymer sequence comprising Pro and Ala (PA#1 which corresponds to SEQ ID NO: 1) were obtained by hybridisation of the two complementary oligodeoxynucleotides (SEQ ID NO: 17 and SEQ ID NO: 18) shown in FIG. 1, followed by concatamer formation in a directed manner via DNA ligation of their mutually compatible but non-palindromic sticky ends. Oligodeoxynucleotides were purchased from ThermoScientific (Ulm, Germany) and purified by preparative urea polyacrylamide gel electrophoresis. The nucleic acid sequences of the oligodesoxynucleotides are depicted in FIG. 1 (SEQ ID NOs 17 and 18 comprising an additional GCC codon for alanine, which becomes part of the following PA#1 sequence repeat upon ligation of the corresponding sticky ends. Enzymatic phosphorylation was performed by mixing 200 pmol of both oligodeoxynucleotides in 100 µl 50 mM Tris/HCl pH 7.6, 10 mM MgCl$_2$, 5 mM DTT, 1 mM ATP and incubation for 30 min at 37° C. in the presence of 10 u polynucleotide kinase (MBI Fermentas, St. Leon-Rot, Germany). After denaturation for 10 min at 80° C., the mixture was cooled to room temperature overnight to achieve hybridization. Then 50 µl of this solution was ligated by adding 1 u T4 DNA ligase (MBI Fermentas) and 10 µl 100 mM Tris/HCl pH 7.4, 50 mM MgCl$_2$, 20 mM DTT, 10 mM ATP, and in some cases 5 mM of each dATP, dCTP, dGTP, and dTTP, in a total volume of 100 µl and incubation for 55 min on ice. After 10 min heat inactivation at 70° C. the ligation products were separated by 1.5% (w/v) agarose gel electrophoresis in the presence of TAE buffer (40 mM Tris, 20 mM acetic acid, 1 mM EDTA). After staining with ethidium bromide the band corresponding to the assembled gene segment of 300 bp length was excised and isolated.

Example 2: Construction of PFab-PA#1(200) as Expression Vector for a Fab-PA#1 Fusion Protein For cloning of a 10mer repeat of the synthetic gene fragment coding for the 20 amino acid sequence of PA#1 from Example 1 the plasmid vector pASK88-Fab-2xSapI (SEQ ID NO: 22), an expression plasmid for an Fab fragment (Schlapschy (2007) Protein Eng. Des. Sel. 20:273-284) harboring a nucleotide sequence with two SapI restriction sites in reverse complementary orientation at the 3-'end of the light chain (FIG. 2A), was employed. This vector, which is a derivative of pASK75 (Skerra, A. (1994) Gene 151: 131-135), was cut with SapI, dephosphorylated with shrimp alkaline phosphatase (USB, Cleveland, Ohio), and ligated with a 300 bp cassette of the synthetic DNA fragment obtained from Example 1. The resulting intermediate plasmid pFab-PA#1(100) was again cut with SapI, dephosphorylated with shrimp alkaline phosphatase, and ligated with a 300 bp cassette of the synthetic DNA fragment obtained from Example 1 (as exemplified in FIG. 2B, however with only a PA#1(20) polymer/polypeptide cassette). The resulting plasmid was designated pFab-PA#1(200) (SEQ ID NO: 28) (FIG. 2C). It should be noted that on this plasmid the coding region for the 200 residue PA#1 sequence repeat was flanked by two SapI restriction, which enables precise excision and further subcloning of the entire sequence cassette, carrying 5'-GCC nucleotide overhangs.

After transformation of E. coli XL1-Blue (Bullock (1987) Biotechniques 5: 376-378), plasmid was prepared and the sequence of the cloned synthetic nucleic acid insert was confirmed by restriction analysis and double-stranded DNA sequencing (ABI-Prism™310 Genetic analyzer, Perkin-Elmer Applied Biosystems, Weiterstadt, Germany) using the BigDye™ terminator kit as well as oligodeoxynucleotide primers that enabled sequencing from both sides.

Example 3: Construction of PASK-PA#1(200)-IFNa2b as an Expression Vector for a PA#1(200)-IFNa2b Fusion Protein For the construction of an expression plasmid encoding IFNa2b as fusion with a 200 residue PA#1 sequence repeat, PA#1(200), pASK-IFNa2b (SEQ ID NO: 32) (FIG. 2D) was cut with SapI, dephosphorylated with shrimp alkaline phosphatase, and ligated with the gene fragment encoding the 200 residue PA#1 polypeptide excised from the previously constructed plasmid pFab-PA#1(200) (Example 2) by restriction digest with SapI (as exemplified in FIG. 2E, however with only a PA#1(20) polymer/polypeptide cassette). After transformation of *E. coli* JM83 (Yanisch-Perron. (1985) Gene 33:103-119), plasmid was prepared and the presence of the correct insert was confirmed by restriction analysis. The resulting plasmid was designated pPA#1(200)-IFNa2b (SEQ ID NO: 37) (FIG. 2F).

Example 4: Bacterial Production and Purification of Fusion Proteins Between an Fab Fragment and a Genetically Encoded PA#1 Polymer/Polypeptide The Fab fragment (calculated mass: 48.0 kDa) and the Fab-PA#1(200) fusion (calculated mass: 64.3 kDa) were produced at 22° C. in *E. coli* KS272 harboring the corresponding expression plasmids from Example 3, together with the folding helper plasmid pTUM4 (Schlapschy (2006) Protein Eng. Des. Sel. 19:385-390), using shaker flask cultures with 2 L LB medium containing 100 mg/l ampicillin and 30 mg/l chloramphenicol. Induction of recombinant gene expression was performed by addition of 0.4 mg anhydrotetracycline at $OD_{550}$=0.5 over night (typically resulting in $OD_{550}$ of ca. 1.0 at harvest). Periplasmic extraction in the presence of 500 mM sucrose, 1 mM EDTA, 100 mM Tris/HCl pH 8.0 containing 50 µg/ml lysozyme was performed as described elsewhere (Breustedt (2005) Biochim. Biophys. Acta 1764:161-173) and followed by purification by means of the $His_6$-tag using immobilized metal affinity chromatography (Skerra (1994) Gene 141: 79-84) with an imidazole gradient from 0 to 200 mM in 500 mM betaine, 50 mM Na-phosphate pH 7.5).

Homogeneous protein preparations were obtained for both recombinant Fab fragments (FIG. 3A) with yields of 0.2 mg $L^{-1}$ $OD^{-1}$ for the unfused Fab and 0.1 mg $L^{-1}$ $OD^{-1}$ for Fab-PA#1(200). SDS-PAGE was performed using a high molarity Tris buffer system (Fling (1986) Anal. Biochem. 155: 83-88). Protein concentrations were determined according to the absorption at 280 nm using calculated extinction coefficients (Gill (1989) Anal. Biochem. 182: 319-326) of 68290 $M^{-1}$ $cm^{-1}$ both for the unfused Fab and its PA#1 polymer fusion as the Pro/Ala polymer did not contribute to UV absorption because of its lack of aromatic amino acids.

Example 5: Bacterial Production and Purification of Fusion Proteins Between IFNa2b and a Genetically Encoded PA#1 Polymer/Polypeptide IFNa2b (calculated mass: 20.9 kDa) and PA#1(200)-IFNa2b (calculated mass: 37.0 kDa) were produced at 22° C. in *E. coli* KS272 harboring the corresponding expression plasmids from Example 3, together with the folding helper plasmid pTUM4 (Schlapschy (2006) loc. cit.), using shaker flask cultures with 2 L LB medium containing 100 mg/l ampicillin and 30 mg/l chloramphenicol. Induction of recombinant gene expression was performed by addition of 0.4 mg anhydrotetracycline at $OD_{550}$=0.5 over night (typically resulting in $OD_{550}$ of ca. 1.0 at harvest). Periplasmic extraction in the presence of 500 mM sucrose, 1 mM EDTA, 100 mM Tris/HCl pH 8.0 containing 50 µg/ml lysozyme was performed as described elsewhere (Breustedt (2005) loc. cit.) and followed by purification via the Strep-tag II using streptavidin affinity chromatography (Schmidt (2007) Nat. Protoc. 2:1528-1535) in the presence of 150 mM NaCl mM EDTA, 100 mM Tris/HCl pH 8.0.

Homogeneous protein preparations were obtained for both recombinant IFNa2b proteins (FIG. 3B) with yields of 0.15 mg $L^{-1}$ $OD^{-1}$ for IFNa2b and 0.1 mg $L^{-1}$ $OD^{-1}$ for PA#1(200)-IFNa2b. SDS-PAGE was performed using a high molarity Tris buffer system (Fling (1986) loc. cit.). Protein concentrations were determined according to the absorption at 280 nm using calculated extinction coefficients (Gill (1989) loc. cit.) of 23590 $M^{-1}$ $cm^{-1}$ both for the unfused IFNa2b and its PA#1 polymer fusion.

Example 6: Measurement of the Hydrodynamic Volume for the Recombinant Fusion Protein Between a Fab Fragment and a Genetically Encoded PA#1 Polymer of 200 Residues By Analytical Gel Filtration Size exclusion chromatography (SEC) was carried out on a Superdex S200 HR 10/300 GL column (GE Healthcare Europe, Freiburg, Germany) at a flow rate of 1 ml/min using an Äkta Purifier 10 system (GE Healthcare) with PBS (115 mM NaCl, 4 mM $KH_2PO_4$, 16 mM $Na_2HPO_4$; pH 7.4) as running buffer. 250 µl samples of the purified Fab fragment and its 200 residue PA#1 fusion, obtained from the metal affinity affinity chromatography as described in Example 4, were individually applied at a concentration of 0.25 mg/ml in PBS. Both proteins eluted in a single homogenous peak as shown in FIG. 4A.

For column calibration (FIG. 4B), 250 µl of an appropriate mixture of the following globular proteins (Sigma, Deisenhofen, Germany) were applied in PBS at protein concentrations between 0.2 mg/ml and 0.5 mg/ml: cytochrome c, 12.4 kDa; carbonic anhydrase, 29.0 kDa; ovalbumin, 43.0 kDa; bovine serum albumin, 66.3 kDa; alcohol dehydrogenase, 150 kDa; β-amylase, 200 kDa; apo-ferritin, 440 kDa.

As result, the fusion protein with the 200 residue PA#1 polymer/polypeptide exhibited a significantly larger size than corresponding globular proteins with the same molecular weight. The apparent size increase for Fab-PA#1(200) was 7.4-fold compared with the unfused Fab fragment whereas the true mass was only larger by 1.3-fold. This observation clearly indicates a much increased hydrodynamic volume conferred to the biologically active Fab fragment by the Pro/Ala polypeptide segment according to this invention.

Example 7: Measurement of the Hydrodynamic Volume for the Recombinant Fusion Protein Between IFNa2b and a Genetically Encoded PA#1 Polymer of 200 Residues by Analytical Gel Filtration Size exclusion chromatography was carried out with IFNa2b and PA#1(200)-IFNa2b on a Superdex S200 HR 10/300 GL column (GE Healthcare) at a flow rate of 1 ml/min using an Äkta Purifier 10 system (GE Healthcare) similarly as described in Example 6. Both proteins eluted in a single homogenous peak as shown in FIG. 4C.

As result, the fusion protein with the 200 residue PA#1 polymer/polypeptide exhibited a significantly larger size than corresponding globular proteins with the same molecular weight (FIG. 4D). The apparent size increase for PA#1 (200)-IFNa2b was 10.2-fold compared with the unfused IFNa2b protein whereas the true mass was only larger by 1.8-fold. This observation clearly indicates a much increased hydrodynamic volume conferred to the biologically active interferon by the Pro/Ala polymer/polypeptide according to this invention.

Example 8: Detection of Random Coil Conformation for the Biosynthetic PA#1 Polymer Fused to a Fab Fragment Via Circular Dichroism Spectroscopy Secondary structure was analysed using a J-810 spectropolarimeter (Jasco, Groβ-Umstadt, Germany) equipped with a quartz cuvette 106-QS (0.1 mm path length; Hellma, Müllheim, Germany). Spectra were recorded from 190 to 250 nm at room temperature by accumulating 16 runs (bandwidth 1 nm, scan speed 100 nm/min, response 4 s) using 3.12 to 15.4 μM protein solutions obtained from Example 4 in 50 mM $K_2SO_4$, 20 mM K-phosphate pH 7.5. After correction for solution blanks, spectra were smoothed using the instrument software, and the molar ellipticity $\Theta_M$ was calculated according to the equation:

$$\Theta_M = \frac{\Theta_{obs}}{c \cdot d}$$

whereby $\Theta_{obs}$ denotes the measured ellipticity, c the protein concentration [mol/l], d the path length of the quartz cuvette [cm]. The $\Theta_M$ values were plotted against the wavelength using Kaleidagraph (Synergy Software, Reading, Pa.).

The measured circular dichroism (CD) spectrum for the recombinant Fab was in accordance with the β-sheet dominated immunglobuline fold, whereas the spectrum for the Fab-PA#1(200) fusion protein revealed a significant contribution of random coil conformation (FIG. 5A). To analyze the spectroscopic contribution by the Pro/Ala polypeptide segment in greater detail the molar difference CD spectrum with respect to the unfused Fab fragment was calculated (FIG. 5B) by subtraction of the latter spectrum from the one for Fab-PA#1(200). As result, a strong minimum around 200 nm, which is characteristic of random coil conformation, was observed. Thus, the Pro/Ala sequence as part of the recombinant fusion protein appears to be present as a random coil polymer under physiological buffer conditions.

Example 9: Detection of Random Coil Conformation for the Genetically Encoded PA#1 Polymer Fused to IFNa2b Via Circular Dichroism Spectroscopy Secondary structure was analysed by CD measurements for IFNa2b and PA#1(200)-IFNa2b (obtained from Example 5) as described in Example 8 using 3.6 to 38.7 μM protein solutions. The spectrum of PA#1(200)-IFNa2b revealed significant contributions of α-helical secondary structure, indicative of the known α-helix bundle fold of interferon, as well as of random coil conformation (FIG. 5C). To analyze the spectroscopic contributions by the Pro/Ala polymer fusion partner in greater detail the molar difference CD spectrum with respect to the unfused IFNa2b was calculated by subtraction of the two individual spectra (FIG. 5D). As result, a strong minimum around 200 nm characteristic of random coil conformation was observed. Thus, the Pro/Ala polypeptide segment as part of the recombinant fusion protein appears to be present as a random coil polymer under aqueous buffer conditions.

Example 10: Quantitative Analysis of the Secondary Structure of the Fab Fragment, of IFNa2b and of Their 200 Residue PA#1 Polymer Fusions The secondary structure content of the Fab fragment, Fab-PA#1(200), IFNa2b, and PA#1(200)-IFNa2b was individually quantified from the corresponding CD spectra measured in Examples 8 and 9 using the secondary structure deconvolution program CDNN ver. 2.1 (Böhm (1992) Protein Eng. 5:191-195) with a set of 33 base spectra for the deconvolution of complex CD spectra The results of this analysis are provided in the following Table:

| | Fab | Fab-PA#1(200) | Diff: PA#1(200) | IFNa2b | PA#1 (100)-IFNa2b | Diff: PA#1(200) |
|---|---|---|---|---|---|---|
| α-helix | 9.5% | 7.5% | 2.1% | 38.2% | 31.0% | 0.7% |
| anti-parallel β-sheet | 40.4% | 3.1% | 0% | 1.8% | 0.2% | 4.6% |
| parallel β-sheet | 6.9% | 1.3% | 0.3% | 8.4% | 0.7% | 0.6% |
| β-turn | 6.2% | 50.4% | 78.6% | 19.2% | 75.2% | 69.7% |
| random coil | 37.2% | 63.4% | 94.8% | 35.9% | 64.4% | 97.5% |
| Σ total | 100.2% | 125.8% | 175.8% | 103.5% | 171.4% | 170.0% |
| Σ β-turn and random coil | 43.4% | 113.8% | 173.4% | 55.1% | 139.6% | 169.1% |

Compared with the predominantly β-sheet secondary structure content of the recombinant Fab fragment, which is in accordance with its known immunoglobulin fold (see Eigenbrot (1993) J. Mol. Biol. 229:969-995), the fraction of unstructured conformation (comprising random coil and β-turn) clearly increases if the PA#1 polymer is fused to the Fab fragment. The difference CD spectrum for the Pro/Ala polypeptide segment reveals a clear random coil conformation. Analysis of the secondary structure shows the presence of a high fraction of unstructured conformations (comprising random coil and β-turn) which nearly comprise 100% of the total secondary structure. Similarly, compared with the predominantly α-helical secondary structure content of the recombinant IFNa2b, which is in accordance with its known three-dimensional structure as an α-helix bundle protein (Radhakrishnan (1996) Structure 4:1453-1463), the fraction of unstructured conformation for the whole protein clearly increases if the PA#1 polymer is fused to IFNa2b. The difference CD spectrum for the Pro/Ala polypeptide segment reveals a clear random coil conformation. Analysis of the secondary structure shows the presence of a high fraction of unstructured conformations (comprising random coil and (β-turn) which nearly comprise 100% of the total secondary structure.

Different results were obtained when a theoretical analysis of the PA#1 polymer sequence was performed using the Chou-Fasman algorithm (Chou and Fasman (1974) Biochemistry 13: 222-245). The results of this analysis are illustrated in FIG. 7. This algorithm predicts 100% α-helical secondary structure, which is in clear contrast with the experimental data. Thus, this algorithm is not useful to confidently predict unstructured conformation for an amino acid polymer according to the invention.

Example 11: Construction of PASK75-His6-PA#1(200)-hGH as an Expression Vector for a His6-PA#1(200)-hGH Fusion Protein For the construction of an expression plasmid encoding hGH as fusion with a 200 residue PA#1 sequence repeat, PA#1(200), pASK75-His6-hGH (SEQ ID NO: 41) (FIG. 6A) was cut with SapI, dephosphorylated with shrimp alkaline phosphatase, and ligated with the gene fragment encoding the 200 residue PA#1 polypeptide excised from the previously constructed plasmid pFab-PA#1(200) (Example 2) by restriction digest with SapI (as exemplified in FIG. 6B, with only a PA#1(20) polymer/polypeptide cassette). After transformation of E. coli JM83 (Yanisch-Perron. (1985) loc. cit.), plasmid was prepared and the presence of the correct insert was confirmed by restriction analysis. The resulting plasmid was designated pASK75-His6-PA#1(200)-hGH (SEQ ID NO: 46) (FIG. 6C).

Example 12: Construction of an Expression Vector for the Secretory Production of Human Growth Hormone Fused with a 200 Residue PA#1 Polymer/Polypeptide in Chinese Hamster Ovary Cells The vector pASK75-His6-PA#1(200)-hGH (SEQ ID NO: 46), a derivative of pASK75 (Skerra (1994) loc. cit.), allowing prokaryotic production of the hGH PA#1 fusion protein, was cut with NheI and HindIII. This fragment was purified via agarose gel electrophoresis and ligated with the correspondingly cut vector pCHO (SEQ ID NO: 50). After transformation of E. coli XL1-Blue (Bullock (1987) loc. cit.), plasmid was prepared and the correct insertion of the fragment was verified via restriction analysis. The resulting plasmid, which codes for the hGH signal peptide fused to the His$_6$ tag, a PA#1(200) polypeptide segment, and the human growth hormone (hGH), was designated pCHO-PA#1(200)-hGH SEQ ID NO: 48) and is depicted in FIG. 6D.

Example 13: Secretory Production of a Fusion Protein Between Human Growth Hormone (hGH) and the Genetically Encoded PA#1 Polymer in CHO Cells CHO-K1 cells ATCC No. CCL-61 were cultured in Quantum 263 medium (PAA Laboratories, Colbe, Germany) in a 100 mm plastic dish until 50% confluency was reached. Cells were transfected with 8 μg pCHO-PA#1(200)-hGH (SEQ ID NO: 48) or, for control, pCHO-hGH (SEQ ID NO: 49), a similar plasmid encoding hGH without the PA#1(200) sequence, using the Nanofectin Kit (PAA Laboratories, Colbe, Germany). After 6 h, cell culture medium was exchanged by 7 ml Opti-MEM®-I reduced serum medium (Invitrogen, Darmstadt, Germany) and cells were incubated at 37° C. in a humidified atmosphere with 5% $CO_2$. After two days, 20 μl of the cell culture supernatant was taken and diluted with 5 μl SDS-PAGE loading buffer containing β-mercaptoethanol. After 5 min heating at 95° C., 15 μl of each sample was subjected to 12% SDS-PAGE. Following electro-transfer onto a nitrocellulose membrane (Schleicher & Schuell, Dassel, Germany) by means of a semi-dry blotting apparatus, the membrane was washed 3 times for 15 min with 10 ml PBST (PBS containing 0.1% v/v Tween 20). The membrane was incubated with 10 ml of a 1:1000 dilution of anti human growth hormone antibody ab1956 conjugated with horse radish peroxidase (Abcam, Cambridge, UK). After incubation for 1 h and washing the membrane twice for 5 min with 20 ml PBST and twice for 5 min with PBS, the chromogenic reaction was performed in the presence of 15 ml of SIGMAFAST™ 3,3-diaminobenzidine solution (Sigma-Aldrich Chemie, Munich, Germany). The reaction was stopped by washing with water and air-drying of the membrane. The blot revealed signals for both recombinant protein samples (FIG. 6E), thus proving secretory production of the hGH fusion protein with the PA#1 polypeptide in CHO cells.

Example 14: Bacterial Production and Purification of Fusion Proteins Between HGH and a Genetically Encoded PA#1 Polymer/Polypeptide Human growth hormone (hGH) (calculated mass: 23.4 kDa), PA#1(200)-hGH (calculated mass: 39.6 kDa), PA#1(400)-hGH (calculated mass: 55.8 kDa) and PA#1(600)-hGH (calculated mass: 72.0 kDa) were produced in E. coli KS272 harboring the corresponding expression plasmids from Example 11 or their derivatives with a double (encoding 400 residues) or triple (600 residues) PA#1 sequence cassette, respectively. Bacterial production was performed at 22° C. in shaker flask cultures with 2 L LB medium containing 2.5 g/L glucose, 0.5 g/L proline and 100 mg/l ampicillin. Induction of recombinant gene expression was performed by addition of 0.4 mg anhydrotetracycline at $OD_{550}$=0.5 for 3 h. Periplasmic extraction in the presence of 500 mM sucrose, 1 mM EDTA, 100 mM Tris/HCl pH 8.0 containing 50 μg/ml lysozyme was carried out as described elsewhere (Breustedt (2005) loc. cit.) and followed by purification via the His$_6$-tag using the HisTrap High Performance affinity column (GE Healthcare) with 40 mM Na-phosphate pH 7.5, 0.5 M NaCl as buffer. Proteins were eluted using an imidazole concentration gradient from 0 to 150 mM (dissolved in the running buffer and adjusted with HCl to pH 7.5) and further purified via size exclusion chromatography using a Superdex 200-HR10/30 column (GE Healthcare) equilibrated with PBS (115 mM NaCl, 4 mM $KH_2PO_4$, 16 mM $Na_2HPO_4$, pH 7.4).

After size exclusion chromatography homogeneous protein preparations were obtained for all recombinant hGH fusion proteins without signs of aggregation and with yields of 1 mg $L^{-1}$ $OD^{-1}$ for hGH, 0.3 mg $L^{-1}$ $OD^{-1}$ for PA#1(200)-hGH, 0.3 mg $L^{-1}$ $OD^{-1}$ for PA#1(400)-hGH and 0.2 mg $L^{-1}$ $OD^{-1}$ for PA#1(600)-hGH. SDS-PAGE was performed using a high molarity Tris buffer system (Fling (1986) loc. cit.). Protein concentrations were determined according to the absorption at 280 nm using calculated extinction coefficients (Gill (1989) loc. cit.) of 16050 $M^{-1}$ $cm^{-1}$ for the unfused hGH and all its PA#1 polypeptide fusions.

Example 15: Measurement of Binding Affinity of Human Growth Hormone and its PA#1 Polymer Fusions Towards the Extracellular Domain of Human Growth Hormone Receptor Using Surface Plasmon Resonance The affinity of hGH and its PA#1 polypeptide fusions to a human growth hormone receptor Fc fusion protein (hGHR-Fc; R&D Systems) was determined via surface plasmon resonance (SPR) real time measurements on a Biacore 2000 system (GE Healthcare). First, 15 µl mouse anti-human IgG-Fc capture antibody (Jackson Immuno Research) at a concentration of 100 µg/m in 10 mM Na-acetate pH 5.0 was immobilized to the surface of two flow channels of a CMDP chip (XanTec bioanalytics) using an amine coupling kit (GE Healthcare). This resulted in ca. 2700 response units (RU). After equilibration with PBS/T (PBS containing 0.05% (v/v) Tween 20) as flow buffer, one channel of the chip was charged with 2 µg/ml hGHR-Fc at a flow rate of 5 µl/min until an additional signal of ca. 300 RU was reached. Then, 75 µl of hGH or its PA#1 polypeptide fusions in PBS/T was injected at varying concentrations and the association and dissociation phases were measured under continuous buffer flow of 20 µl/min. For regeneration, three 6 µl pulses of 10 mM glycine/HCl pH 2.7 were applied. The sensograms were corrected by double subtraction of the corresponding signals measured for the channel without immobilized receptor and an averaged baseline determined from several buffer blank injections (Myszka (1999) Mol. Recognit. 12: 279-284). Kinetic data evaluation was performed by a global fit of the traces from at least seven different sample injections according to the 1:1 Langmuir binding model using BlAevaluation software version 3.1 (GE Healthcare). The values obtained from SPR measurements for the kinetic and derived equilibrium constants of the complexes between hGH or its PA#1 fusions and the human growth hormone receptor are summarized in the following Table:

| hGH variant | $k_{on}$ [$10^5$ M$^{-1}$ s$^{-1}$] | $k_{off}$ [$10^{-6}$ s$^{-1}$] | $K_D$ [pM] |
|---|---|---|---|
| hGH | 10.2 | 10.6 | 10.4 |
| PA#1(200)-hGH | 4.75 | 9.18 | 19.3 |
| PA#1(400)-hGH | 3.26 | 14.0 | 42.9 |
| PA#1(600)-hGH | 3.29 | 12.5 | 38.0 |

These data show that the fusion of hGH with PA#1 polypeptides of different lengths does not significantly interfere with receptor binding. All hGH PA#1 polypeptide fusions retain receptor binding activity within a factor 5 compared with the recombinant hGH lacking a PA#1 polypeptide.

Example 16: Detection of Prolonged Plasma Half-Life In Vivo for the Recombinant Fusion Proteins Between a Fab Fragment and Genetically Encoded PA#1 Polymers Adult BALB/c mice (SPF stock breeding; TU München, Freising, Germany) were intravenously injected according to the following Table:

| Group | A | B | D |
|---|---|---|---|
| Test item | Fab | Fab-PA#1(200) | Fab-PA#1(600) |
| Administration route | | intravenous | |
| Dose [mg/kg b.w.] | 5.0 | 5.0 | 5.0 |
| Concentration [mg/ml] | 1.0 | 1.0 | 1.0 |
| Application volume [ml/kg b.w.] | | 5.0 | |
| No. of animals/group | 9 | 9 | 9 |
| No. of blood sampling time points | 12 | 12 | 12 |
| No. of animals/sampling time point | 3 | 3 | 3 |
| No. of blood samplings/animal | 4/1 | 4/1 | 4/1 |

The total volume of intravenously administered test item was calculated according to the individual body weight (b.w.) recorded on the day of administration (e.g. an animal with 20 g body weight received 100 µl of 1 mg/ml test item). Blood sampling was performed according to the following Table:

| Test item | Subgroup | 10 min | 30 min | 1 h | 2 h | 3 h | 4 h | 6 h | 8 h | 12 h | 24 h | 36 h | 48 h |
|---|---|---|---|---|---|---|---|---|---|---|---|---|---|
| Fab | 1 | x | | x | | x | | x | | | | | |
| Fab-PA#1(200) | | x | | x | | x | | x | | | | | |
| Fab-PA#1(600) | | x | | x | | x | | x | | | | | |
| | 2 | | x | | x | | x | | x | | | | |
| | | | x | | x | | x | | x | | | | |
| | | | x | | x | | x | | x | | | | |
| | 3 | | | x | | x | | | x | | x | | |
| | | | | x | | x | | | x | | x | | |
| | | | | x | | x | | | x | | x | | |

For each substance (Test item) altogether nine animals—divided into three subgroups 1-3 with each three animals—were injected, each providing four samples at different time points. Blood samples (approximately 50 µl) were taken from the tail vene and stored at 4° C. for 30 min. After centrifugation for 10 min at 10 000 g and 4° C. the supernatant (plasma) was immediately frozen and stored at −20° C.

For quantitative detection of the Fab fusion protein in an ELISA, the wells of a 96 well microtiter plate (Maxisorb, NUNC, Denmark) were coated overnight at 4° C. with 50 µl of a 10 µg/ml solution of recombinant Her2/ErbB2 ectodomain antigen in 50 mM NaHCO$_3$ pH 9.6. Then, the wells were blocked with 200 µl of 3% (w/v) BSA in PBS for 1 h and washed three times with PBS/T (PBS containing 0.1% (v/v) Tween 20). The plasma samples were applied in dilution series in PBS/T containing 0.5% (v/v) mouse plasma from an untreated animal and incubated for 1 h. The wells were then washed three times with PBS/T and incubated for 1 h with 50 μl of a 1:1000 diluted solution of an anti-human CK antibody alkaline phosphatase conjugate in PBS/T. After washing twice with PBS/T and twice with PBS the chromogenic reaction was started by adding 50 μl of 0.5 μg/ml p-nitrophenyl phosphate in 100 mM Tris/HCl pH 8.8, 100 mM NaCl, 5 mM MgCl$_2$ as substrate, and after 15 min at 25° C. the absorbance at 405 nm was measured. Concentrations of Fab, Fab-PA#1(200), and Fab-PA#1(600) in the plasma samples were quantified by comparison of the measured signals with standard curves which were determined for dilution series for the corresponding purified proteins at defined concentrations in PBS/T containing 0.5% (v/v) mouse plasma from untreated animals.

To estimate the plasma half-life of Fab, Fab-PA#1(200), and Fab-PA#1(600), the concentration values, c(t), were determined for each time point from the ELISA measurements and plotted against time post intravenous injection, t. These data were numerically fitted using KaleidaGraph software assuming a bi-exponential decay according to the equation $$c(t) = c_\alpha e^{-\ln 2 \frac{t}{\tau^\alpha_{1/2}}} + (c_0 - c_\alpha) e^{-\ln 2 \frac{t}{\tau^\beta_{1/2}}}$$

whereby $\tau^\alpha_{1/2}$ and $\tau^\beta_{1/2}$ are the half-life values of the distribution phase α and the elimination phase β, respectively. $c_0$ is the total blood concentration at time point zero while $c_\alpha$ is the concentration amplitude for the distribution phase.

FIG. 8 depicts the pharmacokinetics for the three test items in BALB/c mice. While the recombinant Fab shows a rapid blood clearance with an elimination half-life of just ca. 1.3 h, the Fab-PA#1(200) and Fab-PA#1(600) fusion proteins have a more than 3-fold and 29-fold extended half-life with corresponding values of ca. 4.1 h and 38.8 h, respectively. These data prove that the in vivo plasma half-life of a Fab fragment is significantly prolonged due to fusion with a Pro/Ala polymer/polypeptide, whereby the half-life becomes longer with increasing length of the amino acid polymer.

Example 17: Gene Synthesis for P1A1 and P1A3 Amino Acid Polymers/Polypeptides and Construction of PFab-P1A1(200) and PFab-P1A3(200) as Expression Vectors for Fab-P1A1(200) and Fab-P1A3(200) Fusion Proteins Gene fragments encoding a repetitive polymer sequence comprising the Pro/Ala polypeptides/polymers P1A1 (SEQ ID NO: 51) and P1A3, also designated PA#3, (SEQ ID NO: 3) were obtained by hybridisation of pairs of complementary oligodeoxynucleotides, respectively, SEQ ID NO: 52 and SEQ ID NO: 53 for P1A1 and SEQ ID NO: 54 and SEQ ID NO: 55 for P1A3 as described in Example 1. pFab-P1A1(200) (Seq ID NO: 58) and pFab-P1A3(200) (Seq ID NO: 59) coding for Fab fragments with the corresponding Pro/Ala polymers/polypeptide segments of 200 residues at the C-terminus of the light chain (LC) (amino acid sequence of LC Fab-P1A1(200): SEQ ID NO: 56; amino acid sequence of LC Fab-P1A3(200): SEQ ID NO: 57) were constructed in an analogous manner to pFab-PA#1(200), which has been described in Example 2.

In the following SEQ ID NOs: 56, 57, 58 and 59 are also reproduced. However, these sequences are also comprised in the appended sequence listing which is a specific part of this disclosure and the description of the present invention.

SEQ ID NO: 56

```
Asp Ile Glu Leu Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190
```

```
Ala Cys Glu Val Thr His Gln Gly Leu Ser Ser Pro Val Thr Lys Ser
            195                 200                 205

Phe Asn Arg Gly Glu Cys Ser Ser Ala Pro Ala Pro Ala Pro Ala Pro
        210                 215                 220

Ala Pro Ala Pro Ala Pro Ala Pro Ala Pro Ala Pro Ala Pro Ala Pro
225                 230                 235                 240

Ala Pro Ala Pro Ala Pro Ala Pro Ala Pro Ala Pro Ala Pro Ala Pro
                245                 250                 255

Ala Pro Ala Pro Ala Pro Ala Pro Ala Pro Ala Pro Ala Pro Ala Pro
            260                 265                 270

Ala Pro Ala Pro Ala Pro Ala Pro Ala Pro Ala Pro Ala Pro Ala Pro
        275                 280                 285

Ala Pro Ala Pro Ala Pro Ala Pro Ala Pro Ala Pro Ala Pro Ala Pro
    290                 295                 300

Ala Pro Ala Pro Ala Pro Ala Pro Ala Pro Ala Pro Ala Pro Ala Pro
305                 310                 315                 320

Ala Pro Ala Pro Ala Pro Ala Pro Ala Pro Ala Pro Ala Pro Ala Pro
                325                 330                 335

Ala Pro Ala Pro Ala Pro Ala Pro Ala Pro Ala Pro Ala Pro Ala Pro
            340                 345                 350

Ala Pro Ala Pro Ala Pro Ala Pro Ala Pro Ala Pro Ala Pro Ala Pro
        355                 360                 365

Ala Pro Ala Pro Ala Pro Ala Pro Ala Pro Ala Pro Ala Pro Ala Pro
    370                 375                 380

Ala Pro Ala Pro Ala Pro Ala Pro Ala Pro Ala Pro Ala Pro Ala Pro
385                 390                 395                 400

Ala Pro Ala Pro Ala Pro Ala Pro Ala Pro Ala Pro Ala Pro Ala Pro
                405                 410                 415

Ala
```

SEQ ID NO: 57
```
Asp Ile Glu Leu Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

-continued

```
Ala Cys Glu Val Thr His Gln Gly Leu Ser Ser Pro Val Thr Lys Ser
            195                 200                 205

Phe Asn Arg Gly Glu Cys Ser Ser Ala Ala Ala Pro Ala Ala Ala Pro
        210                 215                 220

Ala Ala Ala Pro Ala Ala Ala Pro Ala Ala Ala Pro Ala Ala Ala Pro
225                 230                 235                 240

Ala Ala Ala Pro Ala Ala Ala Pro Ala Ala Ala Pro Ala Ala Ala Pro
                245                 250                 255

Ala Ala Ala Pro Ala Ala Ala Pro Ala Ala Ala Pro Ala Ala Ala Pro
            260                 265                 270

Ala Ala Ala Pro Ala Ala Ala Pro Ala Ala Ala Pro Ala Ala Ala Pro
        275                 280                 285

Ala Ala Ala Pro Ala Ala Ala Pro Ala Ala Ala Pro Ala Ala Ala Pro
    290                 295                 300

Ala Ala Ala Pro Ala Ala Ala Pro Ala Ala Ala Pro Ala Ala Ala Pro
305                 310                 315                 320

Ala Ala Ala Pro Ala Ala Ala Pro Ala Ala Ala Pro Ala Ala Ala Pro
                325                 330                 335

Ala Ala Ala Pro Ala Ala Ala Pro Ala Ala Ala Pro Ala Ala Ala Pro
            340                 345                 350

Ala Ala Ala Pro Ala Ala Ala Pro Ala Ala Ala Pro Ala Ala Ala Pro
        355                 360                 365

Ala Ala Ala Pro Ala Ala Ala Pro Ala Ala Ala Pro Ala Ala Ala Pro
    370                 375                 380

Ala Ala Ala Pro Ala Ala Ala Pro Ala Ala Ala Pro Ala Ala Ala Pro
385                 390                 395                 400

Ala Ala Ala Pro Ala Ala Ala Pro Ala Ala Ala Pro Ala Ala Ala Pro
                405                 410                 415

Ala
```

SEQ ID NO: 58

```
acccgacacc atcgaatggc cagatgatta attcctaatt tttgttgaca ctctatcatt    60
gatagagtta ttttaccact ccctatcagt gatagagaaa agtgaaatga atagttcgac   120
aaaaatctag ataacgaggg caaaaaatga aaaagacagc tatcgcgatt gcagtggcac   180
tggctggttt cgctaccgta gcgcaggccg aagttaaact gcaggaatcc ggtggtggtc   240
tggttcagcc aggtggttcc ctgcggctct cgtgtgctgc ttccggtttc aacatcaaag   300
acacctacat ccactgggtt cgtcaggctc cgggtaaagg cctggaatgg gttgctcgta   360
tctacccgac caacggttac accaggtatg ccgattcagt taaaggtcgt ttcaccatct   420
cggccgacac ttccaaaaac accgcttacc tccagatgaa ctccctgcgt gctgaagaca   480
cagctgttta ttattgctcc cgttggggtg gtgacggttt ctacgctatg gactactggg   540
gtcagggtac cctggtcacc gtctcctcag cctccaccaa gggcccatcg gtcttccccc   600
tggcaccctc ctccaagagc acctctgggg gcacagcggc cctgggctgc ctggtcaagg   660
actacttccc cgaaccggtg acggtgtcgt ggaactcagg cgccctgacc agcggcgtgc   720
acaccttccc ggctgtccta cagtcctcag gactctactc cctcagcagc gtggtgactg   780
tgccctccag cagcttgggc acccagacct acatctgcaa cgttaatcac aaacccagca   840
acaccaaggt cgacaagaaa gttgagccca atcttgccat caccaccat caccattaat   900
aaccatggag aaaataaagt gaaacaaagc actattgcac tggcactctt accgttactg   960
tttacccctg tgacaaaagc cgacatcgag ctcacccaat cccgtcctc cctgtccgct  1020
tccgttggcg accgtgttac catcacgtgt agggcctcgc aagacgtaaa caccgccgta  1080
```

-continued

```
gcgtggtatc agcagaaacc cgggaaagct ccgaaactgc tgatctatag cgcttccttc    1140
ctgtattccg gagttccgag caggttcagt ggttcccgtt ccggtaccga cttcaccctg    1200
acgatatcct ccctccagcc ggaagacttc gctacctact actgtcaaca gcactacacc    1260
accccgccga ccttcggtca gggtaccaaa ctcgagatca aacggactgt ggctgcacca    1320
tctgtcttca tcttcccgcc atctgatgag cagttgaaat ctggaactgc ctctgttgtg    1380
tgcctgctga ataacttcta tcccagagag gccaaagtac agtggaaggt ggataacgcc    1440
ctccaatcgg gtaactccca ggagagtgtc acagagcagg acagcaagga cagcacctac    1500
agcctcagca gcaccctgac gctgagcaaa gcagactacg agaaacacaa agtctacgcc    1560
tgcgaagtca cccatcaggg cctgagttcg cccgtcacaa agagcttcaa ccgcggagag    1620
tgctcttctg cccctgctcc tgctccagca cctgcaccag cacctgctcc agcaccagct    1680
cctgcaccag cccctgctcc tgctccagca cctgcaccag cacctgctcc agcaccagct    1740
cctgcaccag cccctgctcc tgctccagca cctgcaccag cacctgctcc agcaccagct    1800
cctgcaccag cccctgctcc tgctccagca cctgcaccag cacctgctcc agcaccagct    1860
cctgcaccag cccctgctcc tgctccagca cctgcaccag cacctgctcc agcaccagct    1920
cctgcaccag cccctgctcc tgctccagca cctgcaccag cacctgctcc agcaccagct    1980
cctgcaccag cccctgctcc tgctccagca cctgcaccag cacctgctcc agcaccagct    2040
cctgcaccag cccctgctcc tgctccagca cctgcaccag cacctgctcc agcaccagct    2100
cctgcaccag cccctgctcc tgctccagca cctgcaccag cacctgctcc agcaccagct    2160
cctgcaccag cccctgctcc tgctccagca cctgcaccag cacctgctcc agcaccagct    2220
cctgcaccag cctgaagagc ttaagcttga cctgtgaagt gaaaaatggc gcacattgtg    2280
cgacattttt tttgtctgcc gtttaccgct actgcgtcac ggatctccac gcgccctgta    2340
gcggcgcatt aagcgcggcg ggtgtggtgg ttacgcgcag cgtgaccgct acacttgcca    2400
gcgccctagc gcccgctcct ttcgctttct tcccttcctt tctcgccacg ttcgccggct    2460
ttccccgtca agctctaaat cgggggctcc ctttagggtt ccgatttagt gctttacggc    2520
acctcgaccc caaaaaactt gattagggtg atggttcacg tagtgggcca tcgccctgat    2580
agacggtttt tcgccctttg acgttggagt ccacgttctt taatagtgga ctcttgttcc    2640
aaactggaac aacactcaac cctatctcgg tctattcttt tgatttataa gggattttgc    2700
cgatttcggc ctattggtta aaaaatgagc tgatttaaca aaaatttaac gcgaatttta    2760
acaaaatatt aacgtttaca atttcaggtg gcacttttcg gggaaatgtg cgcggaaccc    2820
ctatttgttt atttttctaa atacattcaa atatgtatcc gctcatgaga caataaccct    2880
gataaatgct tcaataatat tgaaaaagga agagtatgag tattcaacat ttccgtgtcg    2940
cccttattcc cttttttgcg gcattttgcc ttcctgtttt tgctcaccca gaaacgctgg    3000
tgaaagtaaa agatgctgaa gatcagttgg gtgcacgagt gggttacatc gaactggatc    3060
tcaacagcgg taagatcctt gagagttttc gccccgaaga acgttttcca atgatgagca    3120
cttttaaagt tctgctatgt ggcgcggtat tatcccgtat tgacgccggg caagagcaac    3180
tcggtcgccg catacactat tctcagaatg acttggttga gtactcacca gtcacagaaa    3240
agcatcttac ggatggcatg acagtaagag aattatgcag tgctgccata accatgagtg    3300
ataacactgc ggccaactta cttctgacaa cgatcggagg accgaaggag ctaaccgctt    3360
ttttgcacaa catgggggat catgtaactc gccttgatcg ttgggaaccg gagctgaatg    3420
aagccatacc aaacgacgag cgtgacacca cgatgcctgt agcaatggca acaacgttgc    3480
gcaaactatt aactggcgaa ctacttactc tagcttcccg gcaacaattg atagactgga    3540
```

-continued

```
tggaggcgga taaagttgca ggaccacttc tgcgctcggc ccttccggct ggctggttta    3600
ttgctgataa atctggagcc ggtgagcgtg gctctcgcgg tatcattgca gcactggggc    3660
cagatggtaa gccctcccgt atcgtagtta tctacacgac ggggagtcag gcaactatgg    3720
atgaacgaaa tagacagatc gctgagatag gtgcctcact gattaagcat tggtaggaat    3780
taatgatgtc tcgtttagat aaaagtaaag tgattaacag cgcattagag ctgcttaatg    3840
aggtcggaat cgaaggttta acaacccgta aactcgccca gaagctaggt gtagagcagc    3900
ctacattgta ttggcatgta aaaaataagc gggctttgct cgacgcctta gccattgaga    3960
tgttagatag gcaccatact cacttttgcc ctttagaagg ggaaagctgg caagattttt    4020
tacgtaataa cgctaaaagt tttagatgtg ctttactaag tcatcgcgat ggagcaaaag    4080
tacatttagg tacacggcct acagaaaaac agtatgaaac tctcgaaaat caattagcct    4140
ttttatgcca acaaggtttt tcactagaga atgcattata tgcactcagc gcagtggggc    4200
attttacttt aggttgcgta ttggaagatc aagagcatca agtcgctaaa gaagaaaggg    4260
aaacacctac tactgatagt atgccgccat tattacgaca agctatcgaa ttatttgatc    4320
accaaggtgc agagccogcc ttcttattcg gccttgaatt gatcatatgc ggattagaaa    4380
aacaacttaa atgtgaaagt gggtcttaaa agcagcataa cctttttccg tgatggtaac    4440
ttcactagtt taaaggatc taggtgaaga tccttttga taatcccatg accaaaatcc    4500
cttaacgtga gttttcgctc caccgagcgt cagacccgt agaaaagacc aaaggatctt    4560
cttgagatcc tttttttctg cgcgtaatct gctgcttgca acaaaaaaa ccaccgctac    4620 cagcggtggt ttgtttgccg gatcaagagc taccaactct ttttccgaag gtaactggct    4680
tcagcagagc gcagatacca atatctgtcc ttctagtgta gccgtagtta ggccaccact    4740
tcaagaactc tgtagcaccg cctacatacc tcgctctgct aatcctgtta ccagtggctg    4800
ctgccagtgg cgataagtcg tgtcttaccg ggttggactc aagacgatag ttaccggata    4860
aggcgcagcg gtcgggctga acgggggggtt cgtgcacaca gcccagcttg gagcgaacga    4920
cctacaccga actgagatac ctacagcgtg agctatgaga aagcgccacg cttcccgaag    4980
ggagaaaggc ggacaggtat ccggtaagcg gcagggtcgg aacaggagag cgcacgaggg    5040
agcttccagg gggaaacgcc tggtatcttt atagtcctgt cgggtttcgc cacctctgac    5100
ctgagcgtcg atttttgtga tgctcgtcag ggggcggag cctatggaaa aacgccagca    5160
acgcggcctt tttacggttc ctggcctttt gctggccttt tgctcacatg                5210
```

```
                                                         SEQ ID NO: 59
acccgacacc atcgaatggc cagatgatta attcctaatt tttgttgaca ctctatcatt      60
gatagagtta ttttaccact ccctatcagt gatagagaaa agtgaaatga atagttcgac    120
aaaaatctag ataacgaggg caaaaaatga aaaagacagc tatcgcgatt gcagtggcac    180
tggctggttt cgctaccgta gcgcaggccg aagttaaact gcaggaatcc ggtggtggtc    240
tggttcagcc aggtggttcc ctgcggctct cgtgtgctgc ttccggtttc aacatcaaag    300
acacctacat ccactgggtt cgtcaggctc cgggtaaagg cctggaatgg gttgctcgta    360
tctacccgac caacggttac accaggtatg ccgattcagt taaaggtcgt cccaccatct    420
cggccgacac ttccaaaaac accgcttacc tccagatgaa ctccctgcgt gctgaagaca    480
cagctgttta ttattgctcc cgttggggtg gtgacggttt ctocgctatg gactactggg    540 gtcagggtac cctggtcacc gtctcctcag cctccaccaa gggcccatcg gtcttccccc    600
tggcaccctc ctccaagagc acctctgggg gcacagcggc cctgggctgc ctggtcaagg    660
actacttccc cgaaccggtg acggtgtcgt ggaactcagg cgccctgacc agcggcgtgc    720
```

```
acaccttccc ggctgtccta cagtcctcag gactctactc cctcagcagc gtggtgactg  780
tgccctccag cagcttgggc acccagacct acatctgcaa cgttaaccac aaacccagca  840
acaccaaggt cgacaagaaa gttgagccca atcttgcca tcaccaccat caccattaat   900
aaccatggag aaaataaagt gaaacaaagc actattgcac tggcactctt accgttactg  960
tttaccctg tgacaaaagc cgacatcgag ctcacccaat ccccgCcctc cctgtccgct  1020
tccgttggcg accgtgtcac catcacgtgt agggcctcgc aagacgcaaa caccgccgta 1080
gcgtggtatc agcagaaacc cgggaaagct ccgaaactgc tgatctatag cgcttccttc 1140
ctgtattccg gagttccgag caggttcagt ggttcccgtt ccggtaccga cttcaccctg 1200
acgatatcct ccctccagcc ggaagacttc gctacctact actgtcaaca gcactacacc 1260
accccgccga ccttcggtca gggtaccaaa ctcgagatca acggactgt ggctgcacca  1320
tctgtcttca tcttcccgcc atctgatgag cagttgaaat ctggaactgc ctctgttgtg 1380
tgcctgctga taacttcta cccagagag gccaaagtac agtggaaggt ggataacgcc  1440
ctccaatcgg gtaactccca ggagagtgtc acagagcagg acagcaagga cagcacctac 1500
agcctcagca gcaccctgac gctgagcaaa gcagactacg agaaacacaa agtctacgcc 1560
tgcgaagtca cccatcaggg cctgagttcg cccgtcacaa agagcttcaa ccgcggagag 1620
tgctcttctg ccgctgcacc tgctgcagca cctgctgcag ctccagcagc tgctcctgca 1680
gcagctccag ccgctgcacc tgctgcagca cctgctgcag ctccagcagc tgctcctgca 1740
gcagctccag ccgctgcacc tgctgcagca cctgctgcag ctccagcagc tgctcctgca 1800
gcagctccag ccgctgcacc tgctgcagca cctgctgcag ctccagcagc tgctcctgca 1860
gcagctccag ccgctgcacc tgctgcagca cctgctgcag ctccagcagc tgctcctgca 1920
gcagctccag ccgctgcacc tgctgcagca cctgctgcag ctccagcagc tgctcctgca 1980
gcagctccag ccgctgcacc tgctgcagca cctgctgcag ctccagcagc tgctcctgca 2040
gcagctccag ccgctgcacc tgctgcagca cctgctgcag ctccagcagc tgctcctgca 2100
gcagctccag ccgctgcacc tgctgcagca cctgctgcag ctccagcagc tgctcctgca 2160
gcagctccag ccgctgcacc tgctgcagca cctgctgcag ctccagcagc tgctcctgca 2220
gcagctccag cctgaagagc ttaagcttga cctgtgaagt gaaaaatggc gcacattgtg  2280
cgacattttt tttgtctgcc gtttaccgct actgcgtcac ggatctccac gcgccctgta  2340
gcggcgcatt aagcgcggcg ggtgtggtgg ttacgcgcag cgtgaccgct acacttgcca  2400
gcgcccctagc gcccgctcct ttcgctttct tcccttcctt tctcgccacg ttcgccggct 2460
ttccccgtca gctctaaat cgggggctcc ctttagggtt ccgatttagt gctttacggc  2520
acctcgaccc caaaaaactt gattagggtg atggttcacg tagtgggcca tcgccctgat  2580
agacggtttt tcgccctttg acgttggagt ccacgttctt taatagtgga ctcttgttcc  2640
aaactggaac aacactcaac cctatctcgg tctattcttt tgatttataa gggattttgc  2700
cgatttcggc ctattggtta aaaatgagc tgatttaaca aaaatttaac gcgaatttta   2760
acaaaatatt aacgtttaca atttcaggtg gcacttttcg gggaaatgtg cgcggaaccc  2820
ctatttgttt attttctaa atacattcaa atatgtatcc gctcatgaga caataaccct   2880
gataaatgct tcaataatat tgaaaaagga agagtatgag tattcaacat ttccgtgtcg  2940
cccttattcc ctttttgcg gcattttgcc ttcctgtttt tgctcaccca gaaacgctgg  3000
tgaaagtaaa agatgctgaa gatcagttgg gtgcacgagt gggttacatc gaactggatc  3060
tcaacagcgg taagatcctt gagagttttc gccccgaaga acgttttcca atgatgagca  3120
```

```
cttttaaagt tctgctatgt ggcgcggtat tatcccgtat tgacgccggg caagagcaac 3180
tcggtcgccg catacactat tctcagaatg acttggttga gtactcacca gtcacagaaa 3240
agcatcttac ggatggcatg acagtaagag aattatgcag tgctgccata accatgagtg 3300
ataacactgc ggccaactta cttctgacaa cgatcggagg accgaaggag ctaaccgctt 3360
ttttgcacaa catgggggat catgtaactc gccttgatcg ttgggaaccg gagctgaatg 3420
aagccatacc aaacgacgag cgtgacacca cgatgcctgt agcaatggca acaacgttgc 3480
gcaaactatt aactggcgaa ctacttactc tagcttcccg gcaacaattg atagactgga 3540
tggaggcgga taaagttgca ggaccacttc tgcgctcggc ccttccggct ggctggttta 3600
ttgctgataa atctggagcc ggtgagcgtg gctctcgcgg tatcattgca gcactggggc 3660
cagatggtaa gccctcccgt atcgtagtta tctacacgac ggggagtcag gcaactatgg 3720
atgaacgaaa tagacagatc gctgagatag gtgcctcact gattaagcat tggtaggaat 3780
taatgatgtc tcgtttagat aaaagtaaag tgattaacag cgcattagag ctgcttaatg 3840
aggtcggaat cgaaggttta acaacccgta aactcgccca gaagctaggt gtagagcagc 3900
ctacattgta ttggcatgta aaaaataagc gggctttgct cgacgcctta gccattgaga 3960
tgttagatag gcaccatact cacttttgcc ctttagaagg ggaaagctgg caagattttt 4020
tacgtaataa cgctaaaagt tttagatgtg ctttactaag tcatcgcgat ggagcaaaag 4080
tacatttagg tacacggcct acagaaaaac agtatgaaac tctcgaaaat caattagcct 4140
ttttatgcca acaaggtttt tcactagaga atgcattata tgcactcagc gcagtggggc 4200
attttacttt aggttgcgta ttggaagatc aagagcatca agtcgctaaa gaagaaaggg 4260
aaacacctac tactgatagt atgccgccat tattacgaca agctatcgaa ttatttgatc 4320
accaaggtgc agagccagcc ttcttattcg gccttgaatt gatcatatgc ggattagaaa 4380
aacaacttaa atgtgaaagt gggtcttaaa agcagcataa cctttttccg tgatggtaac 4440
ttcactagtt taaaggatc taggtgaaga tccttttttga taatctcatg accaaaatcc 4500
cttaacgtga gttttcgttc cactgagcgt cagacccccgt agaaaagatc aaaggatctt 4560
cttgagatcc ttttttttctg cgcgtaatct gctgcttgca acaaaaaaaa ccaccgctac 4620
cagcggtggt ttgtttgccg gatcaagagc taccaactct ttttccgaag gtaactggct 4680
tcagcagagc gcagatacca aatactgtcc ttctagtgta gccgtagtta ggccaccact 4740
tcaagaactc tgtagcaccg cctacatacc tcgctctgct aatcctgtta ccagtggctg 4800
ctgccagtgg cgataagtcg tgtcttaccg ggttggactc aagacgatag ttaccggata 4860
aggcgcagcg gtcgggctga acggggggtt cgtgcacaca gcccagcttg gagcgaacga 4920
cctacaccga actgagatac ctacagcgtg agctatgaga aagcgccacg cttcccgaag 4980
ggagaaaggc ggacaggtat ccggtaagcg gcagggtcgg aacaggagag cgcacgaggg 5040
agcttccagg gggaaacgcc tggtatcttt atagtcctgt cgggtttcgc cacctctgac 5100
ttgagcgtcg atttttgtga tgctcgtcag ggggcggag cctatggaaa aacgccagca 5160
acgcggcctt tttacggttc ctggccttt gctggccttt tgctcacatg            5210
```

Example 18: Measurement of the Hydrodynamic Volume for the Recombinant Fusion Protein Between a Fab Fragment and a Genetically Encoded P1A1 or P1A3 Polypeptide/Polymer by Analytical Gel Filtration SEC was carried out on a Superdex S200 HR 10/300 GL column (GE Healthcare Europe, Freiburg, Germany) at a flow rate of 1 ml/min using an Äkta Purifier 10 system (GE Healthcare) with PBS as running buffer. 250 µl samples of the Fab-P1A1(200) and Fab-P1A3(200) fusion proteins, which were similarly produced and purified (FIG. 9) as described for Fab-PA#1(200) in Example 4, were individually applied at a concentration of 0.25 mg/ml in PBS. Both proteins eluted in a single homogenous peak as shown in FIG. 10.

As result, the fusion proteins with the 200 residue P1A1 or P1A3 polymers/polypeptides exhibited significantly larger sizes than the corresponding unfused Fab fragment. The apparent size increase for Fab-P1A1(200) and Fab-P1A3(200) was 5.8-fold and 5.2-fold, respectively, compared with the Fab fragment (cf. FIG. 4B) whereas the true mass was only larger by 1.4-fold and 1.3-fold. This observation clearly indicates a much increased hydrodynamic volume conferred to the biologically active Fab fragment by the biosynthetic P1A1 and P1A3 polypeptide segments according to this invention.

Example 19: Detection of Random Coil Conformation for the Biosynthetic P1A1 and P1A3 Polymers/Polypeptides Fused to a Fab Fragment Via Circular Dichroism (CD) Spectroscopy CD spectra for Fab-P1A1(200) and Fab-P1A3(200) were recorded as described in Example 8 using 4.2 and 6.5 µM protein solutions, respectively, prepared similary as described in Example 4 using 50 mM $K_2SO_4$, 20 mM K-phosphate pH 7.5 as buffer.

The spectra for the Fab-P1A1(200) and Fab-P1A3(200) fusion proteins revealed a significant fraction of random coil conformation (FIG. 11A). To analyze the spectroscopic contribution by the Pro/Ala polypeptide segment in greater detail the molar difference CD spectrum with respect to the unfused Fab fragment (see Example 8) was calculated (FIG. 11B) by subtracting the latter spectrum from the one for Fab-P1A1(200) and Fab-P1A3(200), respectively, after normalization to the same molar concentration. As result, a strong minimum at a wavelength of approximately 200 nm, which is characteristic of random coil conformation, was observed. Thus, the P1A1 and the P1A3 sequences as part of the recombinant fusion protein appear to be present in random coil conformation under physiological buffer conditions.

Example 20: Construction of PSUMO-PA#1(200) as Expression Vector for a His(6)-SUMO-PA#1(200) Fusion Protein For the construction of an expression plasmid encoding a six-residue His-tag and the small ubiquitin-like modifier (SUMO) protein (Panavas (2009) Methods Mol. Biol. 497: 303-17) fused to a 200 residue PA#1 sequence repeat, the SUMO protein) from *Saccharomyces cerevisiae* [also known as Smt3p; Uniprot: Q12306] was amplified via polymerase chain reaction (PCR) from a cloned cDNA. The 5'-primer introduced an NdeI restriction site, containing a Met start codon (ATG) and an additional Lys codon, as well as the His6-tag encoding sequence while the 3'-primer introduced a HindIII and SapI restriction site into the PCR product. The resulting DNA fragment was digested with NdeI and HindIII and ligated with a correspondingly digested derivative of the plasmid pSA1 (Schmidt (1994) J. Chromatogr. 676: 337-345), wherein the SapI restriction site had been eliminated by silent mutation. The resulting plasmid was cut with SapI, dephosphorylated with shrimp alkaline phosphatase, and ligated with the gene fragment encoding the 200 residue PA#1 polypeptide segment excised from the plasmid pFab-PA#1(200) (described in Example 2) by restriction digest with SapI (in an analogous way as exemplified in FIG. 2E). The resulting plasmid was designated pSUMO-PA#1(200) (SEQ ID NO: 60) and is depicted in FIG. 12A.

Example 21: Bacterial Expression and Isolation of a Genetically Encoded PA#1(200) Polymer/Polypeptide The PA#1(200) polypeptide (calculated mass: 16.1 kDa) was initially produced as fusion protein with the small ubiquitin-like modifier (SUMO) protein (calculated mass: 12.2 kDa) in the cytoplasm of *E. coli* BLR(DE3) (NEB, Ipswich, Mass., USA) harboring the expression plasmid pSUMO-PA#1(200) (described in Example 21) together with the plasmid pLysE (Studier (1991) J. Mol. Biol. 219: 37-44), which suppresses the the T7 promoter. Bacterial production was performed at 30° C. in shake flask cultures with 2 L LB medium containing 2.5 g/L D-glucose, 0.5 g/L L-proline, 100 mg/l ampicillin, and 30 mg/l chloramphenicol. Recombinant gene expression was induced by addition of isopropyl-β-D-thiogalactopyranoside (IPTG) to a final concentration of 0.5 mM. Bacteria were harvested 3 h after induction, resuspended in 100 mM NaCl, 40 mM Na-phosphate pH 7.5 and lysed using a French pressure cell (Thermo Scientific, Waltham, Mass., USA). After centrifugation (15 min, 15000 g) of the lysate no inclusion bodies were observed.

The supernatant containing the soluble fusion protein was incubated at 70° C. for 15 min and centrifuged (15 min, 15000 g) to remove thermally unstable host cell proteins. The His(6)-SUMO-PA#1(200) fusion protein was purified from the supernatant via IMAC (Skerra (1994) Gene 141: 79-84) using a 12 ml $Ni_2^+$ charged HisTrap high performance column (GE Healthcare) connected to an Äkta purifier system (GE Healthcare) and eluted with an imidazole gradient from 0 to 150 mM in 500 mM NaCl, 40 mM Na-phosphate pH 7.5. After a subsequent preparative SEC step a homogeneous preparation of the His(6)-SUMO-PA#1 (200) fusion protein (FIG. 12B) with a yield of approximately 5 mg per 1 L bacterial culture with OD550=1 was obtained. Protein concentration was determined according to the absorption at 280 nm using a calculated extinction coefficient (Gill (1989) loc. cit) of 1280 $M^{-1}$ $cm^{-1}$ for the His(6)-SUMO-PA#1(200) polypeptide fusion. Note that the PA#1(200) polypeptide segment does not contribute to the absorption at 280 nm due to its lack of aromatic or sulfur-containing amino acid side chains.

The biosynthetic PA#1(200) polypeptide was liberated from the fusion protein by site specific proteolytic cleavage (downstream of a Gly-Gly motif preceding the Pro/Ala polypeptide segment) with 2 U/mg Ubl-specific protease 1 from *Saccharomyces cerevisiae* (Invitrogen, Carlsbad, Calif., USA) for 1 h at 30° C. in cleavage buffer (0.2 w/v % Igepal, 1 mM DTT, 150 mM NaCl, 50 mM Tris-HCl pH 8.0). The cleavage process was checked by SDS-PAGE (FIG. 12B) using a high molarity Tris buffer system (Fling (1986) Anal. Biochem. 155: 83-88). In order to remove the cleaved His(6)-SUMO protein, residual uncleaved fusion protein, and also the SUMO protease, all carrying the $His_6$-tag, the reaction mixture was subjected to another IMAC using a 5 ml $Ni_2^+$ charged HisTrap high performance column (GE Healthcare) and 500 M NaCl, 20 mM phosphate, pH 7.5 as running buffer. This time the flow-through contained the pure biosynthetic PA#1(200) polypeptide (FIG. 13E). Note that the biosynthetic PA#1(200) polypeptide/polymer (SEQ ID NO: 61) prepared in this manner comprises altogether 201 amino acid residues, which arise from the encoded combined gene product of 10 ligated double-stranded oligodeoxynucleotide building blocks, each encoding 20 amino acid residues, as shown in FIG. 1, and an additional Ala residue encoded by the triplet DNA overhang of the downstream SapI restriction site that was used for cloning.

Example 22: Preparation and Characterization of Small Molecule/Drug Conjugates with PA#1(200)

The unpurified proteolytic cleavage reaction mixture of the His(6)-SUMO-PA#1(200) fusion protein from Example 21 was twice dialysed at 4° C. against 50 mM NaHCO₃ pH 8.3 and incubated at room temperature for 1 h after mixing with a 10-fold molar excess of a solution of 6-[fluorescein-5(6)-carboxamido] hexanoic acid N-hydroxysuccinimide ester (Fluorescein-NHS ester; Sigma-Aldrich) in dry dimethylformamide (DMF). To this end, 200 µl of a 2.5 mg/ml solution of the His(6)-SUMO-PA#1(200) cleavage mixture was added to 17.6 µl of a 10 mM solution of Fluorescein-NHS ester dissolved in DMF. The resulting mixture was incubated at room temperature for 1 h and applied to IMAC as described in Example 21 to remove the cleaved His(6)-SUMO protein, residual uncleaved fusion protein, and the SUMO protease and further purified by preparative SEC on a Superdex S200 10/300 GL column equilibrated with PBS at a flow rate of 0.5 ml/min.

Samples from the different steps were then analysed via analytical SEC on a Superdex S200 10/300 GL column equilibrated with PBS at a flow rate of 0.5 ml/min. The SUMO protein was detected via its aromatic side chains at 280 nm and the peptide bonds, including those of the Pro/Ala polypeptide or polypeptide segment, were detected at 225 nm while fluorescein was detected at 494 nm (FIG. 13 A-G). For comparison, UV/VIS spectra of a solution of free fluorescein (Sigma-Aldrich) and of fractions from each distinct peak detected in the SEC were measured using a Lambda 9 instrument (Perkin Elmer, Waltham, Mass., USA) (FIG. 13 H-K). For size calibration of the chromatography column (FIG. 13L), 250 µl of an appropriate mixture of the following globular proteins (Sigma-Aldrich) were applied in PBS at concentrations between 0.2 and 0.5 mg/ml: aprotinin, 6.5 kDa; cytochrome c, 12.4 kDa; carbonic anhydrase, 29.0 kDa; bovine serum albumin, 66.3 kDa; alcohol dehydrogenase, 150 kDa; β-amylase, 200 kDa; apo-ferritin, 440 kDa.

As result, after coupling of the biosynthetic PA#1(200) polypeptide/polymer with Fluorescein-NHS ester a macromolecular conjugate was isolated via IMAC and SEC that essentially exhibits the size properties of the PA#1(200) polypeptide/polymer and the spectroscopic signature of the small molecule, i.e. the fluorescein group. This demonstrates that the small molecule was successfully coupled to the biosynthetic Pro/Ala polypeptide/polymer, which according to this invention dramatically increases the hydrodynamic volume of the conjugated small molecule drug or compound.

To prepare a similar conjugate between the biosynthetic Pro/Ala polypeptide/polymer and the plant steroid digoxigenin, 0.1 mg of the purified PA#1(200) polypeptide from Example 21 was dialysed against 50 mM NaHCO₃ pH 8.3 as described above. The concentration of purified PA#1(200) polypeptide was determined according to the absorption at 205 nm (Gill (1989) loc. cit). The PA#1(200) polypeptide was coupled with a 10-fold molar excess of digoxigenin-3-O-methylcarbonyl-ε-aminocaproic acid NHS ester (DIG-NHS ester; Roche Diagnostics, Mannheim, Germany). For this purpose, 100 µl of a 1 mg/ml solution of the purified PA#1(200) polypeptide in 50 mM NaHCO₃ pH 8.3 was added to 2 µl of a 30 mM solution of DIG-NHS ester dissolved in dry DMF and the reaction mix was incubated for 1 h at room temperature. The resulting solution of the conjugate was purified using a Zeba™ spin desalting column with a cutoff of 7 kDa (Thermo Scientific), twice dialysed against 10 mM ammonium acetate buffer pH 6.8 and analysed via ESI mass spectrometry on a Q-Tof Ultima instrument (Waters, Eschbronn, Germany) using the positive ion mode. As result, the spectrum of the Digoxigenin-PA#1 (200) conjugate revealed a mass of 16671.4 Da, which essentially coincides with the calculated mass of 16670.6 Da (FIG. 13M). This clearly demonstrates that a biosynthetic Pro/Ala polypeptide/polymer, in particular PA#1(200), can be efficiently conjugated with a small molecule drug.

The present invention relates to and refers to the following exemplified sequences, whereby the appended sequence listing is presented as part of the description and is, accordingly a part of this specification.

SEQ ID NO: 1 shows the amino acid sequence of PA#1.
SEQ ID NO: 2 shows the amino acid sequence of PA#2.
SEQ ID NO: 3 shows the amino acid sequence of PA#3.
SEQ ID NO: 4 shows the amino acid sequence of PA#4.
SEQ ID NO: 5 shows the amino acid sequence of PA#5.
SEQ ID NO: 6 shows the amino acid sequence of PA#6.
SEQ ID NO: 7 shows an amino acid sequence of a circular permutated version of SEQ ID NO: 1.
SEQ ID NO: 8 shows an amino acid sequence of a circular permutated version of SEQ ID NO: 1.
SEQ ID NO: 9 shows an amino acid sequence of a circular permutated version of SEQ ID NO: 1.
SEQ ID NO: 10 shows an amino acid sequence of a circular permutated version of SEQ ID NO: 1.
SEQ ID NO: 11 shows an amino acid sequence of a circular permutated version of SEQ ID NO: 1.
SEQ ID NO: 12 shows an amino acid sequence of a circular permutated version of SEQ ID NO: 1.
SEQ ID NO: 13 shows an amino acid sequence of a circular permutated version of SEQ ID NO: 1.
SEQ ID NO: 14 shows an amino acid sequence of a circular permutated version of SEQ ID NO: 1.
SEQ ID NO: 15 shows an amino acid sequence of a circular permutated version of SEQ ID NO: 1.
SEQ ID NO: 16 shows an amino acid sequence of a circular permutated version of SEQ ID NO: 1.
SEQ ID NO: 17 shows a nucleic acid sequence of the upper/coding strand oligodeoxynucleotide used for the generation of building block PA#1.
SEQ ID NO: 18 shows a nucleic acid sequence of lower/non-coding strand oligodeoxynucleotide used for the generation of the building block for PA#1.
SEQ ID NO: 19 shows a nucleic acid sequence stretch (upper/coding strand) around the C-terminus of the immunoglobulin light chain of an antibody Fab fragment as encoded on pASK88-Fab-2xSapI.
SEQ ID NO: 20 shows a nucleic acid sequence stretch (lower/non-coding strand) around the C-terminus of the immunoglobulin light chain of an antibody Fab fragment as encoded on pASK88-Fab-2xSapI.
SEQ ID NO: 21 shows an amino acid sequence of the C-terminus of the light chain of the Fab fragment as encoded on pASK88-Fab-2xSapI.
SEQ ID NO: 22 shows the nucleic acid sequence of pASK88-Fab-2xSapI.
SEQ ID NO: 23 shows a nucleic acid sequence stretch (upper/coding strand) encoding amino acid sequence of the C-terminus of the Fab light chain after insertion of one PA#1(20) polymer.
SEQ ID NO: 24 shows a nucleic acid sequence (lower/non-coding strand) for an amino acid stretch of the C-terminus of an Fab light chain after insertion of one PA#1(20) polymer.
SEQ ID NO: 25 shows an amino acid sequence stretch of the C-terminus of an Fab light chain after insertion of one PA#1(20) polymer.
SEQ ID NO: 26 shows the amino acid sequence of the Fab heavy chain as encoded on pFab-PA#1(200).

SEQ ID NO: 27 shows the amino acid sequence of the Fab light chain fused with the PA#1(200) polymer as encoded on pFab-PA#1(200).

SEQ ID NO: 28 shows the nucleic acid sequence of pFab-PA#1(200).

SEQ ID NO: 29 shows the nucleic acid sequence (upper/coding strand) encoding the amino acid sequence of the N-terminus of INFa2b and Strep-tag II (only the last two amino acids).

SEQ ID NO: 30 shows a nucleic acid sequence (lower/non-coding strand) encoding amino acid sequence of the N-terminus of INFa2b and Strep-tag II (only the last two amino acids).

SEQ ID NO: 31 shows the amino acid sequence of the C-terminus of Strep-tag II and the N-terminus of INFa2b.

SEQ ID NO: 32 shows the nucleic acid sequence of pASK-IFNa2b.

SEQ ID NO: 33 shows a nucleic acid sequence stretch (upper/coding strand) encoding the C-terminus of Strep-tag II and the N-terminus of IFNa2b after insertion of one PA#1 polymer sequence cassette.

SEQ ID NO: 34 shows a nucleic acid sequence stretch (lower/non-coding strand) of the C-terminus of Strep-tag II and the N-terminus of IFNa2b after insertion of one PA#1 polymer sequence cassette.

SEQ ID NO: 35 shows an amino acid sequence stretch of the C-terminus of Strep-tag II and the N-terminus of IFNa2b ater fusion with one PA#1 polymer cassette.

SEQ ID NO: 36 shows the amino acid sequence of IFNa2b and Strep-tag II fused with the PA#1(200) polymer as encoded on pPA#1(200)-IFNa2b.

SEQ ID NO: 37 shows the nucleic acid sequence of pPA#1(200)-IFNa2b.

SEQ ID NO: 38 shows a nucleic acid sequence stretch (upper/coding strand) on pASK75-His6-hGH encoding the amino acid sequence around the N-terminus of His6-hGH.

SEQ ID NO: 39 shows a nucleic acid sequence stretch (lower/non-coding strand) on pASK75-His6-hGH encoding the amino acid sequence around the N-terminus of hGH.

SEQ ID NO: 40 shows an amino acid sequence stretch of the N-terminus of His6-hGH as encoded on pASK75-His6-hGH.

SEQ ID NO: 41 shows the nucleic acid sequence of pASK75-His6-hGH.

SEQ ID NO: 42 shows a nucleic acid sequence (upper/coding-strand) stretch encoding amino acid sequence of the N-terminus of His6-hGH after insertion of the PA#1(20) polymer.

SEQ ID NO: 43 shows a nucleic acid sequence (lower/non-coding strand) encoding the N-terminus of hGH after insertion of one PA#1 polymer sequence cassette.

SEQ ID NO: 44 shows the amino acid sequence of the N-terminus of His6-hGH after insertion of the PA#1(20) polymer.

SEQ ID NO: 45 shows the amino acid sequence of mature His6-PA#1(200)-hGH as encoded on pASK75-His6-PA#1(200)-hGH.

SEQ ID NO: 46 shows the nucleic acid sequence of pASK75-His6-PA#1(200)-hGH.

SEQ ID NO: 47 shows the amino acid sequence of His6-PA#1(200)-hGH as encoded on pCHO-PA#1(200)-hGH.

SEQ ID NO: 48 shows the nucleic acid sequence of pCHO-PA#1(200)-hGH.

SEQ ID NO: 49 shows the nucleic acid sequence of pCHO-hGH.

SEQ ID NO: 50 shows the nucleic acid sequence of pCHO.

SEQ ID NO: 51 shows the amino acid sequence of P1A1.

SEQ ID NO: 52 shows the nucleic acid sequence of upper/coding strand oligodesoxynucleotide used for the generation of the building block for P1A1.

SEQ ID NO: 53 shows the nucleic acid sequence of lower/non-coding strand oligodesoxynucleotide used for the generation of the building block for P1A1.

SEQ ID NO: 54 shows the nucleic acid sequence of upper/coding strand oligodesoxynucleotide used for the generation of the building block for P1A3.

SEQ ID NO: 55 shows the nucleic acid sequence of lower/non-coding strand oligodesoxynucleotide used for the generation of the building block for P1A3.

SEQ ID NO: 56 shows the amino acid sequence of the Fab light chain fused with the P1A1(200) polymer as encoded on pFab-P1A1(200).

SEQ ID NO: 57 shows the amino acid sequence of the Fab light chain fused with the P1A3(200) polymer as encoded on pFab-P1A3(200).

SEQ ID NO: 58 shows the nucleic acid sequence of pFab-P1A1(200).

SEQ ID NO: 59 shows the acid sequence of pFab-P1A3 (200).

SEQ ID NO: 60 shows the nucleic acid sequence of pSUMO-PA#1(200).

SEQ ID NO: 61 shows the PA#1(200) polypeptide/polymer used for the preparation of drug conjugates (made by ligation of 10 20mer encoding gene cassettes, including one additional C-terminal Ala residue resulting from the downstream ligation site.

SEQUENCE LISTING

```
<160> NUMBER OF SEQ ID NOS: 61

<210> SEQ ID NO 1
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of PA#1"

<400> SEQUENCE: 1

Ala Ala Pro Ala Ala Pro Ala Pro Ala Ala Pro Ala Ala Pro Ala Pro
1               5                   10                  15
```

-continued

Ala Ala Pro Ala
            20

<210> SEQ ID NO 2
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of PA#2"

<400> SEQUENCE: 2

Ala Ala Pro Ala Ala Ala Pro Ala Pro Ala Ala Pro Ala Ala Pro Ala
1               5                   10                  15

Pro Ala Ala Pro
            20

<210> SEQ ID NO 3
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of PA#3"

<400> SEQUENCE: 3

Ala Ala Ala Pro Ala Ala Ala Pro Ala Ala Ala Pro Ala Ala Ala Pro
1               5                   10                  15

Ala Ala Ala Pro
            20

<210> SEQ ID NO 4
<211> LENGTH: 24
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of PA#4"

<400> SEQUENCE: 4

Ala Ala Pro Ala Ala Pro Ala Ala Pro Ala Ala Pro Ala Ala Pro Ala
1               5                   10                  15

Ala Pro Ala Ala Pro Ala Ala Pro
            20

<210> SEQ ID NO 5
<211> LENGTH: 24
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of PA#5"

<400> SEQUENCE: 5

Ala Pro Ala Ala Ala Pro Ala Pro Ala Ala Pro Ala Pro Ala Ala Ala
1               5                   10                  15

Ala Pro Ala Pro Ala Ala Ala Pro
            20

<210> SEQ ID NO 6
<211> LENGTH: 24
<212> TYPE: PRT

```
<213> ORGANISM: artificial sequence
<220> FEATURE:
<221> NAME/KEY: source
<223> OTHER INFORMATION: /note="Description of artificial sequence:
      amino acid sequence of PA#6"

<400> SEQUENCE: 6

Ala Ala Ala Pro Ala Ala Pro Ala Ala Pro Pro Ala Ala Ala Ala Pro
1               5                   10                  15

Ala Ala Pro Ala Ala Pro Pro Ala
            20

<210> SEQ ID NO 7
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of a circular permutated version of SEQ ID
      NO: 1"

<400> SEQUENCE: 7

Ala Pro Ala Ala Pro Ala Pro Ala Ala Pro Ala Ala Pro Ala Pro Ala
1               5                   10                  15

Ala Pro Ala Ala
            20

<210> SEQ ID NO 8
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of a circular permutated version of SEQ ID
      NO: 1"

<400> SEQUENCE: 8

Pro Ala Ala Pro Ala Pro Ala Ala Pro Ala Ala Pro Ala Pro Ala Ala
1               5                   10                  15

Pro Ala Ala Ala
            20

<210> SEQ ID NO 9
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of a circular permutated version of SEQ ID
      NO: 1"

<400> SEQUENCE: 9

Ala Ala Pro Ala Pro Ala Ala Pro Ala Ala Pro Ala Pro Ala Ala Pro
1               5                   10                  15

Ala Ala Ala Pro
            20

<210> SEQ ID NO 10
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
``` amino acid sequence of a circular permutated version of SEQ ID
NO: 1"

<400> SEQUENCE: 10

Ala Pro Ala Pro Ala Ala Pro Ala Ala Pro Ala Pro Ala Ala Pro Ala
1               5                   10                  15

Ala Ala Pro Ala
            20

<210> SEQ ID NO 11
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of a circular permutated version of SEQ ID
      NO: 1"

<400> SEQUENCE: 11

Pro Ala Pro Ala Ala Pro Ala Ala Pro Ala Pro Ala Ala Pro Ala Ala
1               5                   10                  15

Ala Pro Ala Ala
            20

<210> SEQ ID NO 12
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of a circular permutated version of SEQ ID
      NO: 1"

<400> SEQUENCE: 12

Ala Pro Ala Ala Pro Ala Ala Pro Ala Pro Ala Ala Pro Ala Ala Ala
1               5                   10                  15

Pro Ala Ala Pro
            20

<210> SEQ ID NO 13
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of a circular permutated version of SEQ ID
      NO: 1"

<400> SEQUENCE: 13

Pro Ala Ala Pro Ala Ala Pro Ala Pro Ala Ala Pro Ala Ala Ala Pro
1               5                   10                  15

Ala Ala Pro Ala
            20

<210> SEQ ID NO 14
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of a circular permutated version of SEQ ID
      NO: 1"

<400> SEQUENCE: 14

Ala Ala Pro Ala Ala Pro Ala Pro Ala Ala Pro Ala Ala Ala Pro Ala
1               5                   10                  15

Ala Pro Ala Pro
            20

<210> SEQ ID NO 15
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of a circular permutated version of SEQ ID
      NO: 1"

<400> SEQUENCE: 15

Ala Pro Ala Ala Pro Ala Pro Ala Ala Pro Ala Ala Ala Pro Ala Ala
1               5                   10                  15

Pro Ala Pro Ala
            20

<210> SEQ ID NO 16
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of a circular permutated version of SEQ ID
      NO: 1"

<400> SEQUENCE: 16

Pro Ala Ala Pro Ala Pro Ala Ala Pro Ala Ala Ala Pro Ala Ala Pro
1               5                   10                  15

Ala Pro Ala Ala
            20

<210> SEQ ID NO 17
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence of  the upper/coding strand
      oligodeoxynucleotide used for the generation of building block
      PA#1"

<400> SEQUENCE: 17
gccgctccag ctgcacctgc tccagcagca cctgctgcac cagctccggc tgctcctgct      60

<210> SEQ ID NO 18
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence of lower/non-coding strand
      oligodeoxynucleotide used for the generation of the building block
      for PA#1"

<400> SEQUENCE: 18
ggcagcagga gcagccggag ctggtgcagc aggtgctgct ggagcaggtg cagctggagc      60

```
<210> SEQ ID NO 19
<211> LENGTH: 49
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence stretch (upper/coding strand) around the
      C-terminus of the immunoglobulin light chain of an antibody Fab
      fragment as encoded on pASK88-Fab-2xSapI"

<400> SEQUENCE: 19
aagagcttca accgcggaga gtgctcttct gcctgaagag cttaagctt          49

<210> SEQ ID NO 20
<211> LENGTH: 49
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence stretch (lower/non-coding strand) around the
      C-terminus of the immunoglobulin light chain of an antibody Fab
      fragment as encoded on pASK88-Fab-2xSapI"

<400> SEQUENCE: 20
aagcttaagc tcttcaggca gaagagcact ctccgcggtt gaagctctt          49

<210> SEQ ID NO 21
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of the C-terminus of the light chain of the
      Fab fragment as encoded on pASK88-Fab-2xSapI"

<400> SEQUENCE: 21

Lys Ser Phe Asn Arg Gly Glu Cys Ser Ser Ala
1               5                   10

<210> SEQ ID NO 22
<211> LENGTH: 4610
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence of pASK88-Fab-2xSapI"

<400> SEQUENCE: 22
acccgacacc atcgaatggc cagatgatta attcctaatt tttgttgaca ctctatcatt    60
gatagagtta ttttaccact ccctatcagt gatagagaaa agtgaaatga atagttcgac   120
aaaaatctag ataacgaggg caaaaaatga aaaagacagc tatcgcgatt gcagtggcac   180
tggctggttt cgctaccgta gcgcaggccg aagttaaact gcaggaatcc ggtggtggtc   240
tggttcagcc aggtggttcc ctgcggctct cgtgtgctgc ttccggtttc aacatcaaag   300
acacctacat ccactgggtt cgtcaggctc cgggtaaagg cctggaatgg gttgctcgta   360
tctacccgac caacggttac accaggtatg ccgattcagt taaaggtcgt ttcaccatct   420
cggccgacac ttccaaaaac accgcttacc tccagatgaa ctccctgcgt gctgaagaca   480
cagctgttta ttattgctcc cgttggggtg gtgacggttt ctacgctatg gactactggg   540
gtcagggtac cctggtcacc gtctcctcag cctccaccaa gggcccatcg gtcttccccc   600
```

-continued

```
tggcaccctc ctccaagagc acctctgggg gcacagcggc cctgggctgc ctggtcaagg      660
actacttccc cgaaccggtg acggtgtcgt ggaactcagg cgccctgacc agcggcgtgc      720
acaccttccc ggctgtccta cagtcctcag gactctactc cctcagcagc gtggtgactg      780
tgccctccag cagcttgggc acccagacct acatctgcaa cgttaatcac aaacccagca      840
acaccaaggt cgacaagaaa gttgagccca atcttgcca tcaccaccat caccattaat       900
aaccatggaa aaataaagt gaaacaaagc actattgcac tggcactctt accgttactg       960 tttaccctg tgacaaaagc cgacatcgag ctcacccaat ccccgtcctc cctgtccgct       1020
tccgttggcg accgtgttac catcacgtgt agggcctcgc aagacgtaaa caccgccgta      1080
gcgtggtatc agcagaaacc cgggaaagct ccgaaactgc tgatctatag cgcttccttc      1140
ctgtattccg gagttccgag caggttcagt ggttcccgtt ccggtaccga cttcaccctg      1200
acgatatcct ccctccagcc ggaagacttc gctacctact actgtcaaca gcactacacc      1260
accccgccga ccttcggtca gggtaccaaa ctcgagatca acggactgt ggctgcacca       1320 tctgtcttca tcttcccgcc atctgatgag cagttgaaat ctggaactgc ctctgttgtg      1380
tgcctgctga ataacttcta cccagagagg ccaaagtac agtggaaggt ggataacgcc       1440
ctccaatcgg gtaactccca ggagagtgtc acagagcagg acagcaagga cagcacctac      1500
agcctcagca gcaccctgac gctgagcaaa gcagactacg agaaacacaa agtctacgcc      1560
tgcgaagtca cccatcaggg cctgagttcg cccgtcacaa agagcttcaa ccgcggagag      1620
tgctcttctg cctgaagagc ttaagcttga cctgtgaagt gaaaaatggc gcacattgtg      1680 cgacatttt tttgtctgcc gtttaccgct actgcgtcac ggatctccac gcgccctgta       1740
gcggcgcatt aagcgcggcg ggtgtggtgg ttacgcgcag cgtgaccgct acacttgcca      1800 gcgcccctagc gcccgctcct ttcgctttct tcccttcctt tctcgccacg ttcgccggct     1860
ttccccgtca agctctaaat cggggggctcc ctttagggtt ccgatttagt gctttacggc     1920
acctcgaccc caaaaaactt gattaggtg atggttcacg tagtgggcca tcgccctgat      1980
agacggtttt tcgcccttg acgttggagt ccacgttctt aatagtgga ctcttgttcc       2040 aaactggaac aacactcaac cctatctcgg tctattcttt tgatttataa gggattttgc      2100
cgatttcggc ctattggtta aaaaatgagc tgatttaaca aaaatttaac gcgaatttta     2160
acaaaatatt aacgtttaca atttcaggtg gcacttttcg gggaaatgtg cgcggaaccc      2220
ctatttgttt atttttctaa atacattcaa atatgtatcc gctcatgaga caataaccct      2280
gataaatgct tcaataatat tgaaaaagga agagtatgag tattcaacat ttccgtgtcg      2340
cccttattcc cttttttgcg gcattttgcc ttcctgtttt tgctcaccca gaaacgctgg      2400
tgaaagtaaa agatgctgaa gatcagttgg gtgcacgagt gggttacatc gaactggatc      2460
tcaacagcgg taagatcctt gagagttttc gccccgaaga acgttttcca atgatgagca      2520
cttttaaagt tctgctatgt ggcgcggtat tatcccgtat tgacgccggg caagagcaac      2580
tcggtcgccg catacactat tctcagaatg acttggttga gtactcacca gtcacagaaa      2640
agcatcttac ggatggcatg acagtaagag aattatgcag tgctgccata accatgagtg      2700
ataacactgc ggccaactta cttctgacaa cgatcgagg accgaaggag ctaaccgctt       2760
ttttgcacaa catgggggat catgtaactc gccttgatcg ttgggaaccg gagctgaatg      2820
aagccatacc aaacgacgag cgtgacacca cgatgcctgt agcaatggca acaacgttgc      2880
gcaaactatt aactggcgaa ctacttactc tagcttcccg gcaacaattg atagactgga      2940
tggaggcgga taaagttgca ggaccacttc tgcgctcggc ccttccggct ggctggttta      3000
```

-continued

```
ttgctgataa atctggagcc ggtgagcgtg gctctcgcgg tatcattgca gcactggggc    3060
cagatggtaa gccctcccgt atcgtagtta tctacacgac ggggagtcag caactatgg     3120 atgaacgaaa tagacagatc gctgagatag gtgcctcact gattaagcat tggtaggaat    3180
taatgatgtc tcgtttagat aaaagtaaag tgattaacag cgcattagag ctgcttaatg    3240
aggtcggaat cgaaggttta caacccgta aactcgccca gaagctaggt gtagagcagc     3300
ctacattgta ttggcatgta aaaataagc gggctttgct cgacgcctta gccattgaga     3360
tgttagatag gcaccatact cacttttgcc ctttagaagg ggaaagctgg caagattttt    3420
tacgtaataa cgctaaaagt tttagatgtg ctttactaag tcatcgcgat ggagcaaaag    3480
tacatttagg tacacggcct acagaaaaac agtatgaaac tctcgaaaat caattagcct    3540
ttttatgcca acaaggtttt tcactagaga atgcattata tgcactcagc gcagtggggc    3600
attttacttt aggttgcgta ttggaagatc aagagcatca agtcgctaaa gaagaaaggg    3660
aaacacctac tactgatagt atgccgccat tattacgaca agctatcgaa ttatttgatc    3720
accaaggtgc agagccagcc ttcttattcg gccttgaatt gatcatatgc ggattagaaa    3780
aacaacttaa atgtgaaagt gggtcttaaa agcagcataa ccttttttccg tgatggtaac    3840 ttcactagtt taaaggatc taggtgaaga tcctttttga taatctcatg accaaaatcc     3900
cttaacgtga gttttcgttc cactgagcgt cagacccgt agaaaagatc aaaggatctt    3960
cttgagatcc ttttttttctg cgcgtaatct gctgcttgca acaaaaaaa ccaccgctac    4020 cagcggtggt ttgtttgccg gatcaagagc taccaactct tttccgaag gtaactggct    4080 tcagcagagc gcagatacca aatactgtcc ttctagtgta gccgtagtta ggccaccact    4140
tcaagaactc tgtagcaccg cctacatacc tcgctctgct aatcctgtta ccagtggctg    4200
ctgccagtgg cgataagtcg tgtcttaccg ggttggactc aagacgatag ttaccggata    4260
aggcgcagcg gtcgggctga acggggggtt cgtgcacaca gcccagcttg gagcgaacga    4320
cctacaccga actgagatac ctacagcgtg agctatgaga agcgccacg cttcccgaag     4380 ggagaaaggc ggacaggtat ccggtaagcg gcagggtcgg aacaggagag cgcacgaggg    4440
agcttccagg gggaaacgcc tggtatcttt atagtcctgt cgggtttcgc cacctctgac    4500
ttgagcgtcg attttgtga tgctcgtcag ggggcggag cctatggaaa aacgccagca     4560
acgcggcctt tttacggttc ctggcctttt gctggccttt tgctcacatg               4610
```

<210> SEQ ID NO 23
<211> LENGTH: 85
<212> TYPE: DNA
<213> ORGANISM: artificial sequence
<220> FEATURE:
<221> NAME/KEY: source
<223> OTHER INFORMATION: /note="Description of artificial sequence:
nucleic acid sequence stretch (upper/coding strand) encoding amino
acid sequence of the C-terminus of the Fab light chain after
insertion of one PA#1(20) polymer"

<400> SEQUENCE: 23

```
gagtgctctt ctgccgctcc agctgcacct gctccagcag cacctgctgc accagctccg    60
gctgctcctg ctgcctgaag agctt                                          85
```

<210> SEQ ID NO 24
<211> LENGTH: 85
<212> TYPE: DNA
<213> ORGANISM: artificial sequence
<220> FEATURE:

-continued

```
<221> NAME/KEY: source
<223> OTHER INFORMATION: /note="Description of artificial sequence:
      nucleic acid sequence (lower/non-coding strand) for an amino acid
      stretch of the C-terminus of an Fab light chain after insertion of
      one PA#1(20) polymer"

<400> SEQUENCE: 24
aagctcttca ggcagcagga gcagccggag ctggtgcagc aggtgctgct ggagcaggtg    60
cagctggagc ggcagaagag cactc                                         85

<210> SEQ ID NO 25
<211> LENGTH: 25
<212> TYPE: PRT
<213> ORGANISM: artificial sequence
<220> FEATURE:
<221> NAME/KEY: source
<223> OTHER INFORMATION: /note="Description of artificial sequence:
      amino acid sequence stretch of the C-terminus of an Fab light
      chain after insertion of one PA#1(20) polymer"

<400> SEQUENCE: 25

Glu Cys Ser Ser Ala Ala Pro Ala Ala Pro Ala Ala Pro Ala
1               5                   10                  15

Ala Pro Ala Pro Ala Ala Pro Ala Ala
            20                  25

<210> SEQ ID NO 26
<211> LENGTH: 229
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of a Fab heavy chain as encoded on
      pFab-PA#1(200)"

<400> SEQUENCE: 26

Glu Val Lys Leu Gln Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys His
    210                 215                 220

His His His His His
225

<210> SEQ ID NO 27
<211> LENGTH: 417
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of the Fab light chain fused with the
      PA#1(200) polymer as encoded on pFab-PA#1(200)"

<400> SEQUENCE: 27

Asp Ile Glu Leu Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ser Ser Ala Ala Pro Ala Ala Pro Ala Pro
    210                 215                 220

Ala Ala Pro Ala Ala Pro Ala Pro Ala Pro Ala Ala Pro Ala Ala Pro
225                 230                 235                 240

Ala Pro Ala Pro Ala Ala Pro Ala Ala Pro Ala Pro Ala Ala Pro Ala
                245                 250                 255

Ala Ala Pro Ala Ala Pro Ala Pro Ala Ala Pro Ala Ala Pro Ala Pro
            260                 265                 270

Ala Ala Pro Ala Ala Pro Ala Pro Ala Ala Pro Ala Ala Pro Ala Pro
        275                 280                 285

Ala Pro Ala Pro Ala Ala Pro Ala Ala Pro Ala Ala Pro Ala Ala Pro
    290                 295                 300
```

Ala Ala Pro Ala Ala Pro Ala Pro Ala Pro Ala Ala Pro Ala Pro Ala
305                 310                 315                 320

Ala Pro Ala Pro Ala Pro Ala Pro Ala Pro Ala Pro Ala Ala Pro Ala
                325                 330                 335

Ala Ala Pro Ala Ala Pro Ala Pro Ala Pro Ala Ala Pro Ala Pro Ala Pro
            340                 345                 350

Ala Ala Pro Ala Ala Ala Pro Ala Pro Ala Pro Ala Ala Pro Ala
        355                 360                 365

Ala Pro Ala Pro Ala Pro Ala Ala Ala Pro Ala Ala Pro Ala Pro
    370                 375                 380

Ala Ala Pro Ala Ala Pro Ala Pro Ala Ala Ala Pro Ala Ala Pro Ala
385                 390                 395                 400

Ala Pro Ala Pro Ala Ala Pro Ala Ala Pro Ala Pro Ala Ala Pro Ala
            405                 410                 415

Ala

<210> SEQ ID NO 28
<211> LENGTH: 5210
<212> TYPE: DNA
<213> ORGANISM: artificial sequence
<220> FEATURE:
<221> NAME/KEY: source
<223> OTHER INFORMATION: /note="Description of artificial sequence: nucleic acid sequence of pFab-PA#1(200)"

<400> SEQUENCE: 28

```
acccgacacc atcgaatggc cagatgatta attcctaatt tttgttgaca ctctatcatt      60
gatagagtta ttttaccact ccctatcagt gatagagaaa agtgaaatga atagttcgac     120
aaaaatctag ataacgaggg caaaaaatga aaaagacagc tatcgcgatt gcagtggcac     180
tggctggttt cgctaccgta gcgcaggccg aagttaaact gcaggaatcc ggtggtggtc     240
tggttcagcc aggtggttcc ctgcggctct cgtgtgctgc ttccggtttc aacatcaaag     300
acacctacat ccactgggtt cgtcaggctc cgggtaaagg cctggaatgg gttgctcgta     360
tctacccgac caacggttac accaggtatg ccgattcagt taaaggtcgt ttcaccatct     420
cggccgacac ttccaaaaac accgcttacc tccagatgaa ctccctgcgt gctgaagaca     480
cagctgttta ttattgctcc cgttggggtg gtgacggttt ctacgctatg gactactggg     540
gtcagggtac cctggtcacc gtctcctcag cctccaccaa gggcccatcg gtcttccccc     600
tggcaccctc ctccaagagc acctctgggg gcacagcggc cctgggctgc ctggtcaagg     660
actacttccc cgaaccggtg acggtgtcgt ggaactcagg cgccctgacc agcggcgtgc     720
acaccttccc ggctgtccta cagtcctcag gactctactc cctcagcagc gtggtgactg     780
tgccctccag cagcttgggc acccagacct acatctgcaa cgttaatcac aaacccagca     840
acaccaaggt cgacaagaaa gttgagccca atcttgcca tcaccaccat caccattaat     900
aaccatggag aaaataaagt gaaacaaagc actattgcac tggcactctt accgttactg     960
tttacccctg tgacaaaagc cgacatcgag ctcacccaat cccgtcctc cctgtccgct    1020
tccgttggcg accgtgttac catcacgtgt agggcctcgc aagacgtaaa caccgccgta    1080
gcgtggtatc agcagaaacc cgggaaagct ccgaaactgc tgatctatag cgcttccttc    1140
ctgtattccg gagttccgag caggttcagt ggttcccgtt ccggtaccga cttcaccctg    1200
acgatatcct cctccagcc ggaagacttc gctacctact actgtcaaca gcactacacc    1260
accccgccga ccttcggtca gggtaccaaa ctcgagatca aacggactgt ggctgcacca    1320
```

```
tctgtcttca tcttcccgcc atctgatgag cagttgaaat ctggaactgc ctctgttgtg   1380
tgcctgctga ataacttcta tcccagagag gccaaagtac agtggaaggt ggataacgcc   1440
ctccaatcgg gtaactccca ggagagtgtc acagagcagg acagcaagga cagcacctac   1500
agcctcagca gcaccctgac gctgagcaaa gcagactacg agaaacacaa agtctacgcc   1560
tgcgaagtca cccatcaggg cctgagttcg cccgtcacaa agagcttcaa ccgcggagag   1620
tgctcttctg ccgctccagc tgcacctgct ccagcagcac ctgctgcacc agctccggct   1680
gctcctgctg ccgctccagc tgcacctgct ccagcagcac ctgctgcacc agctccggct   1740
gctcctgctg ccgctccagc tgcacctgct ccagcagcac ctgctgcacc agctccggct   1800
gctcctgctg ccgctccagc tgcacctgct ccagcagcac ctgctgcacc agctccggct   1860
gctcctgctg ccgctccagc tgcacctgct ccagcagcac ctgctgcacc agctccggct   1920
gctcctgctg ccgctccagc tgcacctgct ccagcagcac ctgctgcacc agctccggct   1980
gctcctgctg ccgctccagc tgcacctgct ccagcagcac ctgctgcacc agctccggct   2040
gctcctgctg ccgctccagc tgcacctgct ccagcagcac ctgctgcacc agctccggct   2100
gctcctgctg ccgctccagc tgcacctgct ccagcagcac ctgctgcacc agctccggct   2160
gctcctgctg ccgctccagc tgcacctgct ccagcagcac ctgctgcacc agctccggct   2220
gctcctgctg cctgaagagc ttaagcttga cctgtgaagt gaaaaatggc gcacattgtg   2280
cgacattttt tttgtctgcc gtttaccgct actgcgtcac ggatctccac gcgccctgta   2340
gcggcgcatt aagcgcggcg ggtgtggtgg ttacgcgcag cgtgaccgct acacttgcca   2400
gcgccctagc gcccgctcct ttcgctttct tcccttcctt tctcgccacg ttcgccggct   2460
ttccccgtca gctctaaat cggggggctcc ctttagggtt ccgatttagt gctttacggc   2520
acctcgaccc caaaaaactt gattagggtg atggttcacg tagtgggcca tcgccctgat   2580
agacggtttt tcgccctttg acgttggagt ccacgttctt taatagtgga ctcttgttcc   2640
aaactggaac aacactcaac cctatctcgg tctattcttt tgatttataa gggattttgc   2700
cgatttcggc ctattggtta aaaaatgagc tgatttaaca aaaatttaac gcgaatttta   2760
acaaaatatt aacgtttaca atttcaggtg gcacttttcg gggaaatgtg cgcggaaccc   2820
ctatttgttt attttctaa atacattcaa atatgtatcc gctcatgaga caataaccct   2880
gataaatgct tcaataatat tgaaaagga agagtatgag tattcaacat ttccgtgtcg   2940
cccttattcc cttttttgcg gcattttgcc ttcctgtttt tgctcaccca gaaacgctgg   3000
tgaaagtaaa agatgctgaa gatcagttgg gtgcacgagt gggttacatc gaactggatc   3060
tcaacagcgg taagatcctt gagagttttc gccccgaaga acgttttcca atgatgagca   3120
cttttaaagt tctgctatgt ggcgcggtat tatcccgtat tgacgccggg caagagcaac   3180
tcggtcgccg catacactat tctcagaatg acttggttga gtactcacca gtcacagaaa   3240
agcatcttac ggatggcatg acagtaagag aattatgcag tgctgccata accatgagtg   3300
ataacactgc ggccaactta cttctgacaa cgatcggagg accgaaggag ctaaccgctt   3360
ttttgcacaa catgggggat catgtaactc gccttgatcg ttgggaaccg gagctgaatg   3420
aagccatacc aaacgacgag cgtgacacca cgatgcctgt agcaatggca acaacgttgc   3480
gcaaactatt aactggcgaa ctacttactc tagcttcccg gcaacaattg atagactgga   3540
tggaggcgga taaagttgca ggaccacttc tgcgctcggc ccttccggct ggctggttta   3600
ttgctgataa atctggagcc ggtgagcgtg gctctcgcgg tatcattgca gcactggggc   3660
```

```
cagatggtaa gccctcccgt atcgtagtta tctacacgac ggggagtcag gcaactatgg    3720
atgaacgaaa tagacagatc gctgagatag gtgcctcact gattaagcat tggtaggaat    3780
taatgatgtc tcgtttagat aaaagtaaag tgattaacag cgcattagag ctgcttaatg    3840
aggtcggaat cgaaggttta acaacccgta aactcgccca gaagctaggt gtagagcagc    3900
ctacattgta ttggcatgta aaaaataagc gggctttgct cgacgcctta gccattgaga    3960
tgttagatag gcaccatact cacttttgcc ctttagaagg ggaaagctgg caagattttt    4020
tacgtaataa cgctaaaagt tttagatgtg ctttactaag tcatcgcgat ggagcaaaag    4080
tacatttagg tacacggcct acagaaaaac agtatgaaac tctcgaaaat caattagcct    4140
ttttatgcca acaaggtttt tcactagaga atgcattata tgcactcagc gcagtggggc    4200
attttacttt aggttgcgta ttggaagatc aagagcatca agtcgctaaa gaagaaaggg    4260
aaacacctac tactgatagt atgccgccat tattacgaca agctatcgaa ttatttgatc    4320
accaaggtgc agagccagcc ttcttattcg gccttgaatt gatcatatgc ggattagaaa    4380
aacaacttaa atgtgaaagt gggtcttaaa agcagcataa cctttttccg tgatggtaac    4440
ttcactagtt taaaaggatc taggtgaaga tcctttttga taatctcatg accaaaatcc    4500
cttaacgtga gttttcgttc cactgagcgt cagaccccgt agaaaagatc aaaggatctt    4560
cttgagatcc ttttttttctg cgcgtaatct gctgcttgca acaaaaaaa ccaccgctac    4620 cagcggtggt ttgtttgccg gatcaagagc taccaactct ttttccgaag gtaactggct    4680
tcagcagagc gcagatacca aatactgtcc ttctagtgta gccgtagtta ggccaccact    4740
tcaagaactc tgtagcaccg cctacatacc tcgctctgct aatcctgtta ccagtggctg    4800
ctgccagtgg cgataagtcg tgtcttaccg ggttggactc aagacgatag ttaccggata    4860
aggcgcagcg gtcgggctga acggggggtt cgtgcacaca gcccagcttg gagcgaacga    4920
cctacaccga actgagatac ctacagcgtg agctatgaga aagcgccacg cttcccgaag    4980
ggagaaaggc ggacaggtat ccggtaagcg gcagggtcgg aacaggagag cgcacgaggg    5040
agcttccagg gggaaacgcc tggtatcttt atagtcctgt cgggtttcgc cacctctgac    5100
ttgagcgtcg attttttgtga tgctcgtcag ggggggcggag cctatggaaa aacgccagca    5160
acgcggcctt tttacggttc ctggccttttt gctggccttt tgctcacatg             5210
```

<210> SEQ ID NO 29
<211> LENGTH: 57
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence (upper/coding strand) encoding amino acid
      sequence of the N-terminus of INFa2b and Strep-tag II (only the
      last two amino acids)"

<400> SEQUENCE: 29
gaaaaaggcg ccagctcttc tgcctgtgat ctgcctcaaa cccacagcct gggtagc       57

<210> SEQ ID NO 30
<211> LENGTH: 57
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence (lower/non-coding strand) encoding amino
      acid sequence of the N-terminus of INFa2b and Strep-tag II (only
      the last two amino acids)"

<400> SEQUENCE: 30

```
gctacccagg ctgtgggttt gaggcagatc acaggcagaa gagctggcgc cttttttc    57
```

<210> SEQ ID NO 31
<211> LENGTH: 19
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of the C-terminus of Strep-tag II and the
      N-terminus of INFa2b"

<400> SEQUENCE: 31

```
Glu Lys Gly Ala Ser Ser Ser Ala Cys Asp Leu Pro Gln Thr His Ser
1               5                   10                  15

Leu Gly Ser
```

<210> SEQ ID NO 32
<211> LENGTH: 3721
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence of pASK-IFNa2b"

<400> SEQUENCE: 32

```
ccatcgaatg gccagatgat taattcctaa ttttttgttga cactctatca ttgatagagt    60
tattttacca ctccctatca gtgatagaga aaagtgaaat gaatagttcg acaaaaatct    120
agataacgag gcaaaaaat gaaaagaca gctatcgcga ttgcagtggc actggctggt    180
ttcgctaccg tagcgcaggc cgctagctgg agccaccgc agttcgaaaa aggcgccagc    240
tcttctgcct gtgatctgcc tcaaacccac agcctgggta gcaggaggac cttgatgctc    300
ctggcacaga tgaggagaat ctctcttttc tcctgcttga aggacagaca tgactttgga    360
tttccccagg aggagtttgg caaccagttc caaaaggctg aaaccatccc tgtcctccat    420
gagatgatcc agcagatctt caatctcttc agcacaaagg actcatctgc tgcttgggat    480 gagacccctcc tagacaaatt ctacactgaa ctctaccagc agctgaatga cctggaagcc    540
tgtgtgatac aggggtggg ggtgacagag actccctga tgaaggagga ctccattctg    600
gctgtgagga aatacttcca agaatcact ctctatctga agagaagaa atacagccct    660 tgtgcctggg aggttgtcag agcagaaatc atgagatctt tttctttgtc aacaaacttg    720
caagaaagtt taagaagtaa ggaataagct tgacctgtga agtgaaaat ggcgcacatt    780 gtgcgacatt ttttttgtct gccgtttacc gctactgcgt cacggatctc cacgcgccct    840
gtagcggcgc attaagcgcg gcgggtgtgg tggttacgcg cagcgtgacc gctacacttg    900
ccagcgccct agcgcccgct cctttcgctt tcttcccttc ctttctcgcc acgttcgccg    960
gctttccccg tcaagctcta atcgggggc tcccttagg gttccgattt agtgctttac    1020
ggcacctcga ccccaaaaaa cttgattagg gtgatggttc acgtagtggg ccatcgccct    1080
gatagacggt ttttcgccct tgacgttgg agtccacgtt ctttaatagt ggactcttgt    1140
tccaaactgg aacaacactc aaccctatct cggtctattc ttttgattta agggattt    1200 tgccgatttc ggcctattgg ttaaaaaatg agctgattta caaaatttt aacgcgaatt    1260 ttaacaaaat attaacgctt acaatttcag gtggcacttt tcggaaat gtgcgcggaa    1320
```

```
cccctatttg tttattttc taaatacatt caaatatgta tccgctcatg agacaataac    1380
cctgataaat gcttcaataa tattgaaaaa ggaagagtat gagtattcaa catttccgtg    1440
tcgcccttat tcccttttt gcggcatttt gccttcctgt ttttgctcac ccagaaacgc    1500
tggtgaaagt aaaagatgct gaagatcagt tgggtgcacg agtgggttac atcgaactgg    1560
atctcaacag cggtaagatc cttgagagtt ttcgccccga agaacgtttt ccaatgatga    1620
gcacttttaa agttctgcta tgtggcgcgg tattatcccg tattgacgcc gggcaagagc    1680
aactcggtcg ccgcatacac tattctcaga atgacttggt tgagtactca ccagtcacag    1740
aaaagcatct tacggatggc atgacagtaa gagaattatg cagtgctgcc ataaccatga    1800
gtgataacac tgcggccaac ttacttctga caacgatcgg aggaccgaag gagctaaccg    1860
cttttttgca caacatgggg gatcatgtaa ctcgccttga tcgttgggaa ccggagctga    1920
atgaagccat accaaacgac gagcgtgaca ccacgatgcc tgtagcaatg gcaacaacgt    1980
tgcgcaaact attaactggc gaactactta ctctagcttc ccggcaacaa ttgatagact    2040
ggatggaggc ggataaagtt gcaggaccac ttctgcgctc ggcccttccg gctggctggt    2100
ttattgctga taaatctgga gccggtgagc gtggctctcg cggtatcatt gcagcactgg    2160
ggccagatgg taagccctcc cgtatcgtag ttatctacac gacggggagt caggcaacta    2220
tggatgaacg aaatagacag atcgctgaga taggtgcctc actgattaag cattggtagg    2280
aattaatgat gtctcgttta gataaaagta agtgattaa cagcgcatta gagctgctta    2340
atgaggtcgg aatcgaaggt ttaacaaccc gtaaactcgc ccagaagcta ggtgtagagc    2400
agcctacatt gtattggcat gtaaaaaata agcgggcttt gctcgacgcc ttagccattg    2460
agatgttaga taggcaccat actcactttt gccctttaga aggggaaagc tggcaagatt    2520
ttttacgtaa taacgctaaa agttttagat gtgctttact aagtcatcgc gatggagcaa    2580
aagtacattt aggtacacgg cctacagaaa acagtatga aactctcgaa atcaattag    2640
ccttttatg ccaacaaggt ttttcactag agaatgcatt atatgcactc agcgcagtgg    2700
ggcattttac tttaggttgc gtattggaag atcaagagca tcaagtcgct aaagaagaaa    2760
gggaaacacc tactactgat agtatgccgc cattattacg acaagctatc gaattatttg    2820
atcaccaagg tgcagagcca gccttcttat tcggccttga attgatcata tgcggattag    2880
aaaaacaact aaatgtgaa agtgggtctt aaaagcagca taaccttttt ccgtgatggt    2940
aacttcacta gtttaaaagg atctaggtga agatccttt tgataatctc atgaccaaaa    3000
tcccttaacg tgagttttcg ttccactgag cgtcagaccc cgtagaaaag atcaaaggat    3060
cttcttgaga tccttttttt ctgcgcgtaa tctgctgctt gcaaacaaaa aaaccaccgc    3120
taccagcggt ggtttgtttg ccggatcaag agctaccaac tctttttccg aaggtaactg    3180
gcttcagcag agcgcagata ccaaatactg tccttctagt gtagccgtag ttaggccacc    3240
acttcaagaa ctctgtagca ccgcctacat acctcgctct gctaatcctg ttaccagtgg    3300
ctgctgccag tggcgataag tcgtgtctta ccgggttgga ctcaagacga tagttaccgg    3360
ataaggcgca gcggtcgggc tgaacggggg gttcgtgcac acagcccagc ttggagcgaa    3420
cgacctacac cgaactgaga tacctacagc gtgagctatg agaaagcgcc acgcttcccg    3480
aagggagaaa ggcggacagg tatccggtaa gcggcagggt cggaacagga gagcgcacga    3540
gggagcttcc agggggaaac gcctggtatc tttatagtcc tgtcgggttt cgccacctct    3600
gacttgagcg tcgatttttg tgatgctcgt caggggggcg gagcctatgg aaaaacgcca    3660
gcaacgcggc cttttacgg ttcctggcct tttgctggcc ttttgctcac atgacccgac    3720
```

<210> SEQ ID NO 33
<211> LENGTH: 90
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence stretch (upper/coding strand) encoding the
      C-terminus of Strep-tag II and the N-terminus of IFNa2b after
      insertion of one PA#1 polymer sequence cassette"

<400> SEQUENCE: 33
gaaaaaggcg ccagctcttc tgccgctcca gctgcacctg ctccagcagc acctgctgca    60
ccagctccgg ctgctcctgc tgcctgtgat                                    90

<210> SEQ ID NO 34
<211> LENGTH: 90
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence stretch (lower/non-coding strand) of the
      C-terminus of Strep-tag II and the N-terminus of IFNa2b after
      insertion of one PA#1 polymer sequence cassette"

<400> SEQUENCE: 34
atcacaggca gcaggagcag ccggagctgg tgcagcaggt gctgctggag caggtgcagc    60
tggagcggca gaagagctgg cgcctttttc                                    90

<210> SEQ ID NO 35
<211> LENGTH: 30
<212> TYPE: PRT
<213> ORGANISM: artificial sequence
<220> FEATURE:
<221> NAME/KEY: source
<223> OTHER INFORMATION: /note="Description of artificial sequence:
      amino acid sequence stretch of the C-terminus of Strep-tag II and
      the N-terminus of IFNa2b ater fusion with one PA#1 polymer
      cassette"

<400> SEQUENCE: 35

Glu Lys Gly Ala Ser Ser Ser Ala Ala Pro Ala Ala Pro Ala Pro Ala
1               5                   10                  15

Ala Pro Ala Ala Pro Ala Pro Ala Ala Pro Ala Ala Cys Asp
            20                  25                  30

<210> SEQ ID NO 36
<211> LENGTH: 381
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of IFNa2b and Strep-tag II fused with the
      PA#1(200) polymer as encoded on pPA#1(200)-IFNa2b"

<400> SEQUENCE: 36

Ala Ser Trp Ser His Pro Gln Phe Glu Lys Gly Ala Ser Ser Ser Ala
1               5                   10                  15

Ala Pro Ala Ala Pro Ala Pro Ala Ala Pro Ala Ala Pro Ala Pro Ala
            20                  25                  30

Ala Pro Ala Ala Ala Pro Ala Ala Pro Ala Pro Ala Ala Pro Ala Ala

```
                35                  40                  45
Pro Ala Pro Ala Ala Pro Ala Ala Pro Ala Ala Pro Pro Ala
 50                  55                  60
Ala Pro Ala Ala Pro Ala Pro Ala Ala Pro Ala Ala Pro Ala Ala
 65                  70                  75                  80
Pro Ala Pro Ala Ala Pro Ala Ala Pro Ala Ala Pro Ala Pro Ala
                 85                  90                  95
Ala Pro Ala Ala Pro Ala Pro Ala Ala Pro Ala Ala Pro Ala Pro Ala
                100                 105                 110
Ala Pro Ala Ala Ala Pro Ala Ala Pro Ala Pro Ala Ala Pro Ala Ala
                115                 120                 125
Pro Ala Pro Ala Ala Pro Ala Ala Pro Ala Ala Pro Ala Pro Ala
                130                 135                 140
Ala Pro Ala Ala Pro Ala Pro Ala Ala Pro Ala Ala Pro Ala Ala
 145                 150                 155                 160
Pro Ala Pro Ala Ala Pro Ala Ala Pro Ala Ala Pro Ala Pro Ala
                165                 170                 175
Ala Pro Ala Ala Pro Ala Pro Ala Ala Pro Ala Ala Pro Ala Pro Ala
                180                 185                 190
Ala Pro Ala Ala Ala Pro Ala Ala Pro Ala Pro Ala Ala Pro Ala Ala
                195                 200                 205
Pro Ala Pro Ala Ala Pro Ala Ala Cys Asp Leu Pro Gln Thr His Ser
 210                 215                 220
Leu Gly Ser Arg Arg Thr Leu Met Leu Leu Ala Gln Met Arg Arg Ile
 225                 230                 235                 240
Ser Leu Phe Ser Cys Leu Lys Asp Arg His Asp Phe Gly Phe Pro Gln
                245                 250                 255
Glu Glu Phe Gly Asn Gln Phe Gln Lys Ala Glu Thr Ile Pro Val Leu
                260                 265                 270
His Glu Met Ile Gln Gln Ile Phe Asn Leu Phe Ser Thr Lys Asp Ser
                275                 280                 285
Ser Ala Ala Trp Asp Glu Thr Leu Leu Asp Lys Phe Tyr Thr Glu Leu
 290                 295                 300
Tyr Gln Gln Leu Asn Asp Leu Glu Ala Cys Val Ile Gln Gly Val Gly
 305                 310                 315                 320
Val Thr Glu Thr Pro Leu Met Lys Glu Asp Ser Ile Leu Ala Val Arg
                325                 330                 335
Lys Tyr Phe Gln Arg Ile Thr Leu Tyr Leu Lys Glu Lys Lys Tyr Ser
                340                 345                 350
Pro Cys Ala Trp Glu Val Val Arg Ala Glu Ile Met Arg Ser Phe Ser
                355                 360                 365
Leu Ser Thr Asn Leu Gln Glu Ser Leu Arg Ser Lys Glu
 370                 375                 380

<210> SEQ ID NO 37
<211> LENGTH: 4321
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence of pPA#1(200)-IFNa2b"

<400> SEQUENCE: 37
ccatcgaatg gccagatgat taattcctaa tttttgttga cactctatca ttgatagagt    60
```

```
tattttacca ctccctatca gtgatagaga aaagtgaaat gaatagttcg acaaaaatct      120
agataacgag ggcaaaaaat gaaaaagaca gctatcgcga ttgcagtggc actggctggt      180
ttcgctaccg tagcgcaggc cgctagctgg agccacccgc agttcgaaaa aggcgccagc      240
tcttctgccg ctccagctgc acctgctcca gcagcacctg ctgcaccagc tccggctgct      300
cctgctgccg ctccagctgc acctgctcca gcagcacctg ctgcaccagc tccggctgct      360
cctgctgccg ctccagctgc acctgctcca gcagcacctg ctgcaccagc tccggctgct      420
cctgctgccg ctccagctgc acctgctcca gcagcacctg ctgcaccagc tccggctgct      480
cctgctgccg ctccagctgc acctgctcca gcagcacctg ctgcaccagc tccggctgct      540
cctgctgccg ctccagctgc acctgctcca gcagcacctg ctgcaccagc tccggctgct      600
cctgctgccg ctccagctgc acctgctcca gcagcacctg ctgcaccagc tccggctgct      660
cctgctgccg ctccagctgc acctgctcca gcagcacctg ctgcaccagc tccggctgct      720
cctgctgccg ctccagctgc acctgctcca gcagcacctg ctgcaccagc tccggctgct      780
cctgctgccg ctccagctgc acctgctcca gcagcacctg ctgcaccagc tccggctgct      840
cctgctgcct gtgatctgcc tcaaacccac agcctgggta gcaggaggac cttgatgctc      900
ctggcacaga tgaggagaat ctctcttttc tcctgcttga aggacagaca tgactttgga      960
tttccccagg aggagtttgg caaccagttc caaaaggctg aaaccatccc tgtcctccat     1020
gagatgatcc agcagatctt caatctcttc agcacaaagg actcatctgc tgcttgggat     1080
gagaccctcc tagacaaatt ctacactgaa ctctaccagc agctgaatga cctggaagcc     1140
tgtgtgatac aggggggtggg ggtgacagag actcccctga tgaaggagga ctccattctg     1200
gctgtgagga aatacttcca aagaatcact ctctatctga agagaagaa atacagccct     1260 tgtgcctggg aggttgtcag agcagaaatc atgagatctt tttctttgtc aacaaacttg     1320
caagaaagtt taagaagtaa ggaataagct tgacctgtga agtgaaaaat ggcgcacatt     1380
gtgcgacatt ttttttgtct gccgtttacc gctactgcgt cacgatctc cacgcgccct     1440 gtagcggcgc attaagcgcg gcgggtgtgg tggttacgcg cagcgtgacc gctacacttg     1500
ccagcgccct agcgcccgct cctttcgctt tcttcccttc ctttctcgcc acgttcgccg     1560
gctttccccg tcaagctcta atcgggggc tcccttttagg gttccgattt agtgctttac     1620
ggcacctcga ccccaaaaaa cttgattagg gtgatggttc acgtagtggg ccatcgccct     1680
gatagacggt ttttcgccct ttgacgttgg agtccacgtt ctttaatagt ggactcttgt     1740
tccaaactgg aacaacactc aaccctatct cggtctattc ttttgattta taagggattt     1800
tgccgatttc ggcctattgg ttaaaaaatg agctgattta acaaaaattt aacgcgaatt     1860
ttaacaaaat attaacgctt acaatttcag gtggcacttt tcggggaaat gtgcgcggaa     1920 ccccctatttg tttatttttc taaatacatt caaatatgta tccgctcatg agacaataac     1980
cctgataaat gcttcaataa tattgaaaaa ggaagagtat gagtattcaa catttccgtg     2040
tcgcccttat tccctttttt gcggcatttt gccttcctgt ttttgctcac ccagaaacgc     2100
tggtgaaagt aaaagatgct gaagatcagt tgggtgcacg agtgggttac atcgaactgg     2160
atctcaacag cggtaagatc cttgagagtt ttcgccccga agaacgtttt ccaatgatga     2220
gcacttttaa agttctgcta tgtggcgcgg tattatcccg tattgacgcc gggcaagagc     2280
aactcggtcg ccgcatacac tattctcaga atgacttggt tgagtactca ccagtcacag     2340
aaaagcatct tacggatggc atgacagtaa gagaattatg cagtgctgcc ataaccatga     2400
gtgataacac tgcggccaac ttacttctga caacgatcgg aggaccgaag gagctaaccg     2460
```

```
cttttttgca acatgggg gatcatgtaa ctcgccttga tcgttgggaa ccggagctga    2520
atgaagccat accaaacgac gagcgtgaca ccacgatgcc tgtagcaatg caacaacgt    2580 tgcgcaaact attaactggc gaactactta ctctagcttc ccggcaacaa ttgatagact    2640
ggatggaggc ggataaagtt gcaggaccac ttctgcgctc ggcccttccg gctggctggt    2700
ttattgctga taaatctgga gccggtgagc gtggctctcg cggtatcatt gcagcactgg    2760
ggccagatgg taagccctcc cgtatcgtag ttatctacac gacggggagt caggcaacta    2820
tggatgaacg aaatagacag atcgctgaga taggtgcctc actgattaag cattggtagg    2880
aattaatgat gtctcgttta gataaaagta aagtgattaa cagcgcatta gagctgctta    2940
atgaggtcgg aatcgaaggt ttaacaaccc gtaaactcgc ccagaagcta ggtgtagagc    3000
agcctacatt gtattggcat gtaaaaaata agcgggcttt gctcgacgcc ttagccattg    3060
agatgttaga taggcaccat actcactttt gccctttaga aggggaaagc tggcaagatt    3120
ttttacgtaa taacgctaaa agttttagat gtgctttact aagtcatcgc gatggagcaa    3180
aagtacattt aggtacacgg cctacagaaa acagtatga aactctcgaa atcaattag    3240 ccttttatg ccaacaaggt ttttcactag agaatgcatt atatgcactc agcgcagtgg    3300
ggcattttac tttaggttgc gtattggaag atcaagagca tcaagtcgct aaagaagaaa    3360
gggaaacacc tactactgat agtatgccgc cattattacg acaagctatc gaattatttg    3420
atcaccaagg tgcagagcca gccttcttat tcggccttga attgatcata tgcggattag    3480
aaaaacaact taaatgtgaa agtgggtctt aaaagcagca taacctttttt ccgtgatggt    3540 aacttcacta gtttaaaagg atctaggtga agatcctttt tgataatctc atgaccaaaa    3600
tcccttaacg tgagttttcg ttccactgag cgtcagaccc cgtagaaaag atcaaaggat    3660
cttcttgaga tccttttttt ctgcgcgtaa tctgctgctt gcaaacaaaa aaaccaccgc    3720
taccagcggt ggtttgtttg ccggatcaag agctaccaac tcttttttccg aaggtaactg    3780 gcttcagcag agcgcagata ccaaatactg tccttctagt gtagccgtag ttaggccacc    3840
acttcaagaa ctctgtagca ccgcctacat acctcgctct gctaatcctg ttaccagtgg    3900
ctgctgccag tggcgataag tcgtgtctta ccgggttgga ctcaagacga tagttaccgg    3960
ataaggcgca gcggtcgggc tgaacggggg gttcgtgcac acagcccagc ttggagcgaa    4020
cgacctacac cgaactgaga tacctacagc gtgagctatg agaaagcgcc acgcttcccg    4080
aagggagaaa ggcggacagg tatccggtaa gcggcagggt cggaacagga gagcgcacga    4140
gggagcttcc agggggaaac gcctggtatc tttatagtcc tgtcgggttt cgccacctct    4200
gacttgagcg tcgatttttg tgatgctcgt caggggggcg gagcctatgg aaaaacgcca    4260
gcaacgcggc ctttttacgg ttcctggcct tttgctggcc ttttgctcac atgacccgac    4320
a                                                                   4321
```

<210> SEQ ID NO 38
<211> LENGTH: 54
<212> TYPE: DNA
<213> ORGANISM: artificial sequence
<220> FEATURE:
<221> NAME/KEY: source
<223> OTHER INFORMATION: /note="Description of artificial sequence:
    nucleic acid sequence stretch (upper/ coding strand) on
    pASK75-His6-hGH encoding the amino acid sequence around the
    N-terminus of His6-hGH"

<400> SEQUENCE: 38

```
gccgctagcc atcaccacca tcaccatggc gccagctctt ctgccttccc aacc        54
```

<210> SEQ ID NO 39
<211> LENGTH: 54
<212> TYPE: DNA
<213> ORGANISM: artificial sequence
<220> FEATURE:
<221> NAME/KEY: source
<223> OTHER INFORMATION: /note="Description of artificial sequence:
    nucleic acid sequence stretch (lower/non-coding strand) on
    pASK75-His6-hGH encoding the amino acid sequence around the
    N-terminus of hGH"

<400> SEQUENCE: 39

```
ggttgggaag gcagaagagc tggcgccatg gtgatggtgg tgatggctag cggc        54
```

<210> SEQ ID NO 40
<211> LENGTH: 18
<212> TYPE: PRT
<213> ORGANISM: artificial sequence
<220> FEATURE:
<221> NAME/KEY: source
<223> OTHER INFORMATION: /note="Description of artificial sequence:
    amino acid sequence stretch of the N-terminus of His6-hGH as
    encoded on pASK75-His6-hGH"

<400> SEQUENCE: 40

Ala Ala Ser His His His His His His Gly Ala Ser Ser Ser Ala Phe
1               5                   10                  15

Pro Thr

<210> SEQ ID NO 41
<211> LENGTH: 3793
<212> TYPE: DNA
<213> ORGANISM: artificial sequence
<220> FEATURE:
<221> NAME/KEY: source
<223> OTHER INFORMATION: /note="Description of artificial sequence:
    nucleic acid sequence of pASK75-His6-hGH"

<400> SEQUENCE: 41

```
acccgacacc atcgaatggc cagatgatta attcctaatt tttgttgaca ctctatcatt    60
gatagagtta ttttaccact ccctatcagt gatagagaaa agtgaaatga atagttcgac   120
aaaaatctag ataacgaggg caaaaaatga aaaagacagc tatcgcgatt gcagtggcac   180
tggctggttt cgctaccgta gcgcaggccg ctagccatca ccaccatcac catggcgcca   240
gctcttctgc cttcccaacc attcccttat ccaggctttt tgacaacgct atgctccgcg   300
cccatcgtct gcaccagctg gcctttgaca cctaccagga gtttgaagaa gcctatatcc   360
caaaggaaca gaagtattca ttcctgcaga accccagac ctccctctgt ttctcagagt   420
ctattccgac accctccaac agggaggaaa cacaacagaa atccaaccta gagctgctcc   480
gcatctccct gctgctcatc agtcgtggc tggagcccgt gcagttcctc aggagtgtct   540
tcgccaacag cctggtgtac ggcgcctctg acagcaacgt ctatgacctc taaaggacc   600
tagaggaagg catccaaacg ctgatgggga ggctggaaga tggcagcccc cggactgggc   660
agatcttcaa gcagacctac agcaagttcg acacaaactc acacaacgat gacgcactac   720
tcaagaacta cgggctgctc tactgcttca ggaaggacat ggacaaggtc gagacattcc   780
tgcgcatcgt gcagtgccgc tctgtggagg gcagctgtgg cttctaagct tgacctgtga   840
agtgaaaaat ggcgcacatt gtgcgacatt ttttttgtct gccgtttacc gctactgcgt   900
cacggatctc cacgcgccct gtagcggcgc attaagcgcg gcgggtgtgg tggttacgcg   960
```

```
cagcgtgacc gctacacttg ccagcgccct agcgcccgct cctttcgctt tcttcccttc   1020
ctttctcgcc acgttcgccg gctttccccg tcaagctcta atcgggggc tcccttagg    1080 gttccgattt agtgctttac ggcacctcga ccccaaaaaa cttgattagg gtgatggttc   1140
acgtagtggg ccatcgccct gatagacggt ttttcgccct ttgacgttgg agtccacgtt   1200
ctttaatagt ggactcttgt tccaaactgg aacaacactc aaccctatct cggtctattc   1260
ttttgattta taagggattt tgccgatttc ggcctattgg ttaaaaatg agctgattta    1320 acaaaattt aacgcgaatt ttaacaaaat attaacgttt acaatttcag gtggcacttt    1380
tcggggaaat gtgcgcggaa cccctatttg tttattttc taaatacatt caaatatgta    1440
tccgctcatg agacaataac cctgataaat gcttcaataa tattgaaaaa ggaagagtat   1500
gagtattcaa catttccgtg tcgcccttat tccctttttt gcggcatttt gccttcctgt   1560
ttttgctcac ccagaaacgc tggtgaaagt aaaagatgct gaagatcagt tgggtgcacg   1620
agtgggttac atcgaactgg atctcaacag cggtaagatc cttgagagtt tcgccccga    1680 agaacgtttt ccaatgatga gcacttttaa agttctgcta tgtggcgcgg tattatcccg   1740
tattgacgcc gggcaagagc aactcggtcg ccgcatacac tattctcaga atgacttggt   1800
tgagtactca ccagtcacag aaaagcatct tacggatggc atgacagtaa gagaattatg   1860
cagtgctgcc ataaccatga gtgataacac tgcggccaac ttacttctga caacgatcgg   1920
aggaccgaag gagctaaccg cttttttgca caacatgggg gatcatgtaa ctcgccttga   1980
tcgttgggaa ccggagctga atgaagccat accaaacgac gagcgtgaca ccacgatgcc   2040
tgtagcaatg gcaacaacgt tgcgcaaact attaactggc gaactactta ctctagcttc   2100
ccggcaacaa ttgatagact ggatggaggc ggataaagtt gcaggaccac ttctgcgctc   2160
ggcccttccg gctggctggt ttattgctga taaatctgga gccggtgagc gtggctctcg   2220
cggtatcatt gcagcactgg ggccagatgg taagccctcc cgtatcgtag ttatctacac   2280 gacgggagt caggcaacta tggatgaacg aaatagacag atcgctgaga taggtgcctc    2340
actgattaag cattggtagg aattaatgat gtctcgttta gataaaagta aagtgattaa   2400
cagcgcatta gagctgctta atgaggtcgg aatcgaaggt ttaacaaccc gtaaactcgc   2460
ccagaagcta ggtgtagagc agcctacatt gtattggcat gtaaaaaata gcgggctttg   2520
gctcgacgcc ttagccattg agatgttaga taggcaccat actcactttt gccctttaga   2580
aggggaaagc tggcaagatt ttttacgtaa taacgctaaa agttttagat gtgctttact   2640
aagtcatcgc gatggagcaa aagtacattt aggtacacgg cctacagaaa acagtatga    2700 aactctcgaa aatcaattag ccttttatg ccaacaaggt ttttcactag agaatgcatt    2760
atatgcactc agcgcagtgg gcatttttac tttaggttgc gtattggaag atcaagagca   2820
tcaagtcgct aaagaagaaa gggaaacacc tactactgat agtatgccgc cattattacg   2880
acaagctatc gaattatttg atcaccaagg tgcagagcca gccttcttat tcggccttga   2940
attgatcata tgcggattag aaaaacaact aaatgtgaa agtgggtctt aaaagcagca    3000
taaccttttt ccgtgatggt aacttcacta gtttaaaagg atctaggtga agatcctttt   3060
tgataatctc atgaccaaaa tcccttaacg tgagttttcg ttccactgag cgtcagaccc   3120
cgtagaaaag atcaaaggat cttcttgaga tcctttttt ctgcgcgtaa tctgctgctt    3180
gcaaacaaaa aaaccaccgc taccagcggt ggtttgtttg ccggatcaag agctaccaac   3240
tctttttccg aaggtaactg gcttcagcag agcgcagata ccaaatactg tccttctagt   3300
```

```
gtagccgtag ttaggccacc acttcaagaa ctctgtagca ccgcctacat acctcgctct    3360
gctaatcctg ttaccagtgg ctgctgccag tggcgataag tcgtgtctta ccgggttgga    3420
ctcaagacga tagttaccgg ataaggcgca gcggtcgggc tgaacggggg gttcgtgcac    3480
acagcccagc ttggagcgaa cgacctacac cgaactgaga tacctacagc gtgagctatg    3540
agaaagcgcc acgcttcccg aagggagaaa ggcggacagg tatccggtaa gcggcagggt    3600
cggaacagga gagcgcacga gggagcttcc aggggggaaac gcctggtatc tttatagtcc    3660
tgtcgggttt cgccacctct gacttgagcg tcgattttg tgatgctcgt cagggggggcg    3720 gagcctatgg aaaaacgcca gcaacgcggc ctttttacgg ttcctggcct tttgctggcc    3780
ttttgctcac atg                                                      3793
```

<210> SEQ ID NO 42
<211> LENGTH: 114
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence (upper/coding-strand) stretch encoding amino
      acid sequence of the N-terminus of His6-hGH after insertion of
      the PA#1(20) polymer"

<400> SEQUENCE: 42

```
gccgctagcc atcaccacca tcaccatggc gccagctctt ctgccgctcc agctgcacct    60
gctccagcag cacctgctgc accagctccg gctgctcctg ctgccttccc aacc          114
```

<210> SEQ ID NO 43
<211> LENGTH: 114
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence (lower/non-coding strand) encoding the
      N-terminus of hGH after insertion of one PA#1 polymer sequence
      cassette"

<400> SEQUENCE: 43

```
ggttgggaag gcagcaggag cagccggagc tggtgcagca ggtgctgctg gagcaggtgc    60
agctggagcg gcagaagagc tggcgccatg gtgatggtgg tgatggctag cggc          114
```

<210> SEQ ID NO 44
<211> LENGTH: 38
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of the N-terminus of His6-hGH after insertion
      of the PA#1(20) polymer"

<400> SEQUENCE: 44

```
Ala Ala Ser His His His His His His Gly Ala Ser Ser Ser Ala Ala
1               5                   10                  15

Pro Ala Ala Pro Ala Pro Ala Ala Pro Ala Ala Pro Ala Pro Ala Ala
            20                  25                  30

Pro Ala Ala Phe Pro Thr
        35
```

<210> SEQ ID NO 45
<211> LENGTH: 405

```
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of mature His6-PA#1(200)-hGH as encoded on
      pASK75-His6-PA#1(200)-hGH"

<400> SEQUENCE: 45

Ala Ser His His His His His Gly Ala Ser Ser Ala Ala Pro
1               5                   10                  15

Ala Ala Pro Ala Pro Ala Ala Pro Ala Ala Pro Ala Ala Pro
                20                  25                  30

Ala Ala Ala Pro Ala Ala Pro Ala Pro Ala Ala Pro Ala Ala Pro Ala
            35                  40                  45

Pro Ala Ala Pro Ala Ala Ala Pro Ala Ala Pro Ala Pro Ala Ala Pro
    50                      55                  60

Ala Ala Pro Ala Pro Ala Ala Pro Ala Ala Pro Ala Ala Pro Ala
65                  70                  75                  80

Pro Ala Ala Pro Ala Ala Pro Ala Ala Pro Ala Ala Ala Pro
                85                  90                  95

Ala Ala Pro Ala Pro Ala Ala Pro Ala Ala Pro Ala Ala Pro
                100                 105                 110

Ala Ala Ala Pro Ala Ala Pro Ala Pro Ala Ala Pro Ala Ala Pro Ala
            115                 120                 125

Pro Ala Ala Pro Ala Ala Ala Pro Ala Ala Pro Ala Pro Ala Ala Pro
    130                     135                 140

Ala Ala Pro Ala Pro Ala Ala Pro Ala Ala Pro Ala Ala Pro Ala
145                 150                 155                 160

Pro Ala Ala Pro Ala Ala Pro Ala Ala Pro Ala Ala Ala Pro
                165                 170                 175

Ala Ala Pro Ala Pro Ala Ala Pro Ala Ala Pro Ala Ala Pro
                180                 185                 190

Ala Ala Ala Pro Ala Ala Pro Ala Pro Ala Ala Pro Ala Ala Pro Ala
            195                 200                 205

Pro Ala Ala Pro Ala Ala Phe Pro Thr Ile Pro Leu Ser Arg Leu Phe
    210                     215                 220

Asp Asn Ala Met Leu Arg Ala His Arg Leu His Gln Leu Ala Phe Asp
225                 230                 235                 240

Thr Tyr Gln Glu Phe Glu Glu Ala Tyr Ile Pro Lys Glu Gln Lys Tyr
                245                 250                 255

Ser Phe Leu Gln Asn Pro Gln Thr Ser Leu Cys Phe Ser Glu Ser Ile
                260                 265                 270

Pro Thr Pro Ser Asn Arg Glu Glu Thr Gln Gln Lys Ser Asn Leu Glu
            275                 280                 285

Leu Leu Arg Ile Ser Leu Leu Leu Ile Gln Ser Trp Leu Glu Pro Val
290                 295                 300

Gln Phe Leu Arg Ser Val Phe Ala Asn Ser Leu Val Tyr Gly Ala Ser
305                 310                 315                 320

Asp Ser Asn Val Tyr Asp Leu Leu Lys Asp Leu Glu Glu Gly Ile Gln
                325                 330                 335

Thr Leu Met Gly Arg Leu Glu Asp Gly Ser Pro Arg Thr Gly Gln Ile
            340                 345                 350

Phe Lys Gln Thr Tyr Ser Lys Phe Asp Thr Asn Ser His Asn Asp Asp
            355                 360                 365
```

```
Ala Leu Leu Lys Asn Tyr Gly Leu Leu Tyr Cys Phe Arg Lys Asp Met
        370                 375                 380
Asp Lys Val Glu Thr Phe Leu Arg Ile Val Gln Cys Arg Ser Val Glu
385                 390                 395                 400
Gly Ser Cys Gly Phe
            405

<210> SEQ ID NO 46
<211> LENGTH: 4393
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence of pASK75-His6-PA#1(200)-hGH"

<400> SEQUENCE: 46
```

| | | | | | |
|---|---|---|---|---|---|
| gacccgacac | catcgaatgg | ccagatgatt | aattcctaat | ttttgttgac | actctatcat | 60 |
| tgatagagtt | attttaccac | tccctatcag | tgatagagaa | agtgaaatg | aatagttcga | 120 |
| caaaaatcta | gataacgagg | gcaaaaaatg | aaaagacag | ctatcgcgat | tgcagtggca | 180 |
| ctggctggtt | tcgctaccgt | agcgcaggcc | gctagccatc | accaccatca | ccatggcgcc | 240 |
| agctcttctg | ccgctccagc | tgcacctgct | ccagcagcac | ctgctgcacc | agctccggct | 300 |
| gctcctgctg | ccgctccagc | tgcacctgct | ccagcagcac | ctgctgcacc | agctccggct | 360 |
| gctcctgctg | ccgctccagc | tgcacctgct | ccagcagcac | ctgctgcacc | agctccggct | 420 |
| gctcctgctg | ccgctccagc | tgcacctgct | ccagcagcac | ctgctgcacc | agctccggct | 480 |
| gctcctgctg | ccgctccagc | tgcacctgct | ccagcagcac | ctgctgcacc | agctccggct | 540 |
| gctcctgctg | ccgctccagc | tgcacctgct | ccagcagcac | ctgctgcacc | agctccggct | 600 |
| gctcctgctg | ccgctccagc | tgcacctgct | ccagcagcac | ctgctgcacc | agctccggct | 660 |
| gctcctgctg | ccgctccagc | tgcacctgct | ccagcagcac | ctgctgcacc | agctccggct | 720 |
| gctcctgctg | ccgctccagc | tgcacctgct | ccagcagcac | ctgctgcacc | agctccggct | 780 |
| gctcctgctg | ccgctccagc | tgcacctgct | ccagcagcac | ctgctgcacc | agctccggct | 840 |
| gctcctgctg | ccttcccaac | cattccctta | tccaggcttt | ttgacaacgc | tatgctccgc | 900 |
| gcccatcgtc | tgcaccagct | ggcctttgac | acctaccagg | agtttgaaga | agcctatatc | 960 |
| ccaaaggaac | agaagtattc | attcctgcag | aacccccaga | cctccctctg | tttctcagag | 1020 |
| tctattccga | caccctccaa | cagggaggaa | acacaacaga | atccaacct | agagctgctc | 1080 |
| cgcatctccc | tgctgctcat | ccagtcgtgg | ctggagcccg | tgcagttcct | caggagtgtc | 1140 |
| ttcgccaaca | gcctggtgta | cggcgcctct | gacagcaacg | tctatgacct | cctaaaggac | 1200 |
| ctagaggaag | gcatccaaac | gctgatgggg | aggctggaag | atggcagccc | ccggactggg | 1260 |
| cagatcttca | agcagaccta | cagcaagttc | gacacaaact | cacacaacga | tgacgcacta | 1320 |
| ctcaagaact | acgggctgct | ctactgcttc | aggaaggaca | tggacaaggt | cgagacattc | 1380 |
| ctgcgcatcg | tgcagtgccg | ctctgtggag | ggcagctgtg | gcttctaagc | ttgacctgtg | 1440 |
| aagtgaaaaa | tggcgcacat | tgtgcgacat | ttttttgtc | tgccgtttac | cgctactgcg | 1500 |
| tcacggatct | ccacgcgccc | tgtagcgcg | cattaagcgc | ggcgggtgtg | gtggttacgc | 1560 |
| gcagcgtgac | cgctacactt | gccagcgccc | tagcgcccgc | tcctttcgct | ttcttccctt | 1620 |
| cctttctcgc | cacgttcgcc | ggctttcccc | gtcaagctct | aaatcggggg | ctccctttag | 1680 |
| ggttccgatt | tagtgcttta | cggcacctcg | accccaaaaa | acttgattag | ggtgatggtt | 1740 |

```
cacgtagtgg gccatcgccc tgatagacgg ttttttcgccc tttgacgttg gagtccacgt    1800
tctttaatag tggactcttg ttccaaactg aacaacact  caaccctatc tcggtctatt    1860
cttttgattt ataagggatt ttgccgattt cggcctattg gttaaaaaat gagctgattt    1920
aacaaaaatt taacgcgaat tttaacaaaa tattaacgtt tacaatttca ggtggcactt    1980
ttcggggaaa tgtgcgcgga acccctattt gtttattttt ctaaatacat tcaaatatgt    2040
atccgctcat gagacaataa ccctgataaa tgcttcaata atattgaaaa aggaagagta    2100
tgagtattca acatttccgt gtcgccctta ttccctttttt tgcggcattt tgccttcctg    2160
tttttgctca cccagaaacg ctggtgaaag taaaagatgc tgaagatcag ttgggtgcac    2220
gagtgggtta catcgaactg gatctcaaca gcggtaagat ccttgagagt tttcgccccg    2280
aagaacgttt tccaatgatg agcacttttta aagttctgct atgtggcgcg gtattatccc    2340
gtattgacgc cgggcaagag caactcggtc gccgcataca ctattctcag aatgacttgg    2400
ttgagtactc accagtcaca gaaaagcatc ttacggatgg catgacagta agagaattat    2460
gcagtgctgc cataaccatg agtgataaca ctgcggccaa cttacttctg acaacgatcg    2520
gaggaccgaa ggagctaacc gcttttttgc acaacatggg ggatcatgta actcgccttg    2580
atcgttggga accggagctg aatgaagcca taccaaacga cgagcgtgac accacgatgc    2640
ctgtagcaat ggcaacaacg ttgcgcaaac tattaactgg cgaactactt actctagctt    2700
cccggcaaca attgatagac tggatggagg cggataaagt tgcaggacca cttctgcgct    2760
cggcccttcc ggctggctgg tttattgctg ataaatctgg agccggtgag cgtggctctc    2820
gcggtatcat tgcagcactg gggccagatg gtaagccctc ccgtatcgta gttatctaca    2880
cgacggggag tcaggcaact atggatgaac gaaatagaca gatcgctgag ataggtgcct    2940
cactgattaa gcattggtag gaattaatga tgtctcgttt agataaaagt aaagtgatta    3000
acagcgcatt agagctgctt aatgaggtcg gaatcgaagg tttaacaacc cgtaaactcg    3060
cccagaagct aggtgtagag cagcctacat tgtattggca tgtaaaaaat aagcgggctt    3120
tgctcgacgc cttagccatt gagatgttag ataggcacca tactcacttt tgccctttag    3180
aaggggaaag ctggcaagat ttttttacgta ataacgctaa aagttttaga tgtgctttac    3240
taagtcatcg cgatggagca aaagtacatt taggtacacg gcctacagaa aaacagtatg    3300
aaactctcga aaatcaatta gcctttttat gccaacaagg ttttttcacta gagaatgcat    3360
tatatgcact cagcgcagtg gggcattttta ctttaggttg cgtattggaa gatcaagagc    3420
atcaagtcgc taaagaagaa agggaaacac ctactactga tagtatgccg ccattattac    3480
gacaagctat cgaattattt gatcaccaag gtgcagagcc agccttctta ttcggccttg    3540
aattgatcat atgcggatta gaaaaacaac ttaaatgtga agtgggtct  taaaagcagc    3600
ataaccttttt tccgtgatgg taacttcact agtttaaaag gatctaggtg aagatccttt    3660
ttgataatct catgaccaaa atcccttaac gtgagttttc gttccactga gcgtcagacc    3720
ccgtagaaaa gatcaaagga tcttcttgag atccttttttt tctgcgcgta atctgctgct    3780
tgcaaacaaa aaaaccaccg ctaccagcgg tggtttgttt gccggatcaa gagctaccaa    3840
ctcttttttcc gaaggtaact ggcttcagca gagcgcagat accaaatact gtccttctag    3900
tgtagccgta gttaggccac cacttcaaga actctgtagc accgcctaca tacctcgctc    3960
tgctaatcct gttaccagtg gctgctgcca gtggcgataa gtcgtgtctt accgggttgg    4020
actcaagacg atagttaccg gataaggcgc agcggtcggg ctgaacgggg ggttcgtgca    4080
cacagcccag cttggagcga acgacctaca ccgaactgag atacctacag cgtgagctat    4140
```

```
gagaaagcgc cacgcttccc gaagggagaa aggcggacag gtatccggta agcggcaggg    4200
tcggaacagg agagcgcacg agggagcttc caggggggaaa cgcctggtat ctttatagtc    4260
ctgtcgggtt tcgccacctc tgacttgagc gtcgattttt gtgatgctcg tcagggggc     4320 ggagcctatg aaaaacgcc agcaacgcgg cctttttacg gttcctggcc ttttgctggc     4380
cttttgctca cat                                                        4393
```

<210> SEQ ID NO 47
<211> LENGTH: 404
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of His6-PA#1(200)-hGH as encoded on
      pCHO-PA#1(200)-hGH"

<400> SEQUENCE: 47

```
Ser His His His His His Gly Ala Ser Ser Ala Ala Pro Ala
1               5                   10                  15

Ala Pro Ala Pro Ala Ala Pro Ala Ala Pro Ala Pro Ala Ala Pro Ala
            20                  25                  30

Ala Ala Pro Ala Ala Pro Ala Pro Ala Ala Pro Ala Ala Pro Ala Pro
        35                  40                  45

Ala Ala Pro Ala Ala Ala Pro Ala Ala Pro Ala Pro Ala Ala Pro Ala
    50                  55                  60

Ala Pro Ala Pro Ala Ala Pro Ala Ala Ala Pro Ala Ala Pro Ala Pro
65                  70                  75                  80

Ala Ala Pro Ala Ala Pro Ala Pro Ala Ala Pro Ala Ala Ala Pro Ala
                85                  90                  95

Ala Pro Ala Pro Ala Ala Pro Ala Ala Pro Ala Ala Ala Pro Ala Ala
            100                 105                 110

Ala Ala Pro Ala Ala Pro Ala Pro Ala Ala Pro Ala Ala Pro Ala Pro
        115                 120                 125

Ala Ala Pro Ala Ala Ala Pro Ala Ala Pro Ala Pro Ala Ala Pro Ala
    130                 135                 140

Ala Pro Ala Pro Ala Ala Pro Ala Ala Ala Pro Ala Ala Pro Ala Pro
145                 150                 155                 160

Ala Ala Pro Ala Ala Pro Ala Ala Pro Ala Ala Ala Ala Pro Ala
                165                 170                 175

Ala Pro Ala Pro Ala Ala Pro Ala Ala Pro Ala Ala Ala Pro Ala
            180                 185                 190

Ala Ala Pro Ala Ala Pro Ala Pro Ala Ala Pro Ala Ala Pro Ala Pro
        195                 200                 205

Ala Ala Pro Ala Ala Phe Pro Thr Ile Pro Leu Ser Arg Leu Phe Asp
    210                 215                 220

Asn Ala Met Leu Arg Ala His Arg Leu His Gln Leu Ala Phe Asp Thr
225                 230                 235                 240

Tyr Gln Glu Phe Glu Glu Ala Tyr Ile Pro Lys Glu Gln Lys Tyr Ser
                245                 250                 255

Phe Leu Gln Asn Pro Gln Thr Ser Leu Cys Phe Ser Glu Ser Ile Pro
            260                 265                 270

Thr Pro Ser Asn Arg Glu Glu Thr Gln Gln Lys Ser Asn Leu Glu Leu
        275                 280                 285

Leu Arg Ile Ser Leu Leu Leu Ile Gln Ser Trp Leu Glu Pro Val Gln
```

```
                  290               295                300
Phe Leu Arg Ser Val Phe Ala Asn Ser Leu Val Tyr Gly Ala Ser Asp
305                 310                 315                 320

Ser Asn Val Tyr Asp Leu Leu Lys Asp Leu Glu Glu Gly Ile Gln Thr
            325                 330                 335

Leu Met Gly Arg Leu Glu Asp Gly Ser Pro Arg Thr Gly Gln Ile Phe
            340                 345                 350

Lys Gln Thr Tyr Ser Lys Phe Asp Thr Asn Ser His Asn Asp Asp Ala
        355                 360                 365

Leu Leu Lys Asn Tyr Gly Leu Leu Tyr Cys Phe Arg Lys Asp Met Asp
    370                 375                 380

Lys Val Glu Thr Phe Leu Arg Ile Val Gln Cys Arg Ser Val Glu Gly
385                 390                 395                 400

Ser Cys Gly Phe

<210> SEQ ID NO 48
<211> LENGTH: 6653
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence of pCHO-PA#1(200)-hGH"

<400> SEQUENCE: 48
ctattctata gtgtcaccta aatgctagag ctcgctgatc agcctcgact gtgccttcta      60
gttgccagcc atctgttgtt tgcccctccc ccgtgccttc cttgaccctg gaaggtgcca     120
ctcccactgt cctttcctaa taaaatgagg aaattgcatc gcattgtctg agtaggtgtc     180
attctattct ggggggtggg gtggggcagg acagcaaggg ggaggattgg gaagacaata     240
gcaggcatgc tggggatgcg gtgggctcta tggcttctga ggcggaaaga accagctggg     300
gctctagggg gtatccccac gcgccctgta gcggcgcatt aagcgcggcg ggtgtggtgg     360
ttacgcgcag cgtgaccgct acacttgcca gcgccctagc gcccgctcct ttcgctttct     420
tcccttcctt tctcgccacg ttcgccggct tccccgtcca gctctaaat cggggcatcc     480 ctttagggtt ccgatttagt gctttacggc acctcgaccc caaaaaactt gattagggtg     540
atggttcacg tagtgggcca tcgccctgat agacggtttt tcgccctttg acgttggagt     600
ccacgttctt taatagtgga ctcttgttcc aaactggaac aacactcaac cctatctcgg     660
tctattcttt tgatttataa gggattttgg ggatttcggc ctattggtta aaaaatgagc     720
tgatttaaca aaaatttaac gcgaattaat tctgtggaat gtgtgtcagt tagggtgtgg     780
aaagtcccca ggctcccag gcaggcagaa gtatgcaaag catgcatctc aattagtcag     840
caaccaggtg tggaaagtcc ccaggctccc cagcaggcag aagtatgcaa agcatgcatc     900
tcaattagtc agcaaccata gtcccgcccc taactccgcc catcccgccc ctaactccgc     960
ccagttccgc ccattctccg ccccatggct gactaatttt ttttatttat gcagaggccg    1020
aggccgcctc tgcctctgag ctattccaga agtagtgagg aggcttttttt ggaggcctag    1080 gcttttgcaa aaagctcccg ggagcttgta tatccatttt cggatctgat caagagacag    1140
gatgaggatc gtttcgcatg attgaacaag atggattgca cgcaggttct ccggccgctt    1200
gggtggagag gctattcggc tatgactggg cacaacagac aatcggctgc tctgatgccg    1260
ccgtgttccg gctgtcagcg caggggcgcc cggttctttt tgtcaagacc gacctgtccg    1320
gtgccctgaa tgaactgcag gacgaggcag cgcggctatc gtggctggcc acgacgggcg    1380
```

```
ttccttgcgc agctgtgctc gacgttgtca ctgaagcggg aagggactgg ctgctattgg    1440
gcgaagtgcc ggggcaggat ctcctgtcat ctcaccttgc tcctgccgag aaagtatcca    1500
tcatggctga tgcaatgcgg cggctgcata cgcttgatcc ggctacctgc ccattcgacc    1560
accaagcgaa acatcgcatc gagcgagcac gtactcggat ggaagccggt cttgtcgatc    1620
aggatgatct ggacgaagag catcaggggc tcgcgccagc cgaactgttc gccaggctca    1680
aggcgcgcat gcccgacggc gaggatctcg tcgtgaccca tggcgatgcc tgcttgccga    1740
atatcatggt ggaaaatggc cgcttttctg gattcatcga ctgtggccgg ctgggtgtgg    1800
cggaccgcta tcaggacata gcgttggcta cccgtgatat tgctgaagag cttggcggcg    1860
aatgggctga ccgcttcctc gtgctttacg gtatcgccgc tcccgattcg cagcgcatcg    1920
ccttctatcg ccttcttgac gagttcttct gagcgggact ctggggttcg aaatgaccga    1980
ccaagcgacg cccaacctgc catcacgaga tttcgattcc accgccgcct tctatgaaag    2040
gttgggcttc ggaatcgttt tccgggacgc cggctggatg atcctccagc gcggggatct    2100
catgctggag ttcttcgccc accccaactt gtttattgca gcttataatg gttacaaata    2160
aagcaatagc atcacaaatt tcacaaataa agcattttt  tcactgcatt ctagttgtgg    2220
tttgtccaaa ctcatcaatg tatcttatca tgtctgtata ccgtcgacct ctagctagag    2280
cttggcgtaa tcatggtcat agctgtttcc tgtgtgaaat tgttatccgc tcacaattcc    2340
acacaacata cgagccggaa gcataaagtg taaagcctgg ggtgcctaat gagtgagcta    2400
actcacatta attgcgttgc gctcactgcc cgctttccag tcgggaaacc tgtcgtgcca    2460
gctgcattaa tgaatcggcc aacgcgcggg gagaggcggt ttgcgtattg ggcgctcttc    2520
cgcttcctcg ctcactgact cgctgcgctc ggtcgttcgg ctgcggcgag cggtatcagc    2580
tcactcaaag gcggtaatac ggttatccac agaatcaggg gataacgcag gaaagaacat    2640
gtgagcaaaa ggccagcaaa aggccaggaa ccgtaaaaag gccgcgttgc tggcgttttt    2700
ccataggctc cgcccccctg acgagcatca aaaaatcga  cgctcaagtc agaggtggcg    2760
aaacccgaca ggactataaa gataccaggc gtttccccct ggaagctccc tcgtgcgctc    2820
tcctgttccg accctgccgc ttaccggata cctgtccgcc tttctccctt cgggaagcgt    2880
ggcgctttct caatgctcac gctgtaggta tctcagttcg gtgtaggtcg ttcgctccaa    2940
gctgggctgt gtgcacgaac cccccgttca gcccgaccgc tgcgccttat ccggtaacta    3000
tcgtcttgag tccaacccgg taagacacga cttatcgcca ctggcagcag ccactggtaa    3060
caggattagc agagcgaggt atgtaggcgg tgctacagag ttcttgaagt ggtggcctaa    3120
ctacggctac actagaagga cagtatttgg tatctgcgct ctgctgaagc cagttacctt    3180
cggaaaaaga gttggtagct cttgatccgg caaacaaacc accgctggta gcggtggttt    3240
ttttgtttgc aagcagcaga ttacgcgcag aaaaaaagga tctcaagaag atcctttgat    3300
cttttctacg gggtctgacg ctcagtggaa cgaaaactca cgttaaggga ttttggtcat    3360
gagattatca aaaaggatct tcacctagat ccttttaaat taaaaatgaa gttttaaatc    3420
aatctaaagt atatatgagt aaacttggtc tgacagttac caatgcttaa tcagtgaggc    3480
acctatctca gcgatctgtc tatttcgttc atccatagtt gcctgactcc ccgtcgtgta    3540
gataactacg atacgggagg gcttaccatc tggccccagt gctgcaatga taccgcgaga    3600
cccacgctca ccggctccag atttatcagc aataaaccag ccagccggaa gggccgagcg    3660
cagaagtggt cctgcaactt tatccgcctc catccagtct attaattgtt gccgggaagc    3720
```

```
tagagtaagt agttcgccag ttaatagttt gcgcaacgtt gttgccattg ctacaggcat   3780
cgtggtgtca cgctcgtcgt ttggtatggc ttcattcagc tccggttccc aacgatcaag   3840
gcgagttaca tgatccccca tgttgtgcaa aaagcggtt  agctccttcg gtcctccgat   3900
cgttgtcaga gtaagttgg  ccgcagtgtt atcactcatg gttatggcag cactgcataa   3960
ttctcttact gtcatgccat ccgtaagatg ctttttctgtg actggtgagt actcaaccaa  4020
gtcattctga gaatagtgta tgcggcgacc gagttgctct tgcccggcgt caatacggga   4080
taataccgcg ccacatagca gaactttaaa agtgctcatc attggaaaac gttcttcggg   4140
gcgaaaactc tcaaggatct taccgctgtt gagatccagt tcgatgtaac ccactcgtgc   4200
acccaactga tcttcagcat cttttacttt caccagcgtt tctgggtgag caaaaacagg   4260
aaggcaaaat gccgcaaaaa agggaataag ggcgacacgg aaatgttgaa tactcatact   4320
cttcctttt  caatattatt gaagcattta tcagggttat tgtctcatga gcggatacat   4380
atttgaatgt atttagaaaa ataaacaaat aggggttccg cgcacatttc cccgaaaagt   4440
gccacctgac gtcgacggat cgggagatct cccgatcccc tatggtcgac tctcagtaca   4500
atctgctctg atgccgcata gttaagccag tatctgctcc ctgcttgtgt gttggaggtc   4560
gctgagtagt gcgcgagcaa aatttaagct acaacaaggc aaggcttgac cgacaattgc   4620
atgaagaatc tgcttagggt taggcgtttt gcgctgcttc gcgatgtacg ggccagatat   4680
acgcgttgac attgattatt gactagttat taatagtaat caattacggg gtcattagtt   4740
catagcccat atatggagtt ccgcgttaca taacttacgg taaatggccc gcctggctga   4800
ccgcccaacg acccccgccc attgacgtca ataatgacgt atgttcccat agtaacgcca   4860
atagggactt tccattgacg tcaatgggtg gactatttac ggtaaactgc ccacttggca   4920
gtacatcaag tgtatcatat gccaagtacg ccccctattg acgtcaatga cggtaaatgg   4980
cccgcctggc attatgccca gtacatgacc ttatgggact ttcctacttg gcagtacatc   5040
tacgtattag tcatcgctat taccatggtg atgcggtttt ggcagtacat caatgggcgt   5100
ggatagcggt ttgactcacg gggatttcca agtctccacc ccattgacgt caatgggagt   5160
ttgttttggc accaaaatca acgggacttt ccaaaatgtc gtaacaactc cgccccattg   5220
acgcaaatgg gcggtaggcg tgtacggtgg gaggtctata taagcagagc tctctggcta   5280
actagagaac ccactgctta ctggcttatc gaaattaata cgactcacta tagggagacc   5340
caagctgcca ccatggctac aggctcccgg acgtccctgc tcctggcttt tggcctgctc   5400
tgcctgccct ggcttcaaga gggcagcgct agccatcacc accatcacca tggcgccagc   5460
tcttctgccg ctccagctgc acctgctcca gcagcacctg ctgcaccagc tccggctgct   5520
cctgctgccg ctccagctgc acctgctcca gcagcacctg ctgcaccagc tccggctgct   5580
cctgctgccg ctccagctgc acctgctcca gcagcacctg ctgcaccagc tccggctgct   5640
cctgctgccg ctccagctgc acctgctcca gcagcacctg ctgcaccagc tccggctgct   5700
cctgctgccg ctccagctgc acctgctcca gcagcacctg ctgcaccagc tccggctgct   5760
cctgctgccg ctccagctgc acctgctcca gcagcacctg ctgcaccagc tccggctgct   5820
cctgctgccg ctccagctgc acctgctcca gcagcacctg ctgcaccagc tccggctgct   5880
cctgctgccg ctccagctgc acctgctcca gcagcacctg ctgcaccagc tccggctgct   5940
cctgctgccg ctccagctgc acctgctcca gcagcacctg ctgcaccagc tccggctgct   6000
cctgctgccg ctccagctgc acctgctcca gcagcacctg ctgcaccagc tccggctgct   6060
cctgctgcct tcccaaccat tcccttatcc aggcttttttg acaacgctat gctccgcgcc   6120
```

```
catcgtctgc accagctggc ctttgacacc taccaggagt ttgaagaagc ctatatccca    6180
aaggaacaga agtattcatt cctgcagaac ccccagacct ccctctgttt ctcagagtct    6240
attccgacac cctccaacag ggaggaaaca caacagaaat ccaacctaga gctgctccgc    6300
atctccctgc tgctcatcca gtcgtggctg agcccgtgc agttcctcag gagtgtcttc     6360
gccaacagcc tggtgtacgg cgcctctgac agcaacgtct atgacctcct aaaggaccta    6420
gaggaaggca tccaaacgct gatggggagg ctggaagatg cagccccg gactgggcag     6480 atcttcaagc agacctacag caagttcgac acaaactcac acaacgatga cgcactactc    6540
aagaactacg ggctgctcta ctgcttcagg aaggacatgg acaaggtcga cacattcctg    6600
cgcatcgtgc agtgccgctc tgtggagggc agctgtggct ctaagcttg gcc           6653
```

<210> SEQ ID NO 49
<211> LENGTH: 6041
<212> TYPE: DNA
<213> ORGANISM: artificial sequence
<220> FEATURE:
<221> NAME/KEY: source
<223> OTHER INFORMATION: /note="Description of artificial sequence: nucleic acid sequence of pCHO-hGH"

<400> SEQUENCE: 49

```
ctattctata gtgtcaccta aatgctagag ctcgctgatc agcctcgact gtgccttcta      60
gttgccagcc atctgttgtt tgcccctccc ccgtgccttc cttgaccctg gaaggtgcca     120
ctcccactgt cctttcctaa taaaatgagg aaattgcatc gcattgtctg agtaggtgtc     180
attctattct ggggggtggg gtggggcagg acagcaaggg ggaggattgg gaagacaata     240
gcaggcatgc tggggatgcg gtgggctcta tggcttctga ggcggaaaga accagctggg     300
gctctagggg gtatccccac gcgccctgta gcggcgcatt aagcgcggcg ggtgtggtgg     360
ttacgcgcag cgtgaccgct acacttgcca gcgccctagc gcccgctcct ttcgctttct     420
tcccttcctt tctcgccacg ttcgccggct ttccccgtca gctctaaat cggggcatcc      480 ctttagggtt ccgatttagt gctttacggc acctcgaccc caaaaaactt gattagggtg     540
atggttcacg tagtgggcca tcgccctgat agacggtttt tcgccctttg acgttggagt     600
ccacgttctt taatagtgga ctcttgttcc aaactggaac aacactcaac cctatctcgg     660
tctattcttt tgatttataa gggattttgg ggatttcggc ctattggtta aaaaatgagc     720
tgatttaaca aaaatttaac gcgaattaat tctgtggaat gtgtgtcagt tagggtgtgg     780
aaagtcccca ggctccccag gcaggcagaa gtatgcaaag catgcatctc aattagtcag     840
caaccaggtg tggaaagtcc ccaggctccc cagcaggcag aagtatgcaa agcatgcatc     900
tcaattagtc agcaaccata gtcccgcccc taactccgcc catcccgccc ctaactccgc     960
ccagttccgc ccattctccg ccccatggct gactaatttt ttttatttat gcagaggccg    1020
aggccgcctc tgcctctgag ctattccaga agtagtgagg aggcttttt ggaggcctag     1080 gcttttgcaa aaagctcccg ggagcttgta tatccatttt cggatctgat caagagacag    1140
gatgaggatc gtttcgcatg attgaacaag atggattgca cgcaggttct ccggccgctt    1200
gggtggagag gctattcggc tatgactggg cacaacagac aatcggctgc tctgatgccg    1260
ccgtgttccg gctgtcagcg caggggcgcc cggttctttt tgtcaagacc gacctgtccg    1320
gtgccctgaa tgaactgcag gacgaggcag cgcggctatc gtggctggcc acgacgggcg    1380
ttccttgcgc agctgtgctc gacgttgtca ctgaagcggg aagggactgg ctgctattgg    1440
```

```
gcgaagtgcc ggggcaggat ctcctgtcat ctcaccttgc tcctgccgag aaagtatcca   1500
tcatggctga tgcaatgcgg cggctgcata cgcttgatcc ggctacctgc ccattcgacc   1560
accaagcgaa acatcgcatc gagcgagcac gtactcggat ggaagccggt cttgtcgatc   1620
aggatgatct ggacgaagag catcaggggc tcgcgccagc cgaactgttc gccaggctca   1680
aggcgcgcat gcccgacggc gaggatctcg tcgtgaccca tggcgatgcc tgcttgccga   1740
atatcatggt ggaaaatggc cgcttttctg gattcatcga ctgtggccgg ctgggtgtgg   1800
cggaccgcta tcaggacata cgttggcta cccgtgatat tgctgaagag cttggcggcg   1860
aatgggctga ccgcttcctc gtgctttacg gtatcgccgc tcccgattcg cagcgcatcg   1920
ccttctatcg ccttcttgac gagttcttct gagcgggact ctggggttcg aaatgaccga   1980
ccaagcgacg cccaacctgc catcacgaga tttcgattcc accgccgcct tctatgaaag   2040
gttgggcttc ggaatcgttt tccgggacgc cggctggatg atcctccagc gcggggatct   2100
catgctggag ttcttcgccc accccaactt gtttattgca gcttataatg gttacaaata   2160
aagcaatagc atcacaaatt tcacaaataa agcattttt tcactgcatt ctagttgtgg   2220
tttgtccaaa ctcatcaatg tatcttatca tgtctgtata ccgtcgacct ctagctagag   2280
cttggcgtaa tcatggtcat agctgtttcc tgtgtgaaat tgttatccgc tcacaattcc   2340
acacaacata cgagccggaa gcataaagtg taaagcctgg ggtgcctaat gagtgagcta   2400
actcacatta attgcgttgc gctcactgcc cgctttccag tcgggaaacc tgtcgtgcca   2460
gctgcattaa tgaatcggcc aacgcgcggg gagaggcggt ttgcgtattg ggcgctcttc   2520
cgcttcctcg ctcactgact cgctgcgctc ggtcgttcgg ctgcggcgag cggtatcagc   2580
tcactcaaag gcggtaatac ggttatccac agaatcaggg gataacgcag gaaagaacat   2640
gtgagcaaaa ggccagcaaa aggccaggaa ccgtaaaaag gccgcgttgc tggcgttttt   2700
ccataggctc cgcccccctg acgagcatca aaaaatcga cgctcaagtc agaggtggcg   2760
aaacccgaca ggactataaa gataccaggc gtttccccct ggaagctccc tcgtgcgctc   2820
tcctgttccg accctgccgc ttaccggata cctgtccgcc tttctccctt cgggaagcgt   2880
ggcgctttct caatgctcac gctgtaggta tctcagttcg gtgtaggtcg ttcgctccaa   2940
gctgggctgt gtgcacgaac cccccgttca gcccgaccgc tgcgccttat ccggtaacta   3000
tcgtcttgag tccaacccgg taagacacga cttatcgcca ctggcagcag ccactggtaa   3060
caggattagc agagcgaggt atgtaggcgg tgctacagag ttcttgaagt ggtggcctaa   3120
ctacggctac actagaagga cagtatttgg tatctgcgct ctgctgaagc cagttacctt   3180
cggaaaaaga gttggtagct cttgatccgg caaacaaacc accgctggta gcggtggttt   3240
ttttgtttgc aagcagcaga ttacgcgcag aaaaaaagga tctcaagaag atcctttgat   3300
cttttctacg gggtctgacg ctcagtggaa cgaaaactca cgttaaggga ttttggtcat   3360
gagattatca aaaaggatct tcacctagat ccttttaaat taaaaatgaa gttttaaatc   3420
aatctaaagt atatatgagt aaacttggtc tgacagttac caatgcttaa tcagtgaggc   3480
acctatctca gcgatctgtc tatttcgttc atccatagtt gcctgactcc ccgtcgtgta   3540
gataactacg atacgggagg gcttaccatc tggccccagt gctgcaatga taccgcgaga   3600
cccacgctca ccggctccag atttatcagc aataaaccag ccagccggaa gggccgagcg   3660
cagaagtggt cctgcaactt tatccgcctc catccagtct attaattgtt gccgggaagc   3720
tagagtaagt agttcgccag ttaatagttt gcgcaacgtt gttgccattg ctacaggcat   3780
cgtggtgtca cgctcgtcgt ttggtatggc ttcattcagc tccggttccc aacgatcaag   3840
```

```
gcgagttaca tgatccccca tgttgtgcaa aaaagcggtt agctccttcg gtcctccgat   3900
cgttgtcaga agtaagttgg ccgcagtgtt atcactcatg gttatggcag cactgcataa   3960
ttctcttact gtcatgccat ccgtaagatg cttttctgtg actggtgagt actcaaccaa   4020
gtcattctga gaatagtgta tgcggcgacc gagttgctct tgcccggcgt caatacggga   4080
taataccgcg ccacatagca gaactttaaa agtgctcatc attggaaaac gttcttcggg   4140
gcgaaaactc tcaaggatct taccgctgtt gagatccagt tcgatgtaac ccactcgtgc   4200
acccaactga tcttcagcat cttttacttt caccagcgtt tctgggtgag caaaaacagg   4260
aaggcaaaat gccgcaaaaa agggaataag ggcgacacgg aaatgttgaa tactcatact   4320
cttccttttt caatattatt gaagcattta tcagggttat tgtctcatga gcggatacat   4380
atttgaatgt atttagaaaa ataaacaaat aggggttccg cgcacatttc cccgaaaagt   4440
gccacctgac gtcgacggat cgggagatct cccgatcccc tatggtcgac tctcagtaca   4500
atctgctctg atgccgcata gttaagccag tatctgctcc ctgcttgtgt gttggaggtc   4560
gctgagtagt gcgcgagcaa aatttaagct acaacaaggc aaggcttgac cgacaattgc   4620
atgaagaatc tgcttagggt taggcgtttt gcgctgcttc gcgatgtacg ggccagatat   4680
acgcgttgac attgattatt gactagttat taatagtaat caattacggg gtcattagtt   4740
catagcccat atatggagtt ccgcgttaca taacttacgg taaatggccc gcctggctga   4800
ccgcccaacg acccccgccc attgacgtca ataatgacgt atgttcccat agtaacgcca   4860
atagggactt tccattgacg tcaatgggtg gactatttac ggtaaactgc ccacttggca   4920
gtacatcaag tgtatcatat gccaagtacg ccccctattg acgtcaatga cggtaaatgg   4980
cccgcctggc attatgccca gtacatgacc ttatgggact ttcctacttg gcagtacatc   5040
tacgtattag tcatcgctat taccatggtg atgcggtttt ggcagtacat caatgggcgt   5100
ggatagcggt ttgactcacg gggatttcca agtctccacc ccattgacgt caatgggagt   5160
ttgttttggc accaaaatca acgggacttt ccaaaatgtc gtaacaactc cgccccattg   5220
acgcaaatgg gcggtaggcg tgtacggtgg gaggtctata taagcagagc tctctggcta   5280
actagagaac ccactgctta ctggcttatc gaaattaata cgactcacta tagggagacc   5340
caagctgcca ccatggctac aggctcccgg acgtccctgc tcctggcttt tggcctgctc   5400
tgcctgccct ggcttcaaga gggcagcgct agccatcacc accatcacca tggcgccttc   5460
ccaaccattc ccttatccag gcttttgac aacgctatgc tccgcgccca tcgtctgcac   5520
cagctggcct ttgacaccta ccaggagttt gaagaagcct atatcccaaa ggaacagaag   5580
tattcattcc tgcagaaccc ccagacctcc ctctgtttct cagagtctat tccgacaccc   5640
tccaacagga ggaaacaca acagaaatcc aacctagagc tgctccgcat ctccctgctg   5700
ctcatccagt cgtggctgga gcccgtgcag ttcctcagga gtgtcttcgc caacagcctg   5760
gtgtacggcg cctctgacag caacgtctat gacctcctaa aggacctaga ggaaggcatc   5820
caaacgctga tggggaggct ggaagatggc agcccccgga ctgggcagat cttcaagcag   5880
acctacagca agttcgacac aaactcacac aacgatgacg cactactcaa gaactacggg   5940
ctgctctact gcttcaggaa ggacatggac aaggtcgaga cattcctgcg catcgtgcag   6000
tgccgctctg tggagggcag ctgtggcttc taagcttggc c                       6041
```

<210> SEQ ID NO 50
<211> LENGTH: 5449
<212> TYPE: DNA

<213> ORGANISM: artificial sequence
<220> FEATURE:
<221> NAME/KEY: source
<223> OTHER INFORMATION: /note="Description of artificial sequence: nucleic acid sequence of pCHO"

<400> SEQUENCE: 50

```
ctattctata gtgtcaccta aatgctagag ctcgctgatc agcctcgact gtgccttcta      60
gttgccagcc atctgttgtt tgcccctccc ccgtgccttc cttgaccctg gaaggtgcca     120
ctcccactgt cctttcctaa taaaatgagg aaattgcatc gcattgtctg agtaggtgtc     180
attctattct gggggtgggg gtggggcagg acagcaaggg ggaggattgg gaagacaata     240
gcaggcatgc tggggatgcg gtgggctcta tggcttctga ggcggaaaga accagctggg     300
gctctagggg gtatcccac gcgccctgta gcggcgcatt aagcgcggcg ggtgtggtgg     360
ttacgcgcag cgtgaccgct acacttgcca gcgccctagc gcccgctcct ttcgctttct     420
tcccttcctt tctcgccacg ttcgccggct ttccccgtca agctctaaat cggggcatcc     480
ctttagggtt ccgatttagt gctttacggc acctcgaccc caaaaaactt gattagggtg     540
atggttcacg tagtgggcca tcgccctgat agacggtttt tcgccctttg acgttggagt     600
ccacgttctt aatagtgga ctcttgttcc aaactggaac aacactcaac cctatctcgg     660
tctattcttt tgatttataa gggattttgg ggatttcggc ctattggtta aaaaatgagc     720
tgatttaaca aaaatttaac gcgaattaat tctgtgtgaat gtgtgtcagt tagggtgtgg     780
aaagtcccca ggctccccag gcaggcagaa gtatgcaaag catgcatctc aattagtcag     840
caaccaggtg tggaaagtcc ccaggctccc cagcaggcag aagtatgcaa agcatgcatc     900
tcaattagtc agcaaccata gtcccgcccc taactccgcc catcccgccc ctaactccgc     960
ccagttccgc ccattctccg ccccatggct gactaatttt ttttatttat gcagaggccg    1020
aggccgcctc tgcctctgag ctattccaga agtagtgagg aggcttttt ggaggcctag    1080
gcttttgcaa aaagctcccg ggagcttgta tatccatttt cggatctgat caagagacag    1140
gatgaggatc gtttcgcatg attgaacaag atggattgca cgcaggttct ccggccgctt    1200
gggtggagag gctattcggc tatgactggg cacaacagac aatcggctgc tctgatgccg    1260
ccgtgttccg gctgtcagcg caggggcgcc cggttctttt tgtcaagacc gacctgtccg    1320
gtgccctgaa tgaactgcag gacgaggcag cgcggctatc gtggctggcc acgacgggcg    1380
ttccttgcgc agctgtgctc gacgttgtca ctgaagcggg aagggactgg ctgctattgg    1440
gcgaagtgcc ggggcaggat ctcctgtcat ctcaccttgc tcctgccgag aaagtatcca    1500
tcatggctga tgcaatgcgg cggctgcata cgcttgatcc ggctacctgc ccattcgacc    1560
accaagcgaa acatcgcatc gagcgagcac gtactcggat ggaagccggt cttgtcgatc    1620
aggatgatct ggacgaagag catcaggggc tcgcgccagc cgaactgttc gccaggctca    1680
aggcgcgcat gcccgacggc gaggatctcg tcgtgaccca tggcgatgcc tgcttgccga    1740
atatcatggt ggaaaatggc cgcttttctg gattcatcga ctgtggccgg ctgggtgtgg    1800
cggaccgcta tcaggacata gcgttggcta cccgtgatat tgctgaagag cttggcggcg    1860
aatgggctga ccgcttcctc gtgctttacg gtatcgccgc tcccgattcg cagcgcatcg    1920
ccttctatcg ccttcttgac gagttcttct gagcgggact ctggggttcg aaatgaccga    1980
ccaagcgacg cccaacctgc catcacgaga tttcgattcc accgccgcct tctatgaaag    2040
gttgggcttc ggaatcgttt tccgggacgc cggctggatg atcctccagc gcgggatct    2100
catgctggag ttcttcgccc accccaactt gtttattgca gcttataatg gttacaaata    2160
```

```
aagcaatagc atcacaaatt tcacaaataa agcatttttt tcactgcatt ctagttgtgg    2220
tttgtccaaa ctcatcaatg tatcttatca tgtctgtata ccgtcgacct ctagctagag    2280
cttggcgtaa tcatggtcat agctgttttc tgtgtgaaat tgttatccgc tcacaattcc    2340
acacaacata cgagccggaa gcataaagtg taaagcctgg ggtgcctaat gagtgagcta    2400
actcacatta attgcgttgc gctcactgcc cgctttccag tcgggaaacc tgtcgtgcca    2460
gctgcattaa tgaatcggcc aacgcgcggg gagaggcggt ttgcgtattg ggcgctcttc    2520
cgcttcctcg ctcactgact cgctgcgctc ggtcgttcgg ctgcggcgag cggtatcagc    2580
tcactcaaag gcggtaatac ggttatccac agaatcaggg gataacgcag gaaagaacat    2640
gtgagcaaaa ggccagcaaa aggccaggaa ccgtaaaaag gccgcgttgc tggcgttttt    2700
ccataggctc cgcccccctg acgagcatca caaaaatcga cgctcaagtc agaggtggcg    2760
aaacccgaca ggactataaa gataccaggc gtttccccct ggaagctccc tcgtgcgctc    2820
tcctgttccg accctgccgc ttaccggata cctgtccgcc tttctccctt cgggaagcgt    2880
ggcgctttct caatgctcac gctgtaggta tctcagttcg gtgtaggtcg ttcgctccaa    2940
gctgggctgt gtgcacgaac cccccgttca gcccgaccgc tgcgccttat ccggtaacta    3000
tcgtcttgag tccaacccgg taagacacga cttatcgcca ctggcagcag ccactggtaa    3060
caggattagc agagcgaggt atgtaggcgg tgctacagag ttcttgaagt ggtggcctaa    3120
ctacggctac actagaagga cagtatttgg tatctgcgct ctgctgaagc cagttacctt    3180
cggaaaaaga gttggtagct cttgatccgg caaacaaacc accgctggta gcggtggttt    3240
ttttgtttgc aagcagcaga ttacgcgcag aaaaaaagga tctcaagaag atcctttgat    3300
cttttctacg gggtctgacg ctcagtggaa cgaaaactca cgttaaggga ttttggtcat    3360
gagattatca aaaaggatct tcacctagat ccttttaaat taaaaatgaa gttttaaatc    3420
aatctaaagt atatatgagt aaacttggtc tgacagttac caatgcttaa tcagtgaggc    3480
acctatctca gcgatctgtc tatttcgttc atccatagtt gcctgactcc ccgtcgtgta    3540
gataactacg atacgggagg gcttaccatc tggccccagt gctgcaatga taccgcgaga    3600
cccacgctca ccggctccag atttatcagc aataaaccag ccagccggaa gggccgagcg    3660
cagaagtggt cctgcaactt tatccgcctc catccagtct attaattgtt gccgggaagc    3720
tagagtaagt agttcgccag ttaatagttt gcgcaacgtt gttgccattg ctacaggcat    3780
cgtggtgtca cgctcgtcgt ttggtatggc ttcattcagc tccggttccc aacgatcaag    3840
gcgagttaca tgatccccca tgttgtgcaa aaaagcggtt agctccttcg gtcctccgat    3900
cgttgtcaga agtaagttgg ccgcagtgtt atcactcatg gttatggcag cactgcataa    3960
ttctcttact gtcatgccat ccgtaagatg cttttctgtg actggtgagt actcaaccaa    4020
gtcattctga gaatagtgta tgcggcgacc gagttgctct tgcccggcgt caatacggga    4080
taataccgcg ccacatagca gaactttaaa agtgctcatc attggaaaac gttcttcggg    4140
gcgaaaactc tcaaggatct taccgctgtt gagatccagt tcgatgtaac ccactcgtgc    4200
acccaactga tcttcagcat cttttacttt caccagcgtt tctgggtgag caaaaacagg    4260
aaggcaaaat gccgcaaaaa agggaataag ggcgacacgg aaatgttgaa tactcatact    4320 cttcctttt caatattatt gaagcattta tcagggttat tgtctcatga gcggatacat    4380
atttgaatgt atttagaaaa ataaacaaat aggggttccg cgcacatttc cccgaaaagt    4440
gccacctgac gtcgacggat cgggagatct cccgatcccc tatggtcgac tctcagtaca    4500
```

-continued

```
atctgctctg atgccgcata gttaagccag tatctgctcc ctgcttgtgt gttggaggtc    4560
gctgagtagt gcgcgagcaa aatttaagct acaacaaggc aaggcttgac cgacaattgc    4620
atgaagaatc tgcttagggt taggcgtttt gcgctgcttc gcgatgtacg ggccagatat    4680
acgcgttgac attgattatt gactagttat taatagtaat caattacggg gtcattagtt    4740
catagcccat atatggagtt ccgcgttaca taacttacgg taaatggccc gcctggctga    4800
ccgcccaacg accccccgccc attgacgtca ataatgacgt atgttcccat agtaacgcca    4860
atagggactt tccattgacg tcaatgggtg gactatttac ggtaaactgc ccacttggca    4920
gtacatcaag tgtatcatat gccaagtacg cccctattg acgtcaatga cggtaaatgg    4980
cccgcctggc attatgccca gtacatgacc ttatgggact ttcctacttg gcagtacatc    5040
tacgtattag tcatcgctat taccatggtg atgcggtttt ggcagtacat caatgggcgt    5100
ggatagcggt ttgactcacg gggatttcca agtctccacc ccattgacgt caatgggagt    5160
ttgttttggc accaaaatca acgggacttt ccaaaatgtc gtaacaactc cgccccattg    5220
acgcaaatgg gcggtaggcg tgtacggtgg gaggtctata taagcagagc tctctggcta    5280
actagagaac ccactgctta ctggcttatc gaaattaata cgactcacta tagggagacc    5340
caagctgcca ccatggctac aggctcccgg acgtccctgc tcctggcttt tggcctgctc    5400
tgcctgccct ggcttcaaga gggcagcgct agctctagaa agcttggcc                5449
```

<210> SEQ ID NO 51
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence: amino acid sequence of P1A1"

<400> SEQUENCE: 51

Ala Pro Ala Pro Ala Pro Ala Pro Ala Pro Ala Pro Ala Pro Ala Pro
1               5                   10                  15

Ala Pro Ala Pro
            20

<210> SEQ ID NO 52
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence: nucleic acid sequence of upper/coding strand oligodesoxynucleotide used for the generation of the building block for P1A1"

<400> SEQUENCE: 52
gcccctgctc ctgctccagc acctgcacca gcacctgctc cagcaccagc tcctgcacca    60

<210> SEQ ID NO 53
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence: nucleic acid sequence of lower/non-coding strand oligodesoxynucleotide used for the generation of the building block for P1A1"

<400> SEQUENCE: 53
ggctggtgca ggagctggtg ctggagcagg tgctggtgca ggtgctggag caggagcagg    60

<210> SEQ ID NO 54
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence of upper/coding strand oligodesoxynucleotide
      used for the generation of the building block for P1A3"

<400> SEQUENCE: 54
gccgctgcac ctgctgcagc acctgctgca gctccagcag ctgctcctgc agcagctcca    60

<210> SEQ ID NO 55
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence of lower/non-coding strand
      oligodesoxynucleotide used for the generation of the building
      block for P1A3"

<400> SEQUENCE: 55
ggctggagct gctgcaggag cagctgctgg agctgcagca ggtgctgcag caggtgcagc    60

<210> SEQ ID NO 56
<211> LENGTH: 417
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of the Fab light chain fused with the
      P1A1(200) polymer as encoded on pFab-P1A1(200)"

<400> SEQUENCE: 56

Asp Ile Glu Leu Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

-continued

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ser Ser Ala Pro Ala Pro Ala Pro Ala Pro
    210                 215                 220

Ala Pro Ala Pro Ala Pro Ala Pro Ala Pro Ala Pro Ala Pro Ala Pro
225                 230                 235                 240

Ala Pro Ala Pro Ala Pro Ala Pro Ala Pro Ala Pro Ala Pro Ala Pro
                245                 250                 255

Ala Pro Ala Pro Ala Pro Ala Pro Ala Pro Ala Pro Ala Pro Ala Pro
            260                 265                 270

Ala Pro Ala Pro Ala Pro Ala Pro Ala Pro Ala Pro Ala Pro Ala Pro
        275                 280                 285

Ala Pro Ala Pro Ala Pro Ala Pro Ala Pro Ala Pro Ala Pro Ala Pro
    290                 295                 300

Ala Pro Ala Pro Ala Pro Ala Pro Ala Pro Ala Pro Ala Pro Ala Pro
305                 310                 315                 320

Ala Pro Ala Pro Ala Pro Ala Pro Ala Pro Ala Pro Ala Pro Ala Pro
                325                 330                 335

Ala Pro Ala Pro Ala Pro Ala Pro Ala Pro Ala Pro Ala Pro Ala Pro
            340                 345                 350

Ala Pro Ala Pro Ala Pro Ala Pro Ala Pro Ala Pro Ala Pro Ala Pro
        355                 360                 365

Ala Pro Ala Pro Ala Pro Ala Pro Ala Pro Ala Pro Ala Pro Ala Pro
    370                 375                 380

Ala Pro Ala Pro Ala Pro Ala Pro Ala Pro Ala Pro Ala Pro Ala Pro
385                 390                 395                 400

Ala Pro Ala Pro Ala Pro Ala Pro Ala Pro Ala Pro Ala Pro Ala Pro
                405                 410                 415

Ala
```

<210> SEQ ID NO 57
<211> LENGTH: 417
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of the Fab light chain fused with the
      P1A3(200) polymer as encoded on pFab-P1A3(200)"

<400> SEQUENCE: 57

```
Asp Ile Glu Leu Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Leu Glu Ile Lys Arg Thr Val Ala Ala
```

|  |  |  | 100 |  |  |  | 105 |  |  |  | 110 |  |
|---|---|---|---|---|---|---|---|---|---|---|---|---|

Pro Ser Val Phe Ile Phe Pro Pro Ser Asp Glu Gln Leu Lys Ser Gly
           115                    120                    125

Thr Ala Ser Val Val Cys Leu Leu Asn Asn Phe Tyr Pro Arg Glu Ala
130                  135                    140

Lys Val Gln Trp Lys Val Asp Asn Ala Leu Gln Ser Gly Asn Ser Gln
145                  150                  155                  160

Glu Ser Val Thr Glu Gln Asp Ser Lys Asp Ser Thr Tyr Ser Leu Ser
           165                    170                  175

Ser Thr Leu Thr Leu Ser Lys Ala Asp Tyr Glu Lys His Lys Val Tyr
           180                    185                  190

Ala Cys Glu Val Thr His Gln Gly Leu Ser Ser Pro Val Thr Lys Ser
           195                    200                  205

Phe Asn Arg Gly Glu Cys Ser Ser Ala Ala Ala Pro Ala Ala Ala Pro
           210                    215                  220

Ala Ala Ala Pro Ala Ala Ala Pro Ala Ala Ala Pro Ala Ala Ala Pro
225                  230                  235                  240

Ala Ala Ala Pro Ala Ala Ala Pro Ala Ala Ala Pro Ala Ala Ala Pro
           245                    250                  255

Ala Ala Ala Pro Ala Ala Ala Pro Ala Ala Ala Pro Ala Ala Ala Pro
           260                    265                  270

Ala Ala Ala Pro Ala Ala Ala Pro Ala Ala Ala Pro Ala Ala Ala Pro
           275                    280                  285

Ala Ala Ala Pro Ala Ala Ala Pro Ala Ala Ala Pro Ala Ala Ala Pro
           290                    295                  300

Ala Ala Ala Pro Ala Ala Ala Pro Ala Ala Ala Pro Ala Ala Ala Pro
305                  310                  315                  320

Ala Ala Ala Pro Ala Ala Ala Pro Ala Ala Ala Pro Ala Ala Ala Pro
           325                    330                  335

Ala Ala Ala Pro Ala Ala Ala Pro Ala Ala Ala Pro Ala Ala Ala Pro
           340                    345                  350

Ala Ala Ala Pro Ala Ala Ala Pro Ala Ala Ala Pro Ala Ala Ala Pro
           355                    360                  365

Ala Ala Ala Pro Ala Ala Ala Pro Ala Ala Ala Pro Ala Ala Ala Pro
           370                    375                  380

Ala Ala Ala Pro Ala Ala Ala Pro Ala Ala Ala Pro Ala Ala Ala Pro
385                  390                  395                  400

Ala Ala Ala Pro Ala Ala Ala Pro Ala Ala Ala Pro Ala Ala Ala Pro
           405                    410                  415

Ala

<210> SEQ ID NO 58
<211> LENGTH: 5210
<212> TYPE: DNA
<213> ORGANISM: artificial sequence
<220> FEATURE:
<221> NAME/KEY: source
<223> OTHER INFORMATION: /note="Description of artificial sequence:
    nucleic acid sequence of pFab-P1A1(200)"

<400> SEQUENCE: 58
acccgacacc atcgaatggc cagatgatta attcctaatt tttgttgaca ctctatcatt    60
gatagagtta ttttaccact ccctatcagt gatagagaaa agtgaaatga atagttcgac   120
aaaaatctag ataacgaggg caaaaaatga aaaagacagc tatcgcgatt gcagtggcac   180

```
tggctggttt cgctaccgta gcgcaggccg aagttaaact gcaggaatcc ggtggtggtc    240
tggttcagcc aggtggttcc ctgcggctct cgtgtgctgc ttccggtttc aacatcaaag    300
acacctacat ccactgggtt cgtcaggctc cgggtaaagg cctggaatgg gttgctcgta    360
tctacccgac caacggttac accaggtatg ccgattcagt taaaggtcgt ttcaccatct    420
cggccgacac ttccaaaaac accgcttacc tccagatgaa ctccctgcgt gctgaagaca    480
cagctgttta ttattgctcc cgttggggtg gtgacggttt ctacgctatg gactactggg    540
gtcagggtac cctggtcacc gtctcctcag cctccaccaa gggcccatcg gtcttccccc    600
tggcaccctc ctccaagagc acctctgggg gcacagcggc cctgggctgc ctggtcaagg    660
actacttccc cgaaccggtg acggtgtcgt ggaactcagg cgccctgacc agcggcgtgc    720
acaccttccc ggctgtccta cagtcctcag gactctactc cctcagcagc gtggtgactg    780
tgccctccag cagcttgggc acccagacct acatctgcaa cgttaatcac aaacccagca    840
acaccaaggt cgacaagaaa gttgagccca aatcttgcca tcaccaccat caccattaat    900
aaccatggag aaaataaagt gaaacaaagc actattgcac tggcactctt accgttactg    960 tttaccctg tgacaaaagc cgacatcgag ctcacccaat cccgtcctc cctgtccgct    1020 tccgttggcg accgtgttac catcacgtgt agggcctcgc aagacgtaaa caccgccgta    1080
gcgtggtatc agcagaaacc cgggaaagct ccgaaactgc tgatctatag cgcttccttc    1140
ctgtattccg gagttccgag caggttcagt ggttcccgtt ccggtaccga cttcaccctg    1200
acgatatcct ccctccagcc ggaagacttc gctacctact actgtcaaca gcactacacc    1260
accccgccga ccttcggtca gggtaccaaa ctcgagatca acggactgt ggctgcacca    1320 tctgtcttca tcttcccgcc atctgatgag cagttgaaat ctggaactgc ctctgttgtg    1380
tgcctgctga ataacttcta tcccagagag gccaaagtac agtggaaggt ggataacgcc    1440
ctccaatcgg gtaactccca ggagagtgtc acagagcagg acagcaagga cagcacctac    1500
agcctcagca gcaccctgac gctgagcaaa gcagactacg agaaacacaa agtctacgcc    1560
tgcgaagtca cccatcaggg cctgagttcg cccgtcacaa agagcttcaa ccgcggagag    1620
tgctcttctg cccctgctcc tgctccagca cctgcaccag cacctgctcc agcaccagct    1680
cctgcaccag cccctgctcc tgctccagca cctgcaccag cacctgctcc agcaccagct    1740
cctgcaccag cccctgctcc tgctccagca cctgcaccag cacctgctcc agcaccagct    1800
cctgcaccag cccctgctcc tgctccagca cctgcaccag cacctgctcc agcaccagct    1860
cctgcaccag cccctgctcc tgctccagca cctgcaccag cacctgctcc agcaccagct    1920
cctgcaccag cccctgctcc tgctccagca cctgcaccag cacctgctcc agcaccagct    1980
cctgcaccag cccctgctcc tgctccagca cctgcaccag cacctgctcc agcaccagct    2040
cctgcaccag cccctgctcc tgctccagca cctgcaccag cacctgctcc agcaccagct    2100
cctgcaccag cccctgctcc tgctccagca cctgcaccag cacctgctcc agcaccagct    2160
cctgcaccag cccctgctcc tgctccagca cctgcaccag cacctgctcc agcaccagct    2220
cctgcaccag cctgaagagc ttaagcttga cctgtgaagt gaaaaatggc gcacattgtg    2280
cgacattttt tttgtctgcc gtttaccgct actgcgtcac ggatctccac gcgccctgta    2340
gcggcgcatt aagcgcggcg ggtgtggtgg ttacgcgcag cgtgaccgct acacttgcca    2400
gcgccctagc gcccgctcct ttcgctttct tcccttcctt tctcgccacg ttcgccggct    2460
ttccccgtca agctctaaat cggggggctccc ctttagggtt ccgatttagt gctttacggc    2520
acctcgaccc caaaaaactt gattagggtg atggttcacg tagtgggcca tcgccctgat    2580
```

```
agacggtttt tcgcccttty acgttggagt ccacgttctt taatagtgga ctcttgttcc   2640
aaactggaac aacactcaac cctatctcgg tctattcttt tgatttataa gggattttgc   2700
cgatttcggc ctattggtta aaaaatgagc tgatttaaca aaaatttaac gcgaattta    2760 acaaaatatt aacgtttaca atttcaggtg gcacttttcg gggaaatgtg cgcggaaccc   2820
ctatttgttt attttttctaa atacattcaa atatgtatcc gctcatgaga caataaccct   2880
gataaatgct tcaataatat tgaaaaagga agagtatgag tattcaacat ttccgtgtcg   2940
cccttattcc cttttttgcg gcattttgcc ttcctgtttt tgctcaccca gaaacgctgg   3000
tgaaagtaaa agatgctgaa gatcagttgg gtgcacgagt gggttacatc gaactggatc   3060
tcaacagcgg taagatcctt gagagttttc gccccgaaga acgttttcca atgatgagca   3120
cttttaaagt tctgctatgt ggcgcggtat tatcccgtat tgacgccggg caagagcaac   3180
tcggtcgccg catacactat tctcagaatg acttggttga gtactcacca gtcacagaaa   3240
agcatcttac ggatggcatg acagtaagag aattatgcag tgctgccata accatgagtg   3300
ataacactgc ggccaactta cttctgacaa cgatcggagg accgaaggag ctaaccgctt   3360
ttttgcacaa catgggggat catgtaactc gccttgatcg ttgggaaccg gagctgaatg   3420
aagccatacc aaacgacgag cgtgacacca cgatgcctgt agcaatggca acaacgttgc   3480
gcaaactatt aactggcgaa ctacttactc tagcttcccg gcaacaattg atagactgga   3540
tggaggcgga taaagttgca ggaccacttc tgcgctcggc ccttccggct ggctggttta   3600
ttgctgataa atctggagcc ggtgagcgtg gctctcgcgg tatcattgca gcactggggc   3660
cagatggtaa gccctcccgt atcgtagtta tctacacgac ggggagtcag gcaactatgg   3720
atgaacgaaa tagacagatc gctgagatag gtgcctcact gattaagcat tggtaggaat   3780
taatgatgtc tcgtttagat aaaagtaaag tgattaacag cgcattagag ctgcttaatg   3840
aggtcggaat cgaaggttta acaacccgta aactcgccca gaagctaggt gtagagcagc   3900
ctacattgta ttggcatgta aaaaataagc gggctttgct cgacgcctta gccattgaga   3960
tgttagatag gcaccatact cacttttgcc ctttagaagg ggaaagctgg caagattttt   4020
tacgtaataa cgctaaaagt tttagatgtg ctttactaag tcatcgcgat ggagcaaaag   4080
tacatttagg tacacggcct acagaaaaac agtatgaaac tctcgaaaat caattagcct   4140
ttttatgcca acaaggtttt tcactagaga atgcattata tgcactcagc gcagtggggc   4200
attttacttt aggttgcgta ttggaagatc aagagcatca agtcgctaaa gaagaaaggg   4260
aaacacctac tactgatagt atgccgccat tattacgaca agctatcgaa ttatttgatc   4320
accaaggtgc agagccagcc ttcttattcg gccttgaatt gatcatatgc ggattagaaa   4380
aacaacttaa atgtgaaagt gggtcttaaa agcagcataa ccttttttccg tgatggtaac   4440 ttcactagtt taaaggatc taggtgaaga tcctttttga taatctcatg accaaaatcc   4500
cttaacgtga gttttcgttc cactgagcgt cagacccgt agaaaagatc aaaggatctt   4560
cttgagatcc ttttttttctg cgcgtaatct gctgcttgca acaaaaaaa ccaccgctac   4620 cagcggtggt ttgtttgccg gatcaagagc taccaactct ttttccgaag gtaactggct   4680
tcagcagagc gcagatacca aatactgtcc ttctagtgta gccgtagtta ggccaccact   4740
tcaagaactc tgtagcaccg cctacatacc tcgctctgct aatcctgtta ccagtggctg   4800
ctgccagtgg cgataagtcg tgtcttaccg ggttggactc aagacgatag ttaccggata   4860
aggcgcagcg gtcgggctga acggggggtt cgtgcacaca gcccagcttg gagcgaacga   4920
```

```
cctacaccga actgagatac ctacagcgtg agctatgaga aagcgccacg cttcccgaag    4980
ggagaaaggc ggacaggtat ccggtaagcg gcagggtcgg aacaggagag cgcacgaggg    5040
agcttccagg gggaaacgcc tggtatcttt atagtcctgt cgggtttcgc cacctctgac    5100
ttgagcgtcg attttttgtga tgctcgtcag ggggcggag cctatggaaa acgccagca    5160 acgcggcctt tttacggttc ctggccttt gctggccttt tgctcacatg               5210

<210> SEQ ID NO 59
<211> LENGTH: 5210
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence of pFab-P1A3(200)"

<400> SEQUENCE: 59
acccgacacc atcgaatggc cagatgatta attcctaatt tttgttgaca ctctatcatt      60
gatagagtta ttttaccact ccctatcagt gatagagaaa agtgaaatga atagttcgac     120
aaaaatctag ataacgaggg caaaaaatga aaaagacagc tatcgcgatt gcagtggcac     180
tggctggttt cgctaccgta gcgcaggccg aagttaaact gcaggaatcc ggtggtggtc     240
tggttcagcc aggtggttcc ctgcggctct cgtgtgctgc ttccggtttc aacatcaaag     300
acacctacat ccactgggtt cgtcaggctc cgggtaaagg cctggaatgg gttgctcgta     360
tctacccgac caacggttac accaggtatg ccgattcagt taaaggtcgt ttcaccatct     420
cggccgacac ttccaaaaac accgcttacc tccagatgaa ctccctgcgt gctgaagaca     480
cagctgttta ttattgctcc cgttggggtg gtgacggttt ctacgctatg gactactggg     540
gtcagggtac cctggtcacc gtctcctcag cctccaccaa gggcccatcg gtcttccccc     600
tggcaccctc ctccaagagc acctctgggg gcacagcggc cctgggctgc ctggtcaagg     660
actacttccc cgaaccggtg acggtgtcgt ggaactcagg cgccctgacc agcggcgtgc     720
acaccttccc ggctgtccta cagtcctcag gactctactc cctcagcagc gtggtgactg     780
tgcccctcca gcagcttggg cacccagacc acatctgcaa cgttaatcac aaacccagca     840
acaccaaggt cgacaagaaa gttgagccca atcttgcca tcaccaccat caccattaat     900
aaccatggag aaaataaagt gaaacaaagc actattgcac tggcactctt accgttactg     960 tttaccctg tgacaaaagc cgacatcgag ctcacccaat cccgtcctc cctgtccgct     1020 tccgttggcg accgtgttac catcacgtgt agggcctcgc aagacgtaaa caccgccgta    1080
gcgtggtatc agcagaaacc cgggaaagct ccgaaactgc tgatctatag cgcttccttc    1140
ctgtattccg gagttccgag caggttcagt ggttcccgtt ccggtaccga cttcaccctg    1200
acgatatcct ccctccagcc ggaagacttc gctacctact actgtcaaca gcactacacc    1260
accccgccga ccttcggtca gggtaccaaa ctcgagatca aacggactgt ggctgcacca    1320
tctgtcttca tcttcccgcc atctgatgag cagttgaaat ctggaactgc ctctgttgtg    1380
tgcctgctga ataacttcta tcccagagag gccaaagtac agtggaaggt ggataacgcc    1440
ctccaatcgg gtaactccca ggagagtgtc acagagcagg acagcaagga cagcacctac    1500
agcctcagca gcaccctgac gctgagcaaa gcagactacg agaaacacaa agtctacgcc    1560
tgcgaagtca cccatcaggg cctgagttcg cccgtcacaa agagcttcaa ccgcggagag    1620
tgctcttctg ccgctgcacc tgctgcagca cctgctgcag ctccagcagc tgctcctgca    1680
gcagctccag ccgctgcacc tgctgcagca cctgctgcag ctccagcagc tgctcctgca    1740
```

```
gcagctccag ccgctgcacc tgctgcagca cctgctgcag ctccagcagc tgctcctgca  1800
gcagctccag ccgctgcacc tgctgcagca cctgctgcag ctccagcagc tgctcctgca  1860
gcagctccag ccgctgcacc tgctgcagca cctgctgcag ctccagcagc tgctcctgca  1920
gcagctccag ccgctgcacc tgctgcagca cctgctgcag ctccagcagc tgctcctgca  1980
gcagctccag ccgctgcacc tgctgcagca cctgctgcag ctccagcagc tgctcctgca  2040
gcagctccag ccgctgcacc tgctgcagca cctgctgcag ctccagcagc tgctcctgca  2100
gcagctccag ccgctgcacc tgctgcagca cctgctgcag ctccagcagc tgctcctgca  2160
gcagctccag ccgctgcacc tgctgcagca cctgctgcag ctccagcagc tgctcctgca  2220
gcagctccag cctgaagagc ttaagcttga cctgtgaagt gaaaaatggc gcacattgtg  2280
cgacattttt tttgtctgcc gtttaccgct actgcgtcac ggatctccac gcgccctgta  2340
gcggcgcatt aagcgcggcg ggtgtggtgg ttacgcgcag cgtgaccgct acacttgcca  2400
gcgccctagc gcccgctcct ttcgctttct tcccttcctt tctcgccacg ttcgccggct  2460
ttccccgtca agctctaaat cgggggctcc ctttagggtt ccgatttagt gctttacggc  2520
acctcgaccc caaaaaactt gattagggtg atggttcacg tagtgggcca tcgccctgat  2580
agacggtttt tcgccctttg acgttggagt ccacgttctt aatagtgga ctcttgttcc  2640 aaactggaac aacactcaac cctatctcgg tctattcttt tgatttataa gggattttgc  2700
cgatttcggc ctattggtta aaaaatgagc tgatttaaca aaaatttaac gcgaatttta  2760
acaaaatatt aacgtttaca atttcaggtg gcacttttcg gggaaatgtg cgcggaaccc  2820
ctatttgttt attttctaa atacattcaa atatgtatcc gctcatgaga caataaccct  2880
gataaatgct tcaataatat tgaaaaagga agagtatgag tattcaacat ttccgtgtcg  2940
cccttattcc cttttttgcg gcattttgcc ttcctgtttt tgctcaccca gaaacgctgg  3000
tgaaagtaaa agatgctgaa gatcagttgg gtgcacgagt gggttacatc gaactggatc  3060
tcaacagcgg taagatcctt gagagttttc gccccgaaga acgttttcca atgatgagca  3120
cttttaaagt tctgctatgt ggcgcggtat tatcccgtat tgacgccggg caagagcaac  3180
tcggtcgccg catacactat tctcagaatg acttggttga gtactcacca gtcacagaaa  3240
agcatcttac ggatggcatg acagtaagag aattatgcag tgctgccata accatgagtg  3300
ataacactgc ggccaactta cttctgacaa cgatcggagg accgaaggag ctaaccgctt  3360
ttttgcacaa catgggggat catgtaactc gccttgatcg ttgggaaccg gagctgaatg  3420
aagccatacc aaacgacgag cgtgacacca cgatgcctgt agcaatggca acaacgttgc  3480
gcaaactatt aactggcgaa ctacttactc tagcttcccg gcaacaattg atagactgga  3540
tggaggcgga taaagttgca ggaccacttc tgcgctcggc ccttccggct ggctggttta  3600
ttgctgataa atctggagcc ggtgagcgtg ctctcgcgg tatcattgca gcactggggc  3660
cagatggtaa gccctcccgt atcgtagtta tctacacgac ggggagtcag gcaactatgg  3720
atgaacgaaa tagacagatc gctgagatag gtgcctcact gattaagcat tggtaggaat  3780
taatgatgtc tcgtttagat aaagtaaag tgattaacag cgcattagag ctgcttaatg  3840
aggtcggaat cgaaggttta acaacccgta aactcgccca aagctaggt gtagagcagc  3900 ctacattgta ttggcatgta aaaaataagc gggctttgct cgacgcctta gccattgaga  3960
tgttagatag gcaccatact cacttttgcc ctttagaagg ggaaagctgg caagattttt  4020
tacgtaataa cgctaaaagt tttagatgtg ctttactaag tcatcgcgat ggagcaaaag  4080
```

| | | |
|---|---|---|
| tacatttagg tacacggcct acagaaaaac agtatgaaac tctcgaaaat caattagcct | 4140 | |
| ttttatgcca acaaggtttt tcactagaga atgcattata tgcactcagc gcagtggggc | 4200 | |
| atttacttt aggttgcgta ttggaagatc aagagcatca agtcgctaaa gaagaaaggg | 4260 | |
| aaacacctac tactgatagt atgccgccat tattacgaca agctatcgaa ttatttgatc | 4320 | |
| accaaggtgc agagccagcc ttcttattcg gccttgaatt gatcatatgc ggattagaaa | 4380 | |
| aacaacttaa atgtgaaagt gggtcttaaa agcagcataa ccttttttccg tgatggtaac | 4440 | |
| ttcactagtt taaaggatc taggtgaaga tcctttttga taatctcatg accaaaatcc | 4500 | |
| cttaacgtga gttttcgttc cactgagcgt cagaccccgt agaaaagatc aaaggatctt | 4560 | |
| cttgagatcc ttttttttctg cgcgtaatct gctgcttgca acaaaaaaa ccaccgctac | 4620 | |
| cagcggtggt ttgtttgccg gatcaagagc taccaactct ttttccgaag gtaactggct | 4680 | |
| tcagcagagc gcagatacca aatactgtcc ttctagtgta gccgtagtta ggccaccact | 4740 | |
| tcaagaactc tgtagcaccg cctacatacc tcgctctgct aatcctgtta ccagtggctg | 4800 | |
| ctgccagtgg cgataagtcg tgtcttaccg ggttggactc aagacgatag ttaccggata | 4860 | |
| aggcgcagcg gtcgggctga acggggggtt cgtgcacaca gcccagcttg gagcgaacga | 4920 | |
| cctacaccga actgagatac ctacagcgtg agctatgaga agcgccacg cttcccgaag | 4980 | |
| ggagaaaggc ggacaggtat ccggtaagcg gcagggtcgg aacaggagag cgcacgaggg | 5040 | |
| agcttccagg gggaaacgcc tggtatcttt atagtcctgt cgggtttcgc cacctctgac | 5100 | |
| ttgagcgtcg attttttgtga tgctcgtcag ggggggcggag cctatggaaa aacgccagca | 5160 | |
| acgcggcctt tttacggttc ctggcctttt gctggccttt tgctcacatg | 5210 | |

<210> SEQ ID NO 60
<211> LENGTH: 3680
<212> TYPE: DNA
<213> ORGANISM: artificial sequence
<220> FEATURE:
<221> NAME/KEY: source
<223> OTHER INFORMATION: /note="Description of artificial sequence:
    nucleic acid sequence of pSUMO-PA#1(200)"

<400> SEQUENCE: 60

| | | |
|---|---|---|
| gcactttttcg gggaaatgtg cgcggaaccc ctatttgttt attttttctaa atacattcaa | 60 | |
| atatgtatcc gctcatgaga caataaccct gataaatgct tcaataatat tgaaaaagga | 120 | |
| agagtatgag tattcaacat ttccgtgtcg cccttattcc cttttttgcg gcattttgcc | 180 | |
| ttcctgtttt tgctcaccca gaaacgctgg tgaaagtaaa agatgctgaa gatcagttgg | 240 | |
| gtgcacgagt gggttacatc gaactggatc tcaacagcgg taagatcctt gagagttttc | 300 | |
| gccccgaaga acgttttcca atgatgagca cttttaaagt tctgctatgt ggcgcggtat | 360 | |
| tatcccgtat tgacgccggg caagagcaac tcggtcgccg catacactat tctcagaatg | 420 | |
| acttggttga gtactcacca gtcacagaaa agcatcttac ggatggcatg acagtaagag | 480 | |
| aattatgcag tgctgccata accatgagtg ataacactgc ggccaactta cttctgacaa | 540 | |
| cgatcggagg accgaaggag ctaaccgctt ttttgcacaa catgggggat catgtaactc | 600 | |
| gccttgatcg ttgggaaccg gagctgaatg aagccatacc aaacgacgag cgtgacacca | 660 | |
| cgatgcctgt agcaatggca acaacgttgc gcaaactatt aactggcgaa ctacttactc | 720 | |
| tagcttcccg gcaacaatta atagactgga tggaggcgga taaagttgca ggaccacttc | 780 | |
| tgcgctcggc ccttccggct ggctggttta ttgctgataa atctggagcc ggtgagcgtg | 840 | |
| ggtctcgcgg tatcattgca gcactggggc cagatggtaa gccctcccgt atcgtagtta | 900 | |

```
tctacacgac ggggagtcag gcaactatgg atgaacgaaa tagacagatc gctgagatag    960
gtgcctcact gattaagcat tggtaactgt cagaccaagt ttactcatat atactttaga   1020
ttgatttaaa acttcatttt taatttaaaa ggatctaggt gaagatcctt tttgataatc   1080
tcatgaccaa atcccttaa cgtgagtttt cgttccactg agcgtcagac cccgtagaaa    1140
agatcaaagg atcttcttga tcctttttt ttctgcgcgt aatctgctgc ttgcaaacaa    1200
aaaaaccacc gctaccagcg gtggtttgtt tgccggatca agagctacca actctttttc   1260
cgaaggtaac tggcttcagc agagcgcaga taccaaatac tgtccttcta gtgtagccgt   1320
agttaggcca ccacttcaag aactctgtag caccgcctac atacctcgct ctgctaatcc   1380
tgttaccagt ggctgctgcc agtggcgata agtcgtgtct taccgggttg gactcaagac   1440
gatagttacc ggataaggcg cagcggtcgg gctgaacggg gggttcgtgc acacagccca   1500
gcttggagcg aacgacctac accgaactga gatacctaca gcgtgagcta tgagaaagcg   1560
ccacgcttcc cgaagggaga aaggcggaca ggtatccggt aagcggcagg gtcggaacag   1620
gagagcgcac gagggagctt ccagggggaa acgcctggta tctttatagt cctgtcgggt   1680
ttcgccacct ctgacttgag cgtcgatttt tgtgatgctc gtcaggggggg cggagcctat   1740
ggaaaaacgc cagcaacgcg gcctttttac ggttcctggc cttttgctgg ccttttgctc   1800
acatgttctt tcctgcgtta tcccctgatt ctgtggataa ccgtattacc gcctttgagt   1860
gagctgatac cgctcgccgc agccgaacga ccgagcgcag cgagtcagtg agcgaggaag   1920
cggagaagcg cccaatacgc aaaccgcctc tccccgcgcg ttggccgatt cattaatgca   1980
ggatctcgat cccgcgaaat taatacgact cactataggg agaccacaac ggtttccctc   2040
tagaaataat tttgtttaac tttaagaagg agatatacat atgaaacatc accaccatca   2100
ccattcggac tcagaagtca atcaagaagc taagccagag gtcaagccag aagtcaagcc   2160
tgagactcac atcaatttaa aggtgtccga tggatcttca gaaatcttct ttaagatcaa   2220
aaagaccact cctttaagaa ggctgatgga agcgttcgct aaaagacagg gtaaggaaat   2280
ggactcctta agattcttgt acgacggtat tagaattcaa gctgatcaga cccctgaaga   2340
tttggacatg gaggataacg atattattga ggctcacaga gaacagattg gtggcgccgc   2400
tccagctgca cctgctccag cagcacctgc tgcaccagct ccggctgctc ctgctgccgc   2460
tccagctgca cctgctccag cagcacctgc tgcaccagct ccggctgctc ctgctgccgc   2520
tccagctgca cctgctccag cagcacctgc tgcaccagct ccggctgctc ctgctgccgc   2580
tccagctgca cctgctccag cagcacctgc tgcaccagct ccggctgctc ctgctgccgc   2640
tccagctgca cctgctccag cagcacctgc tgcaccagct ccggctgctc ctgctgccgc   2700
tccagctgca cctgctccag cagcacctgc tgcaccagct ccggctgctc ctgctgccgc   2760
tccagctgca cctgctccag cagcacctgc tgcaccagct ccggctgctc ctgctgccgc   2820
tccagctgca cctgctccag cagcacctgc tgcaccagct ccggctgctc ctgctgccgc   2880
tccagctgca cctgctccag cagcacctgc tgcaccagct ccggctgctc ctgctgccgc   2940
tccagctgca cctgctccag cagcacctgc tgcaccagct ccggctgctc ctgctgcctg   3000
aagagcaagc ttgatccggc tgctaacaaa gcccgaaagg aagctgagtt ggctgctgcc   3060
accgctgagc aataactagc ataaccctt ggggcctcta acgggtctt gaggggtttt    3120
ttgctgaaag gaggaactat atccggatct ggcgtaatag cgaagaggcc cgcaccgatc   3180
gcccttccca acagttgcgc agcctgaatg gcgaatggga cgcgcccgt agcggcgcat    3240
taagcgcggc gggtgtggtg gttacgcgca gcgtgaccgc tacacttgcc agcgccctag   3300
```

```
cgcccgctcc tttcgctttc ttcccttcct ttctcgccac gttcgccggc tttccccgtc    3360
aagctctaaa tcgggggctc cctttagggt tccgatttag tgctttacgg cacctcgacc    3420
ccaaaaaact tgattagggt gatggttcac gtagtgggcc atcgccctga tagacggttt    3480
ttcgcccttt gacgttggag tccacgttct ttaatagtgg actcttgttc caaactggaa    3540
caacactcaa ccctatctcg gtctattctt ttgatttata agggatttg ccgatttcgg     3600 cctattggtt aaaaaatgag ctgatttaac aaaaatttaa cgcgaatttt aacaaaatat    3660
taacgcttac aatttaggtg                                                 3680

<210> SEQ ID NO 61
<211> LENGTH: 201
<212> TYPE: PRT
<213> ORGANISM: artificial sequence
<220> FEATURE:
<221> NAME/KEY: source
<223> OTHER INFORMATION: /note="Description of artificial sequence:
      PA#1(200) polypeptide/polymer used for the preparation of drug
      conjugates (made by ligation of 10 20mer encoding gene cassettes,
      including one additional C-terminal Ala residue resulting from
      the downstream ligation site)"

<400> SEQUENCE: 61

Ala Ala Pro Ala Ala Pro Ala Pro Ala Ala Pro Ala Ala Pro Ala Pro
1               5                  10                  15

Ala Ala Pro Ala Ala Ala Pro Ala Ala Pro Ala Pro Ala Ala Pro Ala
            20                  25                  30

Ala Pro Ala Pro Ala Ala Pro Ala Ala Ala Pro Ala Ala Pro Ala Pro
        35                  40                  45

Ala Ala Pro Ala Ala Pro Ala Pro Ala Ala Pro Ala Ala Ala Pro Ala
    50                  55                  60

Ala Pro Ala Pro Ala Ala Pro Ala Ala Pro Ala Ala Pro Ala Ala Pro
65                  70                  75                  80

Ala Ala Pro Ala Ala Pro Ala Pro Ala Ala Pro Ala Ala Ala Pro Ala
                85                  90                  95

Ala Pro Ala Ala Ala Pro Ala Ala Pro Ala Pro Ala Ala Pro Ala Ala
            100                 105                 110

Ala Pro Ala Pro Ala Ala Pro Ala Ala Ala Pro Ala Ala Pro Ala Pro
        115                 120                 125

Ala Ala Pro Ala Ala Pro Ala Pro Ala Ala Pro Ala Ala Ala Pro Ala
    130                 135                 140

Ala Pro Ala Pro Ala Ala Pro Ala Ala Pro Ala Ala Pro Ala Ala Pro
145                 150                 155                 160

Ala Ala Pro Ala Ala Pro Ala Pro Ala Ala Pro Ala Ala Ala Pro Ala
                165                 170                 175

Ala Ala Pro Ala Ala Pro Ala Ala Pro Ala Pro Ala Ala Pro Ala Ala
            180                 185                 190

Ala Pro Ala Pro Ala Ala Pro Ala Ala
        195                 200
```

The invention claimed is:

1. A drug conjugate comprising
   (i) a biosynthetic random coil polypeptide or polypeptide segment comprising an amino acid sequence consisting of proline and alanine amino acid residues, wherein said amino acid sequence consists of at least 150 proline (Pro) and alanine (Ala) amino acid residues, and
   (ii) a drug selected from the group consisting of (a) a biologically active protein or a polypeptide that comprises or that is an amino acid sequence that has or mediates a biological activity and (b) a small molecule drug.

2. The drug conjugate according to claim 1, wherein said random coil polypeptide or polypeptide segment comprises an amino acid sequence consisting of 150 to 3000 amino acid residues.

3. The drug conjugate according to claim 1, wherein said proline residues constitute more than 10% and less than 75% of the amino acid sequence.

4. The drug conjugate according to claim 1, wherein said random coil polypeptide or polypeptide segment comprises a plurality of amino acid repeats, wherein said repeat consists of proline and alanine residues and wherein no more than 6 consecutive amino acid residues are identical.

5. The drug conjugate according to claim 1, wherein said random coil polypeptide or polypeptide segment comprises an amino acid sequence selected from the group consisting of

AAPAAPAPAAPAAPAPAAPA; (SEQ ID NO: 1)

AAPAAAPAPAAPAAPAPAAP; (SEQ ID NO: 2)

AAAPAAAPAAAPAAAPAAAP; (SEQ ID NO: 3)

AAPAAPAAPAAPAAPAAPAAP; (SEQ ID NO: 4)

APAAAPAPAAAPAPAAAPAPAAAP; (SEQ ID NO: 5)

AAAPAAPAAPPAAAAPAAPAAPPA; (SEQ ID NO: 6)
and

APAPAPAPAPAPAPAPAPAP (SEQ ID NO: 51)

or circular permuted versions or (a) multimers(s) of these sequences as a whole or parts of these sequences.

6. The drug conjugate according to claim 1, wherein said polypeptide with biological activity, said biologically active protein or said polypeptide that comprises or that is an amino acid sequence that has or that mediates a biological activity is selected from the group consisting of binding proteins, antibody fragments, cytokines, growth factors, hormones or enzymes.

7. The drug conjugate of claim 6, wherein said polypeptide with biological activity is a binding protein and wherein said binding molecule is selected from the group consisting of antibodies, Fab fragments, F(ab')$_2$ fragments, CDR-derived peptidomimetics, single chain variable fragments (scFv), domain antibodies, lectins, immunoglobulin domains, fibronectin domains, protein A domains, SH3 domains, ankyrin repeat domains, and lipocalins.

8. The drug conjugate of claim 1, wherein said biologically active protein is selected from the group consisting of granulocyte colony stimulating factor, human growth hormone, alpha-interferon, beta-interferon, gamma-interferon, tumor necrosis factor, erythropoietin, coagulation factor VIII, gp120/gp160, soluble tumor necrosis factor I and II receptor, reteplase, exendin-4, anakinra, interleukin-2, neutrophil gelatinase-associated lipocalin, follicle-stimulating hormone, glucocerebrosidase, thymosin alpha 1, glucagon, somatostatin, adenosine deaminase, interleukine 11, coagulation factor VIIa, coagulation factor IX, hematide, lambda-interferone, leptin, interleukine-22 receptor subunit alpha (IL-22ra), interleukine-22, hyaluronidase, fibroblast growth factor 18, fibroblast growth factor 21, glucagon-like peptide 1, osteoprotegerin, IL-18 binding protein, growth hormone releasing factor, soluble TACI receptor, thrombospondin-1, soluble VEGF receptor Flt-1, and IL-4 mutein.

9. The drug conjugate according to claim 1, whereby said biosynthetic random coil polypeptide or polypeptide mediates an increased in vivo and/or in vitro stability of said drug conjugate.

10. The drug conjugate according to claim 9, wherein said increased in vivo stability is a prolonged plasma half-life of said drug conjugate when compared to the stability of a control polypeptide or a control conjugate lacking said random coil random coil polypeptide or polypeptide segment.

11. The drug conjugate according to claim 1, wherein said small molecule is selected from the group consisting of digoxigenin, fluorescein, doxorubicin, calicheamicin, camptothecin, fumagillin, dexamethasone, geldanamycin, paclitaxel, docetaxel, irinotecan, cyclosporine, buprenorphine, naltrexone, naloxone, vindesine, vancomycin, risperidone, aripiprazole, palonosetron, granisetron, cytarabine NX1838, leuprolide, goserelin, buserelin, octreotide, teduglutide, cilengitide, abarelix, enfuvirtide, ghrelin, alpha 4 integrin inhibitors, antisense nucleic acids, small interference RNAs, micro RNAs, steroids, DNA or RNA aptamers and peptides and/or peptidomimetics.

12. A composition comprising the drug conjugate according to claim 1.

13. The composition according to claim 12 which is a pharmaceutical composition or a diagnostic composition, optionally further comprising a pharmaceutically acceptable carrier(s).

14. The drug conjugate according to claim 1, wherein the biologically active protein is selected from the group consisting of binding proteins, antibody fragments, cytokines, growth factors, hormones and enzymes.

* * * * *